(12) United States Patent
Hummer et al.

(10) Patent No.: US 12,092,629 B2
(45) Date of Patent: Sep. 17, 2024

(54) SIMULTANEOUS DISEASE DETECTION SYSTEM METHOD AND DEVICES

(71) Applicants: Matthew Hummer, Shaker Heights, OH (US); Gregory J. Hummer, Shaker Heights, OH (US)

(72) Inventors: Matthew Hummer, Shaker Heights, OH (US); Gregory J. Hummer, Shaker Heights, OH (US)

(*) Notice: Subject to any disclaimer, the term of this patent is extended or adjusted under 35 U.S.C. 154(b) by 0 days.

(21) Appl. No.: 18/243,088

(22) Filed: Sep. 6, 2023

(65) Prior Publication Data
US 2023/0417732 A1 Dec. 28, 2023

Related U.S. Application Data

(63) Continuation-in-part of application No. 17/832,632, filed on Jun. 4, 2022, now abandoned, which is a continuation-in-part of application No. 17/733,902, filed on Apr. 29, 2022, now Pat. No. 11,614,439, which is a continuation of application No. 17/324,085, filed on May 18, 2021, now Pat. No. 11,340,210, which is a continuation-in-part of application No. 16/926,701, filed on Jul. 11, 2020, now Pat. No. 11,179,061.

(51) Int. Cl.
G01N 33/48     (2006.01)
G01N 33/487    (2006.01)
G01N 33/569    (2006.01)
G16H 10/40     (2018.01)

(52) U.S. Cl.
CPC .. *G01N 33/48792* (2013.01); *G01N 33/48714* (2013.01); *G01N 33/4875* (2013.01); *G01N 33/56983* (2013.01); *G16H 10/40* (2018.01)

(58) Field of Classification Search
CPC ....... G01N 33/48792; G01N 33/48714; G01N 33/4875; G01N 33/56983; G16H 10/40
USPC ..................................... 702/19; 422/500, 50
See application file for complete search history.

(56) References Cited

U.S. PATENT DOCUMENTS 8,629,770 B2 * 1/2014 Hummer ............. G08B 25/012
                                                340/539.1

* cited by examiner

*Primary Examiner* — Christine T Mui
(74) *Attorney, Agent, or Firm* — Edmond DeFrank

(57) ABSTRACT

The embodiments disclose a process for manufacturing a sensor including depositing a first conductive layer on a substrate followed by curing the first conductive layer and, depositing a temperature controlling conductive ink on top of a portion of the first conductive layer followed by curing the temperature controlling conductive ink and, depositing an insulating layer on top of the temperature controlling conductive ink layer and a portion of the first conductive layer followed by curing the insulating layer and, depositing a second conductive layer on top of a portion of first conductive layer followed by curing the second conductive layer and, depositing an adhesive layer on top of a portion of the first conductive layer for adhering a memory chip to the first conductive layer followed by curing the adhesive layer and, depositing at least one biomolecule layer on top of the second conductive layer followed by drying the at least one biomolecule layer.

12 Claims, 120 Drawing Sheets

FIG. 33

┌─────────────────────────────────────────────────────────────┐
│ THE BIOLOGICAL PATHOGEN APP CAN BE CONFIGURED TO DETECT OR  │
│ TRIGGER AN ALARM WHEN A PATHOGEN WHICH IS CONSIDERED        │
│ HIGHLY INFECTIOUS IS DETECTED                               │
└─────────────────────────────────────────────────────────────┘
3400

3410
┌─────────────────────────────────────────────────────────────┐
│ THE BIOLOGICAL PATHOGEN APP IS CONFIGURED TO, ONCE A HIGHLY │
│ INFECTIOUS PATHOGEN IS DETECTED, SHARE THE DETECTION        │
│ INFORMATION                                                 │
└─────────────────────────────────────────────────────────────┘

3420
┌─────────────────────────────────────────────────────────────┐
│ FOR EXAMPLE, THE BIOLOGICAL PATHOGEN APP IS CONFIGURED TO   │
│ USE THE COMMUNICATION CIRCUITRY TO BROADCAST AN ALERT (OR   │
│ GENERATE A NOTIFICATION) VIA ANY SUITABLE COMMUNICATIONS    │
│ NETWORK E.G., WIFI, NFC, BLUETOOTH, CELL, AND OTHER NETWORKS│
└─────────────────────────────────────────────────────────────┘

3430
┌─────────────────────────────────────────────────────────────┐
│ THE ALERT MAY BE DIRECTLY SENT TO OTHER CELL PHONES AND/OR  │
│ PERSONAL COMMUNICATION DEVICES IN THE AREA, OR MAY BE SENT  │
│ TO A SERVER (OR THROUGH A NETWORK) AND THEN ON TO DEVICES   │
│ WITHIN A RANGE OF A GIVEN LOCATION                          │
└─────────────────────────────────────────────────────────────┘

3440
┌─────────────────────────────────────────────────────────────┐
│ THE BIOLOGICAL PATHOGEN APP IS CONFIGURED TO USE LOCATION   │
│ INFORMATION FROM A GPS CHIP, WIFI OR ANY OTHER LOCATION     │
│ INFORMATION AVAILABLE TO THE CELL PHONE TO IDENTIFY THE     │
│ LOCATION OF THE DETECTED HIGHLY INFECTIOUS PATHOGEN         │
└─────────────────────────────────────────────────────────────┘

3450
┌─────────────────────────────────────────────────────────────┐
│ THE BIOLOGICAL PATHOGEN APP CAN BE CONFIGURED TO ALERT THE  │
│ AUTHORITIES IN THE EVENT CERTAIN HIGHLY INFECTIOUS PATHOGENS│
│ ARE DETECTED                                                │
└─────────────────────────────────────────────────────────────┘

3460
┌─────────────────────────────────────────────────────────────┐
│ FOR EXAMPLE, THE DETECTION OF SARS-CoV-2 CAN TRIGGER        │
│ INFORMATION RELATING TO THE LOCATION, TIME, AND OTHER DATA  │
│ OF THE DETECTION TO BE FORWARDED TO CERTAIN DESIGNATED      │
│ AUTHORITIES FOR PUBLIC HEALTH THREAT MANAGEMENT/MITIGATION  │
└─────────────────────────────────────────────────────────────┘

FIG. 34

3700 — A MONITOR SYSTEM WITH AT LEAST ONE MONITOR/DETECTOR COMPONENT

4140 — A PLURALITY OF NANOSENSORS

2730 — A PLURALITY OF BIOLOGICAL SENSORS

2750 — A PLURALITY OF ANALYTE SENSORS

4142 — FOR ANALYTIC DETECTION

2740 — FOR DETECTING CERTAIN BIOLOGICAL PATHOGENS

4142 — FOR ANALYTIC DETECTION

4100 — MONITOR SYSTEMS ARE PLACED IN AIR HANDLERS TO DETECT PATHOGENS IN THE AIR

4120 — MONITOR SYSTEMS GPS CHIPS RECORD THE GPS COORDINATES IN A MEMORY DEVICE OF THE DETECTION READER

4110 — MONITOR SYSTEMS ARE CONFIGURED TO ACTIVATE DISINFECTANT DISPERSING DEVICES WHEN PATHOGENS ARE DETECTED IN THE AIR

4130 — MONITOR SYSTEMS ARE CONFIGURED TO TRANSMIT DETECTION LOCATION GPS COORDINATES TO A SENSING PLATFORM SMART PHONE APP

FIG. 41

```
┌─────────────────────────────┐
│  WORKING MECHANISM FOR      │─── 4500
│  CARBON AND VDW SENSORS     │
└─────────────────────────────┘
              ↓
┌─────────────────────────────┐
│  LARGE SURFACE TO VOLUME    │─── 4501
│          RATIO              │
└─────────────────────────────┘
              ↓
┌─────────────────────────────┐
│        SURFACE              │─── 4502
│    FUNCTIONALIZATION        │
└─────────────────────────────┘
              ↓
┌─────────────────────────────┐
│      SELECTIVE DETECTION    │─── 4503
└─────────────────────────────┘
              ↓
4508 ─┌─────────────────────────────┐
      │  IMPROVING REPRODUCIBILITY OF│
      │   CARBON/VDW SENSORS         │
      └─────────────────────────────┘
```

4510 — MICRO-GRAVURE SYSTEM FOR R2R THIN-FILM DEPOSITION

ROLL-TO-ROLL PROCESSING MAY INCLUDE A MULTI-FUNCTIONAL R2R SYSTEM, INCLUDING IN-LINE ELECTROSPRAY, DRYING, CURING AND SINTERING PROCESSES — 4520

SCALED PRODUCTION OF CARBON/VDW-BASED SENSORS BY USING R2R THIN FILM DEPOSITION SYSTEM — 4530

4532 — INTEGRATED STRUCTURE OF CARBON AND VDW SENSORS

4534 — A SELECTABLE BIOLOGIC TARGET DETECTION SYSTEM THAT IS FIELD-DEPLOYABLE WITH RAPID DETECTION OF SARS-COV-2 DEVICES

4600 — CONDUCTIVE-BASED SENSORS MANUFACTURING PARAMETERS

4602 — CONDUCTIVE NANOSENSOR BONDED TO POLYIMIDE OR PET SUBSTRATE
- 4603 — VDW MATERIAL
- 4604 — GRAPHENE

4610 — JET PRINTING, SCREEN PRINTING, INKJET PRINTING, DIGITAL PRINTING, 3D PRINTING, MICRO-CONTACT PRINTING, AEROSOL PRINTING AND ADDITIVE MANUFACTURING OF CONDUCTIVE ELECTRODES
- 4615 — NICKEL
- 4616 — CARBON
- 4611 — GOLD
- 4612 — SILVER
- 4613 — COPPER
- 4614 — PLATINUM

4630 — BINDING SENSORS AND OPTIMIZING SENSOR CONDUCTIVITY USING VARIOUS INK DEPOSITION, DRYING, CURING, CLEANING, WASHING AND FUNCTIONALIZATION METHODS

4632 — AEROSOL SPRAY/AIR-SPRAY

4634 — ELECTROSTATIC SPRAY

4633 — SPRAY COATING BIOLOGICALLY SENSITIVE MOLECULES SOLUTION ON CONDUCTIVE CARBON SENSOR SURFACE

4635 — NOZZLE SIZE, OPERATING PRESSURE/VOLTAGE, OPERATING DISTANCE BETWEEN THE SPRAY NOZZLE AND THE SUBSTRATE, DRYING TEMPERATURE

4636 — PIEZO-DRIVEN DISPENSING BIOLOGICALLY SENSITIVE MOLECULES SOLUTION ON CONDUCTIVE CARBON SENSOR SURFACE

4637 — DIP COATING BIOLOGICALLY SENSITIVE MOLECULES SOLUTION ON CONDUCTIVE CARBON SENSOR SURFACE

FIG. 46

4700 — DETECTION SENSOR FOR ELECTROCHEMICAL DETECTION OF SARS-CoV2 BIOLOGIC ANALYTICAL TARGET

4725 — PRINTED ELECTRODES

4724 — A PLURALITY OF TARGET BIOLOGICALLY SENSITIVE MOLECULES SPECIFIC FOR SARS-CoV2 ARE BOUND TO THE CARBON SENSOR AND STABILIZED INDUCTIVELY

4702 — CARBON SENSOR IS BONDED TO THE POLYIMIDE OR PET SUBSTRATE

4722 — PRINTED IDES

4720 — POLYIMIDE OR PET OR PAPER AND OTHER PLASTIC SUBSTRATES, DIELECTRIC FLEXIBLE FILM SUBSTRATE

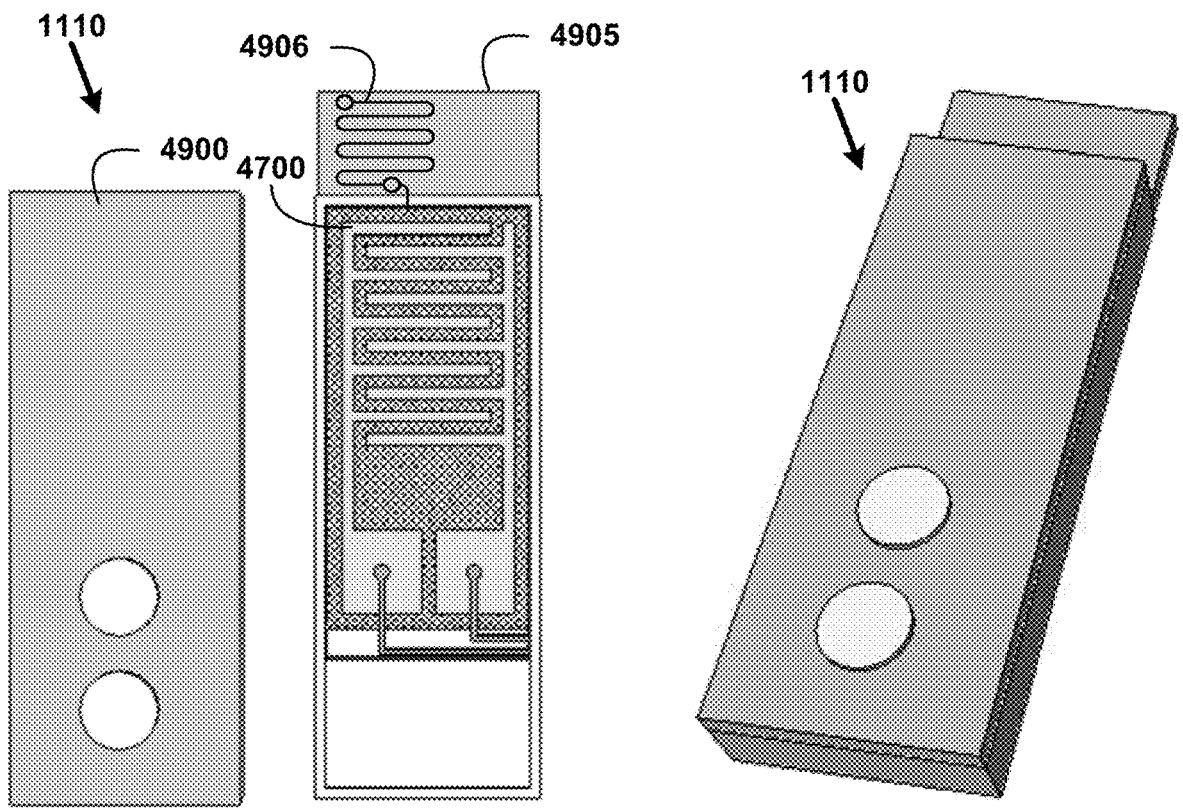
FIG. 49A
FIG. 49B
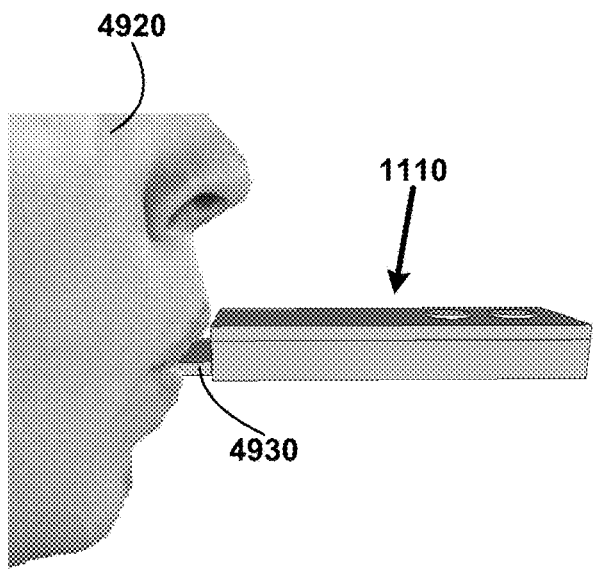
FIG. 49C
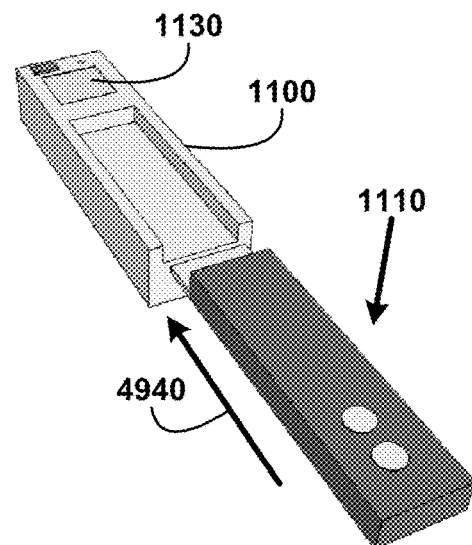
FIG. 49D

5400 — PROCESS FOR ANALYTE AND PATHOGEN DETECTION IN AIR SAMPLE AND HVAC

5410 — AIR SAMPLE COLLECTED AND ELECTRICALLY CHANGED (USUALLY NEGATIVELY CHARGED)

5420 — NEBULIZER CONTAINING SOLUTION (BUFFER OR OTHER SOLUTIONS) CREATES ELECTRICALLY CHARGED (USUALLY POSITIVELY CHARGED) AEROSOLS

5430 — THE NEGATIVELY CHARGED AIR SAMPLE IS ATTRACTED TO THE POSITIVELY CHARGED AEROSOLS FORMING A UNIFORM AEROSOLIZED TEST SAMPLE

5440 — THE AEROSOLIZED TEST SAMPLE IS TRANSFORMED INTO A LIQUID TEST SAMPLE USING AN IMPACTOR JET NOZZLE TO SPRAY THE AEROSOLIZED SAMPLE INTO AN IMPACTION PLATE, WHICH CAUSES THE SAMPLE TO TRANSFORM INTO A LIQUID

5450 — THE LIQUID TEST SAMPLE IS CAPTURED BY A TEMPERATURE CONTROLLED FLUIDIC PATH OR CHAMBER WHERE THE LIQUID SAMPLE CAN BE ELECTRICALLY CHARGED AGAIN IF NECESSARY

5460 — THE LIQUID TEST SAMPLE IS PRESENTED TO THE SENSOR ARRAY FOR MEASUREMENT THROUGH THE TEMPERATURE CONTROLLED FLUIDIC PATH OR CHAMBER

5470 — THE TEST SAMPLE IS DISPOSED OF IN A WASTE RESERVOIR USING VARIOUS ACTIVE OR PASSIVE INDUCTION DEVICES SUCH AS VACUUMS OR PUMPS

FIG. 54

```
┌─────────────────────────┐
│   ULTRASONIC SPRAY      │
│  COATING IS USED FOR    │──7600
│      TIGHT DROP         │
│     DISTRIBUTION        │
│   WITHOUT CLOGGING      │
└───────────┬─────────────┘
            ▼
┌─────────────────────────────┐
│ ULTRASONIC SPRAY COATING, A │
│ LOW-VELOCITY SPRAY THAT     │──7610
│ CREATES UNIFORM MICRON AND  │
│ SUB-MICRON THICKNESS LAYERS │
│  RANGING FROM 10M TO 39M    │
└─────────────┬───────────────┘
              ▼
┌─────────────────────────┐
│   ULTRASONIC NOZZLE     │──7620
│      FREQUENCY IS       │
│    MEASURED IN KHZ      │
└───────────┬─────────────┘
            ▼
┌──────────────────────────────────┐
│ ULTRASONIC NOZZLES OPERATE AT    │──7630
│ A SPECIFIC RESONANCE FREQUENCY,  │
│ WHICH DICTATES THE MEDIAN        │
│       DROPLET SIZE               │
└──────────────────────────────────┘
```

FIG. 75

SIMULTANEOUS DISEASE DETECTION SYSTEM METHOD AND DEVICES

This patent application is a Continuation-in-part and claims priority to United States patent application entitled: "SIMULTANEOUS DISEASE DETECTION SYSTEM METHOD AND DEVICES", U.S. Ser. No. 17/832,632 filed on Jun. 4, 2022, by Matthew Hummer, which is a Continuation-in-part and claims priority to the United States patent application entitled: "METHOD AND DEVICES FOR DETECTING VIRUSES AND BACTERIAL PATHOGENS", U.S. Ser. No. 17/733,902 filed on Apr. 29, 2022 by Matthew Hummer, which is a Continuation of United States patent application entitled: "METHOD AND DEVICES FOR DETECTING VIRUSES AND BACTERIAL PATHOGENS", U.S. patent application Ser. No. 17/324,085 filed on May 18, 2021 by Matthew Hummer, which is a Continuation-in-part of "METHOD AND DEVICES FOR DETECTING CHEMICAL COMPOSITIONS AND BIOLOGICAL PATHOGENS", U.S. Ser. No. 16/926,701 filed on Jul. 11, 2020 by Gregory J. Hummer, which all of the above are incorporated herein by reference.

BACKGROUND

There is a great need for rapid and accurate detection of analytes that is cost-effective. Detection should be personalized for early diagnosis of a targeted disease, enabling early treatment for improved health outcomes. Detection should provide real-time analysis of infectious diseases outbreak and community spread allowing for rapid implementation of mitigation tactics and healthcare resource alignment. The rapid and accurate detection of infections or associated biomarkers is also needed for general wellness, other known diseases, infectious viruses, and bacterial pathogens, including new infectious viruses, diseases, and bacterial pathogens that may appear. A major challenge to achieving the cost-effectiveness of a rapid and accurate detection system is deposition methods or transfer methods of nanosensor materials along with drying, curing, and preparing those materials in a volume production process.

BRIEF SUMMARY OF THE INVENTION

The invention is a manufacturing process of an analyte detection system. The manufacturing process deposits analyte sensor liquid materials contained in a tank being flowed into a deposition device. The deposition device deposits the analyte sensor materials to form a multi-layered analyte sensor. In a separate process occurring simultaneously, a layering device is used to build multiple layers of analyte detection liquid materials contained in a tank to fabricate into an analyte monitor/detection device. An assembly device couples the multi-layered analyte sensor and the analyte monitor/detection device into an analyte monitor/detection system.

In another separate process occurring simultaneously, multiple receiver reader components are positioned into a receiver reader assembly device. The receiver reader assembly device couples the components to create a receiver reader. A connection assembly device connects the analyte monitor/detection system to the receiver reader to create an analyte detection system. The analyte detection system is used to process an analyte test sample. The analyte detection system identifies and measures the analyte test sample to identify a detected targeted analyte.

The receiver reader processes the detection data and displays the analyte sensing detection results. In one embodiment, the receiver reader transmits the analyte sensing detection results to remote servers. The remote servers record the data and results into a database. The remote servers transmit the data and results to a user's computer to allow the user to review the analyte sensing detection results.

BRIEF DESCRIPTION OF THE DRAWINGS

FIG. 34 shows a block diagram of an overview of communication circuitry to broadcast an alert of one embodiment.

FIG. 41 shows a block diagram of an overview of monitor systems placed in air handlers of one embodiment.

FIG. 45A shows a block diagram of an overview of the working mechanism for carbon sensors of one embodiment.

FIG. 46 shows a block diagram of an overview of conductive-based sensors manufacturing parameters of one embodiment.

FIG. 47A shows for illustrative purposes only an example of electronic detection of SARS-CoV-2 biologic analytical target of one embodiment.

FIG. 47B shows for illustrative purposes only an example of breath moisture test sampling of one embodiment.

FIG. 49A shows for illustrative purposes only an example of an opened test cartridge showing a sensor of one embodiment.

FIG. 49B shows for illustrative purposes only an example of a closed test cartridge of one embodiment.

FIG. 49C shows for illustrative purposes only an example of a test subject depositing a sample of one embodiment.

FIG. 49D shows for illustrative purposes only an example of a test cartridge inserted into a portable detection cartridge reader of one embodiment.

FIG. 54 shows a block diagram of an overview of chemical and pathogen detection in an air sample and HVAC system of one embodiment.

FIG. 75 shows a block diagram of an overview of ultrasonic spray coating of one embodiment.

FIG. 97 shows for illustrative purposes only an example of a dual-film sensor.

FIG. 98 shows for illustrative purposes only an example of a dual-film material layers and stack-up of one embodiment.

FIG. 99 shows for illustrative purposes only an example of a dual-film sensor material layers and stack-up with swapped first and second conductive layers of one embodiment.

FIG. 100 shows for illustrative purposes only an example of a mono-film sensor of one embodiment.

FIG. 101 shows for illustrative purposes only an example of a mono-film sensor material layers and stack-up of one embodiment.

FIG. 102 shows for illustrative purposes only an example of mono-film sensor material layers and stack-up with swapped first and second conductive layers of one embodiment.

FIG. 103 shows for illustrative purposes only an example of a mono-film sensor material deposition sequence and relative thickness of one embodiment.

FIG. 104 shows a block diagram of an overview of a sensor material manufacturing process of one embodiment.

FIG. 105 shows for illustrative purposes only an example of analyte detection system components of one embodiment.

FIG. 106A shows for illustrative purposes only an example of a sample collector of one embodiment.

FIG. 106B shows for illustrative purposes only an example of a sample collector continuation of one embodiment.

FIG. 107 shows for illustrative purposes only an example of sensor cartridge components of one embodiment.

Figure 108A:
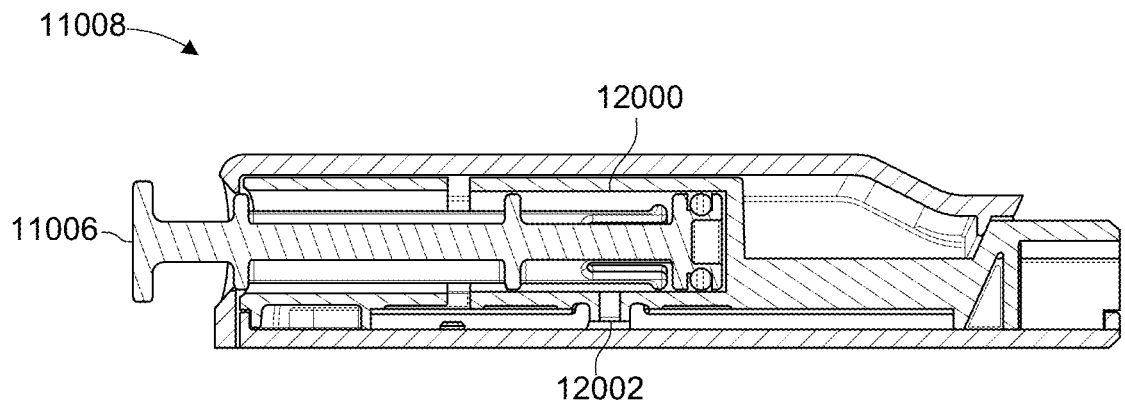

FIG. 108A shows for illustrative purposes only an example of the flow induction mechanism of one embodiment.

Figure 108B:
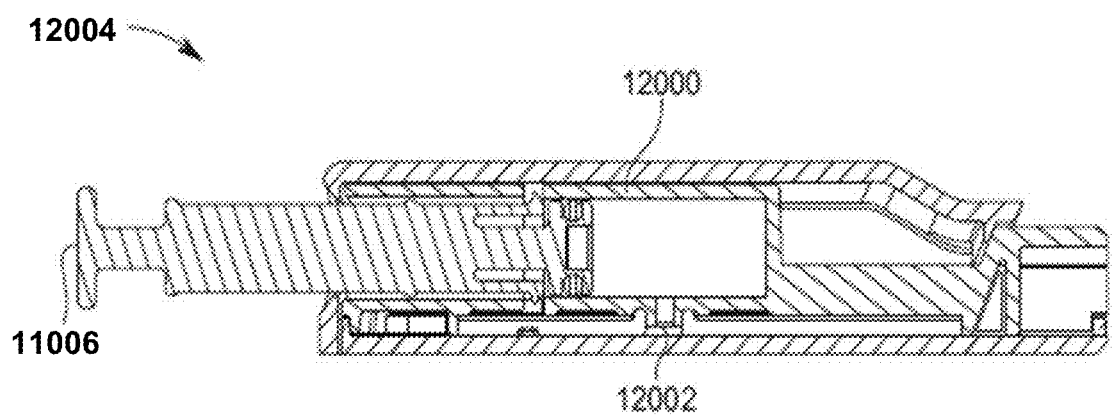

FIG. 108B shows for illustrative purposes only an example of the flow induction mechanism continuation of one embodiment.

Figure 109:
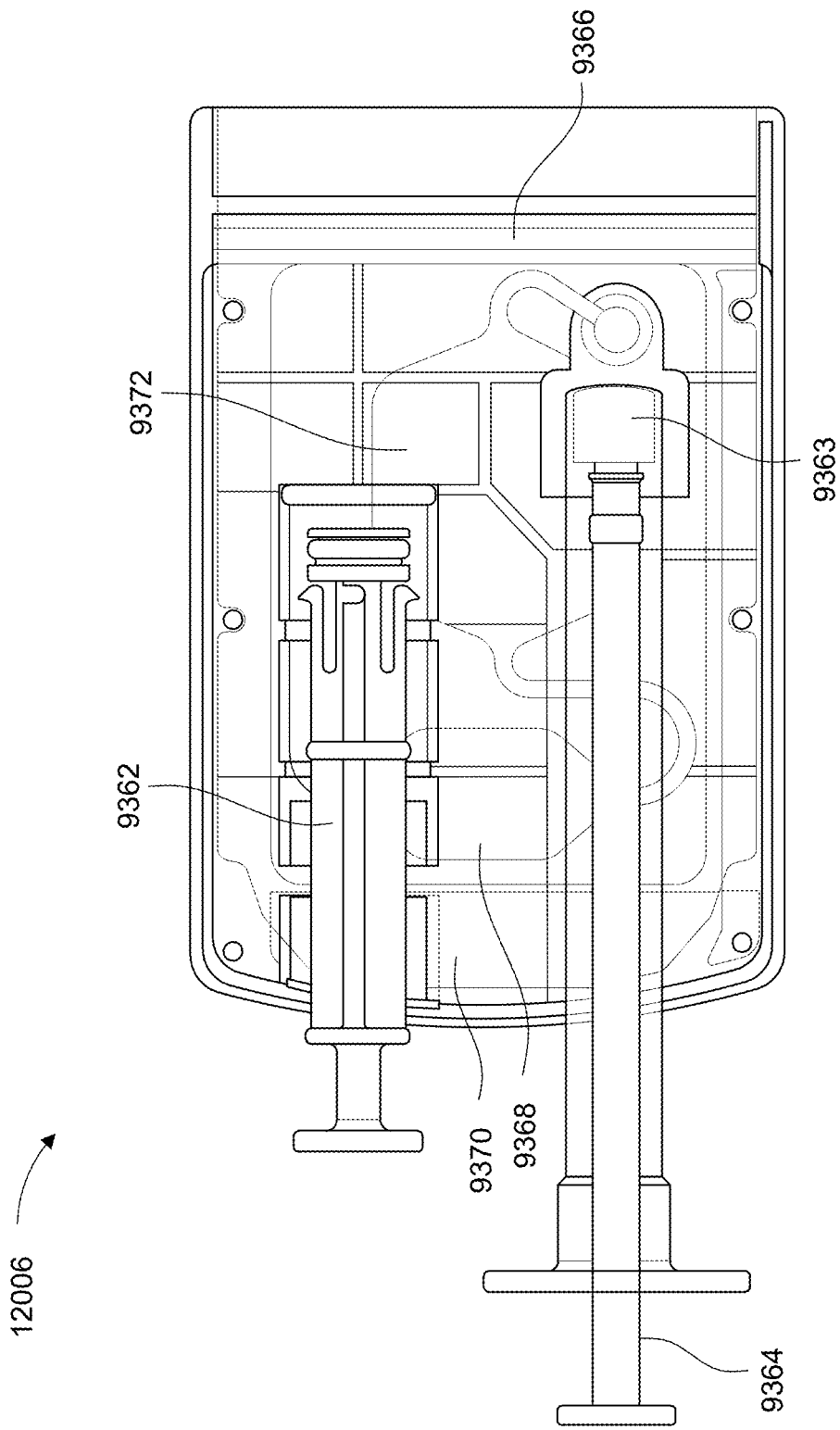

FIG. 109 shows for illustrative purposes only an example of the sensor cartridge assembled components of one embodiment.

Figure 110:
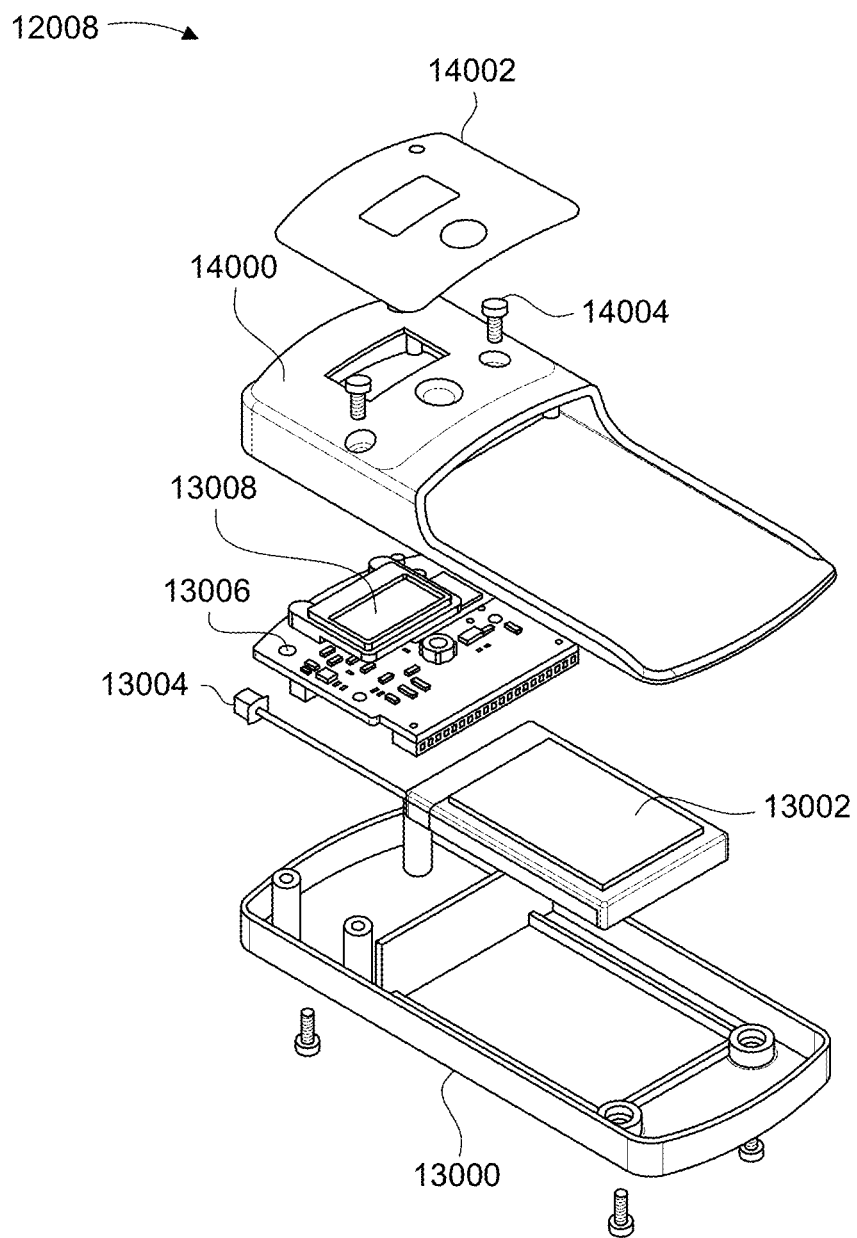

FIG. 110 shows for illustrative purposes only an example of analyte detection reader components of one embodiment.

DETAILED DESCRIPTION OF THE INVENTION

In the following description, reference is made to the accompanying drawings, which form a part hereof, and which are shown by way of illustration a specific example in which the invention may be practiced. It is to be understood that other embodiments may be utilized and structural changes may be made without departing from the scope of the present invention.

General Overview

It should be noted that the descriptions that follow, for example, in terms of a simultaneous disease detection system, method, and devices are described for illustrative purposes and the underlying system can apply to any number and multiple types of disease or target analytes. In one embodiment of the present invention, the method and devices for detecting diseases or target analytes can be configured using simultaneous detection of a plurality of diseases or target analytes. The method and devices for detecting diseases or target analytes can be configured to include a single-use test cartridge and can be configured to include a plurality of impedimetric biosensors for detecting multiple different diseases or target analytes simultaneously using the present invention.

Detection of analytes includes infectious diseases, deficiency diseases, heredity diseases and physiological diseases, and other conditions detectable with biosensing. Biosensing provides a device that detects an analyte (tissue, microorganisms, organelles, cell receptors, enzymes, antibodies, nanobodies, antigens, proteins, amino acids, nucleic acids, genetic material, other biologically sensitive molecules, large molecules, and small molecules) by transducing a biological response into an electrical signal.

The present exemplary embodiment relates to the rapid and accurate detection of biomarkers and disease that is cost-effective and finds application in conjunction with monitoring systems and diagnostic systems that use a nanosensor and will be described with particular reference thereto. However, it is to be appreciated that the present exemplary embodiment is also amenable to other like applications.

Such a system is simple enough that the system could be operated without assistance or supervision from a medical operator and in some applications is completely automated. The system is to provide personalized and early diagnosis of targeted diseases, enabling early treatment for improved health outcomes. The system would also provide real-time analysis of infectious diseases outbreak and community spread allowing for rapid implementation of mitigation tactics and healthcare resource alignment. The rapid and accurate detection of infections or biomarkers is also needed for general wellness, other known diseases, infectious viruses, and bacterial pathogens, including new infectious viruses, diseases, and bacterial pathogens that may appear.

The embodiments that describe achieving the cost-effectiveness of a rapid and accurate detection system are deposition methods or transfer methods of nanosensor materials along with drying, curing, and preparing those materials in a volume production process.

There are two general categories of deposition methods of the exemplary embodiment: direct deposition or patterning of material onto a desired substrate and transfer deposition of pre-patterned material onto the substrate. Direct deposition can be achieved by contact and non-contact printing, while the latter is achieved by a transfer print after the patterns are brought about via conventional lithography, plasma-modified techniques, or other techniques. There are two general categories of curing: thermal curing using furnaces and radiative heat transfer or energy transfer. Exemplary embodiments show how known deposition, drying, curing, and manufacturing methods are modified to produce highly accurate nanosensors for rapid and cost-effective detection of diseases, pathogens, and target analytes.

The following terms and phrases immobilized, stabilized inductively, polarized, conductively oriented, electrokinetically oriented, and inductively aligned are used herein interchangeably without any change in meaning.

Figure 1A:
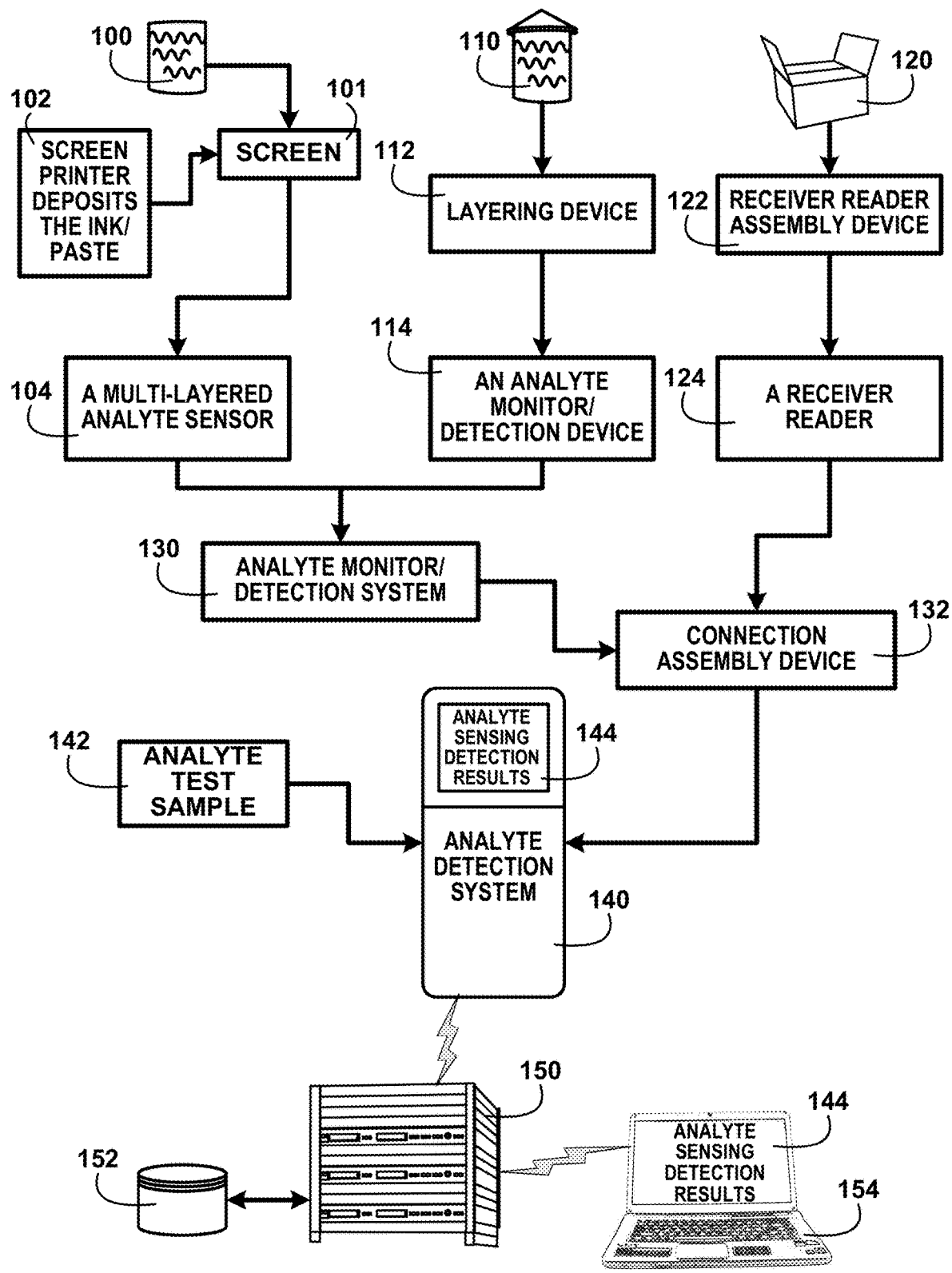
FIG. 1A shows for illustrative purposes only an example of an analyte detection system fabrication system of one embodiment.
Figure 1B:
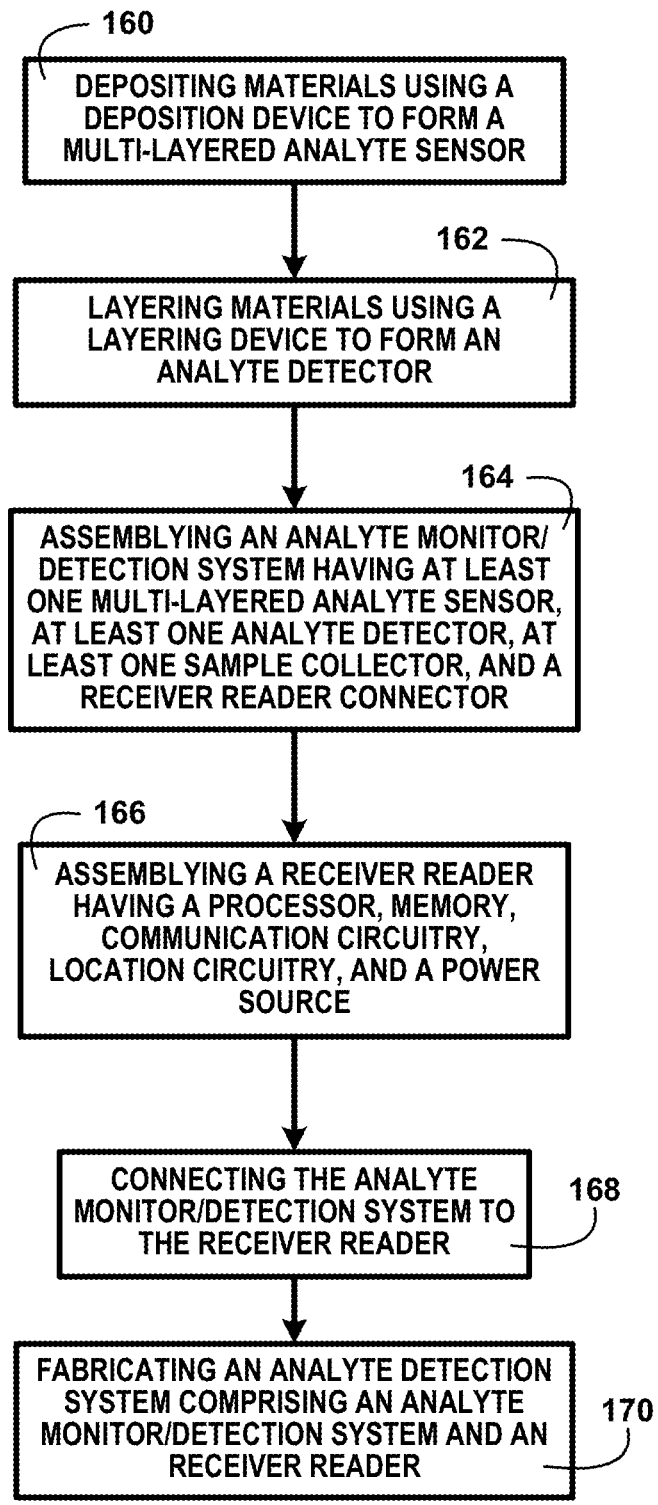
FIG. 1B shows a block diagram of an overview flow chart of analyte detection system fabrication system of one embodiment.

An Analyte Detection System Fabrication System:

In one embodiment FIG. 1A and FIG. 1B describe the manufacturing steps to create the analyte detection system of the invention.

FIG. 1A shows for illustrative purposes only an example of an analyte detection system fabrication system of one embodiment. In one embodiment, FIG. 1A shows analyte sensor liquid materials 100 contained in a tank being flowed into a deposition device 102 in an automated screen printing system where the ink or paste could be stored in a tank. In another embodiment, ink or paste can be placed on the screen 101 and the screen printer can perform the function of depositing the ink or paste.

The deposition device 102 deposits the analyte sensor materials 100 to form a multi-layered analyte sensor 104. Multiple analyte detection liquid materials 110 contained in a tank being flowed into a layering device 112. The layering device 112 fabricates the multiple analyte detection liquid materials 110 into an analyte monitor/detection device 114. An assembly device couples the multi-layered analyte sensor 104 and the analyte monitor/detection device 114 into an analyte monitor/detection system 130.

Multiple receiver reader components 120 are joined in a receiver reader assembly device 122 to create a receiver reader 124. A connection assembly device 132 connects the analyte monitor/detection system 130 to the receiver reader 124 to create an analyte detection system 140. The analyte detection system 140 is used to process an analyte test sample 142. The analyte detection system 140 identifies and measures the analyte test sample 142 to identify a detected targeted analyte.

The receiver reader 124 processes the detection data and displays the analyte sensing detection results on user's computer 154. The receiver reader 124 transmits the analyte sensing detection results 144 to remote servers 150. The remote servers 150 record the data and results into a database 152. The remote servers 150 transmits the data and results to a user's computer 154 to allow the user to review the analyte sensing detection results 144.

The multi-layered analyte sensor 104 is a five layered multilayered analyte sensor structure. A plurality of materials to sense analytes joined in a multi-layered analyte sensor. The analyte monitor/detection device 114 is a plurality of materials including a lysing component layered to form at least one analyte detector. A monitor/detection system assembled includes at least one sensor, at least one detector, at least one sample collector, and a receiver connector. A receiver reader assembled includes a processor, memory, communication circuitry, location circuitry, and a power source. The monitor/detection system is connected to the receiver reader. The deposition, layering, and joining operations are an analyte detection system fabrication process comprising a sensor and an associated receiver of one embodiment.

A plurality of materials to sense analytes are included in the multi-layered analyte sensor. A plurality of materials including a lysing component, are layered to form at least one analyte detector. The plurality of materials are deposited and infused into the five layered analyte sensor. A detection device assembly comprises a receiver connector, at least one monitor detector, a plurality of at least one analyte detector, a memory device, and a lysing function component. A monitor/detection system assembled includes at least one sensor, at least one detection device, at least one sample collector, flow induction mechanism, a sensor detector cartridge, and a receiver connector. A receiver reader assembled included a processor, a memory device, communication circuitry, location circuitry, a lower molded housing, a power source with a rechargeable port, a printed circuit board assembly (PCBA), a display, an upper molded housing and a display cover. The monitor/detection system is connected to the receiver reader. An analyte detection system fabrication process comprises a sensor and an associated receiver reader to detect analytes of one embodiment.

DETAILED DESCRIPTION

FIG. 1B shows a block diagram of an overview flow chart of analyte detection system fabrication system of one embodiment. FIG. 1B shows depositing materials using a deposition device to form a multi-layered analyte sensor 160. Layering materials using a layering device to form an analyte detector 162. Assembling an analyte monitor/detection system having at least one multi-layered analyte sensor, at least one analyte detector, at least one sample collector, and a receiver reader connector 164. Assembling a receiver reader having a processor, memory, communication circuitry, location circuitry, and a power source 166. Connecting the analyte monitor/detection system to the receiver reader 168. Fabricating an analyte detection system comprising an analyte monitor/detection system and a receiver reader 170.

Depositing materials forms a multi-layered analyte sensor. Layering materials forms at least one analyte detector having a lysing component. Assembling using an assembly device creates a monitor/detection system having at least one sensor, at least one detector, at least one sample collector, and a receiver connector. Assembling a receiver reader using an assembly device includes a processor, memory, communication circuitry, location circuitry, and a power source. A connection device is used for connecting the monitor/detection system to the receiver reader. Fabricating an analyte detection system comprises connecting a monitor/detection system to an associated receiver reader of one embodiment.

Figure 2A:
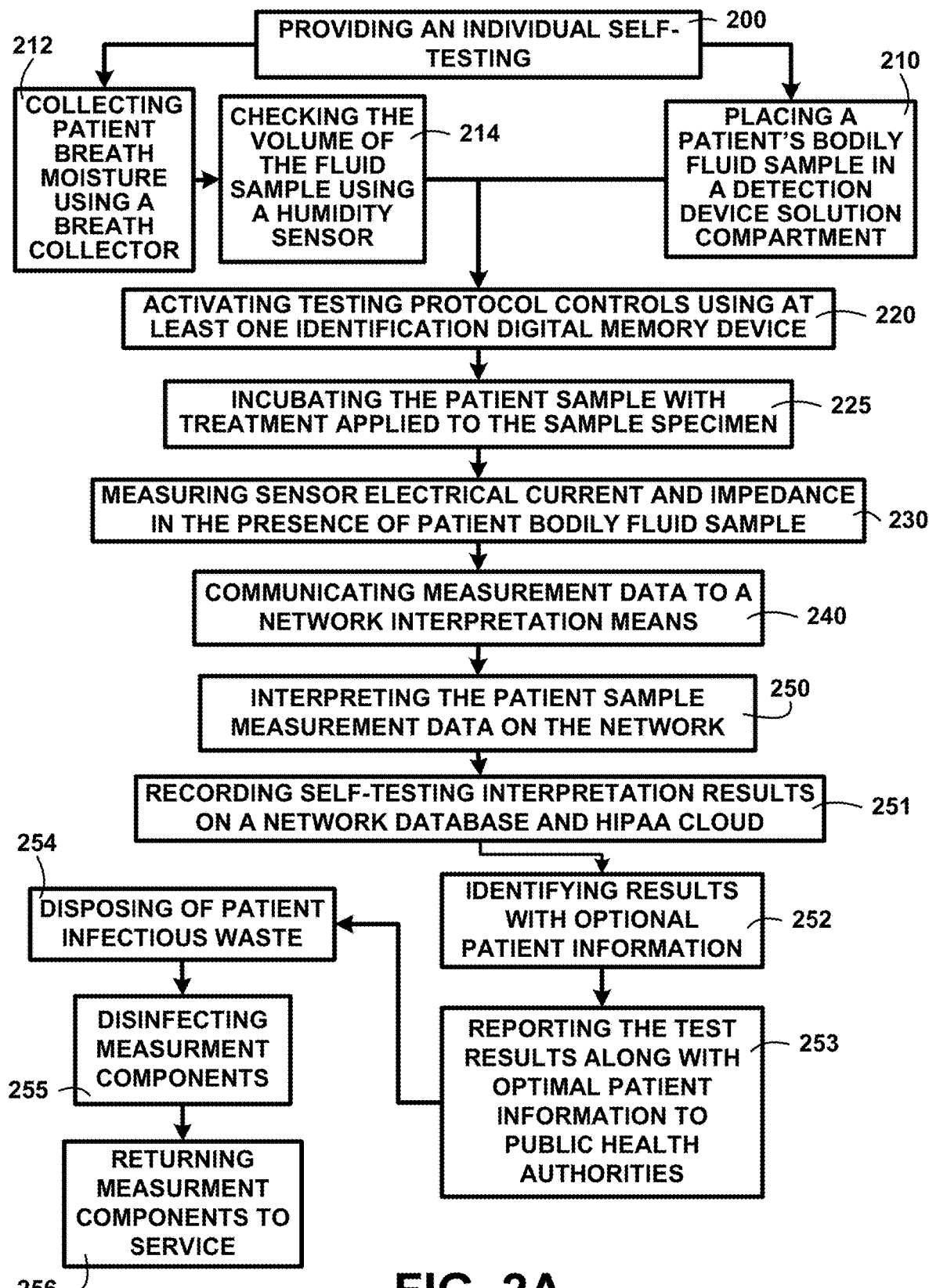
FIG. 2A shows a block diagram of an overview flow chart of an individual self-testing at the home of one embodiment.
Figure 91A:
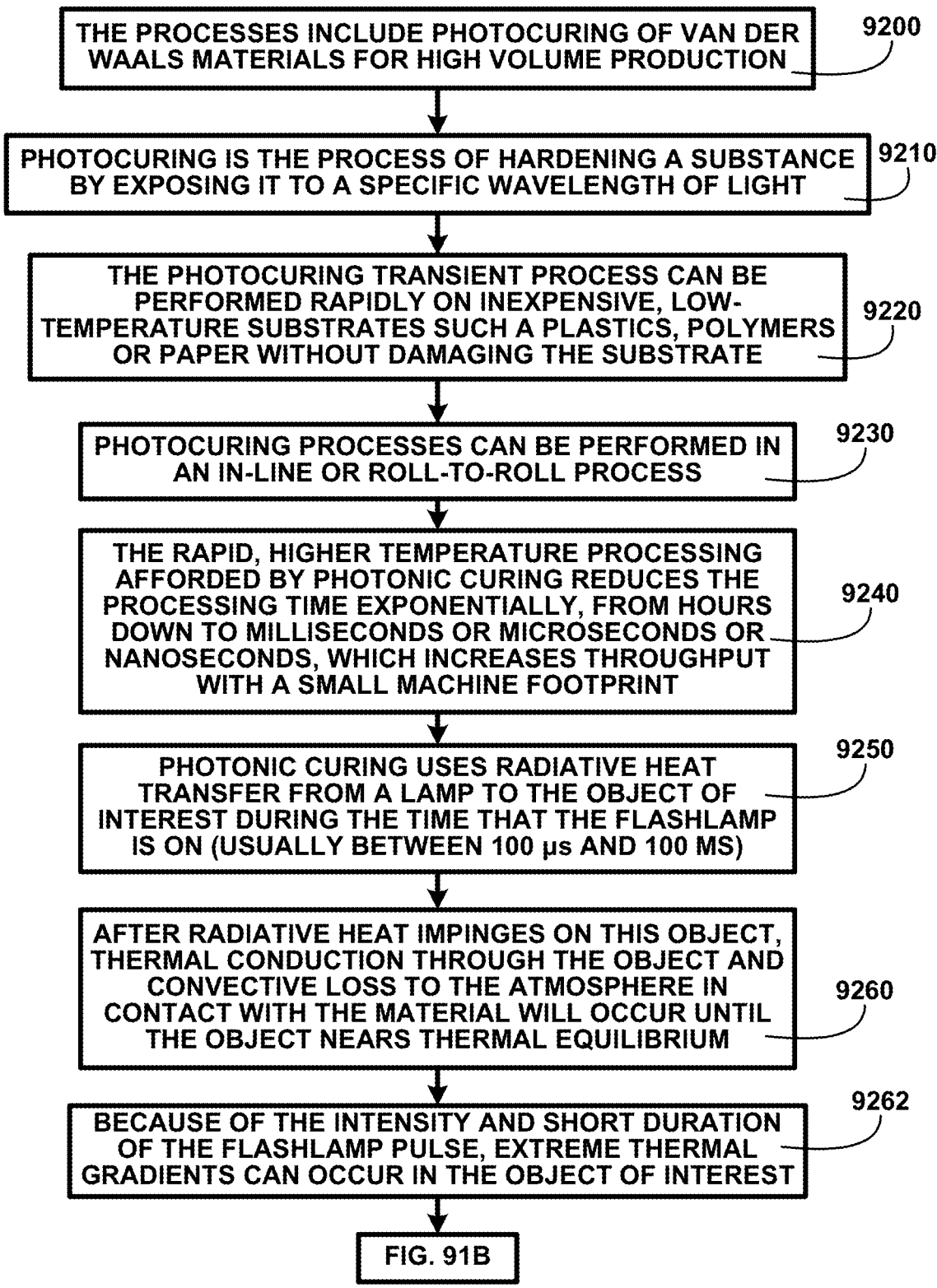
FIG. 91A shows a block diagram of an overview of the photocuring of Van Der Waals materials for high-volume production of one embodiment.
Figure 91B:
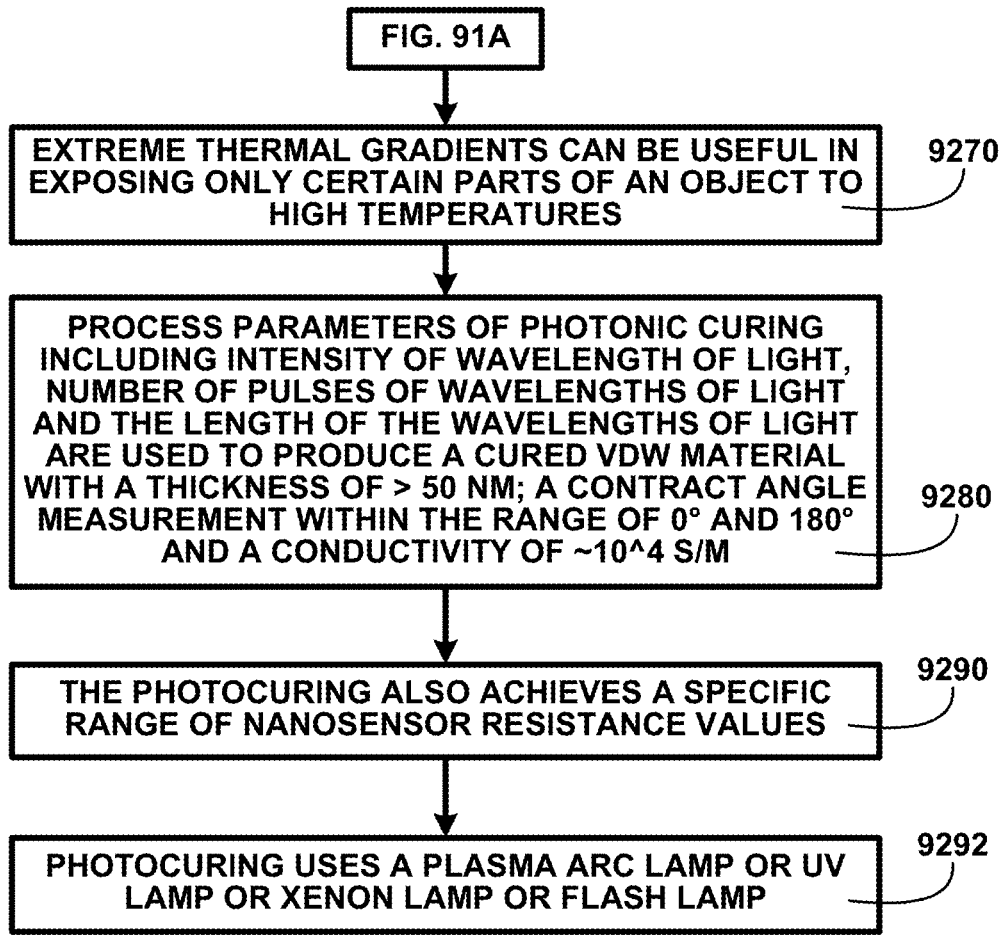
FIG. 91B shows a block diagram of an overview of the photocuring of Van Der Waals materials for high-volume production of one embodiment.

In one embodiment FIGS. 2A through 91B describe the sensing and detection methods and processes taken to identify and measure a targeted analyte using the analyte detection system of the invention.

DETAILED DESCRIPTION

FIG. 2A shows a block diagram of an overview flow chart of an individual self-testing at the home of one embodiment. FIG. 2A shows providing an individual self-testing 200 at home. Providing an individual self-testing 200 at home includes placing a patient's bodily fluid sample in a detection device solution compartment 210. A patient's bodily fluid sample may consist of any one of a group consisting of a drop of blood, saliva, sputum, urine, breathe moisture, nasopharyngeal, serum, semen, vaginal fluid, mucus, plasma, lymph, cells, tissue, clots, coagulants, amniotic fluid or other bodily fluid, tissue samples or other fluid from a human or animal body. In another embodiment, a sample is obtained by collecting patient breath moisture using a breath collector 212. The breath collector includes for example a process of checking the volume of the fluid sample using a humidity sensor 214 of one embodiment.

Data Flow for a Self-Testing Process:

Federal law may require any test for disease to be reported to local and state health officials and then to Federal agencies like CDC which is part of HHS. Infectious disease test results in the reporting transmission required data fields. Laboratories or diagnostic platform manufacturers should make every reasonable effort to provide the following data elements to state and jurisdictional health departments. The test ordered use harmonized LOINC codes provided by CDC, Device Identifier, Test result-use appropriate LOINC and SNOMED codes, as defined by the Laboratory In Vitro Diagnostics (LIVD) Test Code Mapping for SARS-CoV-2 Tests provided by CDC, Test Result date (date format), Accession #/Specimen ID, Patient age, Patient race, Patient ethnicity, Patient sex, Patient residence zip code, Patient residence county, Ordering provider name and nonpharmaceutical interventions (as applicable), Ordering provider zip code, Performing facility name and CLIA number, Performing facility zip code, Specimen Source—use appropriate LOINC, SNOMED-CT, or SPM4 codes, or equivalently detailed alternative codes, Date test ordered (date format), and Date specimen collected (date format).

The following additional demographic data elements should also be collected and reported to state or local public health departments: Patient name (Last name, First name, Middle Initial), Patient street address, Patient phone number with area code, Patient date of birth, Ordering provider address, and Ordering provider phone number.

To protect patient privacy, any data that state and jurisdictional health departments send to CDC will be de-identified and will not include some patient-level information. The de-identified data shared with CDC will contribute to understanding COVID-19's impact, case rate positivity trends, and testing coverage, and will help identify supply chain issues for reagents and other materials critical to disease treatment and prevention.

The nanosensor platform devices and processes 100 of FIG. 1 are configured for detecting any number and multiple types of viruses and bacterial pathogens using impedimetric detection of analytical targets. The nanosensor platform devices and processes 100 of FIG. 1 include activating testing protocol controls using at least one identification digital memory device 220, for example, but not limited to the SARS-CoV-2 virus that causes Covid-19, MRSA, other viruses, and bacteria, pathogens on food and general analytes and biomarkers. In one embodiment, the nanosensor platform devices and processes 100 of FIG. 1 including incubating the patient sample with treatment applied to the sample specimen 225. Heated incubation processing prepares the testing for measuring sensor electrical current and impedance in the presence of patient bodily fluid sample 230. Heated incubation processing prepares the testing for blood, serum, saliva, and other test samples for measuring impedance and electrical current. One purpose of treating the sample is to break down the membrane of a cell, often by viral, enzymatic, or osmotic mechanisms that compromise the cell structure; this process is known as lysis.

There are at least three ways of conducting lysis including: 1) heat treatment 2) chemical treatment or 3) treatment with materials. Heat treatment involves raising the temperature of the test sample to a specific set point for a predetermined period of time, causing a breakdown of cell membranes. Chemical treatment involves adding chemicals such as detergents, ionic surfactants, organic solvents, enzymes, hypotonic solutions and solutions with pH extremes for cell lysis to the sample. Detergents are a class of molecules whose unique properties enable manipulation (disruption or formation) of hydrophobic-hydrophilic interactions among molecules in biological samples. Detergents are amphipathic molecules, meaning they contain both a non-polar "tail" having an aliphatic or aromatic character and a polar "head". The ionic character of the polar head group forms the basis for the broad classification of detergents; they may be ionic (charged, either anionic or cationic), non-ionic (uncharged), or zwitterionic (having both positively and negatively charged groups but with a net charge of zero). For detecting proteins, detergents are used to lyse cells (release soluble proteins), solubilize membrane proteins and lipids, control protein crystallization, prevent non-specific binding in affinity purification and immunoassay procedures, and are used as additives in electrophoresis. All three treatment types are intended to optimize the sample for evaluation. Optimal samples have appropriate levels of volume, viscosity, pH, diluent, and concentrations of biologically sensitive molecules.

The nanosensor platform devices and processes 100 of FIG. 1 include communication devices for communicating measurement data to a network Interpretation means 240. Processing includes interpreting the patient sample measurement data on network 250. The network interpretation includes recording self-testing interpretation results on a network database and HIPAA Cloud 251. In one embodiment recording self-testing interpretation results includes identifying results with optional patient information 252 and reporting the test results along with optimal patient information to public health authorities 253. After the results are determined the processing continues with disposing of patient infectious waste 254, disinfecting measurement components 255, and returning measurement components to service 256 of one embodiment.

Figure 2B:
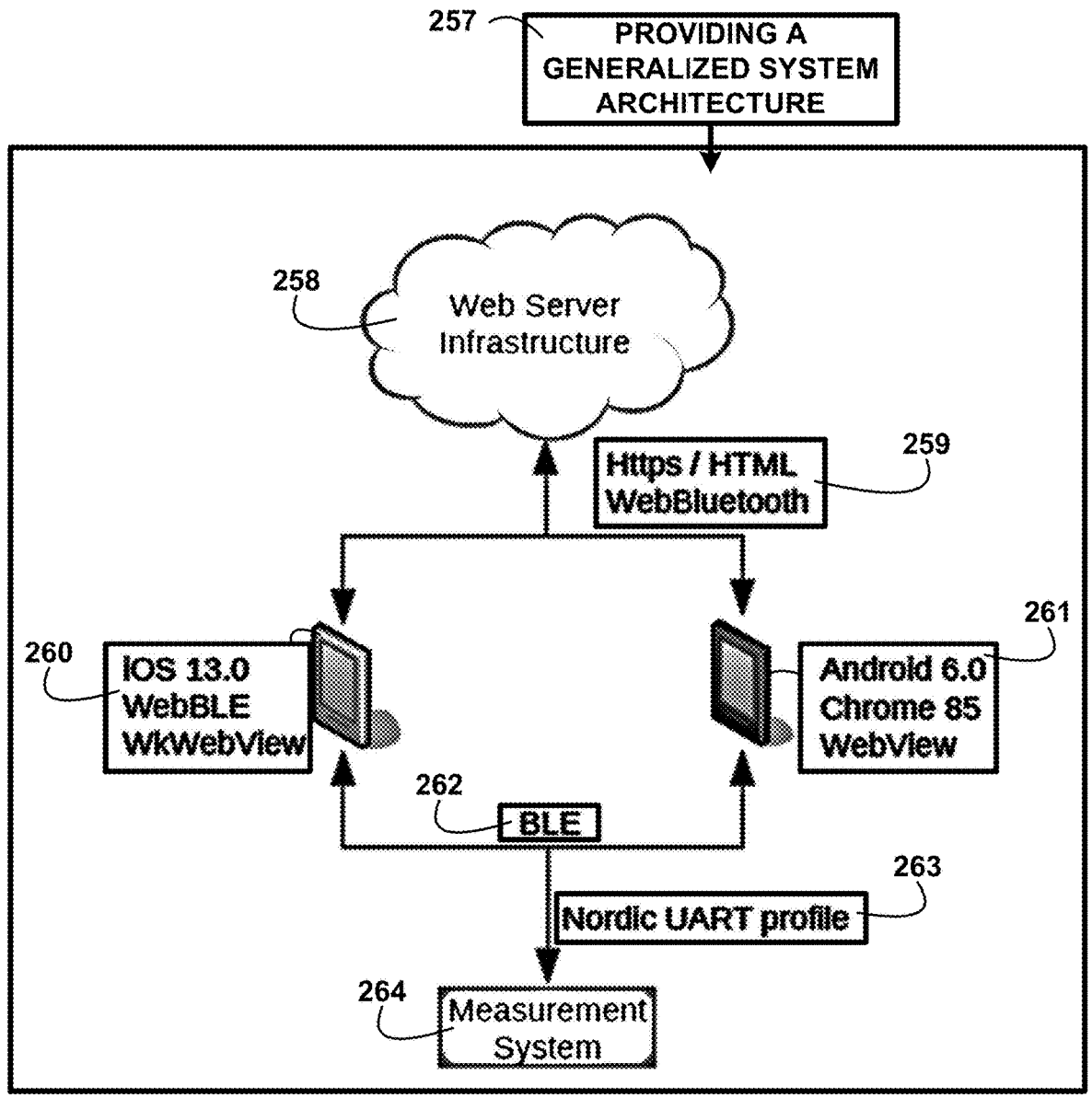
FIG. 2B shows for illustrative purposes only an example of a generalized system infrastructure of one embodiment.

Generalized System Infrastructure:

FIG. 2B shows for illustrative purposes only an example of a generalized system infrastructure of one embodiment. FIG. 2B shows providing a generalized system architecture 257. Providing a generalized system architecture 257 includes a Web Server Infrastructure 258. The Web Server Infrastructure 258 supports both the client-facing applets as well as the back-end interpretation, database, and reporting structures. A Web Server Infrastructure 258 includes an HTTPS/HTML WebBluetooth 259. An IOS 13.0 Webble WkWebView 260 supports a viable subset of Web Bluetooth, allowing the server side to access a BLE device. An Android 6.0 Chrome 85 WebView 261 directly supports Web Bluetooth APIs to allow server-side access to a BLE device. A BLE 262 device, referring to a Bluetooth Low Energy (BLE) device.

Nordic UART profile 263 wherein Nordic UART profile 263 service receives and writes data and serves as a bridge to the Universal Asynchronous Receiver-Transmitter (UART) interface. These devices and services provide data to a measurement system 264. The measurement system 264 accepts a test cassette, executes the stored instructions within the test cassette, and provides a feature vector of the measurements of the tests. The smartphone client-side application "app" displays the client-testing information provided by the web server infrastructure 258 and provides a communication path between the web server infrastructure 258 and the measurement system 264 of one embodiment. Both iOS ("WKWebView") and Android ("WebView") allow apps to embed web pages in Apps. This approach allows the development of what appears to be an App but is still essentially a web browser. Especially with the iOS-side development, this allows the app to implement the WebBluetooth API and allow the operation of one embodiment.

Figure 2C:
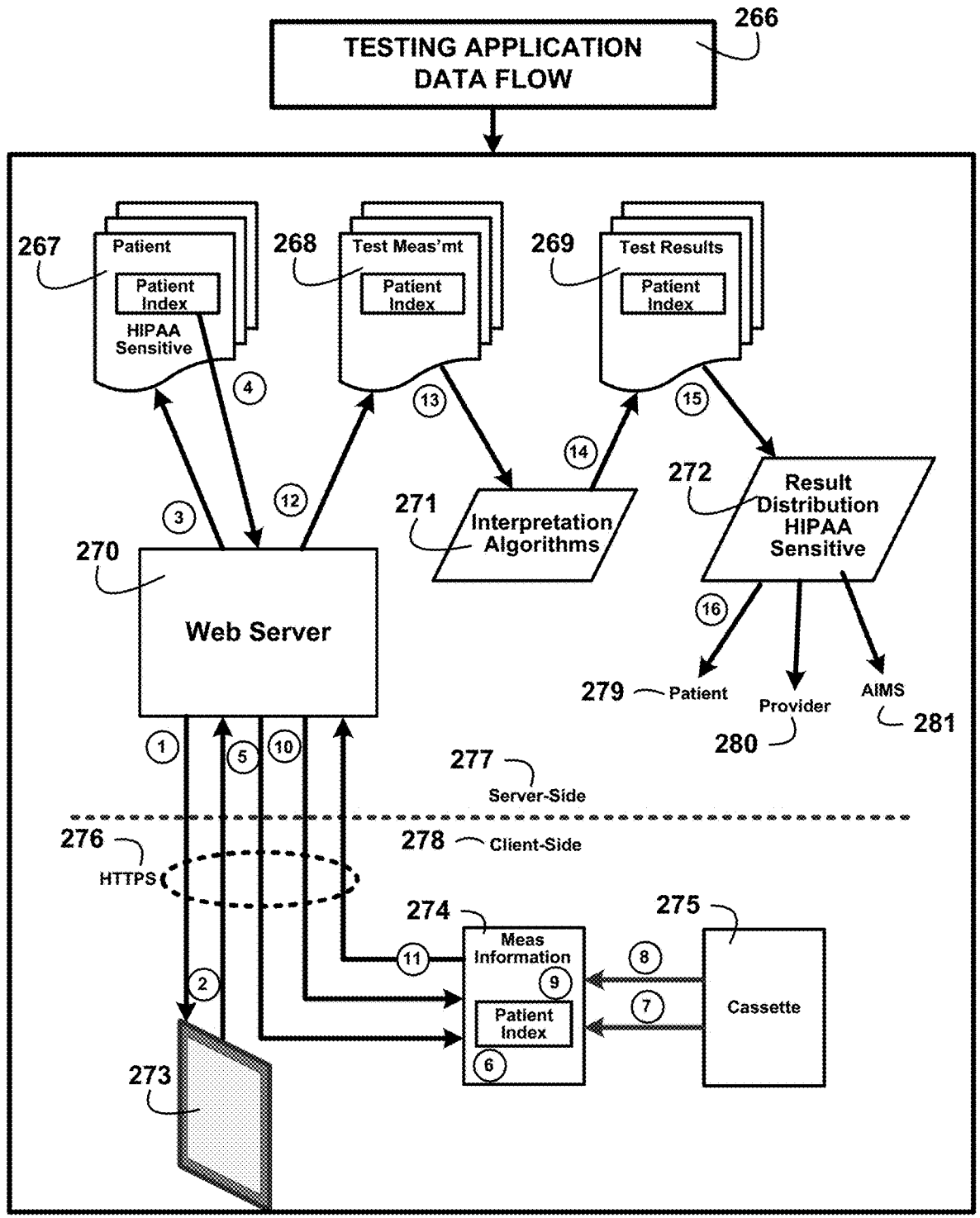
FIG. 2C shows for illustrative purposes only an example of a testing application data flow of one embodiment.

Testing Application Data Flow:

FIG. 2C shows for illustrative purposes only an example of a testing application data flow of one embodiment. FIG. 2C shows a testing application data flow 266. FIG. 2C shows the server side 277 features including a patient HIPAA sensitive patient index 267, test measurement patient index 268, test results patient index 269, web server 270, interpretation algorithms 271, result distribution HIPAA sensitive 272, to patient 279, to provider 280, and to AIMS 281.

FIG. 2C shows processes within the server side 277 including step 3. A patient record is stored, 3.1 and assigned a new ID Number if a patient doesn't exist, 3.2 recovers an existing ID Number if a patient does already exist in the records, 4. Patient ID Number information is sent through Web Server, 12. Web Server stores "test Record" (linked to the patient through Patient Index), 13. Interpretation Algorithms retrieve "test Record" and interpret feature vector(s) to determine test results, 14. Test Results are stored (linked to the patient through Patient Index), 15. Results Distribution collects new Test Results and fuses information with Patient records, and 16. Results Distribution sends appropriately formatted results to the Patient, Provider, AIMS, and others (as required).

FIG. 2C shows the client-side 278 features including for example a patient tablet 273, measurement information patent index 274, cassette 275, and HTTPS 276. FIG. 2C shows processes within the client side 278 including step 7. Measurement System retrieves "sensor Platform" information from Cassette, 8. Measurement System executes "protocol" on Cassette and collects measurements, and 9. Measurement System executes "vector" on collected measurements. The client-side application "app" displays the client-facing information provided by the Web Server Infrastructure and provides a communication path between the Web Server Infrastructure 258 of FIG. 2B and the Measurement System 264 of FIG. 2B.

The testing application data flow 266 includes processes between a server-side 277 and a client-side 278. The processes between a server-side 277 and a client-side 278 include step 1. Web Server provides a form for the patient to fill out on an electronic device such as a smartphone, 2. smartphone submits a patient form, 5. Optional step Using Web Bluetooth Send Patient ID Number through the smartphone to Measurement System (Reader), 6. Patient ID Number is stored locally on Measurement System, 10. Optional step Using Web Bluetooth, Web Sewer periodically polls Measurement System for test completed, 11. Using Web Bluetooth, Web Server retrieves a "test Record" from Measurement System upon completion. The Measurement System accepts a Test Cassette, executes the stored instructions within the Test Cassette, and provides a feature vector of the measurements of the tests. The "test Record" from the measurement system is also sent to BLE 262 of FIG. 2B device using a cookie of one embodiment.

Figure 3:
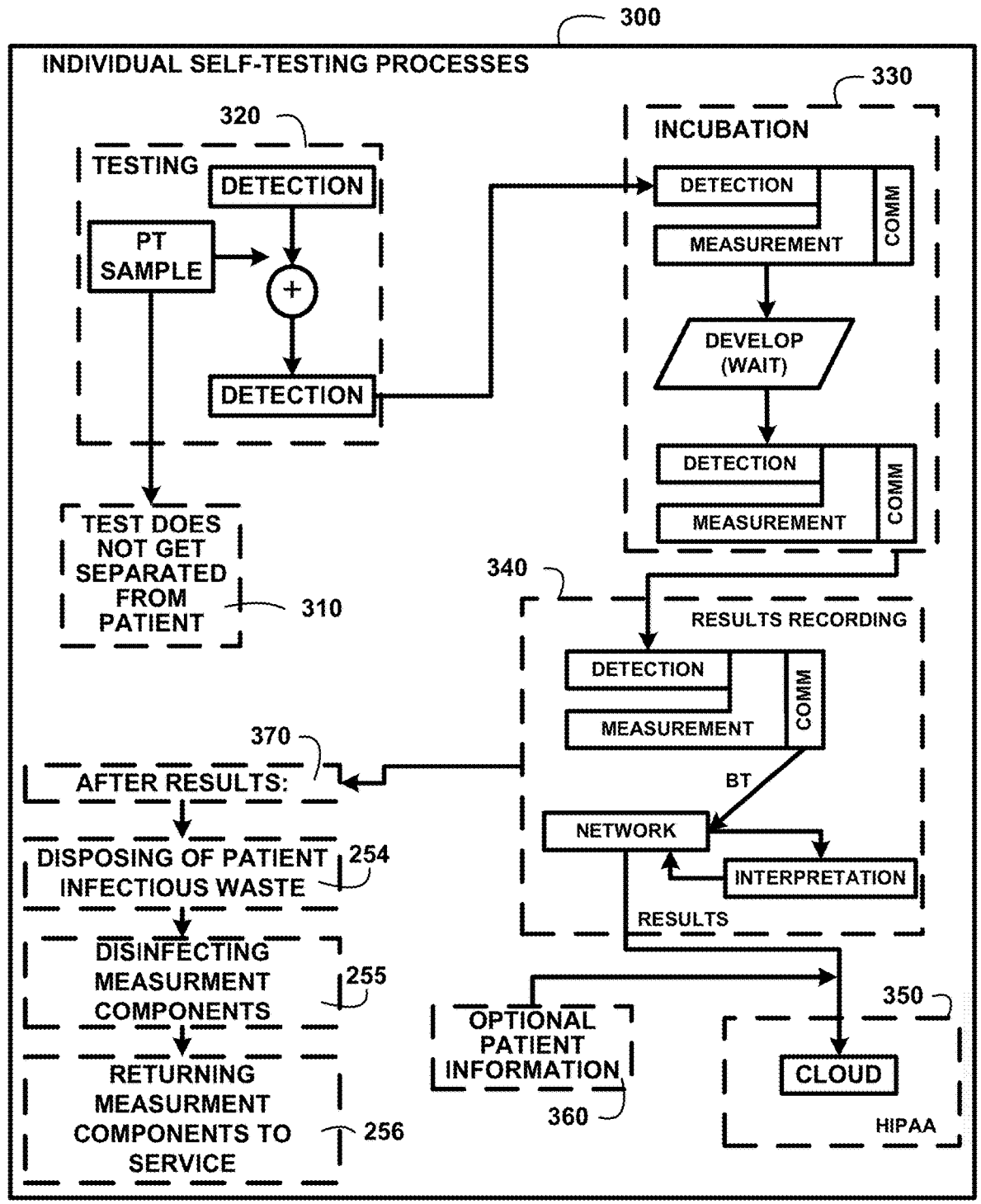
FIG. 3 shows for illustrative purposes only an example of an individual self-testing process of one embodiment.

An Individual Self-Testing Process:

FIG. 3 shows for illustrative purposes only an example of an individual self-testing process of one embodiment. FIG. 3 shows individual self-testing processes 300. The test does not get separated from patient 310. The testing 320 processes include detection before placing the patient sample to confirm a clear base. Upon placing the patient sample, the detection process continues. A second detection process is conducted and the measurement of any changes in the impedance of the detection electrode. In one example the patient sample is processed with incubation 330. A comm device is used to transmit the multiple detection measurements to the sensing platform smartphone app 132 of FIG. 1 or other means for reading and interpreting test data. During incubation, the patient sample is heated over a predetermined time and at a predetermined heat level then cooled over a predetermined time and at a predetermined cooling level to develop the patient sample. In another embodiment, the sample is not cooled over a predetermined time and at a predetermined cooling level to develop the patient sample. Other methods of sample preparation could be used including chemical treatment and treatment using materials. In some embodiments, the cell lysis step is not required. In such embodiments, the test sample is directly transmitted for multiple detection measurements. After the development period, another detection measurement is processed and transmitted over comm.

The results recording 340 will include the detection and measurement. The comm will transmit the detection and measurement data for BT interpretation on the network for reading and interpreting test data. The results of the test for disease will also be transmitted to a HIPAA cloud 350, to local and state health officials than to Federal agencies like CDC. The results reporting will include all agency-required data and include optional patient information 360. After results: 370 have been recorded, detection devices are disposing of patient infectious waste 254, disinfecting measurement components 255, and returning measurement components to service 256 of one embodiment.

Figure 4:
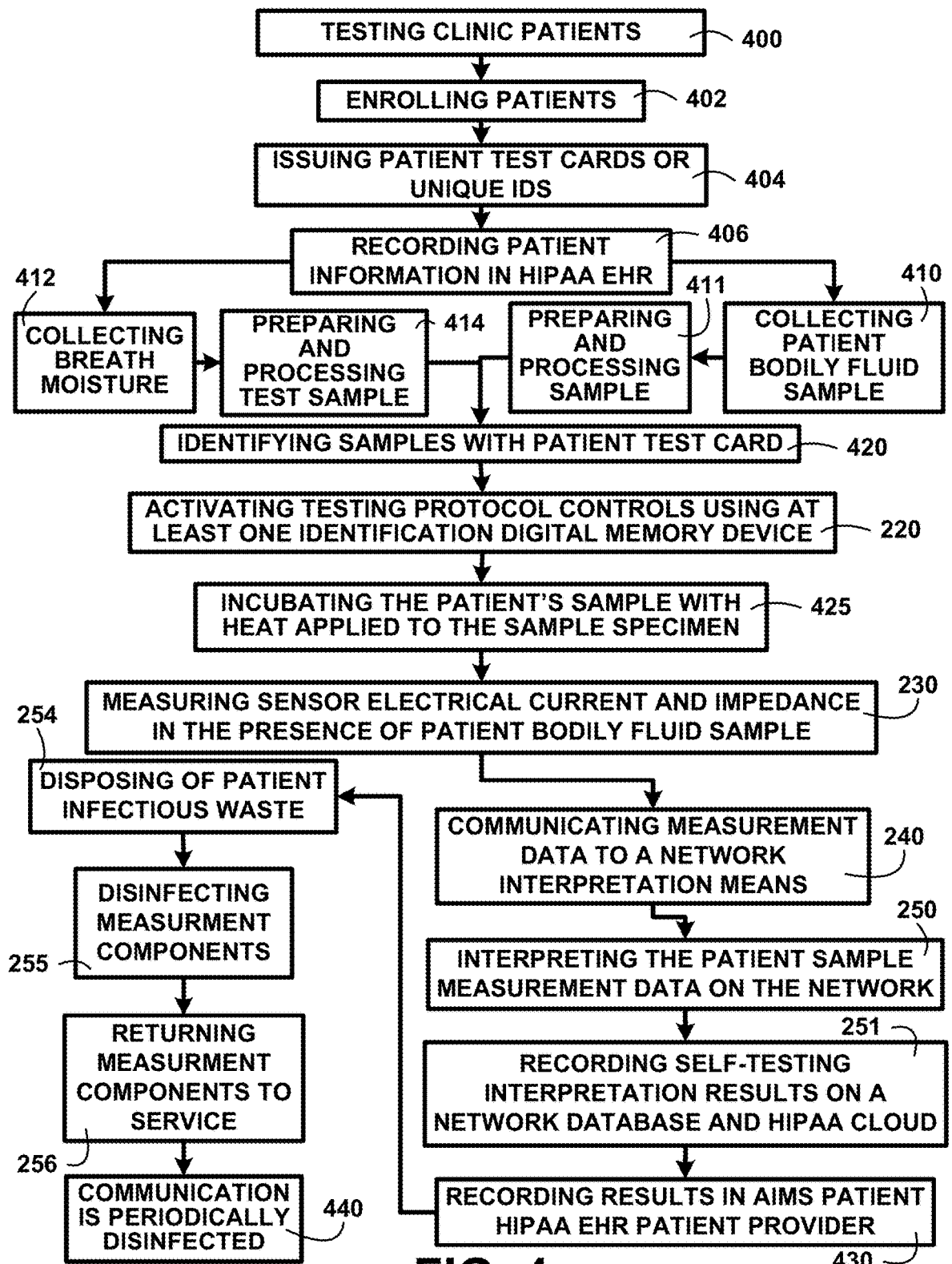
FIG. 4 shows a block diagram of an overview flow chart of testing clinic patients of one embodiment.

Testing Clinic Patients:

FIG. 4 shows a block diagram of an overview flow chart of testing clinic patients of one embodiment. FIG. 4 shows testing clinic patients 400 processing. Testing clinic patients 400 processing begins with enrolling patients 402 and issuing patient test cards or unique IDs 404. The patient test cards include a unique identifying code and patient information. The processing continues with recording patient information in HIPAA EHR 406.

Collecting patient bodily fluid sample 410 for testing. In another embodiment, a patient sample includes collecting breath moisture 412, preparing and processing test sample 414, and preparing and processing sample 411 including checking the volume of the fluid sample using a humidity sensor 214 of FIG. 2A for a sufficient sample specimen and may require additional patient exhalations into the device. The process includes identifying samples with patient test card 420. The testing process is prepared by activating testing protocol controls using at least one identification digital memory device 220. The processing proceeds with incubating the patient's sample with a heat applied to the sample specimen 425 or chemicals applied to the sample specimen or materials applied to the sample specimen. When incubation is completed, the process continues with measuring sensor impedance and electrical current in the presence of patient bodily fluid sample 230. The impedance and electrical current of the electrode is affected by the presence of the incubated patient sample.

Communicating measurement data to a network interpretation means 240 for interpreting the patient sample measurements with interpreting the patient sample measurement data on the network 250. Recording self-testing interpretation results on a network database and HIPAA cloud 251. The process includes recording testing interpretation results on an IOS 13.0 Webble WkWebView 260 and recording results in AIMS patient HIPAA EHR patient-provider 430 and to local and state health officials then to Federal agencies like CDC. After the results are recorded the process includes disposing of patient infectious waste 254, disinfecting measurement components 255, returning measurement components to service 256, and communication is periodically disinfected 440 of one embodiment.

Figure 5:
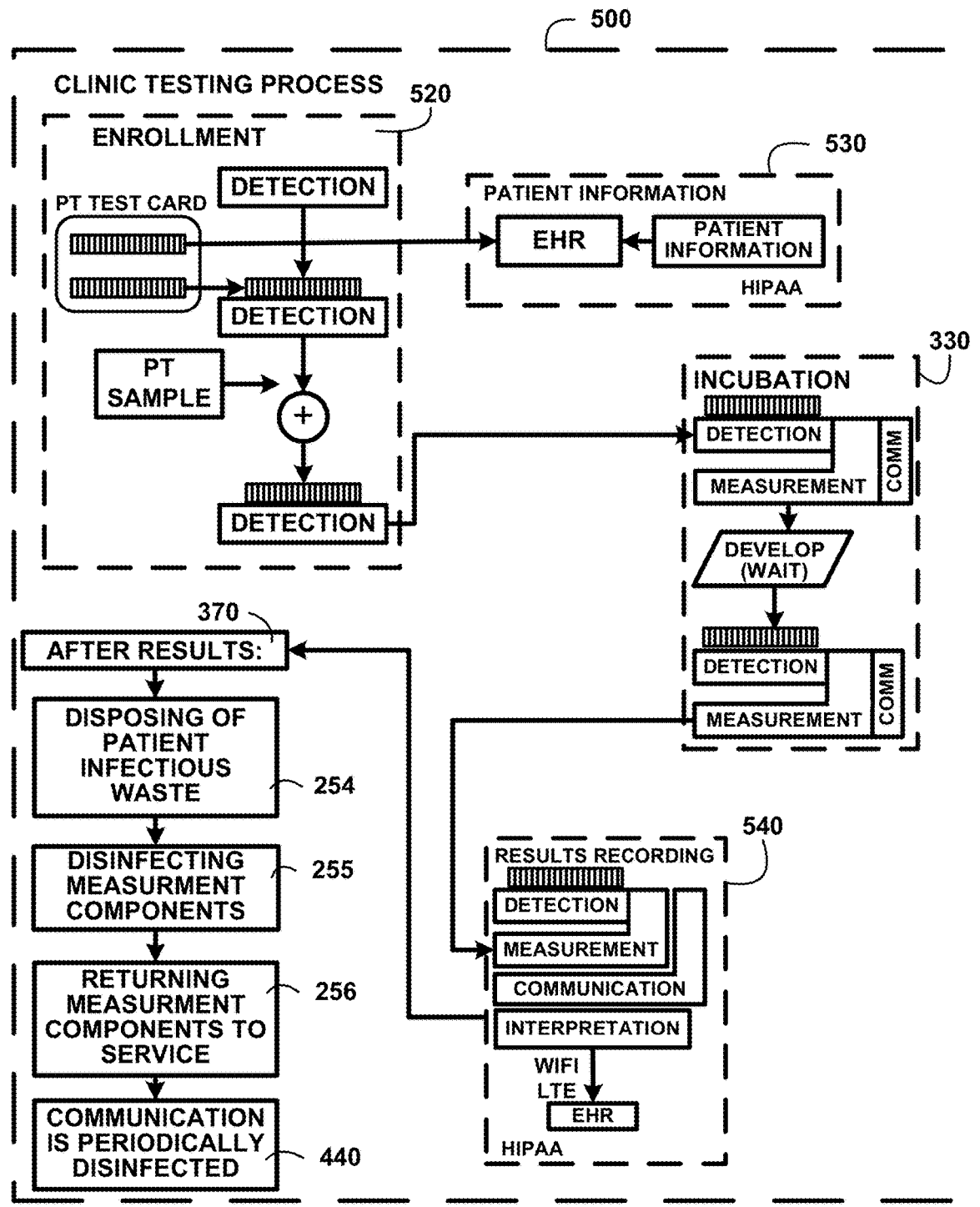
FIG. 5 shows for illustrative purposes only an example of a clinic testing process of one embodiment.

A Clinic Testing Process:

FIG. 5 shows for illustrative purposes only an example of a clinic testing process of one embodiment. FIG. 5 shows a clinic testing process 500 and enrollment 520 of patients being tested and issuing a patient test card. The patient test card assigns a unique identifying testing code and records patient information 530 on the card. The patient card is used for transmitting to the patient EHR the patient information and testing results according to HIPAA. The card can also be a virtual token or scannable such as a QR code or another method of verification such as biometric or other.

The process includes detection where the detection with patient ID is first performed before placing a patient sample. After placing the patient sample detection with patient ID proceeds to incubation 330 of the patient sample with heat applied to the sample. Other treatments can be used such as chemical treatment or treatment using advanced materials. The detection with patient ID is followed by a measurement of the electrode impedance and electrical current after a predetermined "develop" time of the incubated patient sample.

Results recording 540 is performed after the detection with patient ID measurement is transmitted with communication to the interpretation means. The results recording 540 after interpretation is transmitted via WIFI LTE to the patient EHR under HIPAA. After the results: 370 are recorded and reported to local and state health officials then to Federal agencies like CDC which is part of HHS, detection is disposing of patient infectious waste 254, disinfecting measurement components 255, and returning measurement components to service 256, and communication is periodically disinfected 440. The data flow process for the clinic testing application is the same as shown in FIG. 2C of one embodiment.

Figure 6:
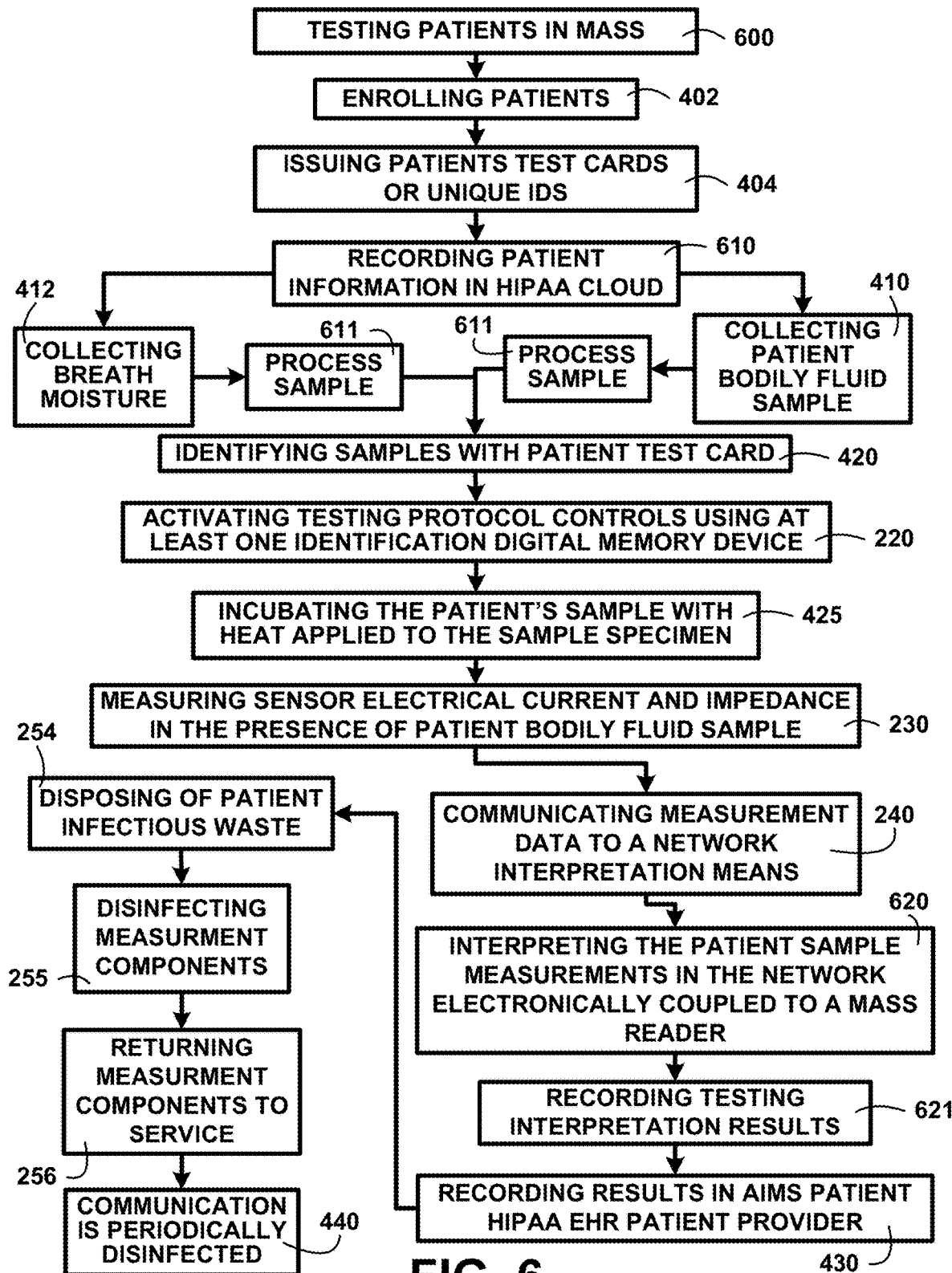
FIG. 6 shows a block diagram of an overview flow chart of testing patients in a mass of one embodiment.

Testing Patients in Mass:

FIG. 6 shows a block diagram of an overview flow chart of testing patients in a mass of one embodiment. FIG. 6 shows testing patients in mass 600 using the nanosensor platform devices and processes 100 of FIG. 1. A process is used for enrolling patients 402 and issuing patients test cards or unique IDs 404. The patient's test cards include a unique testing code and patient information. The processing includes recording patient information on a HIPAA cloud 610.

The processing continues with collecting patient bodily fluid sample 410 testing specimen to process sample 611 for testing. In another embodiment, the process is collecting breath moisture 412 from a patient to process sample 611 for testing and checking the volume of breath fluid sample 414. Collecting patient samples includes identifying samples with patient test card 420. Processing continues with activating testing protocol controls using at least one identification digital memory device 220. A process is used for incubating the patient's sample with heat or other treatment applied to sample specimen 425. After incubation, a process is used for measuring sensor impedance in the presence of patient bodily fluid sample 230 of the detection electrode. Processing for communicating measurement data to a network interpretation means 240 for interpreting the patient sample measurements in the network electronically coupled to a mass reader 620 and recording testing interpretation results on an IOS 13.0 Webble WkWebView 260. Recording testing interpretation results from 621 on an IOS 13.0 Webble WkWebView 260 includes recording results on a HIPAA cloud. After the results are recorded the process continues with disposing of patient infectious waste 254, disinfecting measurement components 255, returning measurement components to service 256, and communication is periodically disinfected 440. The data flow process for the clinic testing application is the same as shown in FIG. 2C of one embodiment.

Figure 7:
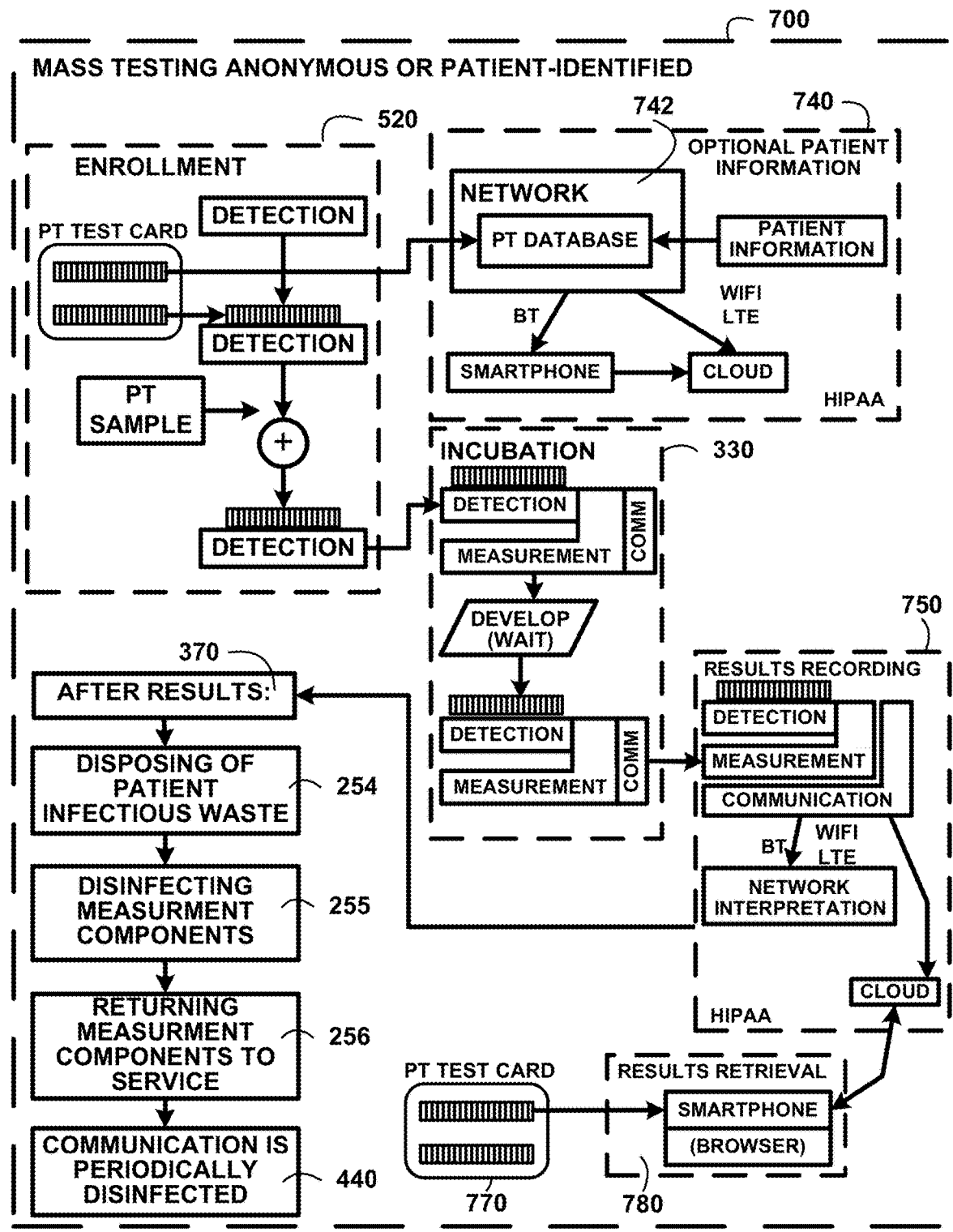
FIG. 7 shows for illustrative purposes only an example of mass testing anonymously or patient-identified of one embodiment.

Mass Testing Anonymously or Patient-Identified:

FIG. 7 shows for illustrative purposes only an example of mass testing anonymously or patient-identified of one embodiment. FIG. 7 shows mass testing anonymously or patient-identified 700. Mass testing processing begins with the enrollment 520 of patients and issuing a patient test card to each patient. The patient test card includes optional patient information 740 that may be transmitted to a network 742 and recorded on a patient database. The optional patient information 740 may be transmitted to a BT smartphone for accessing patient information transmitted via WIFI LTE to a HIPAA cloud.

Detection with a patient ID labeled patient sample is followed by incubation 330 with applied heat or other test sample treatments to develop for a predetermined time the patient sample. Detection with a patient ID sample after development is then processed for measurement of electrode impedance. The detection measurement results recording 750 are communicated using a communication device to an interpretation system for the determination of the concentration of any detected virus or bacterial pathogen.

The interpretation results are transmitted via BT smartphone and WIFI LTE to a patient EHR HIPAA file. A patient test ID card 770 is used by a patient who logs in to a HIPAA cloud for results retrieval 780 using a smartphone/browser. After results: 370 are recorded and reported detection is disposing of patient infectious waste 254, disinfecting measurement components 255, and returning measurement components to service 256, and communication is periodically disinfected 440. The data flow process for mass-testing is the same as shown in FIG. 2C of one embodiment.

Figure 8:
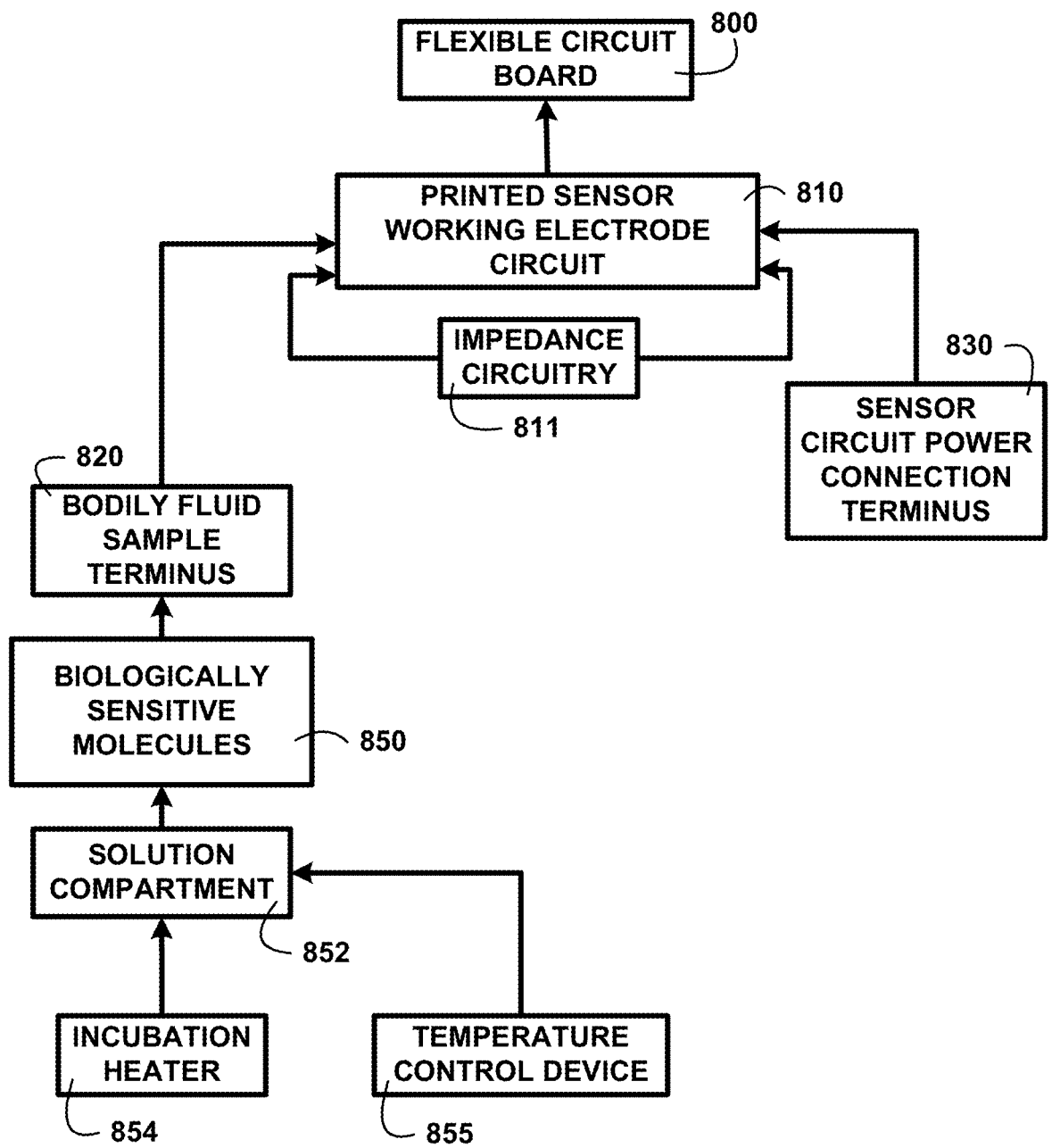
FIG. 8 shows a block diagram of an overview of a printed sensor electrode circuit of one embodiment.

A Printed Sensor Electrode Circuit:

FIG. 8 shows a block diagram of an overview of a printed sensor electrode circuit of one embodiment. FIG. 8 shows a flexible circuit board 800 with a printed sensor working electrode circuit 810 deposited on the surface. The printed sensor electrode circuit 810 can be made using printers including an inkjet printer, aerosol printer, spin coating, screen printer, gravure printer, offset printer, roll-to-roll printer, 3D printer, or other forms of material deposition or material transfer. The electrode is composed of an electrically conductive material of one embodiment.

The printed sensor electrode impedance circuitry 811 is configured with a bodily fluid sample terminus 820. The bodily fluid sample terminus 820 includes biologically sensitive molecules such as DNA probes 850 that will be in contact with the patient bodily fluid sample when placed. A solution compartment 852 is coupled over the biologically sensitive molecules such as DNA probes 850 for receiving a bodily fluid sample. An incubation heater 854 is placed under the solution compartment 852. The incubation temperature control device 855 may include a temperature-controlling element 855 using conductive printable inks. Temperature-controlling conductive inks such as positive temperature coefficient (PTC) inks heat up to a certain temperature threshold called a "switch-off" temperature. The "switch-off" temperature can range between ±30° C. and ±150° C. Temperature control devices are self-regulating heaters that run open-loop without any external diagnostic controls. A deposit of the bodily fluid sample is tested on the bodily fluid sample terminus 820. This test is to determine the valid functioning of the sensor prior to release to other processing.

Other methods of sample treatment can be used including treatment using chemicals and materials. The opposite end of the printed sensor working electrode circuit 810 includes a sensor circuit power connection terminus 830 for connecting a power source of one embodiment.

Figure 9:
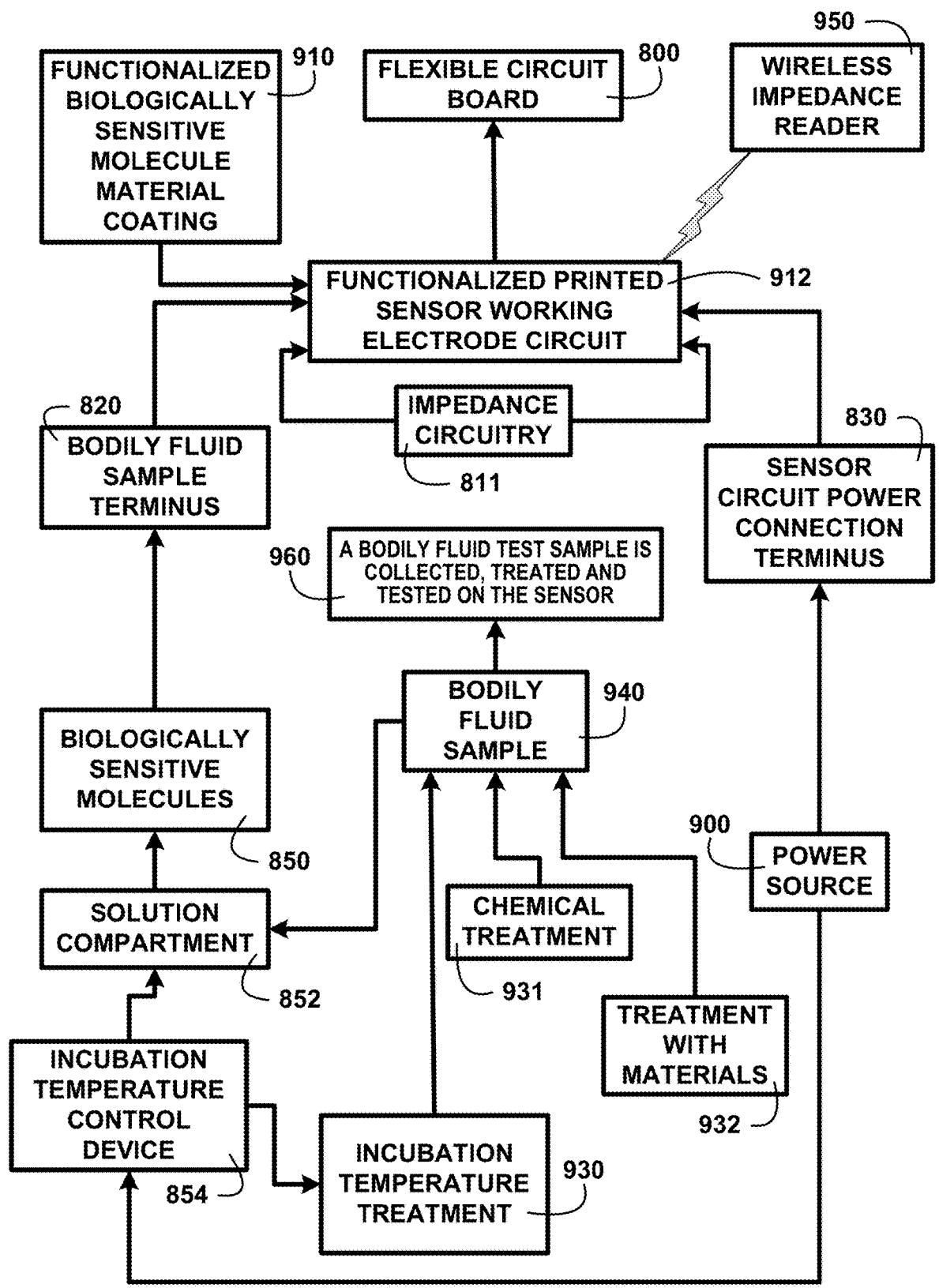
FIG. 9 shows a block diagram of an overview of a functionalized printed sensor working electrode circuit of one embodiment.

A Functionalized Printed Sensor Working Electrode Circuit:

FIG. 9 shows a block diagram of an overview of a functionalized printed sensor working electrode circuit of one embodiment. FIG. 9 shows the flexible circuit board 800, a printed sensor working electrode circuit 810, impedance circuitry 811, bodily fluid sample terminus 820, biologically sensitive molecules such as DNA probes 850, solution compartment 852, incubation temperature control device 854, and sensor circuit power connection terminus 830. A functionalized biologically sensitive molecule material coating 910 is deposited on the surface of the printed sensor working electrode circuit 810 to form a functionalized printed sensor working electrode circuit 912. A bodily fluid sample 940 is shown placed in the solution compartment 852 and contacting the biologically sensitive molecules such as DNA probes 850. A power source 900 is coupled to the sensor circuit power connection terminus 830 for providing power to the incubation temperature control device 854 and other types of heaters including a temperature control device 855 of FIG. 8 for incubation temperature treatment 930 to the bodily fluid sample 940 during incubation of one embodiment. A chemical treatment 931 or treatment with materials 932 can be applied to the bodily fluid sample 940 in other embodiments. A bodily fluid test sample is collected, treated and tested on the sensor 960. The power source 900 also provides power for impedance and electrical current testing that is read using a wireless impedance reader 950 of one embodiment.

Figure 10A:
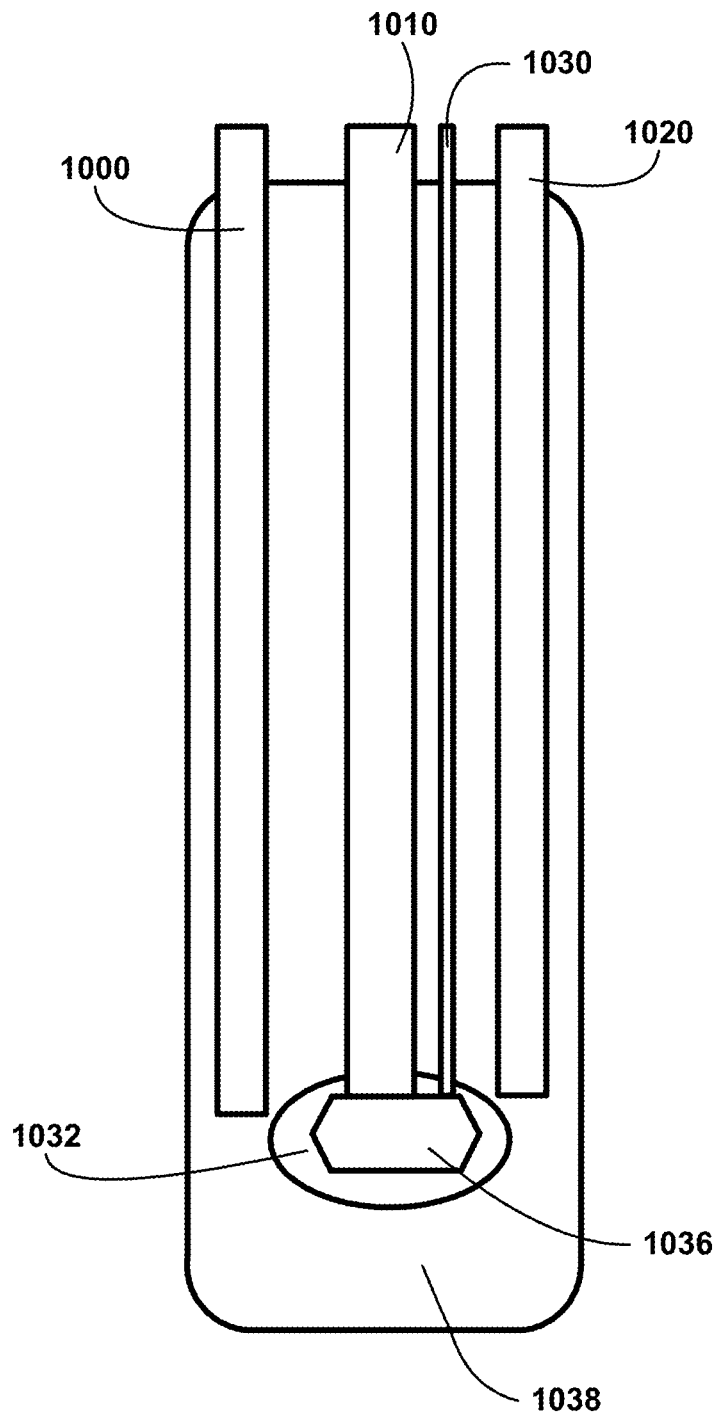
FIG. 10A shows for illustrative purposes only an example of an incubation heater of one embodiment.

An Incubation Heater:

FIG. 10A shows for illustrative purposes only an example of an incubation heater of one embodiment. FIG. 10A shows a heater below working electrode head 1036 that is used for heating a bodily fluid sample during incubation. In one embodiment the detection device includes a reference electrode 1000, working electrode 1010, and counter electrode 1020. The working electrode head 1036 is shown coupled to a heated fluid tube 1030. In another embodiment, the detection device includes only a working electrode 1010, and a counter electrode 1020.

A solution compartment 1038 is used for placing the bodily fluid sample. The solution compartment can be located in the sidewall next to the head of the working electrode separated by a thin film that melts away or directly above the working electrode such that when the sample is placed in the hole from above the heater then melts the top membrane so the sample mixes then the bottom member melts, allowing the mixed sample to pour down on the working electrode surface 1032. All fluids will be able to be tested, however, different test strips will need different combinations of test fluids and treatment or none at all of one embodiment. It should be appreciate that other methods of incubating the test sample using gravity or a vacuum source are contemplated.

Figure 10B:
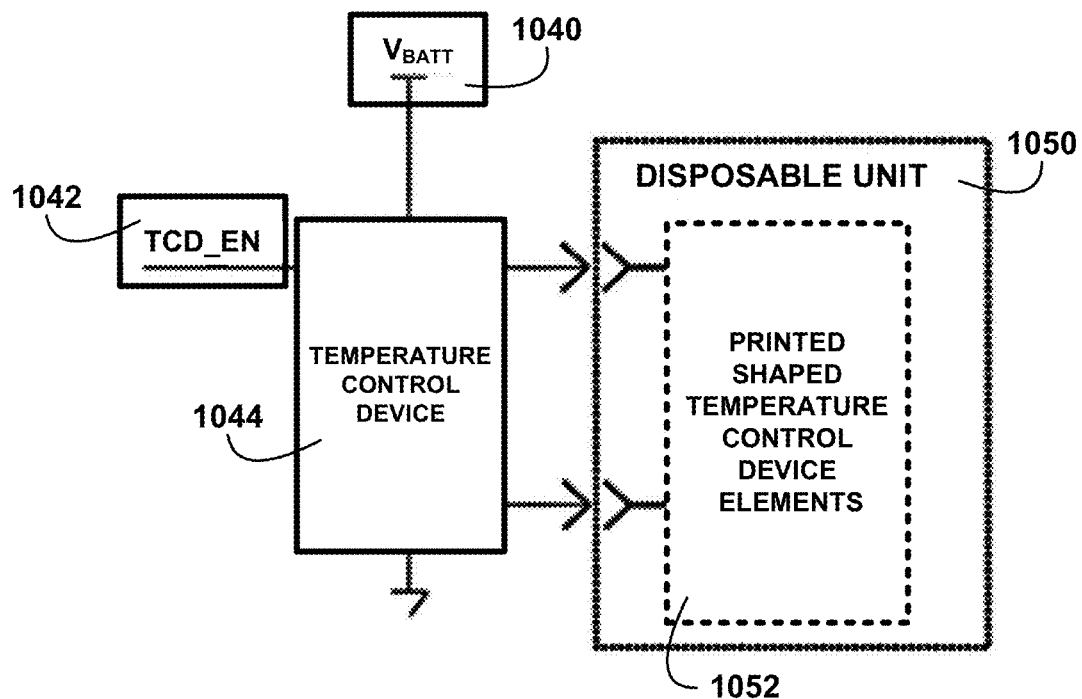
FIG. 10B shows for illustrative purposes only an example of a printed temperature control device of one embodiment.

A Printed Heater:

FIG. 10B shows for illustrative purposes only an example of a printed temperature control device of one embodiment. FIG. 10B shows a Vbatt 1040 power source, a TCD en 1042, and a temperature control drive 1044 that operates the heating/cooling system of a disposable unit 1050. The disposable unit 1050 consists of a temperature control device, for example, a printed temperature control device 1052 with, for example, a printed-shaped temperature control device element. A drive circuit for a printed temperature control device is used for heating a bodily fluid sample. The drive circuit can be microcontroller-based, analog, or a combination. The temperature control device resistance itself is used to determine temperature. In one embodiment a temperature control device can include, for example, a shaped printed element based on printable conductive ink otherwise known as a positive temperature coefficient (PTC) temperature control device. The base resistance can be scaled linearly by adjusting the size of the shaped printed element of one embodiment.

Figure 10C:
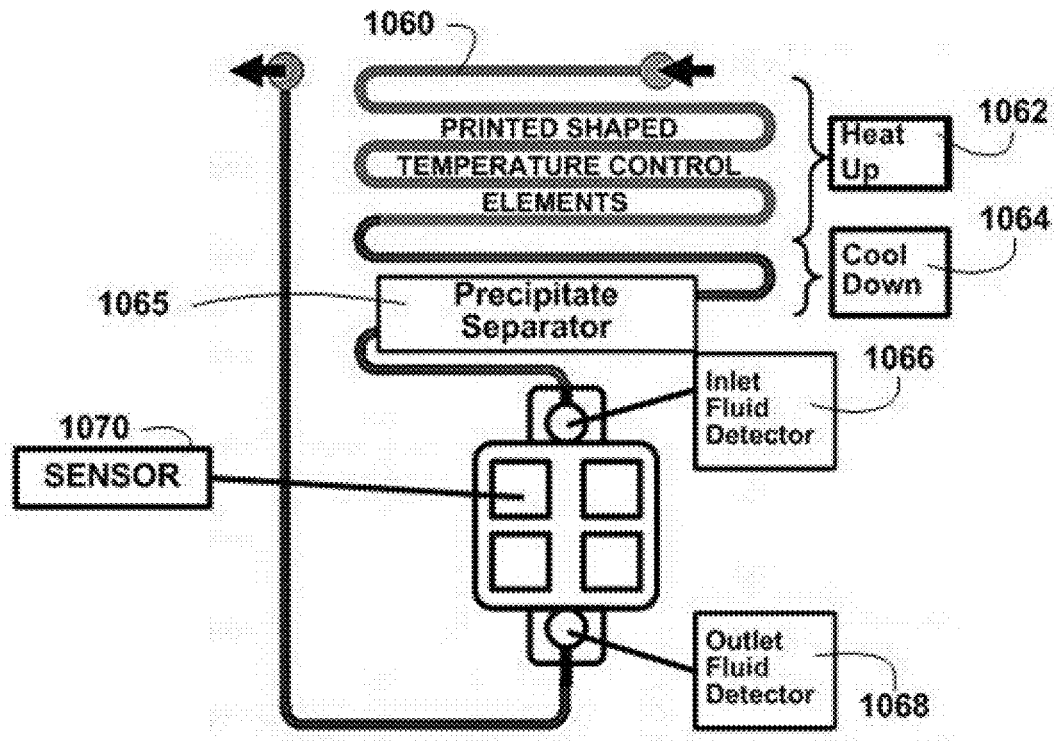
FIG. 10C shows for illustrative purposes only an example of a printed temperature control device and printed sensor of one embodiment.

A Printed Heater and Printed Sensor:

FIG. 10C shows for illustrative purposes only an example of a printed temperature control device and printed sensor of one embodiment. FIG. 10C shows a printed temperature control device and printed sensor consisting of a shaped temperature control element 1060, heater 1062, cool down 1064; precipitate separator 1065, inlet fluid detector 1066, outlet fluid detector 1068, and at least one sensor 1070 of one embodiment. In another embodiment, the cool-down 1064 is not included in the printed temperature control device. In yet another embodiment, the printed heater 1062 is not included in the printed sensor film.

Figure 11A:
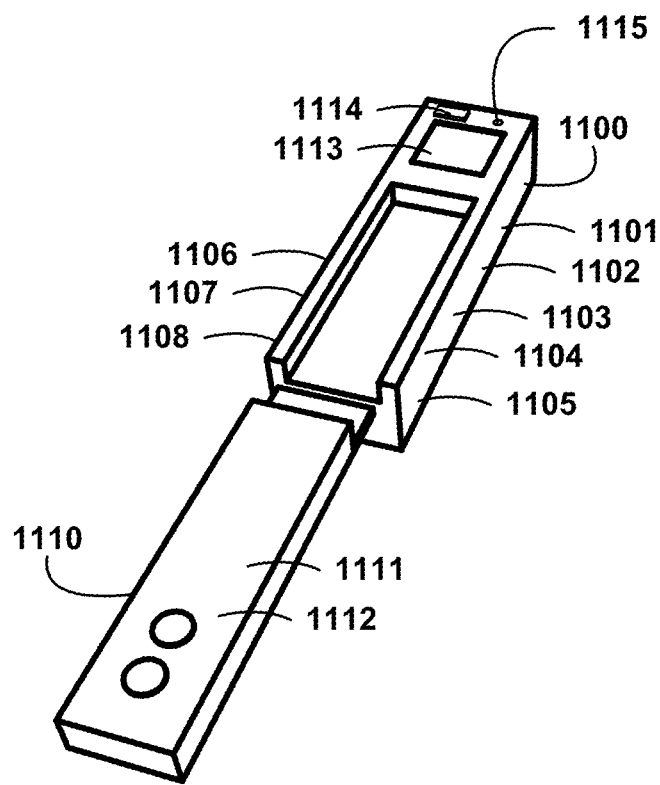
FIG. 11A shows for illustrative purposes only an example of a detection cartridge of one embodiment.

A Detection Cartridge:

FIG. 11A shows for illustrative purposes only an example of a detection cartridge of one embodiment. FIG. 11A shows a nanosensor platform device 1100 including a processor 1101, at least one internal and external power source 1102, at least one communication device 1103, and at least one digital memory device 1104. The nanosensor platform device 1100 is configured to include an impedance measuring device 1105, an interpretation processor 1106, at least one data cartridge reader 1107, and at least one testing protocol that controls digital memory identification activator 1108. The nanosensor platform device 1100 includes a testing status display 1113 for displaying the testing process status and results. An on/off and selection button 1114 is used for turning on the power which is shown in a power-off indicator light 1115 condition. At least one detection cartridge 1110 includes at least one functionalized printed electrode 1111 and an incubation heater 1112 of one embodiment.

Figure 11B:
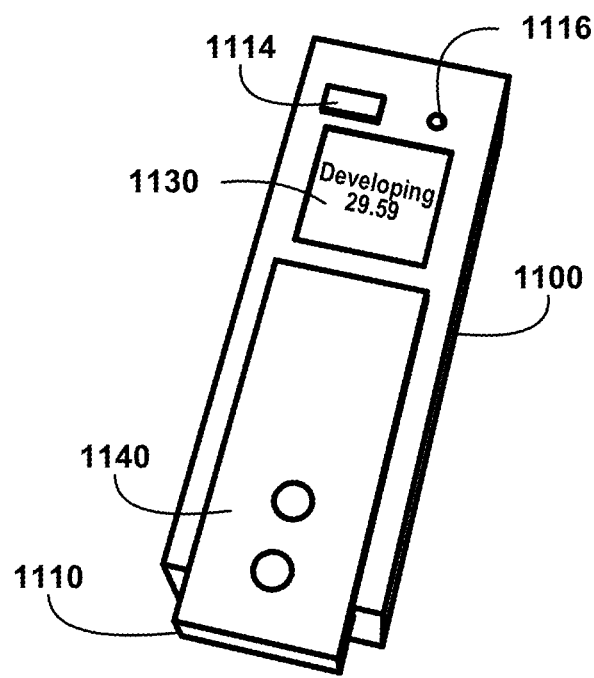
FIG. 11B shows for illustrative purposes only an example of a detection device of one embodiment.

A Detection Device:

FIG. 11B shows for illustrative purposes only an example of a detection device of one embodiment. FIG. 11B shows nanosensor platform device 1100 includes at least one detection cartridge 1110 and an on/off and selection button 1114. In this instance, the power-on indicator light 1116 is lit indicating the power has been turned on. A detection cartridge inserted into the nanosensor platform 1140 produces a testing status display showing developing 29.59 1130 of one embodiment.

Figure 12A:
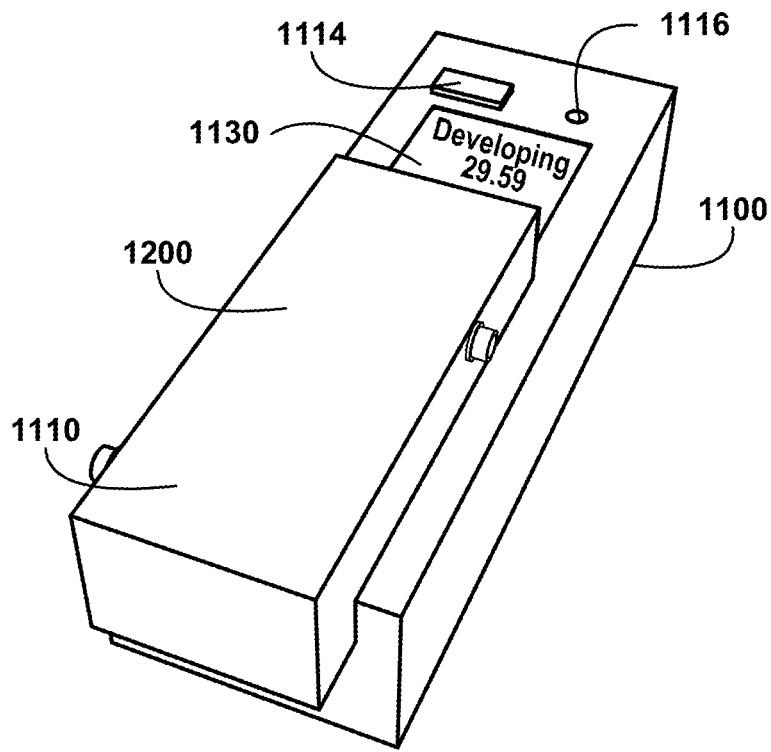
FIG. 12A shows for illustrative purposes only an example of a detection device display developing of one embodiment.

A Detection Device Display Developing:

FIG. 12A shows for illustrative purposes only an example of a detection device display developing of one embodiment. FIG. 12A shows the nanosensor platform device 1100, at least one detection cartridge 1110, on/off and selection button 1114, power-on indicator light 1116, and the testing status display showing developing 29.59 1130 in a high fluid volume detection cartridge 1200 of one embodiment.

Figure 12B:
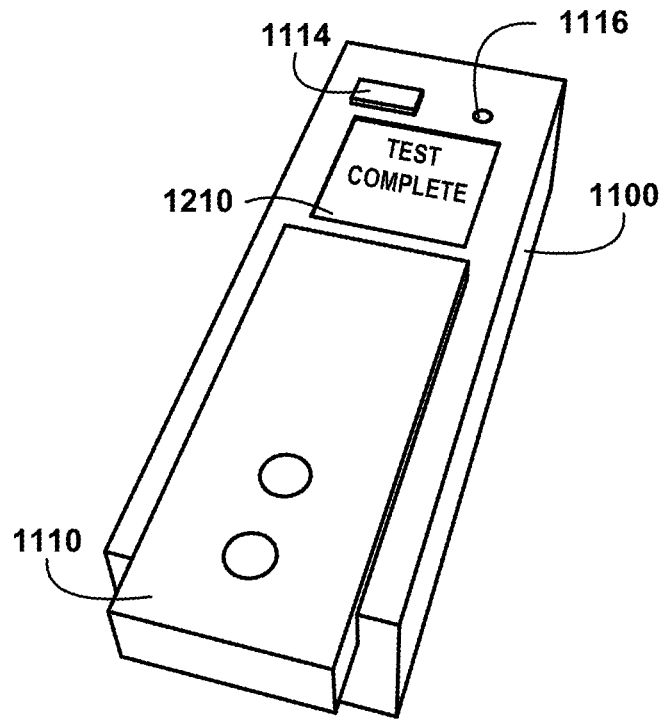
FIG. 12B shows for illustrative purposes only an example of a detection device display test complete of one embodiment.

A Detection Device Display Test Complete:

FIG. 12B shows for illustrative purposes only an example of a detection device display test complete of one embodiment. FIG. 12B shows the nanosensor platform device 1100, at least one detection cartridge 1110, on/off and selection button 1114, and power-on indicator light 1116. A testing status display shows test complete 1210 and the end of a testing process cycle of one embodiment.

Figure 13:
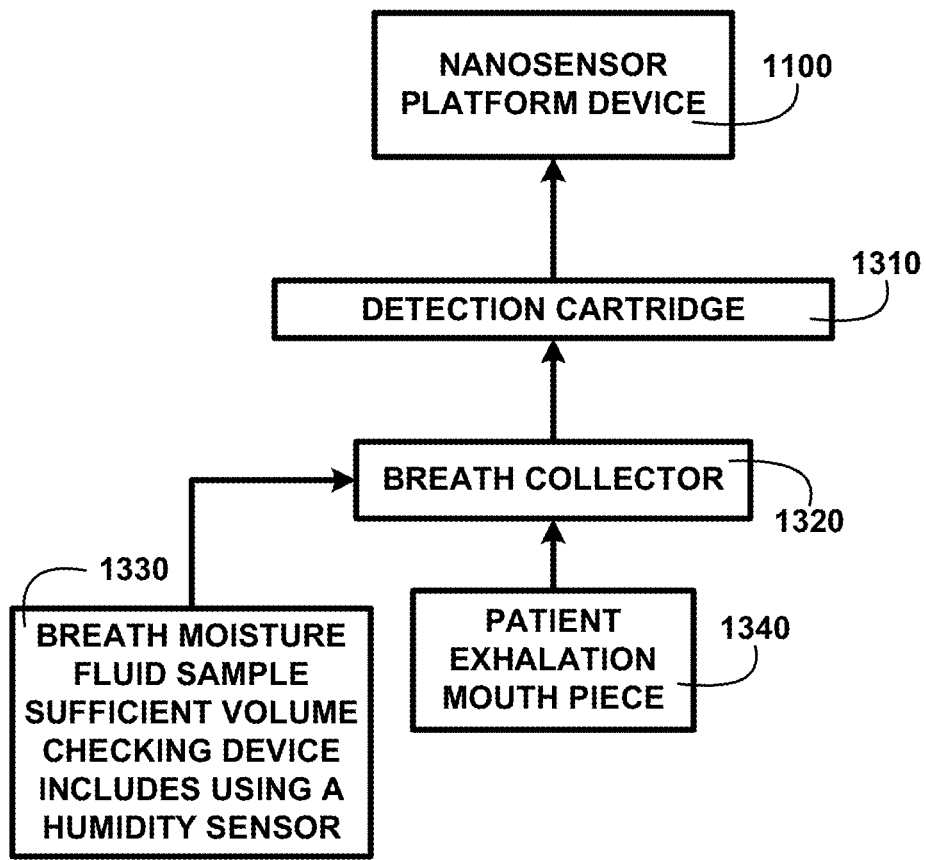
FIG. 13 shows a block diagram of an overview of a detection cartridge breath collector of one embodiment.

A Detection Cartridge Breathe Collector:

FIG. 13 shows a block diagram of an overview of a detection cartridge breath collector of one embodiment. FIG. 13 shows in another embodiment a nanosensor platform device 1300. Coupled to the nanosensor platform device 1300 is a detection cartridge 1310. The detection cartridge 1310 is configured with a patient exhalation mouthpiece 1340. The patient's exhalation mouthpiece 1340 is coupled to a breath collector 1320. The breath collector 1320 is used to collect moisture in the exhaled air of the patient. The breath collector 1320 includes a breath moisture fluid sample sufficient volume checking device includes using a humidity sensor 1330. A patient may need to exhale several times to allow the collection of sufficient moisture to perform the testing of one embodiment.

Figure 14:
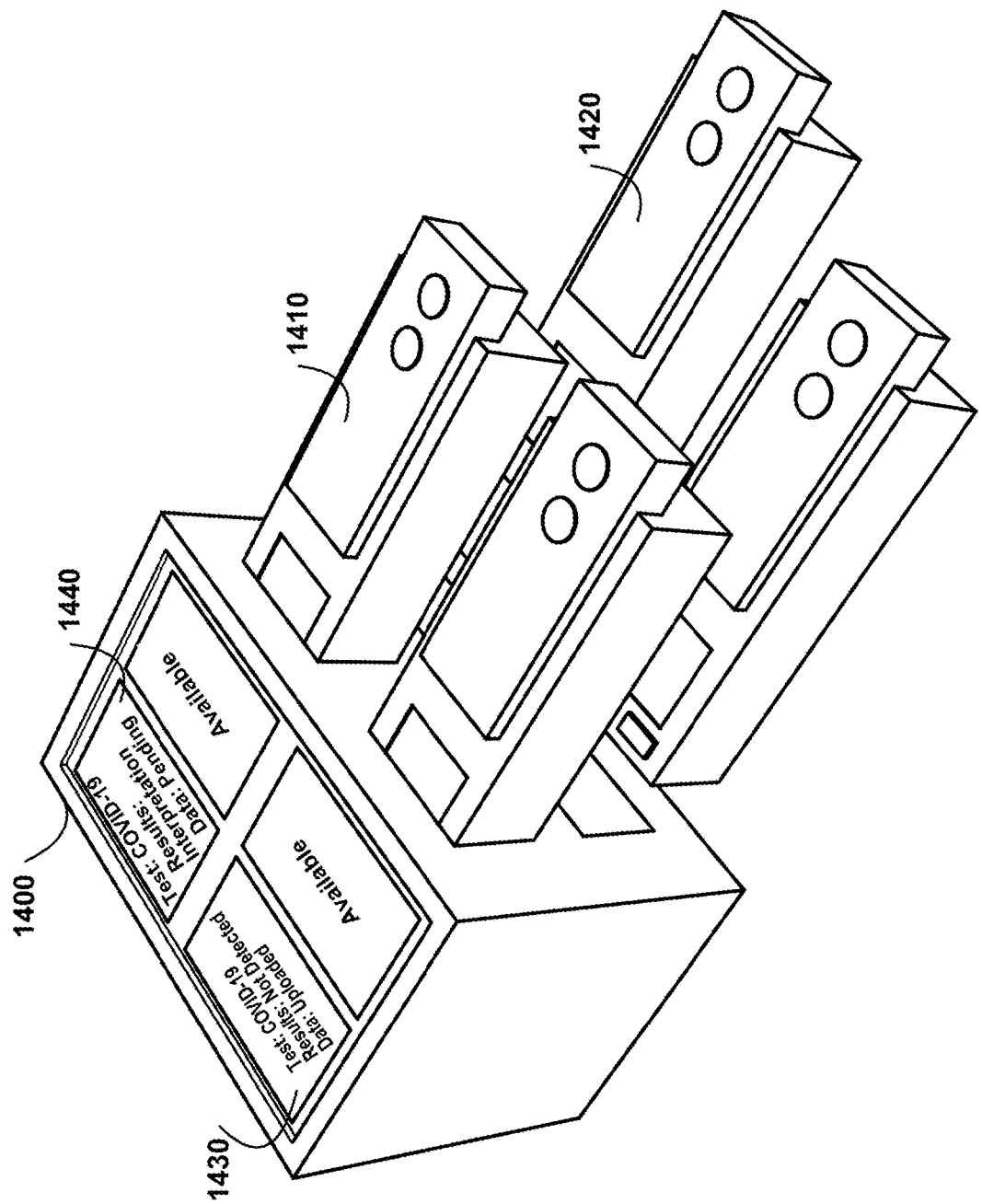
FIG. 14 shows for illustrative purposes only an example of a multi-reader of one embodiment.

A Multi-Reader:

FIG. 14 shows for illustrative purposes only an example of a multi-reader of one embodiment. FIG. 14 shows a multi-detection device reader 1400. The multi-detection device reader 1400 is shown with at least one detection device inserted into the multi-detection device reader 1410. Also showing is at least one detection device not inserted into the multi-detection device reader 1420. The multi-detection device reader 1400 includes test results displays. In this instance, one test results display showing uploaded 1430 and the other test results display showing pending 1440 of one embodiment. In another embodiment, the multi-reader can also be wireless such that the test cartridges sit on the table and transmit the data wirelessly to the multi-reader receiver.

Figure 15:
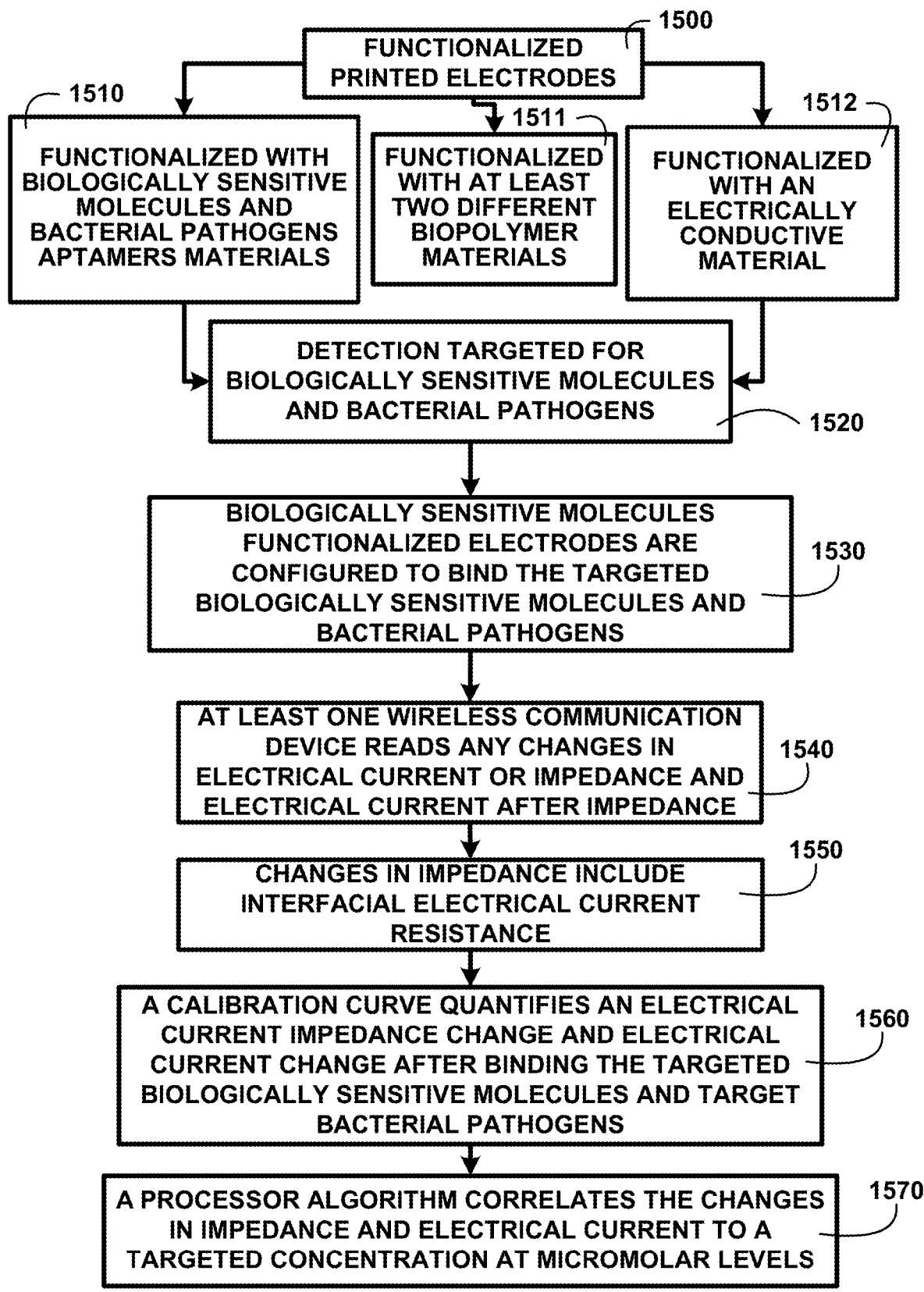
FIG. 15 shows a block diagram of an overview of functionalized printed electrodes of one embodiment.

Functionalized Printed Electrodes:

FIG. 15 shows a block diagram of an overview of functionalized printed electrodes of one embodiment. FIG. 15 shows functionalized printed electrodes 1500. The functionalized printed electrodes 1500 are functionalized with biologically sensitive molecules and bacterial pathogens aptamers materials 1510. In one embodiment the printed electrodes 1500 are functionalized with at least two different biopolymer materials 1511. In another embodiment, printed electrodes 1500 are functionalized with an electrically conductive material 1512. The biologically sensitive molecules such as DNA probes 850 of FIG. 8 consists of materials corresponding to the specific biologically sensitive molecules and bacterial pathogens biologically sensitive molecules and aptamer materials. The functionalized printed electrodes 1500 are configured for detection targeted for biologically sensitive molecules and bacterial pathogens 1520.

Electrodes functionalized with biologically sensitive molecules functionalized electrodes are configured to bind to the targeted biologically sensitive molecules and bacterial pathogens 1530 to the probes and aptamers. At least one wireless communication device reads any changes in electrical current or impedance and electrical current after impedance 1540 and records any changes for transmission to an interpretation means. Changes in impedance include interfacial electrical current resistance 1550. A calibration curve quantifies an electrical current impedance change and electrical current change after binding the targeted biologically sensitive molecules and target bacterial pathogens 1560. A processor algorithm correlates the changes in impedance and electrical current to a targeted concentration at micromolar levels 1570 of one embodiment.

Figure 16:
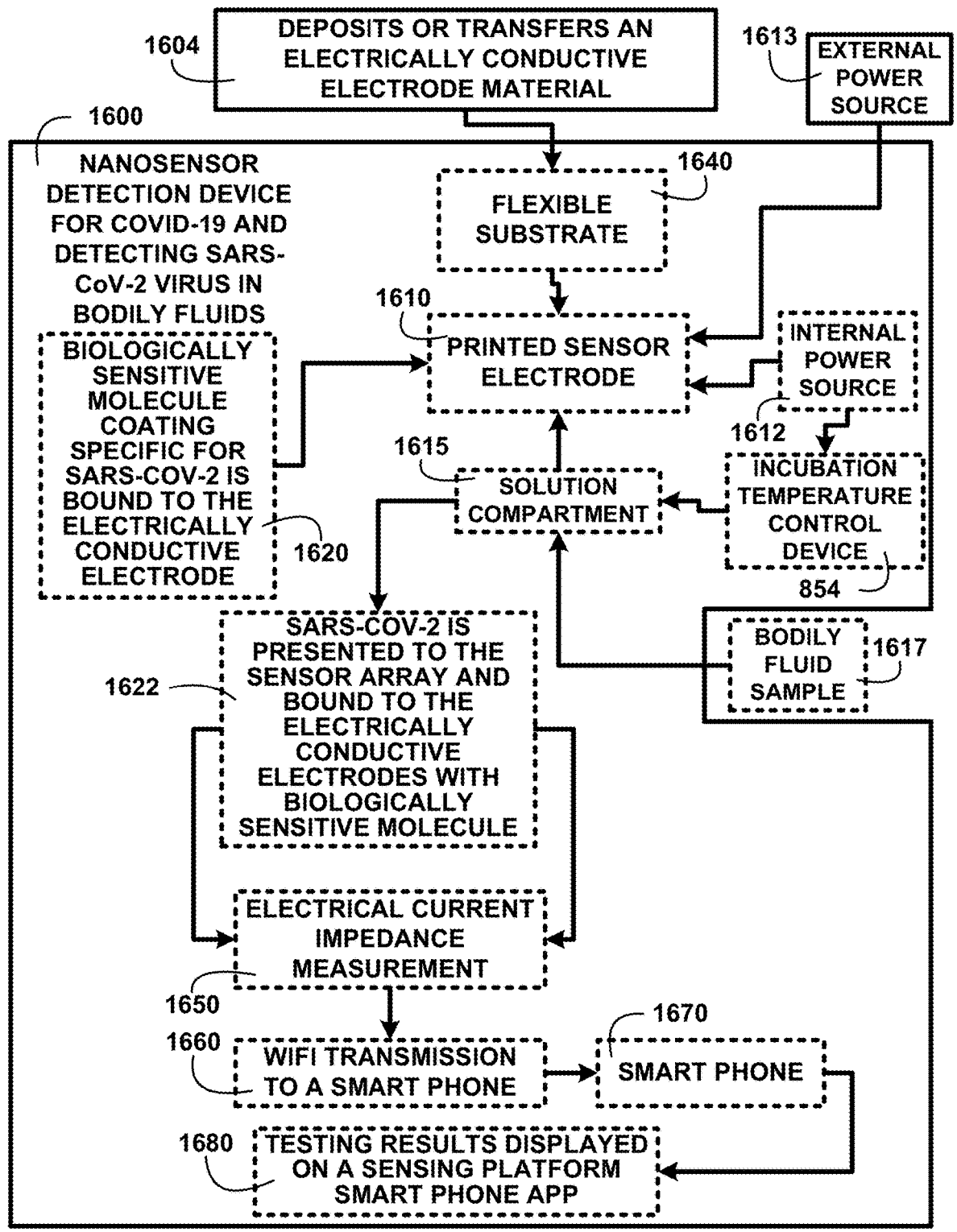
FIG. 16 shows a block diagram of an overview of an example of electrode binding of targeted biologically sensitive molecules and bacterial pathogens of one embodiment.

Electrode Binding of Targeted Biologically Sensitive Molecules and Bacterial Pathogens:

FIG. 16 shows a block diagram of an overview of an example of electrode binding of targeted biologically sensitive molecules and bacterial pathogens of one embodiment. FIG. 16 shows the nanosensor detection device for diagnosing COVID-19 and detecting SARS-CoV-2 virus in bodily fluids 1600. System deposits or transfers an electrically conductive electrode material 1604 on a Polyimide flexible substrate 1640 or other common thermoplastic polymers including Polyethylene terephthalate to make a printed sensor electrode 1610. A biologically sensitive molecule coating specific for SARS-CoV-2 is bound to the electrically conductive electrode 1620 to form a functionalized printed electrode. Coupled to the precision-printed sensor electrode 1610 are an external power source 1613 and an internal power source 1612. Also coupled to the printed sensor electrode 1610 is a solution compartment 1615 the receiver for the bodily fluid sample 1617.

An incubation temperature control device 854 is coupled underneath the solution compartment 1615. The internal power source 1612 is shown connected to the incubation temperature control device 854 for applying heat to the bodily fluid sample during the predetermined incubation time. It should be appreciated that other methods of sample treatment including chemical treatment (e.g. detergents) and treatment using materials are used in other embodiments.

After the incubation period, the positive test sample including SARS-CoV-2 is presented to the sensor array and bound to the electrically conductive electrodes with biologically sensitive molecule 1622. Each terminus of the sensor electrode forms a measurement circuit for processing an electrical current and impedance measurements 1650. The electrical current and impedance measurement 1650 are read with a WIFI transmission to a smartphone 1660. The Interpretation is processed on a sensing platform smartphone app on a patient smartphone 1670. The testing results displayed on a sensing platform smartphone app 1680 quickly informs the patient if they are infected with the COVID-19 because of detecting SARS-CoV-2 virus of one embodiment.

Figure 17:
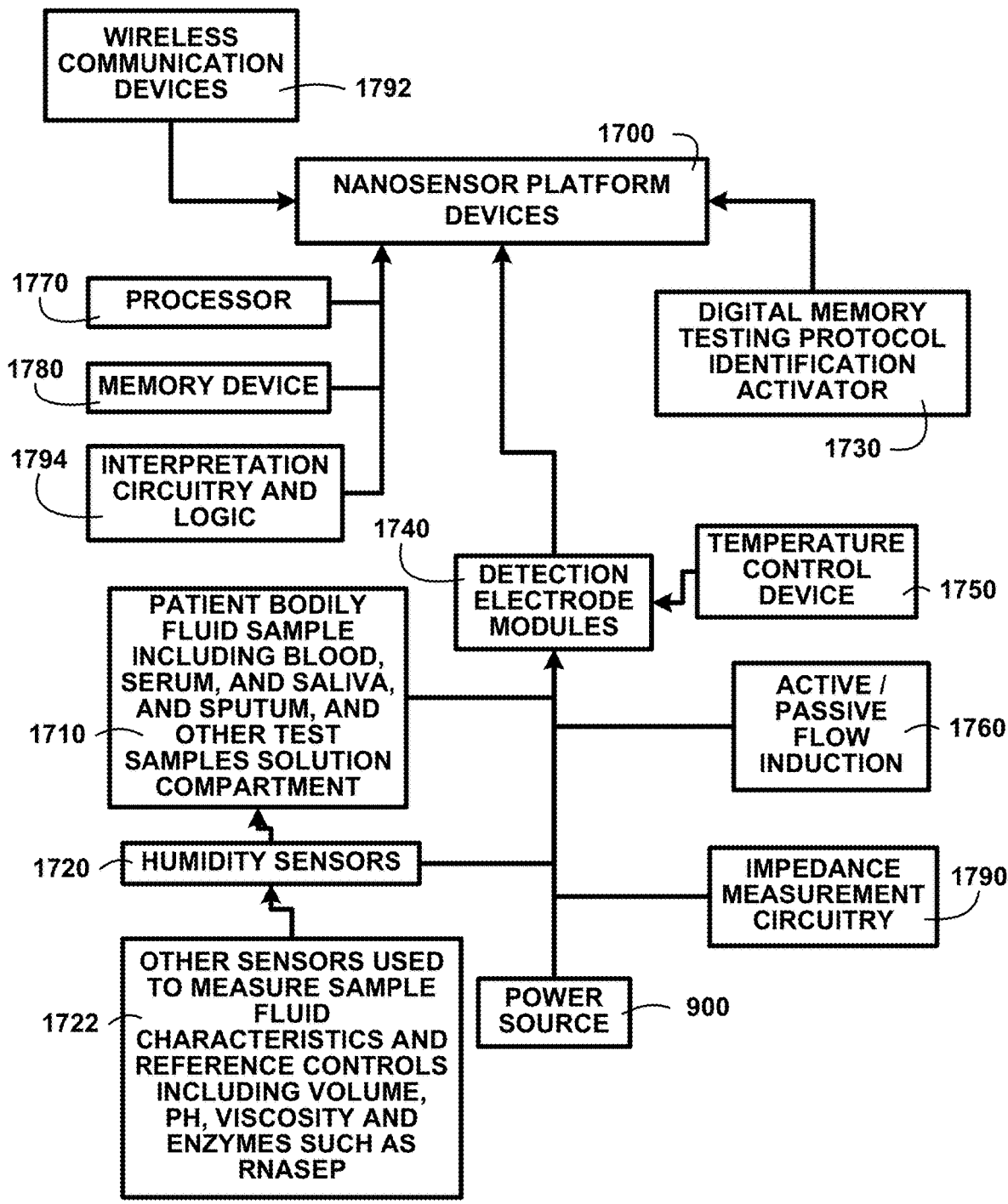
FIG. 17 shows a block diagram of an overview of nanosensor platform devices of one embodiment.

Nanosensor Platform Devices:

FIG. 17 shows a block diagram of an overview of nanosensor platform devices of one embodiment. FIG. 17 shows nanosensor platform devices 1700 that are configured with wireless communication devices 1792, at least one processor 1770, the memory device 1780, interpretation circuitry and logic 1794, and electrical current and impedance measurement circuitry 1790. Detection electrode modules 1740 are inserted into the nanosensor platform devices 1700 for reading and interpretation of the detection testing. Coupled to the detection electrode module 1740 is a patient bodily fluid sample including blood, serum, saliva, sputum and other test samples solution compartment 1710. Coupled to the patient's bodily fluid sample including blood, serum, saliva, sputum and other test samples solution compartment 1710 are humidity sensors 1720 and other sensors used to measure sample fluid characteristics and reference controls including volume, Ph, viscosity, and enzymes such as RNase P 1722. Also coupled to the detection electrode modules 1740 are at least one digital memory testing protocol identification activator 1730, temperature control device 1750, and active/passive flow induction 1760. Another element coupled to the detection electrode module 1740 is a power source 900 of one embodiment.

Figure 18A:
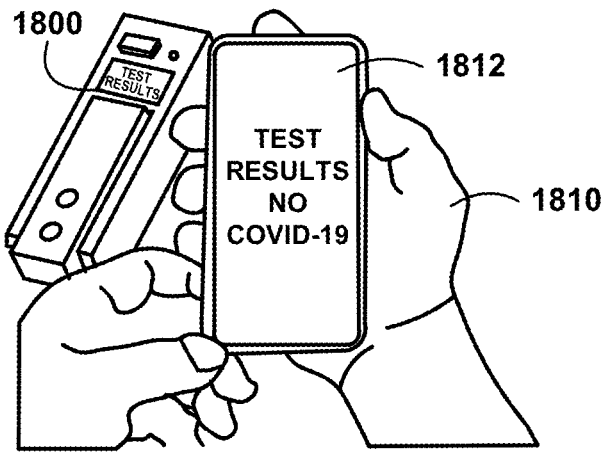
FIG. 18A shows for illustrative purposes only an example of the home use application environment of one embodiment.
Figure 18B:
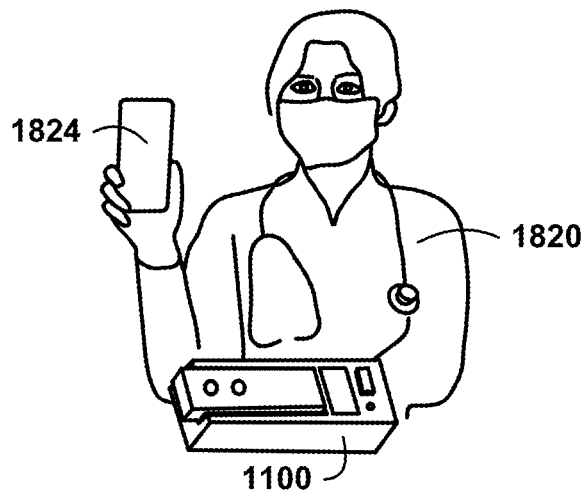
FIG. 18B shows for illustrative purposes only an example of clinic use application environment of one embodiment.
Figure 18C:
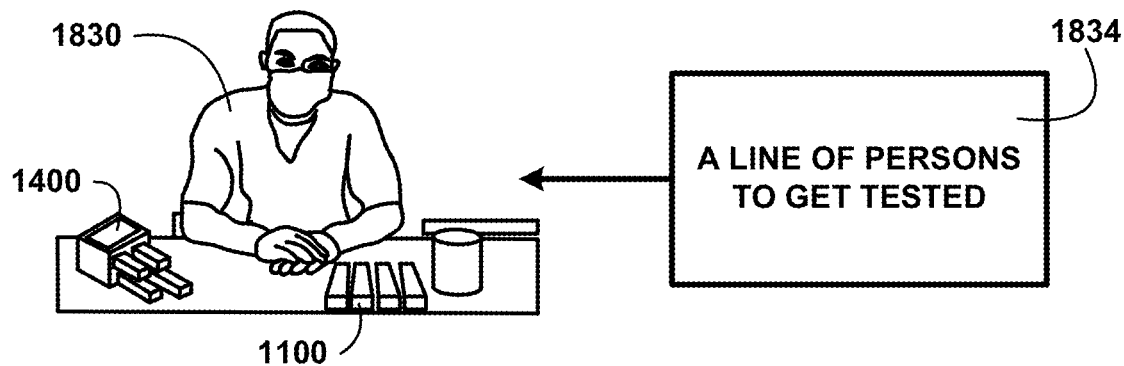
FIG. 18C shows for illustrative purposes only an example of a mass-use application environment of one embodiment.

Application Environments:

FIGS. 18A, 18B, and 18C show application environments for the use of the nanosensor platform devices and processes 100 of FIG. 1.

FIG. 18A shows for illustrative purposes only an example of the home use application environment of one embodiment. FIG. 18A shows in one embodiment the nanosensor platform devices and processes 100 of FIG. 1 are configured for home use with an untrained user, following written instructions 1810. The home use processing of the nanosensor platform device 1800 with detection, measurement, and interpretation means reported to the user via a sensing platform smartphone app 1812 that in this instance reports "Test Results no Covid-19".

FIG. 18B shows for illustrative purposes only an example of clinic use application environment of one embodiment. FIG. 18B shows in another embodiment Clinical Use with a semi-trained user 1824, having previously performed the test and following written instructions 1820. Processing includes nanosensor platform device 1100 with detection, measurement, and test data transmitted over WIFI to a network for reading and interpretation and reporting results on a sensing platform smartphone app in this instance waiting for the results report to be displayed.

FIG. 18C shows for illustrative purposes only an example of a mass-use application environment of one embodiment. FIG. 18C shows in yet another embodiment Mass Use with a trained operator 1830, repeatedly performing the tests from documented procedures, conversant in test sampling and preparation techniques. Mass Use utilizes a nanosensor platform device 1100 with detection, measurement, and using an external multiple device multi-reader and interpretation device transceiver 1400. The interpretation device transceiver can be configured with hard-wire and wireless communication to the network interpretation means. The multiple device multi-reader and interpretation device transceiver 1400 facilitates processing tests of a large number of people 1834 in a short time.

Figure 19:
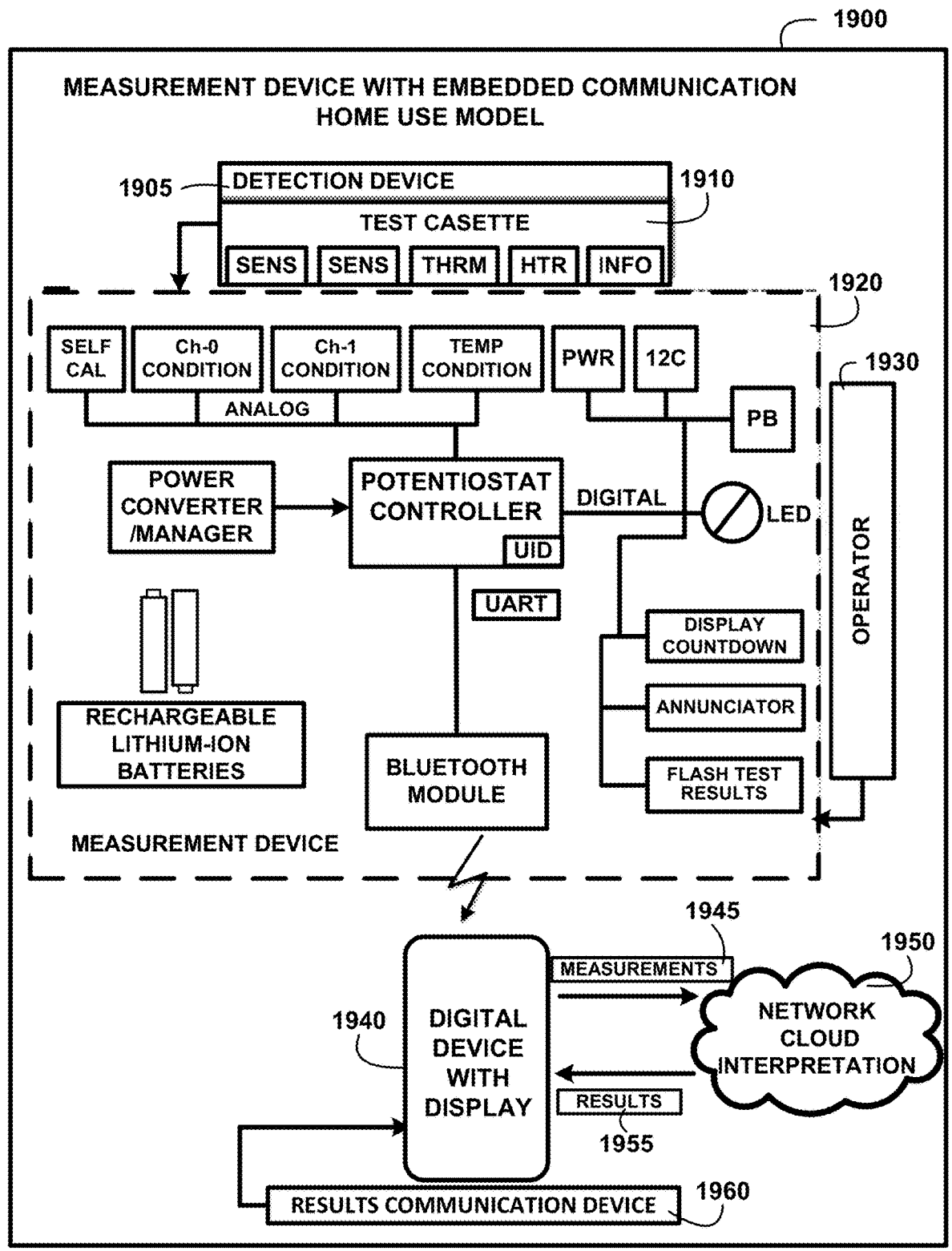
FIG. 19 shows for illustrative purposes only an example of a measurement device with embedded communication home use model of one embodiment.

A Measurement Device with Embedded Communication Home Use Model:

FIG. 19 shows for illustrative purposes only an example of a measurement device with embedded communication home use model of one embodiment. FIG. 19 shows an example of a measurement device with embedded communication home use model 1900. The home-use model includes a detection device 1905 with a test cassette 1910 with modules for SENS, SENS, THRM, HTR, and INFO. A measurement device 1920 is configured with PWR, 12C, PB, and an LED. The measurement device 1920 includes operations of a displayed countdown, annunciator, and flash test results. An operator 1930 turns on and off and makes selections of the operations of the home use model.

The measurement device 1920 includes analog operations for self-cal (calibration), Ch-0 condition, Ch-1 condition, and temp condition. The measurement device 1920 includes a potentiostat controller UID, a power converter/manager for rechargeable batteries, and digital devices. UART and Bluetooth module. The Bluetooth module communicates with at least one communication device including a digital device with display 1940 for transmitting and receiving data including measurements 1945, network cloud interpretation 1950 and results 1955 and results communication device 1960 of one embodiment.

Figure 20:
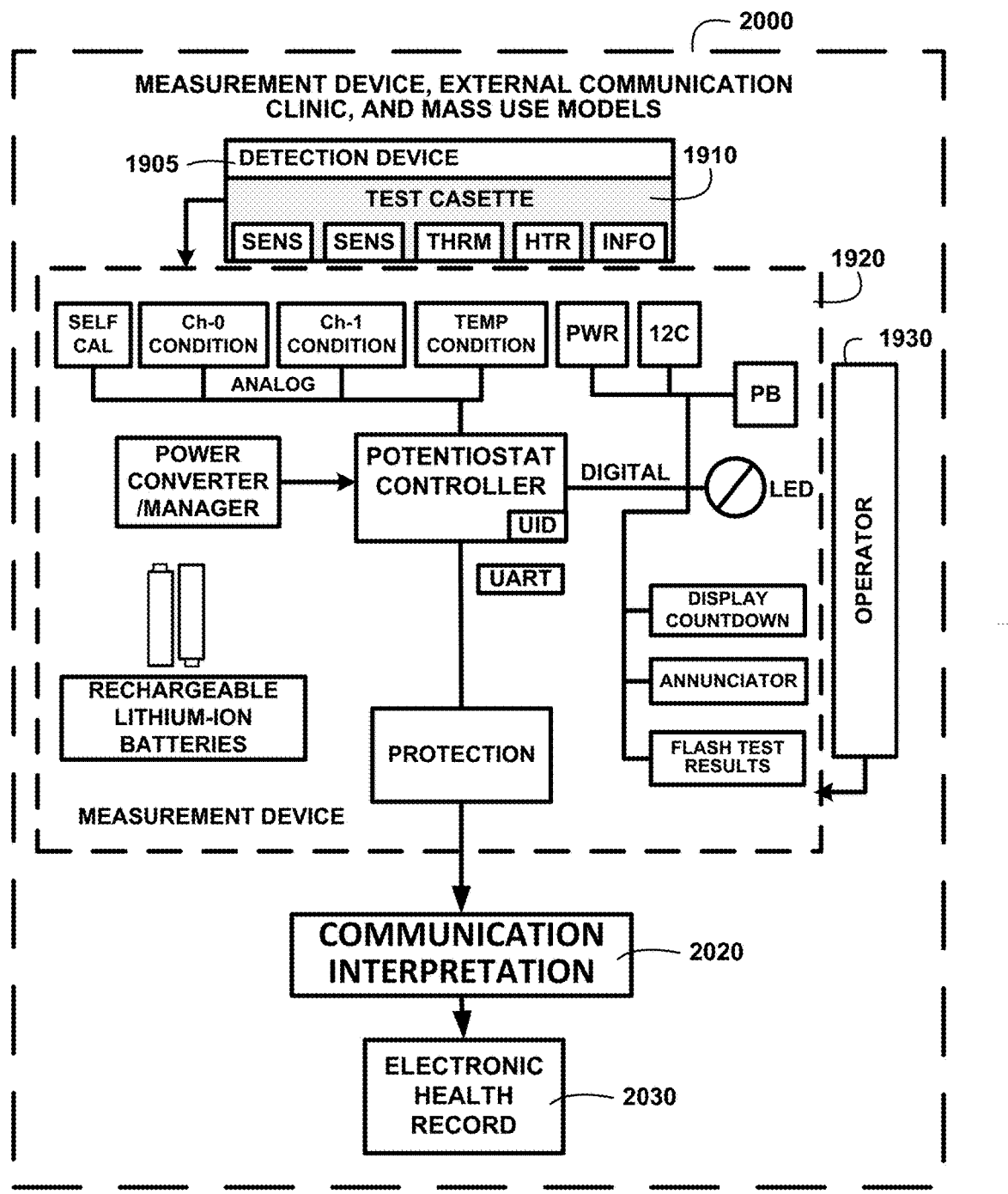
FIG. 20 shows for illustrative purposes only an example of a measurement device, external communication clinic, and mass-use models of one embodiment.

A Measurement Device, External Communication Clinic, and Mass-Use Models:

FIG. 20 shows for illustrative purposes only an example of a measurement device, external communication clinic, and mass-use models of one embodiment. FIG. 20 shows an example of a measurement device, external communication clinic, and mass use models 2000. The clinic and mass-use models include a detection device 1905 with a test cassette 1910 with modules for SENS, SENS, THRM, HTR, and INFO.

A measurement device 1920 is configured with PWR, 12C, PB, and an LED. The measurement device 1920 includes operations of a displayed countdown, annunciator, and flash test results. An operator 1930 turns on and off and makes selections of the operations of the home use model. The measurement device 1920 includes analog operations for self-cal (calibration), Ch-0 condition, Ch-1 condition, and temp condition.

The measurement device 1920 includes a potentiostat controller UID, power converter/manager for rechargeable batteries, and digital devices, UART and protection. Communication interpretation 2020 is performed on external devices wherein the detection and measurement data is communicated to a network for interpretation. The interpretation results are transmitted to a patient electronic health record (her) 2030 of one embodiment.

Figure 21:
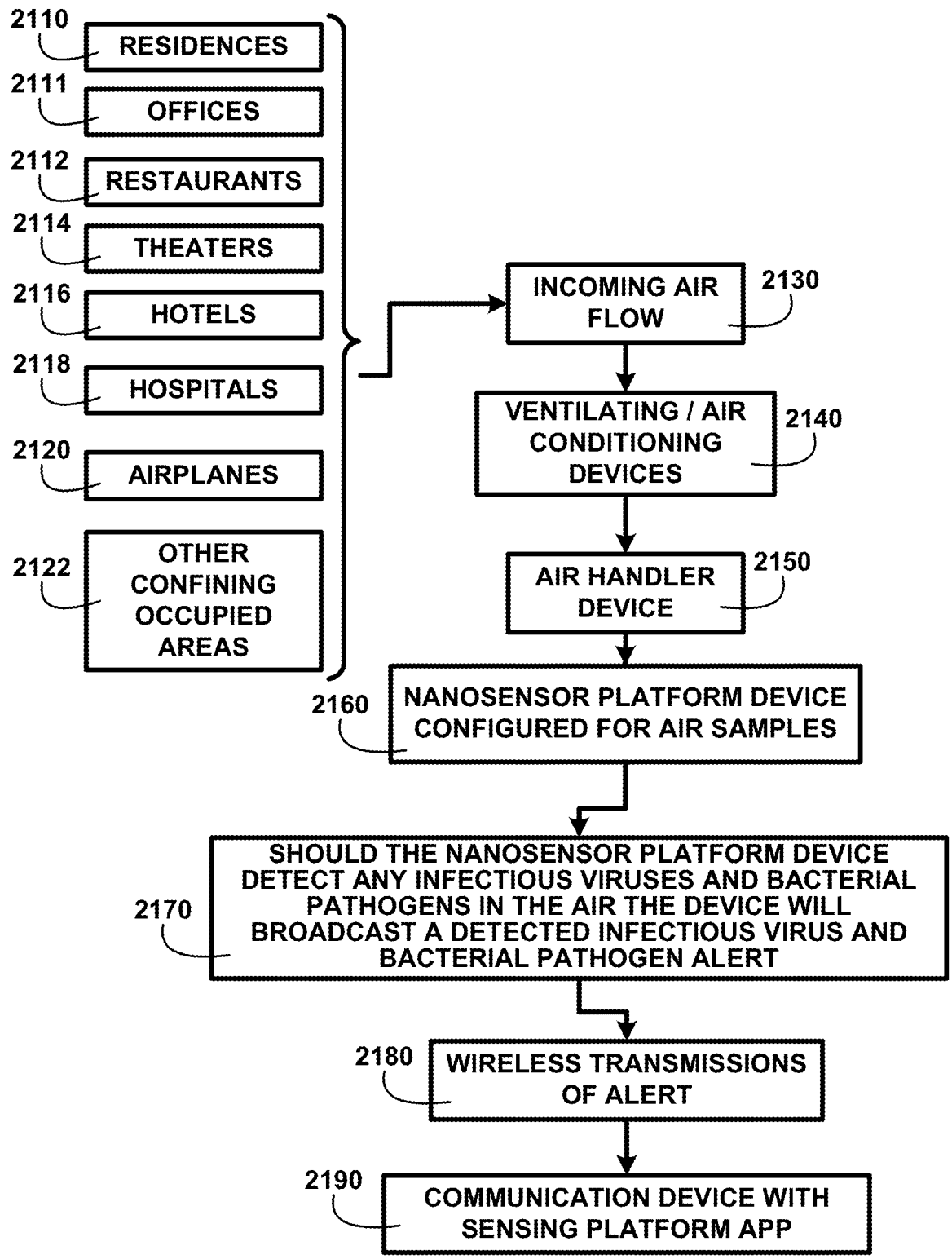
FIG. 21 shows a block diagram of an overview of electrochemical air sampling sensing platform devices of one embodiment.

Electrochemical Air Sampling Sensing Platform Devices:

FIG. 21 shows a block diagram of an overview of electrochemical air sampling sensing platform devices of one embodiment. FIG. 21 shows areas where people congregate frequently including residences 2110, offices 2111, restaurants 2112, theaters 2114, hotels 2116, hospitals 2118, airplanes 2120, and other confining occupied areas 2122.

One commonality of these locations is the ventilating of the indoor air. Incoming airflow 2130 to ventilating/air conditioning devices 2140 is passed through the rooms and other occupied areas by the ventilating/air conditioning devices 2140 air handler device 2150. The testing of this air can detect the presence of infectious viruses and bacterial pathogens or biomarkers indicative of the presence of infectious viruses and bacterial pathogens including SARS-CoV-2 and other viruses, MSRA, Legionnaires770830, and other infectious microorganisms.

In one embodiment, a nanosensor platform device configured for air sample 2160 will test the air as it passes through the nanosensor platform device configured for air sample 2160. The nanosensor platform device configured for air sample 2160 will be placed within the airflow.

Should the nanosensor platform device detect any infectious viruses and bacterial pathogens in the air the device will broadcast a detected infectious virus and bacterial pathogen alert 2170. Communication devices in the nanosensor platform device will initiate wireless transmissions of alert 2180 to a user communication device with sensing platform app 2190 so they can take appropriate actions of one embodiment.

Figure 22:
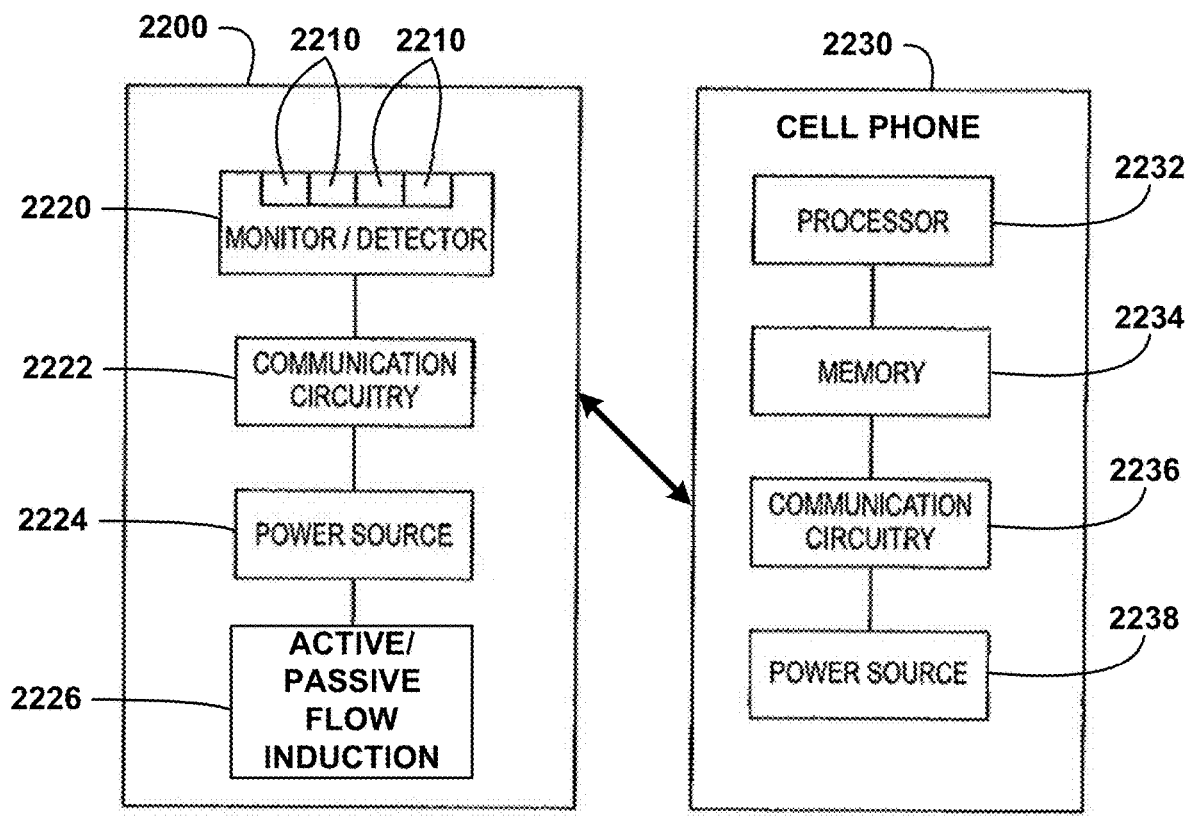
FIG. 22 shows for illustrative purposes only an example of an exemplary system of one embodiment.

Exemplary System:

FIG. 22 shows for illustrative purposes only an example of an exemplary system of one embodiment. FIG. 22 shows a monitor system 2200 generally includes a monitor/detector component 2220. One monitor/detector component 2220 that is particularly well-suited for purposes of the present disclosure is set forth in U.S. Pat. No. 8,629,770 to Hummer et al. and U.S. Pat. No. 7,176,793 to Hummer, both of which are incorporated herein by reference in their entireties. Other types of monitor/detector components can also be used in accordance with the present disclosure.

The monitor system 2200 further includes communication circuitry 2222 and a power source 2224. The monitor system 2200 communication circuitry 2222, in one embodiment, includes at least one of a near-field communication device, Bluetooth communication device, WIFI communication device, or any other suitable communication circuitry for establishing communications with a cell phone. The power source 2224 can be a power supply such as a battery (lithium or other) mounted or otherwise contained within the case of a cell phone 2230. In other embodiments, the power source 2224 can be an antenna configured to receive energy wirelessly and supply the received energy to one or both of the monitor/detector component 2220 and/or communication circuitry 2222 such that no onboard battery is required for the operation of the monitor system 2200. In still other arrangements, the monitor system 2200 power source 2224 can be a connector configured to couple with a port of the cell phone 2230 to receive power from a power source of the cell phone 2230.

An active or passive flow induction device 2226 can be provided for ensuring adequate and or continuous flow of a substance to the monitor/detector component 2220. Such devices can include fans, micro pumps, louvers, vents, etc. An active induction device can be separately replaceable within the system and can include its power supply. Alternatively, an active induction device can be configured to receive power from power supply 2224.

It should be appreciated that the monitor/detector component 2220 can comprise a plurality of sensors 2210. The sensors 2210 can be individually replaceable or can be replaced as a unit. Replacement of the sensors may be necessary due to sensor degradation. In other situations, a user may wish to detect certain chemicals or analytes and will choose which sensors to install in the system. In one embodiment, the entire monitor system 2200 is replaceable as a unit.

The sensors 2210 may detect harmful materials, such as disease, explosives, radioactive materials, harmful chemicals, such as chemical warfare agents, nerve gases, biological materials, such as gases, anthrax, and other germ warfare agents, narcotics, and other illegal drugs, or combinations thereof. At least one of the sensors 2210 can be configured for generating a signal which is indicative of the presence of a nitrogen-based explosive, such as trinitrotoluene (TNT), and/or a peroxide-based explosive, such as triacetone triperoxide (TATP) or hexamethylenetriperoxidediamine (HMTD), or a combination thereof, for example.

It will be appreciated that the monitor system 2200 is configured to communicate with the cell phone 2230. That is the monitor system 2200 collects data and transmits or otherwise shares the collected data with the cell phone 2230 for processing. The cell phone 2230 of the illustrated embodiment includes a processor 2232, a memory 2234, a cell phone 2230 communication circuitry 2236, and a power source 2238. It will be appreciated that the cell phone 2230 can include a wide variety of additional components as is conventional. Such additional components can include a display device, input device, various sensors, various antennas, etc.

Data collected by the monitor/detector 2220 is transmitted via communication circuitry 2222 to communication circuitry 2236 of the cell phone 2230. Other data, such as sensor state, status, performance data, and the like can also be transmitted to the cell phone 2230. Any suitable manner of transmitting the data from the monitor system 2200 to the cell phone 2230 can be employed.

The data collected and transmitted by the monitoring system 2200 is then processed by the phone to detect one or more analytes in accordance with one or more methods set forth in U.S. Pat. No. 8,629,770 to Hummer et al. and U.S. Pat. No. 7,176,793 to Hummer. To this end, suitable software for analyzing the data is stored in memory 2234 of the cell phone 2230. Other detection and/or analyzing methods and techniques may also be used in conjunction with aspects of the present disclosure.

In one embodiment, the software stored in memory 2234 can be in the form of an application, or "app", that is downloaded from an app store or the like. The app can be provided with various "signatures" of analytes. The signatures can be compared to the data to determine whether the analyte signature was detected by the monitoring system 2200. The app can be configured to be automatically updated with new signatures as the need to detect new analytes arise. That is, it is possible to provide new and/or additional analyte signatures for the app to check against the data to detect specific analytes.

The app can further include features such as adjustable thresholds. For example, for some analytes that are routinely present in certain amounts and/or not generally considered dangerous below certain levels, the application can be configured to detect or trigger an alarm when a threshold amount is met or exceeded. For some analytes which are considered dangerous in any amount, the thresholds would not generally be adjustable.

The app can be further configured to, once an analyte is detected, share the detection information. For example, the application can be configured to use the communication circuitry 2236 to broadcast an alert (or generate a notification) via any suitable communications network (e.g., WIFI, NFC, Bluetooth, cell, etc.). The alert may be directly sent to other cell phones and/or personal communication devices in the area or may be sent to a server (or through a network) and then on to devices within a range of a given location. Accordingly, the application can be configured to use location information from a GPS chip, WIFI, or any other location information available to the cell phone 2230 to identify the location of the detected analyte.

The app can be configured to alert the authorities in the event certain analytes are detected. For example, the detection of any amount of sarin gas (or other chemical/biological agents) can trigger information relating to the location, time, etc. of the detection to be forwarded to certain designated authorities for threat management/mitigation.

It should be appreciated that a network of devices having monitoring systems, each detecting a certain analyte, can be configured to share valuable data regarding the dispersion of the particular analyte. For example, devices in close proximity to each other and the point of origin of the analyte may detect a greater concentration of the analyte than devices further away from the point of origin. Using this data and an appropriate dispersion model, a point of origin can be calculated. This can allow responsive action to be taken more quickly than otherwise would be the case.

Similarly, the data (location, concentration, etc.) from a plurality of such devices can be used to predict the dispersion of the analyte so that preemptive action can be taken to minimize exposure of humans to the detected analyte.

Providing the monitoring system 2200 in a separate component that is attachable to a phone or other personal communication device has several advantages. For example, all such devices can become monitors/detectors upon the provision of a suitable case or other components. Accordingly, a consumer can decide whether to add the functionality. In addition, the orientation, location, and other aspects of the positioning of the sensor elements within the case or other components can be standardized to provide more consistent detection as compared to placing the sensor elements within various models of cell phones. In other embodiments, the monitoring system 2200 is embedded in a smart device or phone.

It should be appreciated that, although the monitoring system 2200 is illustrated as part of a case, the monitoring system 2200 can also be provided as a separate unit attachable either directly to a cell phone or the like, or attachable to a case in which a cell phone is contained.

Figure 23:
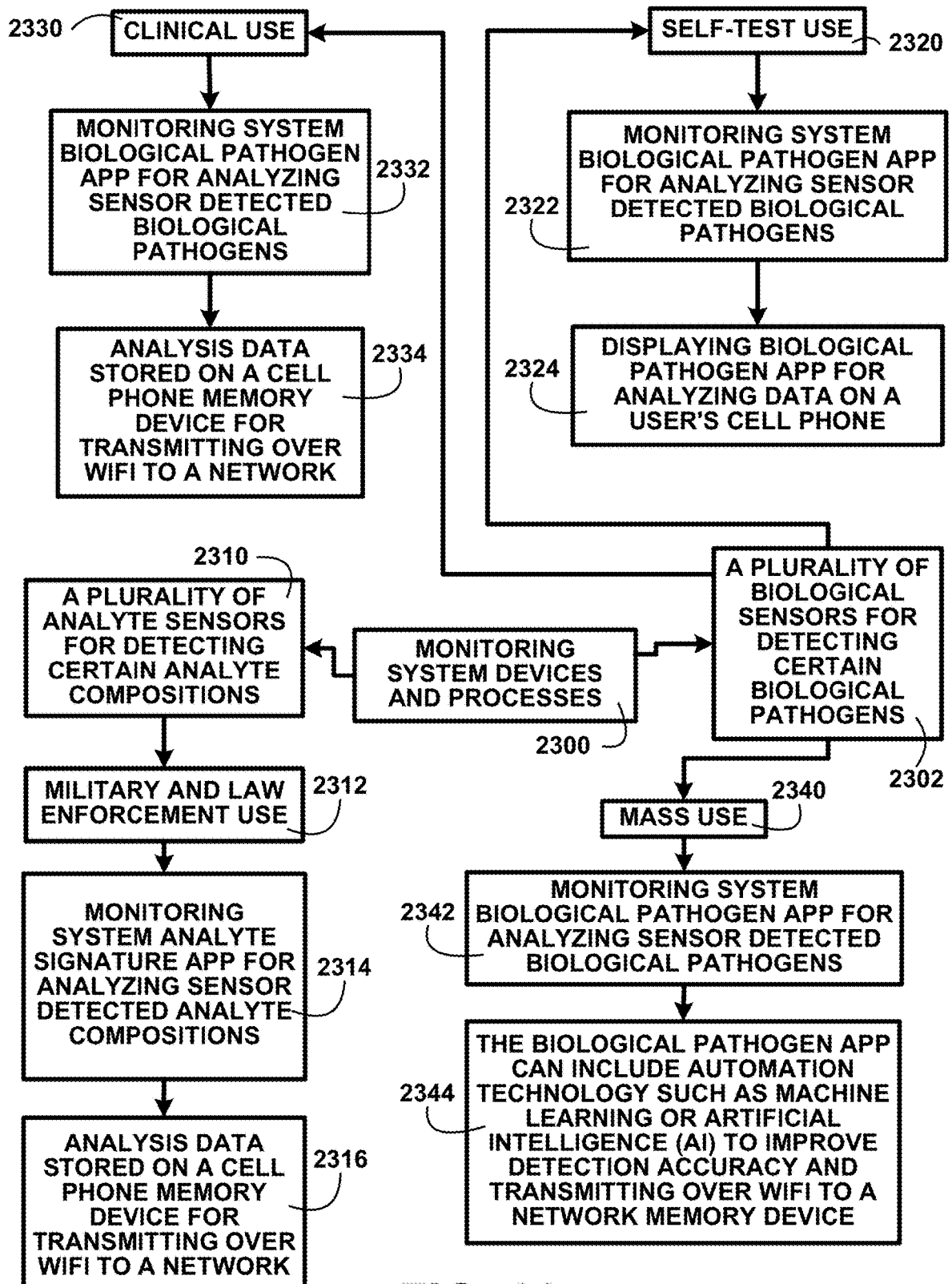
FIG. 23 shows a block diagram of an overview of monitoring system devices and processes of one embodiment.

Monitoring System Devices and Processes:

FIG. 23 shows a block diagram of an overview of monitoring system devices and processes of one embodiment. FIG. 23 shows monitoring system devices and processes 2300 including a plurality of analyte sensors for detecting certain chemical compositions or analytes 2310. In one embodiment, the plurality of analyte sensors for detecting certain analyte compositions 2310 are applied for military and law enforcement use 2312. A monitoring system analyte signature app for analyzing sensor-detected analyte compositions 2314 is also used for analyzing data stored on a cell phone memory device for transmitting over WIFI to a network 2316.

FIG. 23 shows a plurality of biological sensors for detecting certain biological pathogens 2302. In one embodiment, the plurality of biological sensors for detecting certain biological pathogens 2302 is applied for self-test use 2320. A monitoring system biological pathogen app for analyzing sensor-detected biological pathogens 2322 and for displaying biological pathogen app for analyzing data on a user's cell phone 2324.

In another embodiment, a monitoring system biological pathogen app for analyzing sensor-detected biological pathogens 2332 is applied for clinical use 2330. The analysis data is stored on a cell phone memory device for transmitting over WIFI to network 2334. In yet another embodiment a mass use 2340 uses a monitoring system biological pathogen app for analyzing sensor detected biological pathogens 2342. Also uses multiple monitoring systems detection analysis data stored on a cell phone for self-testing, a reader for a clinic, and a reader for mass testing. The biological pathogen app 2332 can include automation technology such as machine learning or artificial intelligence (Ai) to improve detection accuracy and transmitting over WIFI to a network memory device 2344 of one embodiment. In one embodiment, machine learning and AI includes using existing neural networks, such as Bayesian networks, to analyze and compare the collected data with known data for recommending and resolving accuracy based on the analysis and comparisons for quality assurance, quality control and revisionary improvements in results and manufacturing.

Figure 24:
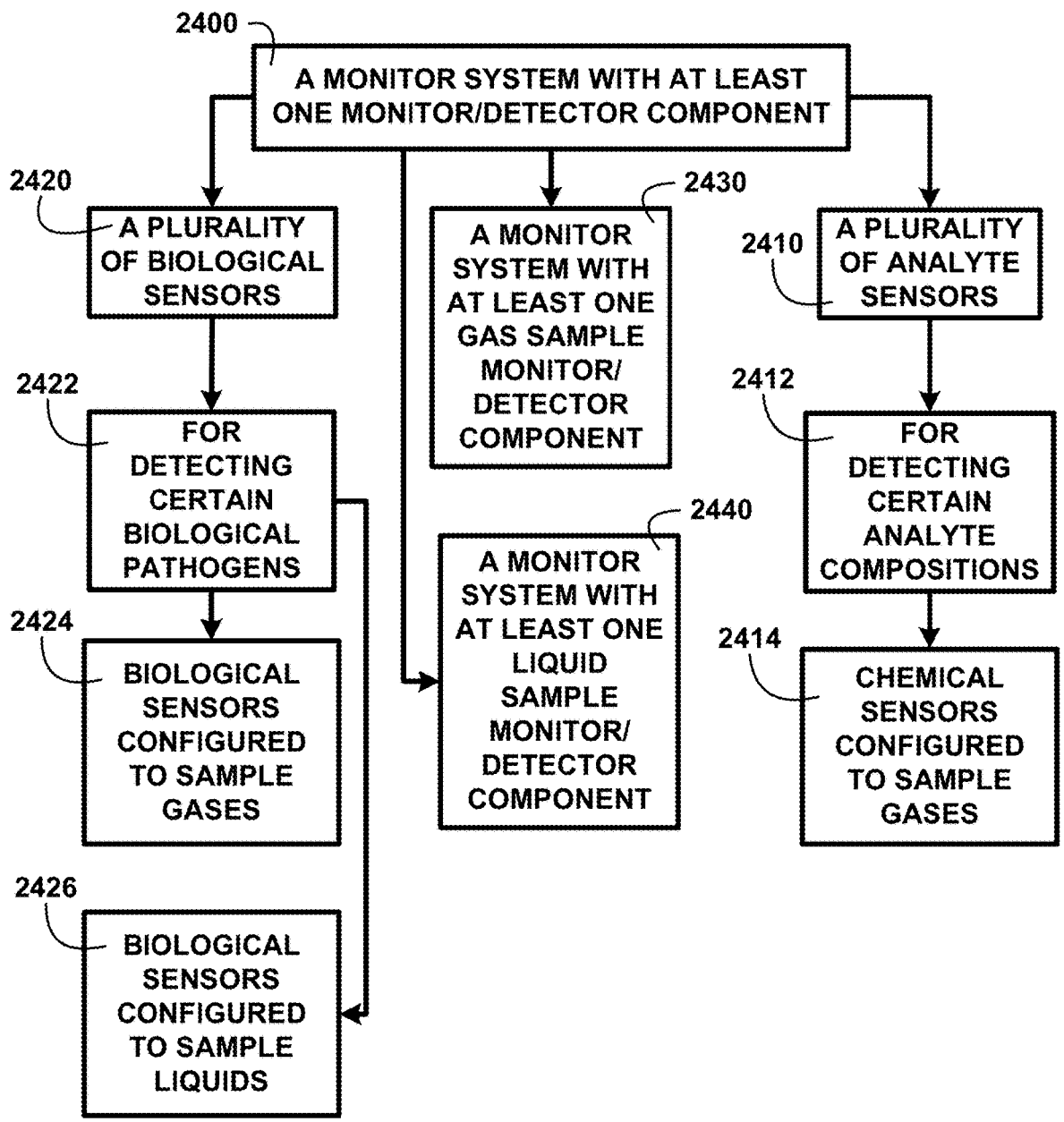
FIG. 24 shows a block diagram of an overview of the monitor/detector component of one embodiment.

Monitor/Detector Component:

FIG. 24 shows a block diagram of an overview of the monitor/detector component of one embodiment. FIG. 24 shows a monitor system with at least one monitor/detector component 2400 with a plurality of analyte sensors 2410 for detecting certain analyte compositions 2412. The plurality of analyte sensors 2410 includes chemical sensors configured to sample gases 2414. The monitor system with at least one monitor/detector component 2400 can be configured with a plurality of biological sensors 2420 for detecting certain biological pathogens 2422. The plurality of biological sensors 2420 includes biological sensors configured to sample gases 2424. The plurality of biological sensors 2420 includes biological sensors configured to sample liquids 2426. The devices include a monitor system with at least one gas sample monitor/detector component 2430. The devices include a monitor system with at least one liquid sample monitor/detector component 2440 of one embodiment.

Figure 25:
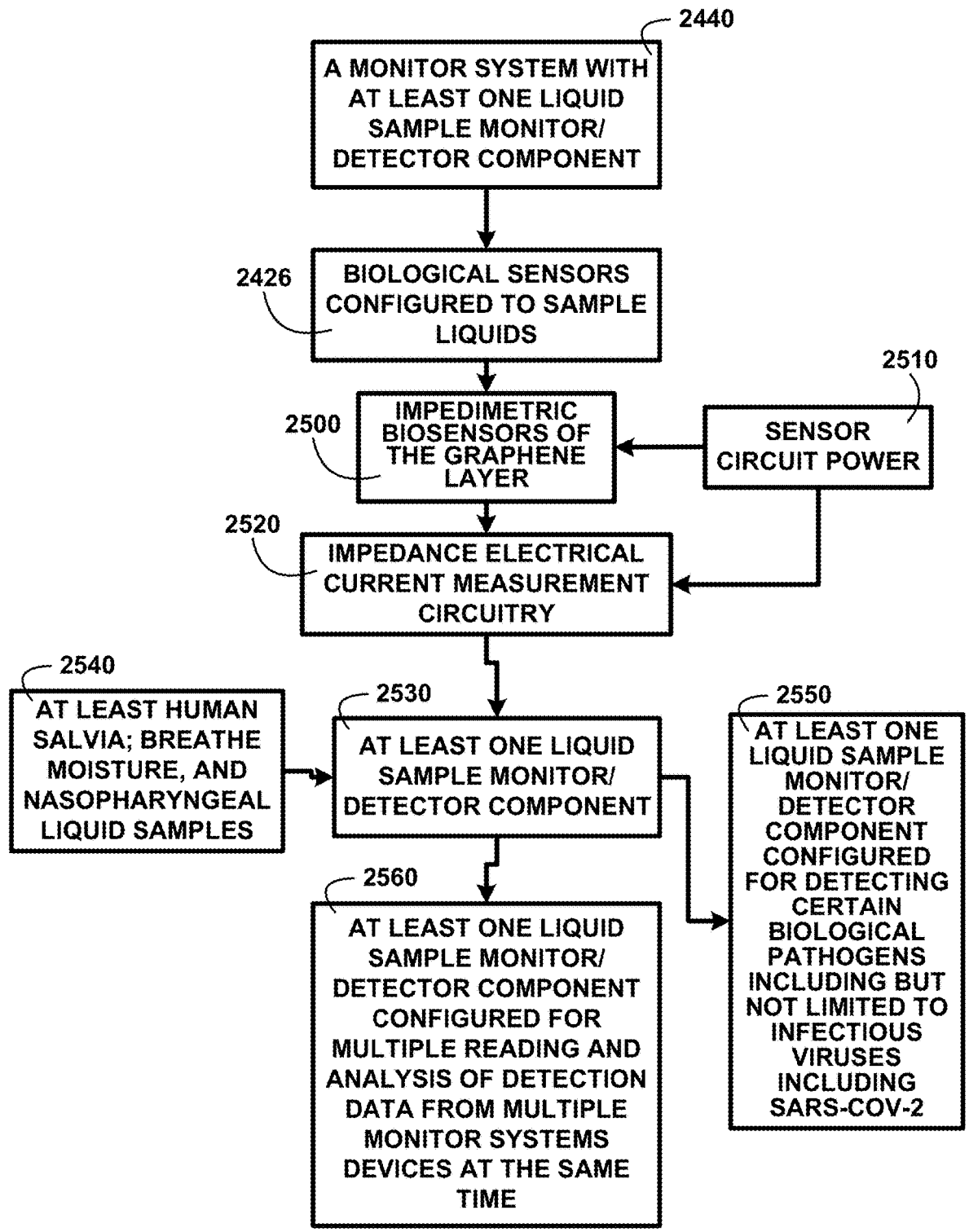
FIG. 25 shows a block diagram of an overview of the liquid sample monitor/detector component of one embodiment.

Liquid Sample Monitor/Detector Component:

FIG. 25 shows a block diagram of an overview of the liquid sample monitor/detector component of one embodiment. FIG. 25 shows a monitor system with at least one liquid sample monitor/detector component 2440 with biological sensors configured to sample liquids 2426. Detection using liquid samples is performed using impedimetric biosensors 2500. The impedimetric biosensors 2500 are powered using sensor circuit power 2510 and use electrical current and impedance electrical current measurement circuitry 2520 for an analysis process. At least one liquid sample monitor/detector component 2530 is configured for at least human *salvia*; breathe moisture, and nasopharyngeal liquid samples 2540.

At least one liquid sample monitor/detector component configured for detecting certain biological pathogens including but not limited to infectious viruses including SARS-CoV-2 2550. In another embodiment, at least one liquid sample monitor/detector component is configured for multiple readings and analysis of detection data from multiple monitor systems devices at the same time 2560 of one embodiment.

Figure 26:
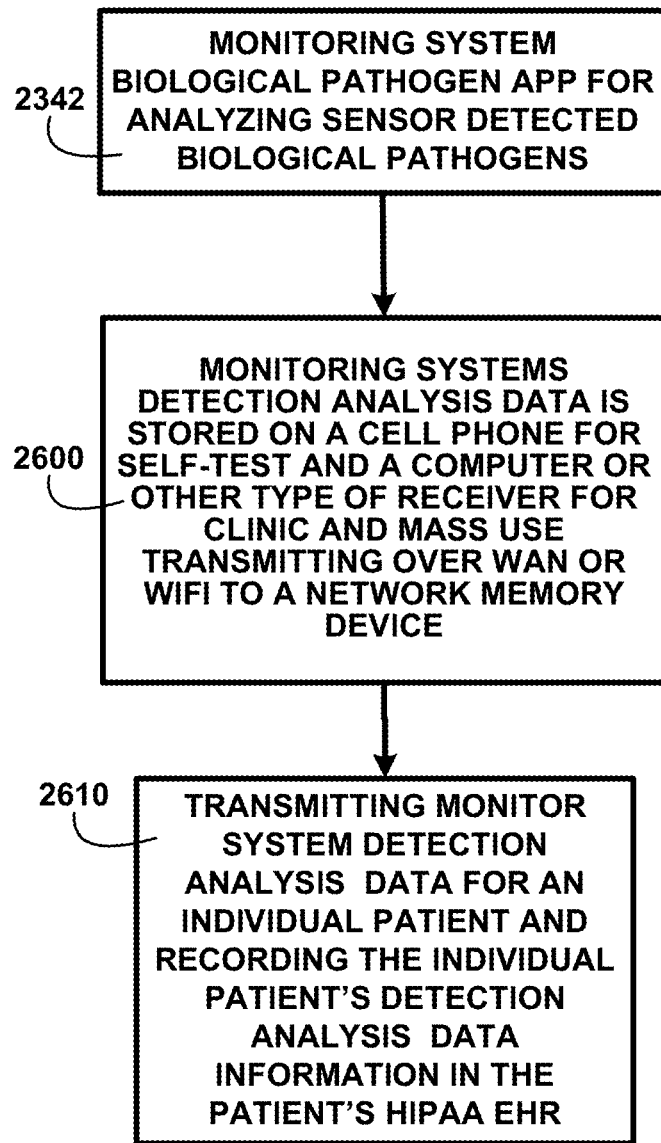
FIG. 26 shows a block diagram of an overview of recording the individual patient's detection analysis data information in the patient's HIPAA EHR of one embodiment.

Recording the Individual Patient's Detection Analysis Data Information in the Patient's HIPAA EHR:

FIG. 26 shows a block diagram of an overview of recording the individual patient's detection analysis data information in the patient's HIPAA EHR of one embodiment. FIG. 26 shows a monitoring system biological pathogen app for analyzing sensor-detected biological pathogens 2342. Monitoring systems detection analysis data is stored on a cell phone for self-test and a computer or other type of receiver for clinic and mass use transmitting over WAN or WIFI to a network memory device 2600. The process includes transmitting monitor system detection analysis data for an individual patient and recording the individual patient's detection analysis data information in the patient's HIPAA EHR 2610.

Figure 27:
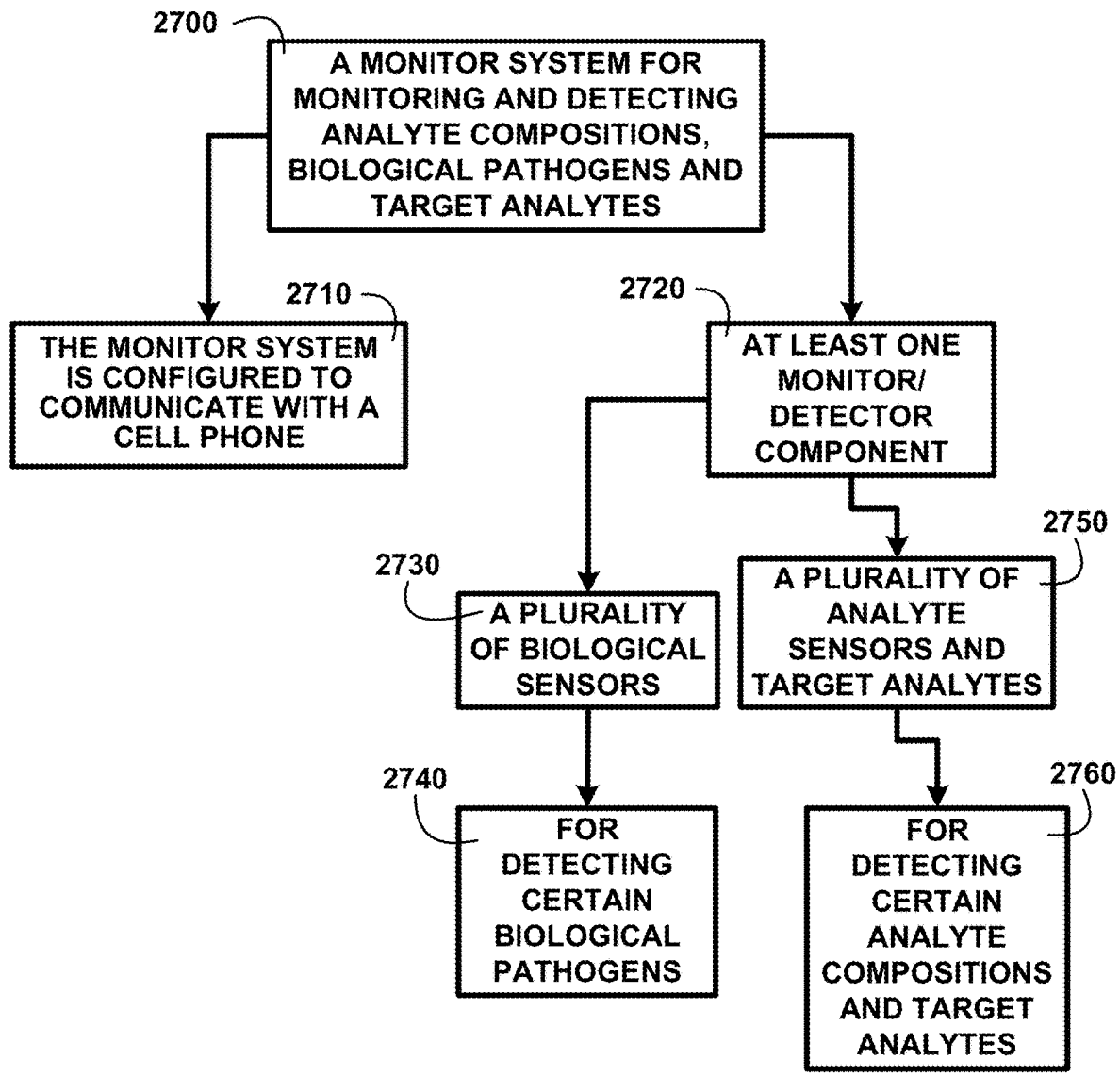
FIG. 27 shows a block diagram of an overview of a monitor system for monitoring and detecting chemical compositions and biological pathogens of one embodiment.

A Monitor System for Monitoring and Detecting Chemical Compositions and Biological Pathogens and Target Analytes:

FIG. 27 shows a block diagram of an overview of a monitor system for monitoring and detecting chemical compositions and biological pathogens of one embodiment. FIG. 27 shows a monitor system for monitoring and detecting analyte compositions, biological pathogens, and target analytes 2700. The monitor system is configured to communicate with a cell phone 2710. The monitor system is configured with at least one monitor/detector component 2720. The monitor system is configured with a plurality of biological sensors 2730 for detecting certain biological pathogens 2740. The monitor system is configured with a plurality of analyte sensors and target analytes 2750 for detecting certain analytes compositions and target analytes 2760 of one embodiment.

Figure 28:
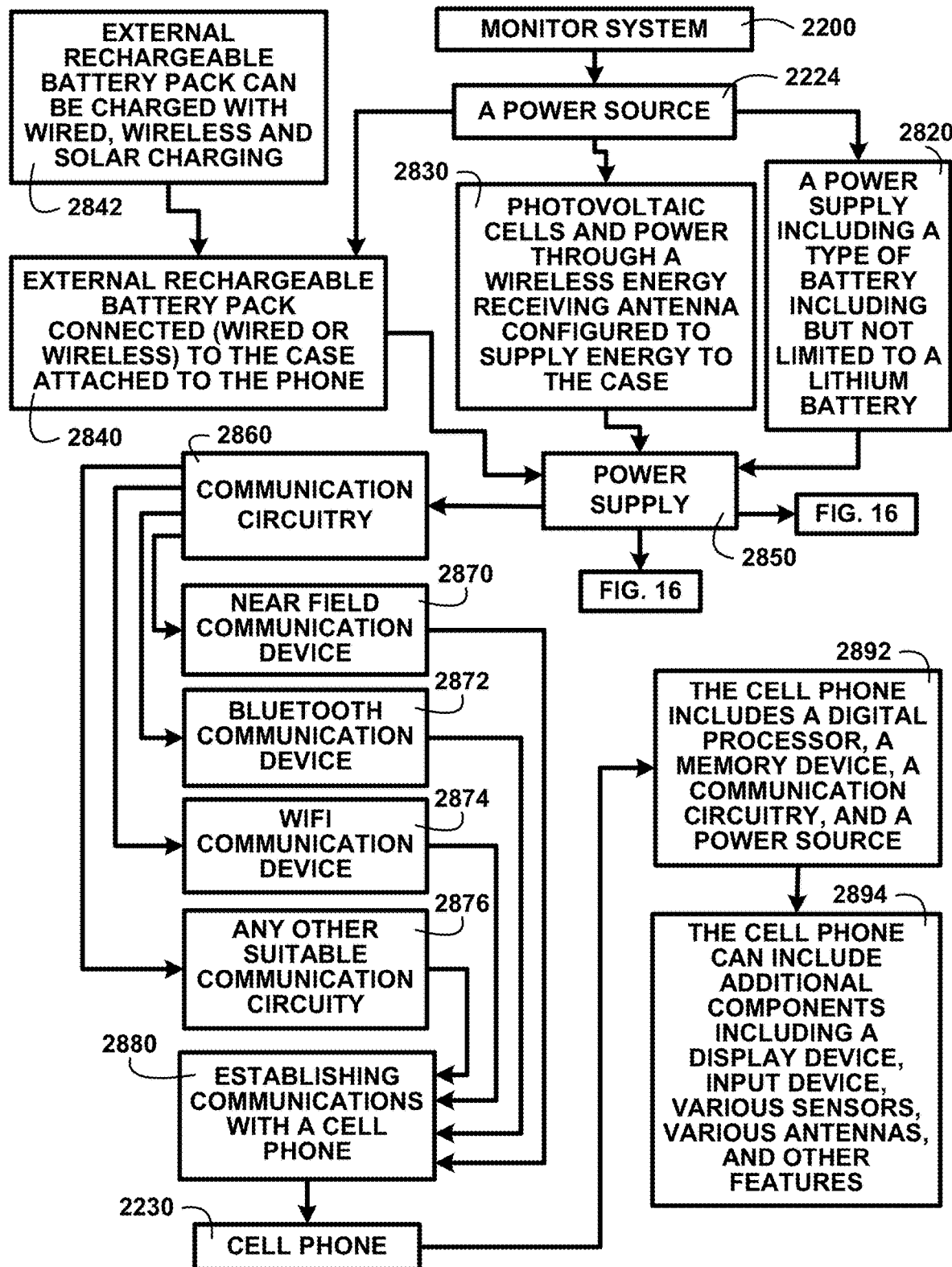
FIG. 28 shows a block diagram of an overview of a power source of one embodiment.

A Power Source:

FIG. 28 shows a block diagram of an overview of a power source of one embodiment. FIG. 28 shows the monitor system 2200 coupled to a power source 2224. The power source 2224 can be configured to include a power supply including a type of battery including but not limited to a lithium battery 2820. The power source 2224 can be configured to include photovoltaic cells and power through a wireless energy receiving antenna configured to supply energy to case 2830. The power source 2224 can be configured to include an external rechargeable battery pack connected (wired or wireless) to the case attached to the phone 2840. The external rechargeable battery pack can be charged with wired, wireless, and solar charging 2842.

The power source 2224 is configured to be a power supply 2850 as shown in FIG. 16. The power source 2224 is configured to be a power supply 2850 for communication circuitry 2860. Communication circuitry 2860 can be configured to include one or more from a group including a near-field communication device 2870, Bluetooth communication device 2872, WIFI communication device 2874, and any other suitable communication circuitry 2876. The communication circuitry 2860 is used for establishing communications with a cell phone 2880.

A cell phone 2230 or other communication device is the communication link to the user. The cell phone includes a digital processor, a memory device, communication circuitry, and a power source 2892. The cell phone 2230 can include additional components including a display device, input device, various sensors, various antennas, and other features 2894 of one embodiment.

Figure 29:
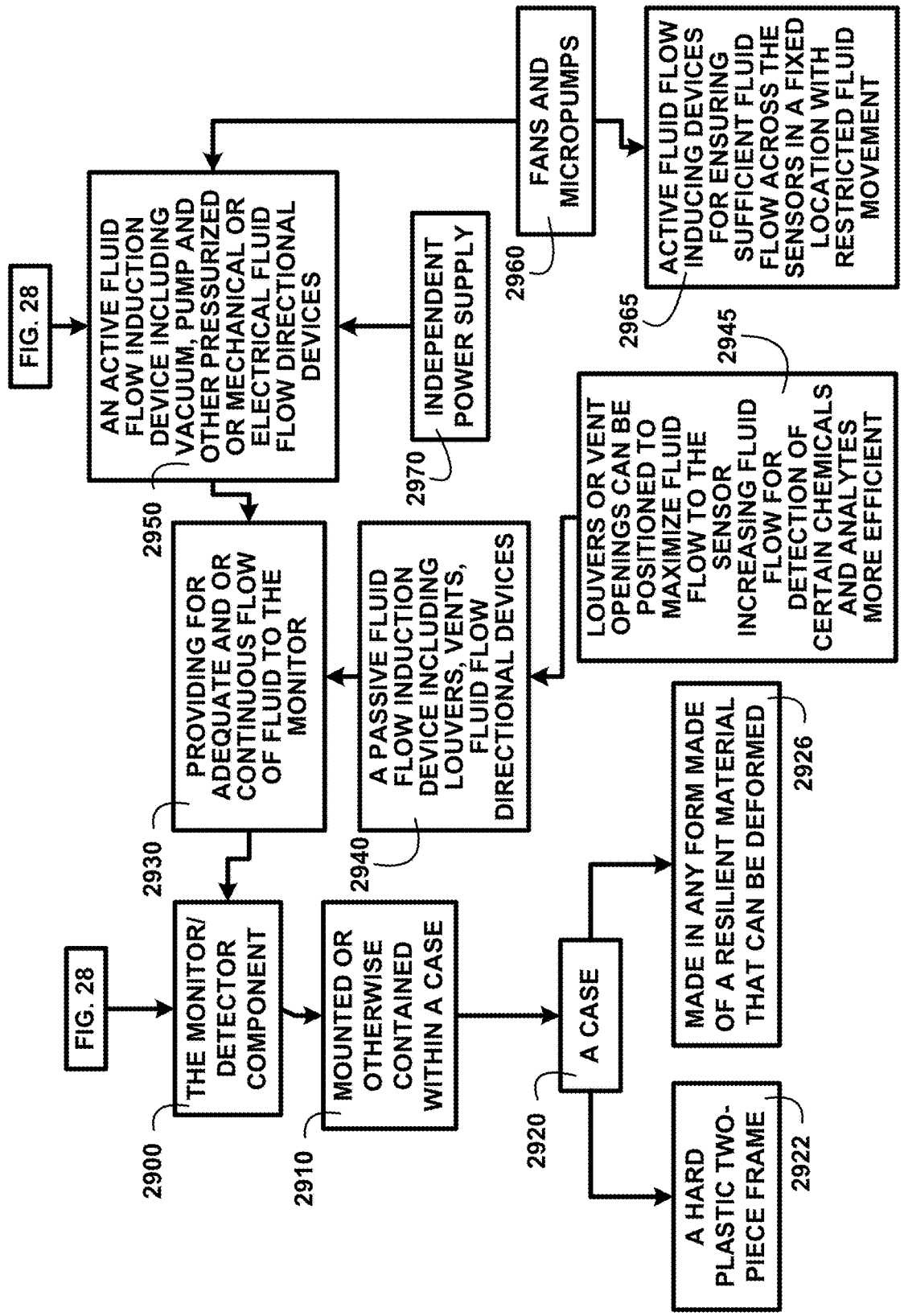
FIG. 29 shows a block diagram of an overview of a fluid flow induction device of one embodiment.

A Fluid Flow Induction Device:

FIG. 29 shows a block diagram of an overview of a fluid flow induction device of one embodiment. FIG. 29 shows a continuation from FIG. 28 the monitor/detector component 2900 mounted or otherwise contained within case 2910. A case can be made of a hard plastic two-piece frame 2922. Case 2920 can be made in any form made of a resilient material that can be deformed 2926. A fluid flow induction device is used for providing an adequate and or continuous flow of fluid to monitor 2930. A passive fluid flow induction device louvers, vents, and fluid flow directional devices 2940. Louvers or vent openings can be positioned to maximize fluid flow to the sensor increasing fluid flow for the detection of certain chemicals or analytes more efficiently 2945.

Also continuing from FIG. 28 is showing an active fluid flow induction device including vacuum, pump and other pressurized, mechanical, electrical or gravitational fluid flow directional devices 2950 with an independent power supply 2970, fans and micro-pumps 2960, and active fluid flow inducing devices for ensuring sufficient fluid flow across the sensors in a fixed location with restricted fluid movement 2965 of one embodiment.

Figure 30:
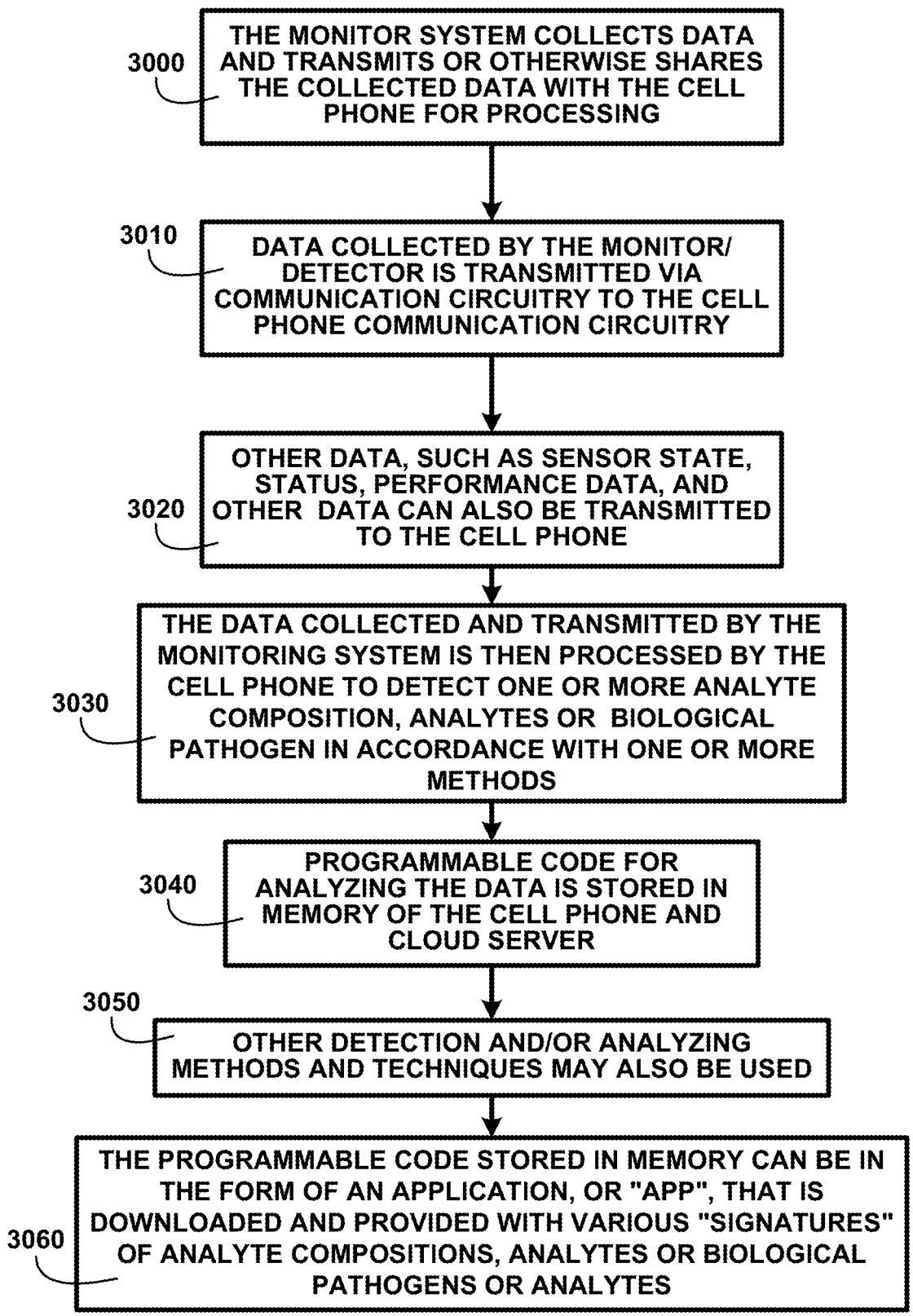
FIG. 30 shows a block diagram of an overview of a cell phone for processing of one embodiment.

A Cell Phone for Processing:

FIG. 30 shows a block diagram of an overview of a cell phone for processing of one embodiment. FIG. 30 shows the monitor system collects data and transmits or otherwise shares the collected data with the cell phone for processing 3000. The data collected by the monitor/detector is transmitted via communication circuitry to the cell phone communication circuitry 3010. Other data, such as sensor state, status, performance data, and other data can also be transmitted to the cell phone 3020. The data collected and transmitted by the monitoring system is then processed by the cell phone to detect one or more analyte compositions or biological pathogens or analytes in accordance with one or more methods 3030.

Programmable code for analyzing the data is stored in the memory of the cell phone and cloud server 3040. Other detection and/or analyzing methods and techniques may also be used 3050. The programmable code stored in memory can be in the form of an application, or "app", that is downloaded and provided with various "signatures" of analyte compositions, analytes or biological pathogens or analytes 3060 of one embodiment.

Figure 31:
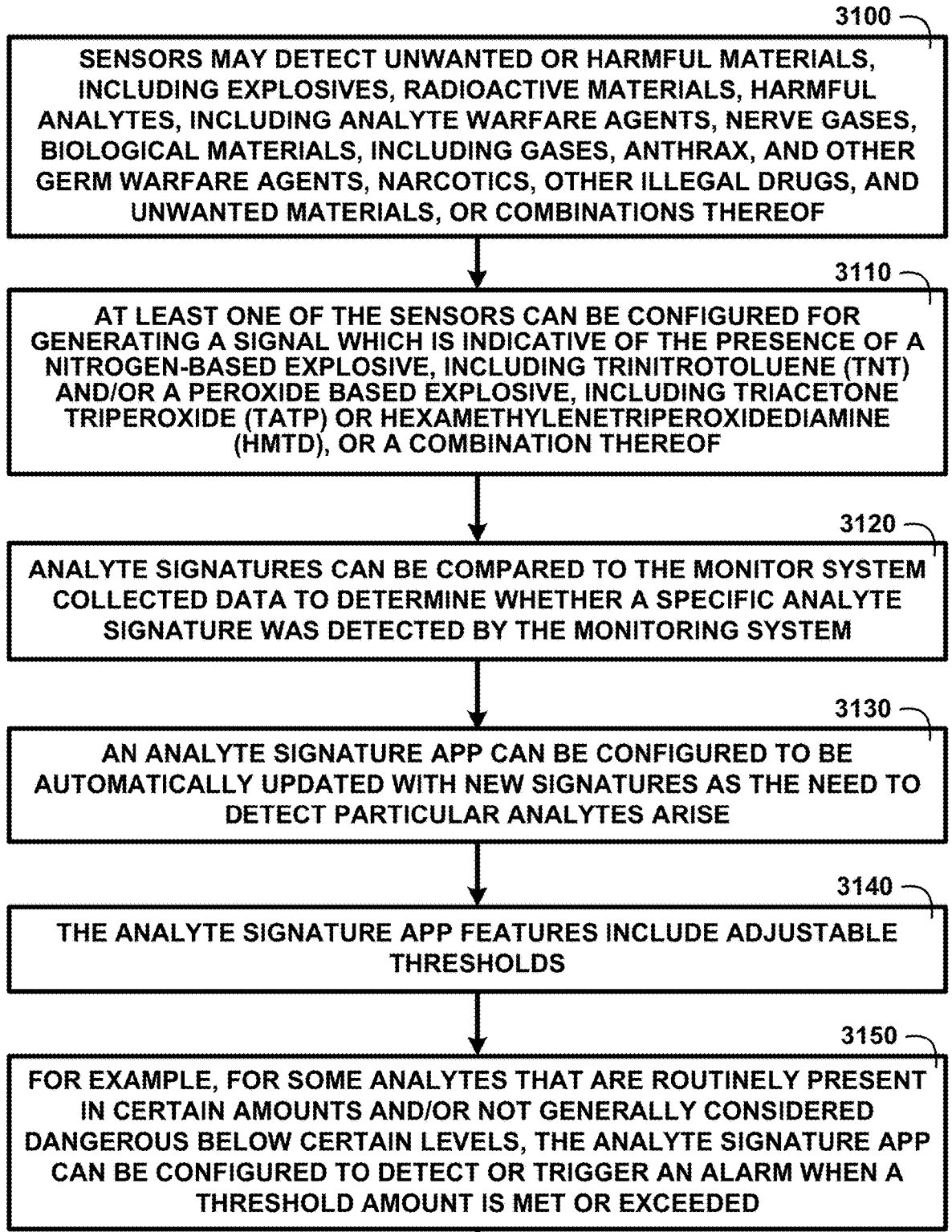
FIG. 31 shows a block diagram of an overview of sensors that may detect harmful materials of one embodiment.

Sensors May Detect Harmful Materials:

FIG. 31 shows a block diagram of an overview of sensors that may detect harmful or unwanted materials of one embodiment. FIG. 31 shows sensors may detect unwanted or harmful materials, including explosives, radioactive materials, harmful analytes, including analyte warfare agents, nerve gases, biological materials, including gases, anthrax, and other germ warfare agents, narcotics, other illegal drugs, and unwanted materials, or combinations thereof 3100. At least one of the sensors can be configured for generating a signal which is indicative of the presence of a nitrogen-based explosive, including trinitrotoluene (TNT) and/or a peroxide-based explosive, including triacetone triperoxide (TATP) or hexamethylenetriperoxidediamine (HMTD), or a combination thereof 3110.

Analyte signatures can be compared to the monitor system collected data to determine whether a specific analyte signature was detected by the monitoring system 3120. An analyte signature app can be configured to be automatically updated with new signatures as the need to detect particular analytes arise 3130. The analyte signature app features include adjustable thresholds 3140, for example, for some analytes that are routinely present in certain amounts and/or not generally considered dangerous below certain levels, the analyte signature app can be configured to detect or trigger an alarm when a threshold amount is met or exceeded 3150. The description is continued in FIG. 32.

Figure 32:
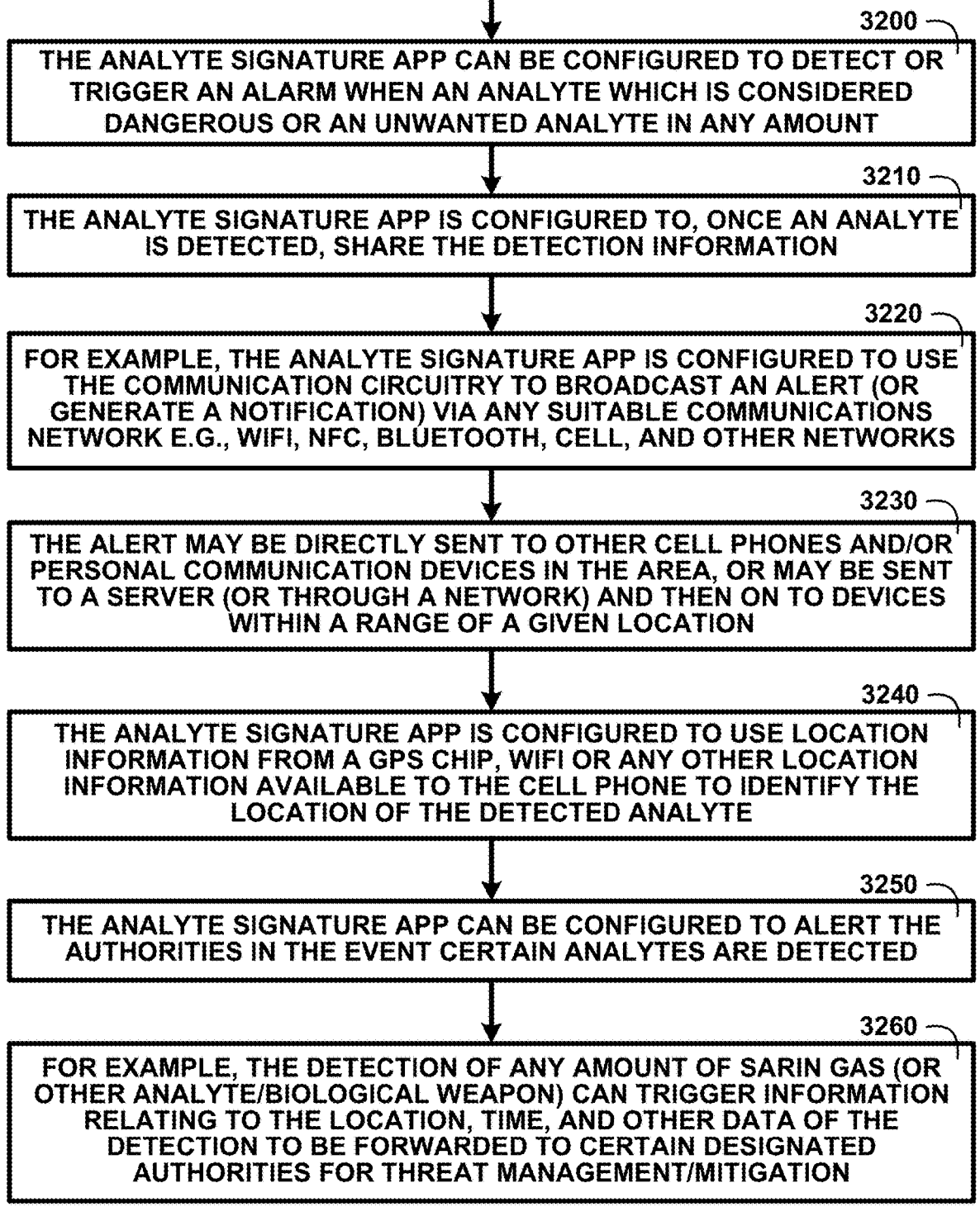
FIG. 32 shows a block diagram of an overview of a chemical signature app of one embodiment.

An Analyte Signature App:

FIG. 32 shows a block diagram of an overview of a analyte signature app of one embodiment. FIG. 32 shows a continuation from FIG. 31 shows the analyte signature app can be configured to detect or trigger an alarm when a analyte is considered dangerous or an unwanted analyte in any amount 3200. The analyte signature app is configured to, once a analyte is detected, share the detection information 3210, for example, the analyte signature app is configured to use the communication circuitry to broadcast an alert (or generate a notification) via any suitable communications network e.g., WIFI, NFC, Bluetooth, cell, and other networks 3220. The alert may be directly sent to other cell phones and/or personal communication devices in the area, or may be sent to a server (or through a network) and then on to devices within a range of a given location 3230.

The analyte signature app is configured to use location information from a GPS chip, WIFI, or any other location information available to the cell phone to identify the location of the detected analyte 3240. The analyte signature app can be configured to alert the authorities in the event certain analytes are detected 3250, for example, the detection of any amount of sarin gas (or other chemical/biological weapons) can trigger information relating to the location, time, and other data of the detection to be forwarded to certain designated authorities for threat management/mitigation 3260 of one embodiment.

Figure 33:
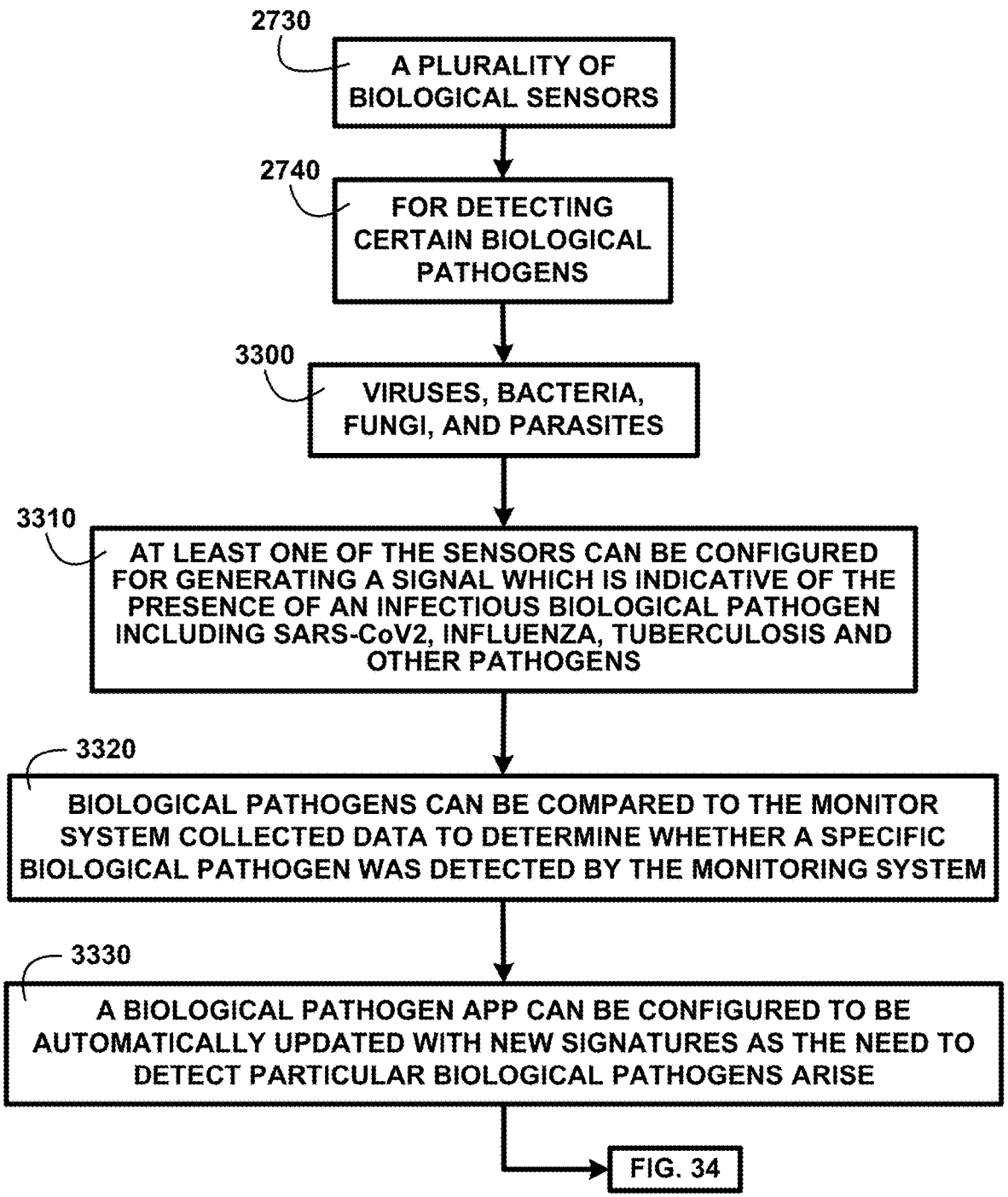
FIG. 33 shows a block diagram of an overview of a biological pathogen app of one embodiment.

A Biological Pathogen App:

FIG. 33 shows a block diagram of an overview of a biological pathogen app of one embodiment. FIG. 33 shows a plurality of biological sensors 2730 for detecting certain biological pathogens 2740 including viruses, bacteria, fungi, and parasites 3300. At least one of the sensors can be configured for generating a signal which is indicative of the presence of an infectious biological pathogen including SARS-CoV-2, influenza, tuberculosis, and other pathogens 3310. Biological pathogens can be compared to the monitor system collected data to determine whether a specific biological pathogen was detected by the monitoring system 3320. A biological pathogen app can be configured to be automatically updated with new signatures as the need to detect particular biological pathogens arise 3330. The description is continued in FIG. 34.

Communication Circuitry to Broadcast an Alert:

FIG. 34 shows a block diagram of an overview of communication circuitry to broadcast an alert of one embodiment. FIG. 34 shows a continuation from FIG. 33 the biological pathogen app can be configured to detect or trigger an alarm when a pathogen that is considered highly infectious is detected 3400. The biological pathogen app is configured to, once a highly infectious pathogen is detected, share the detection information 3410, for example, the biological pathogen app is configured to use the communication circuitry to broadcast an alert (or generate a notification) via any suitable communications network e.g., WIFI, NFC, Bluetooth, cell, and other networks 3420. The alert may be directly sent to other cell phones and/or personal communication devices in the area, or may be sent to a server (or through a network) and then on to devices within a range of a given location 3430 of one embodiment. The biological pathogen app is configured to use location information from a GPS chip, WIFI, or any other location information available to the cell phone to identify the location of the detected highly infectious pathogen 3440. The biological pathogen app can be configured to alert the authorities in the event certain highly infectious pathogens are detected 3450. For example, the detection of SARS-COV-2 can trigger information relating to the location, time, and other data of the detection to be forwarded to certain designated authorities for public health threat management/mitigation 3460.

Figure 35:
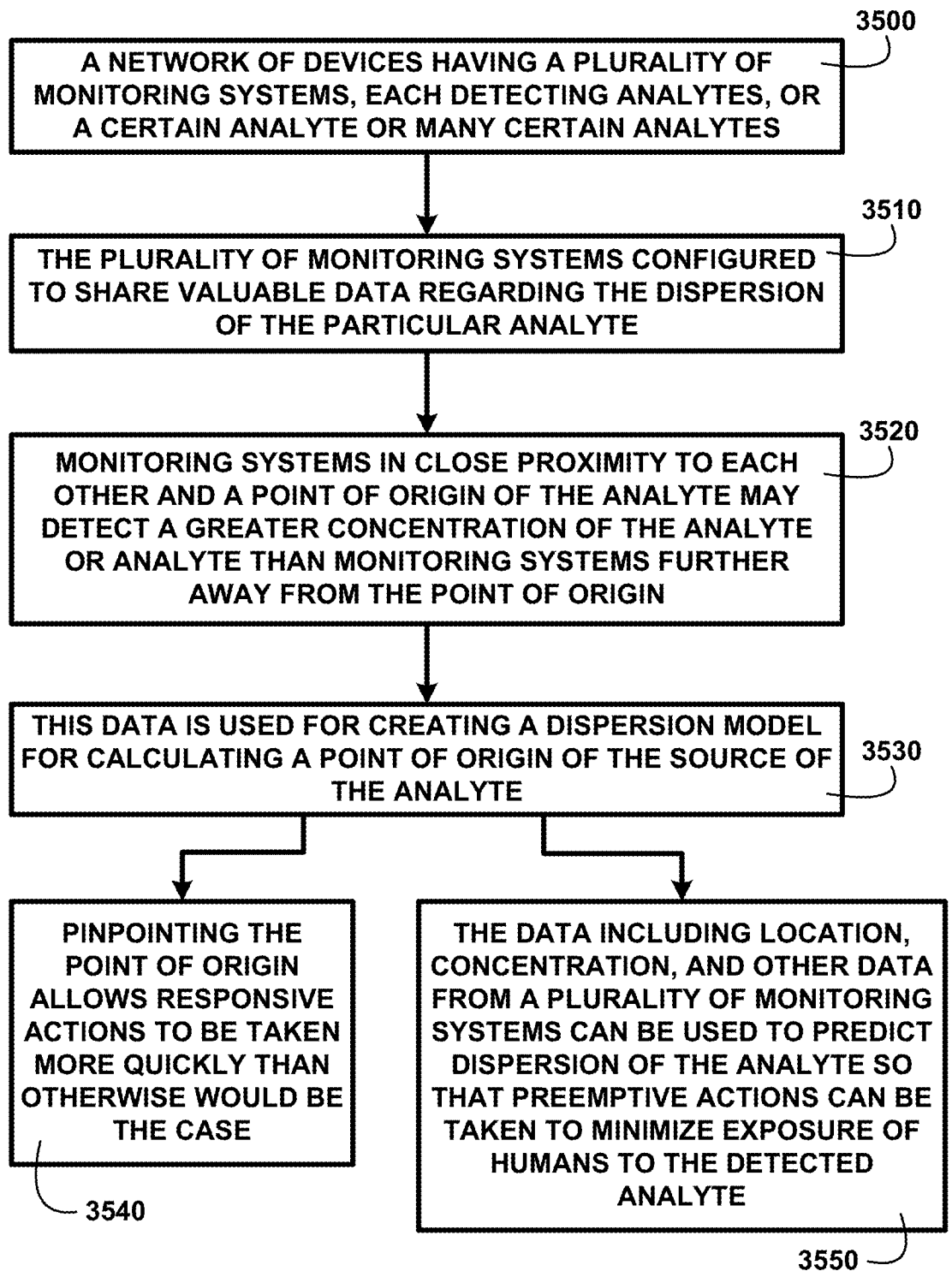
FIG. 35 shows for illustrative purposes only an example of a network of devices having a plurality of monitoring systems of one embodiment.

A Network of Devices Having a Plurality of Monitoring Systems:

FIG. 35 shows for illustrative purposes only an example of a network of devices having a plurality of monitoring systems of one embodiment. FIG. 35 shows a network of devices having a plurality of monitoring systems, each detecting analytes, or a certain analyte or many certain analytes 3500. The plurality of monitoring systems configured to share valuable data regarding the dispersion of the particular analyte 3510. Monitoring systems in close proximity to each other and a point of origin of the analyte may detect a greater concentration of the analyte than monitoring systems further away from the point of origin 3520. This data is used for creating a dispersion model for calculating the point of origin of the source of the analyte 3530. Pinpointing the point of origin allows responsive actions to be taken more quickly than otherwise would be the case 3540. The data including location, concentration, and other data from a plurality of monitoring systems can be used to predict the dispersion of the analyte so that preemptive actions can be taken to minimize exposure of humans to the detected analyte 3550 of one embodiment.

Figure 36:
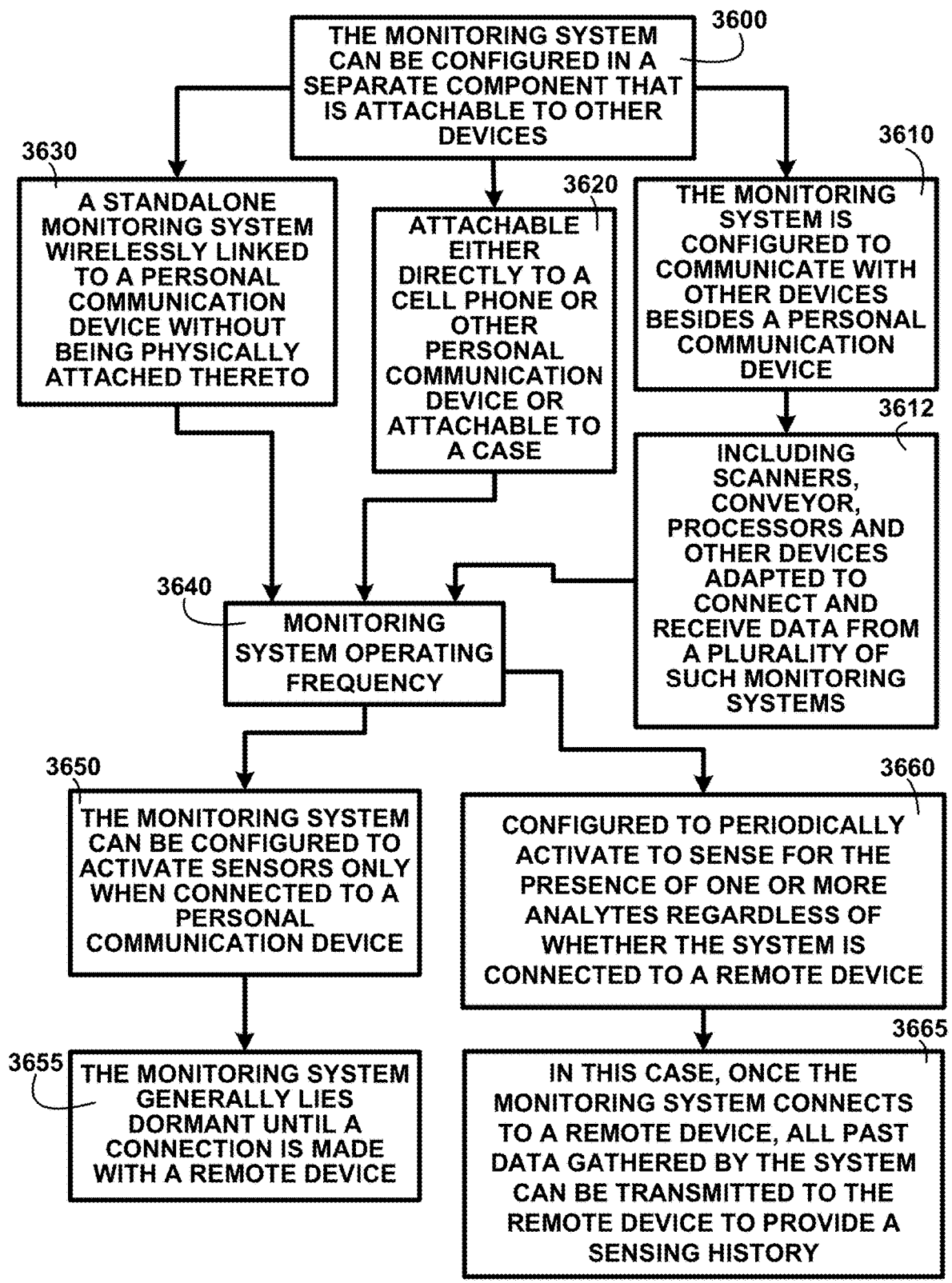
FIG. 36 shows a block diagram of an overview of the monitoring system configured in a separate component of one embodiment.

The Monitoring System is Configured in a Separate Component:

FIG. 36 shows a block diagram of an overview of the monitoring system configured in a separate component of one embodiment. FIG. 36 shows the monitoring system can be configured in a separate component that is attachable to other devices 3600. The monitoring system is configured to communicate with other devices besides a personal communication device 3610 including scanners, conveyors, processors and other devices adapted to connect and receive data from a plurality of such monitoring systems 3612. It should be appreciated that the other devices besides a personal communication device 3610 also includes smart equipment or infrastructure. Smart equipment refers to machinery, devices or systems that incorporate advanced technologies, connectivity and often artificial intelligence to enhance their functionality and capabilities. These technologies enable these devices to gather, analyze, and utilize data to improve performance, automate processes, and provide valuable insights. Smart equipment can be found in various industries and applications, including: smart home devices, industrial automation, healthcare, transportation, agriculture, energy management, consumer electronics, environmental monitoring, smart cities and research and laboratory equipment.

Smart infrastructure includes: transportation equipment, energy grids, water and waste water infrastructure, communication networks, buildings and urban spaces, safety and security, healthcare and education facilities, emergency management, data analytics and visualization. The monitoring system is attachable either directly to a cell phone or other personal communication device or attachable to a case 3620. A standalone monitoring system wirelessly linked to a personal communication device without being physically attached thereto 3630 can be used. The monitoring system operating frequency 3640 can be varied for a particular use. The monitoring system can be configured to activate sensors only when connected to a personal communication device 3650. In this operating frequency, the monitoring system generally lies dormant until a connection is made with a remote device 3655. The monitoring system operating frequency 3640 can be configured to periodically activate to sense the presence of one or more analytes regardless of whether the system is connected to a remote device 3660. In this case, once the monitoring system connects to a remote device, all past data gathered by the system can be transmitted to the remote device to provide a sensing history 3665 of one embodiment.

Figure 37:
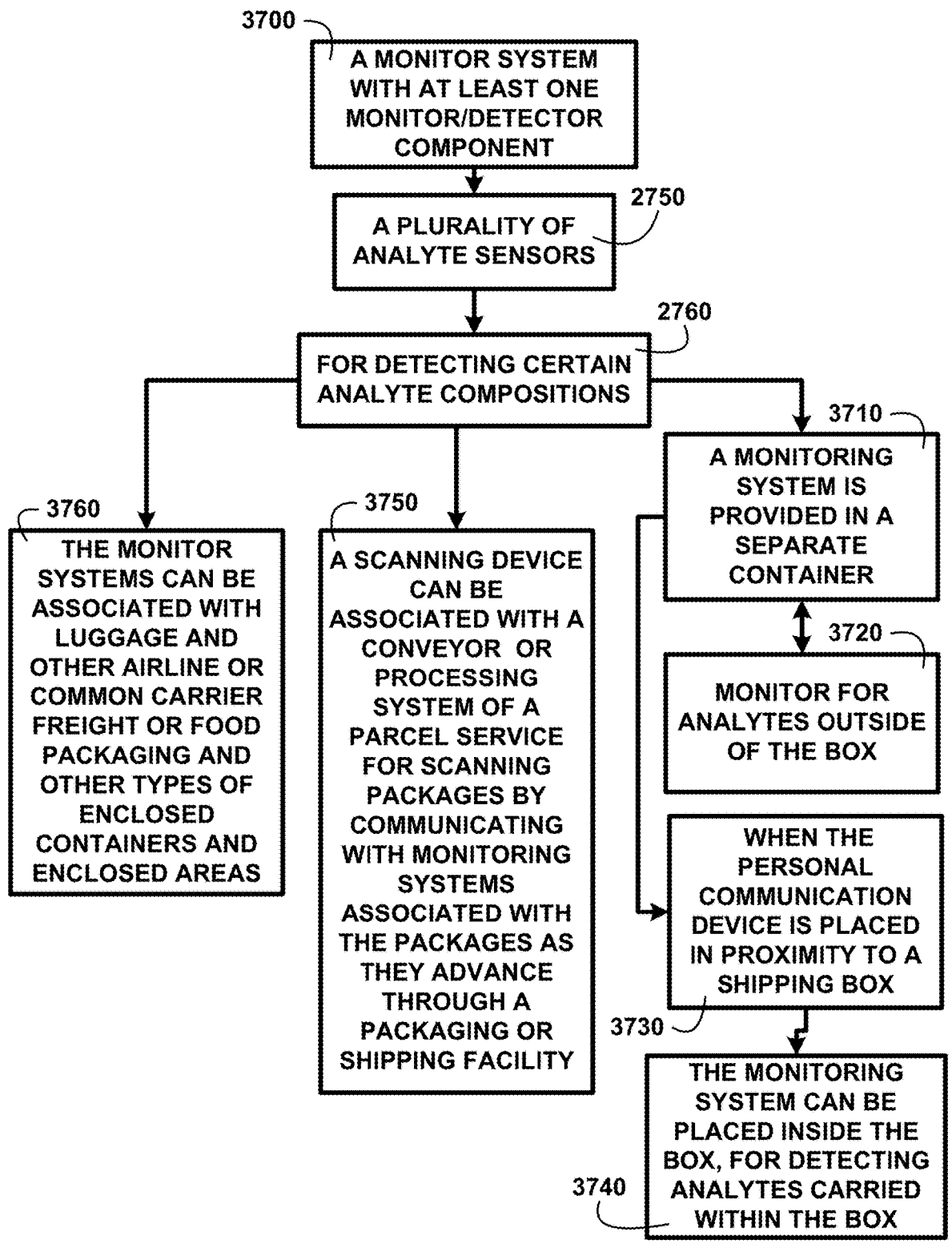
FIG. 37 shows a block diagram of an overview of a scanning device of one embodiment.

A Scanning Device:

FIG. 37 shows a block diagram of an overview of a scanning device of one embodiment. FIG. 37 shows a monitor system with at least one monitor/detector component 3700 and a plurality of analyte sensors 2750 for detecting certain analyte compositions 2760. A monitoring system is provided in a separate container 3710 to monitor for analytes outside of the box 3720. When the personal communication device is placed in proximity to a shipping box 3730 the monitoring system transmits the data to the personal communication device. The monitoring system can be placed inside the box, for detecting analytes carried within the box 3740. A scanning device can be associated with a conveyor or processing system of a parcel service for scanning packages by communicating with monitoring systems associated with the packages as they advance through a packaging or shipping facility 3750. The monitor systems can be associated with luggage and other airline or common carrier freight or food packaging and other types of enclosed containers and enclosed areas 3760 of one embodiment.

Figure 38:
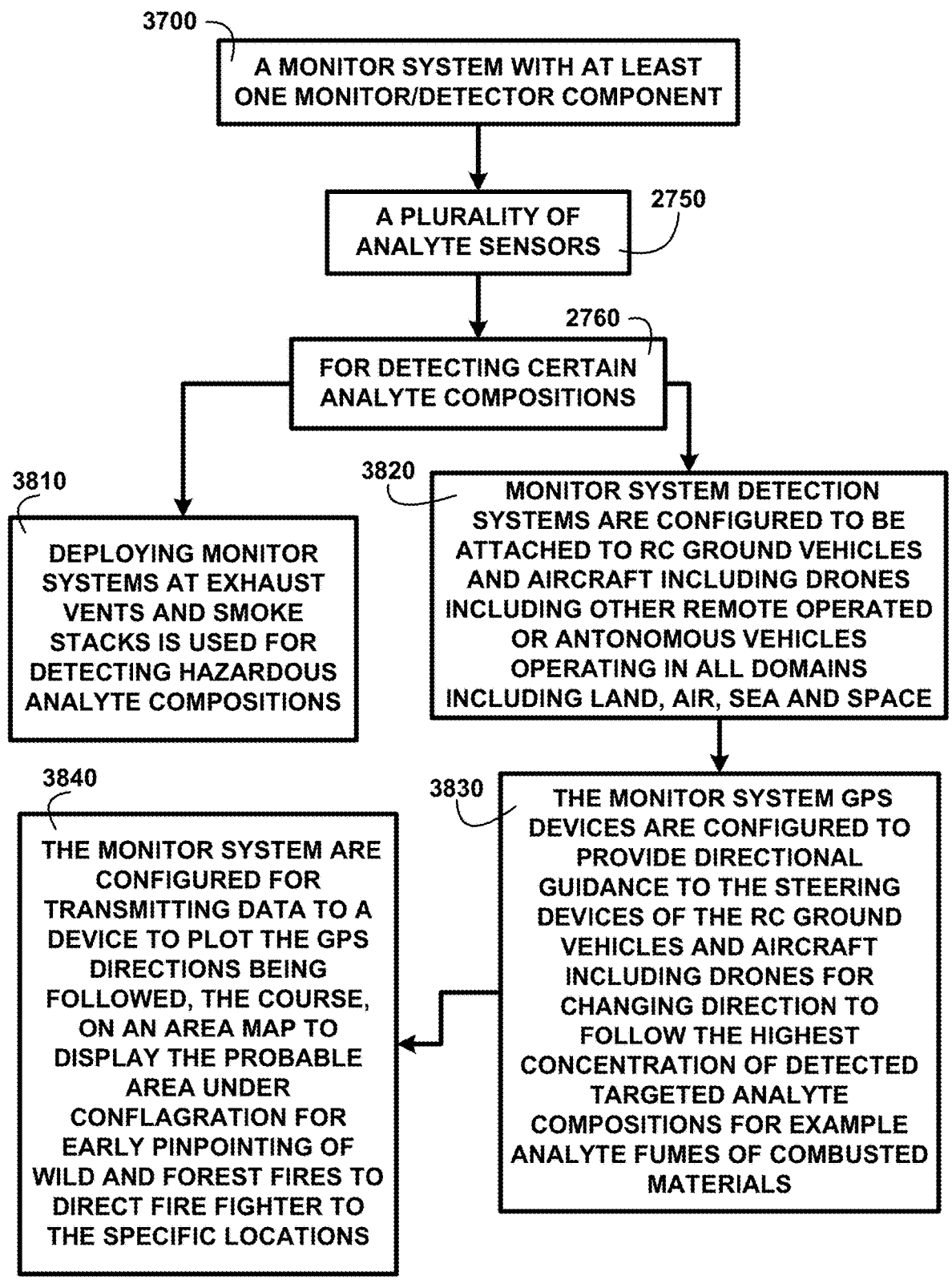
FIG. 38 shows a block diagram of an overview of RC ground vehicles and aircraft of one embodiment.

RC Ground Vehicles and Aircraft:

FIG. 38 shows a block diagram of an overview of RC ground vehicles and aircraft of one embodiment. FIG. 38 shows a monitor system with at least one monitor/detector component 3700 and a plurality of analyte sensors 2750 for detecting certain analyte compositions 2760. In one embodiment, deploying monitor systems at exhaust vents and smokestacks is used for detecting hazardous analyte compositions 3810. Monitor system detection systems are configured to be attached to RC ground vehicles and aircraft including drones including other remote-operated or autonomous vehicles operating in all domains including land, air, sea, and space 3820. The monitor system GPS devices are configured to provide directional guidance to the steering devices of the RC ground vehicles and aircraft including drones for changing direction to follow the highest concentration of detected targeted chemical compositions, for example, analyte fumes of combusted materials 3830. The monitor system is configured for transmitting data to a device to plot the GPS directions being followed, the course, on an area map to display the probable area under conflagration for early pinpointing of wild and forest fires to direct firefighters to the specific locations 3840 of one embodiment.

Figure 39:
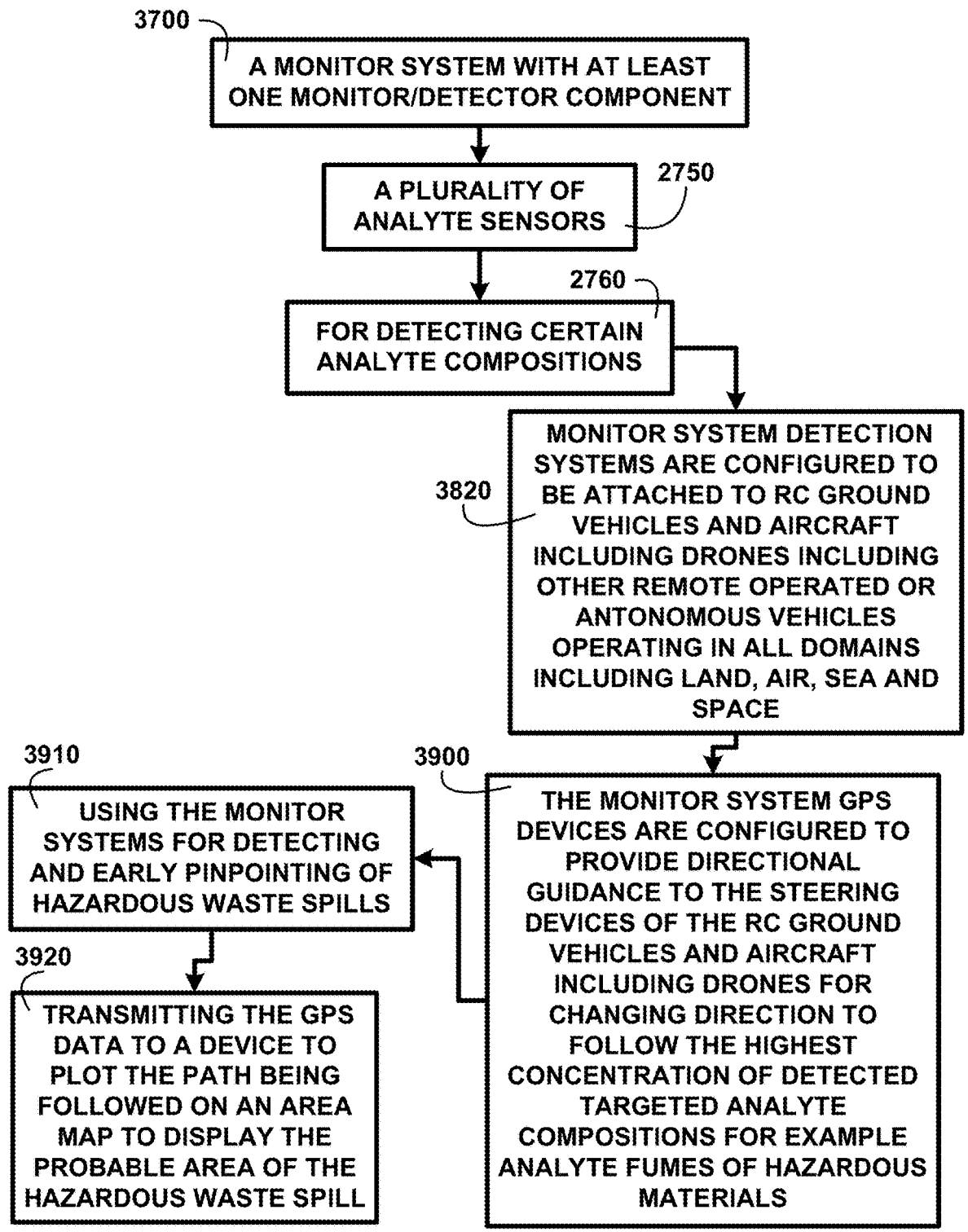
FIG. 39 shows a block diagram of an overview of directional guidance to the steering devices of one embodiment.

Directional Guidance to the Steering Devices:

FIG. 39 shows a block diagram of an overview of directional guidance to the steering devices of one embodiment. FIG. 39 shows a monitor system with at least one monitor/detector component 3700 with a plurality of analyte sensors 2750 for detecting certain analyte compositions 2760. Monitor system detection systems are configured to be attached to RC ground vehicles and aircraft including drones including other remote-operated or autonomous vehicles operating in all domains including land, air, sea, and space 3820. The monitor system GPS devices are configured to provide directional guidance to the steering devices of the RC ground vehicles and aircraft including drones for changing direction to follow the highest concentration of detected targeted analyte compositions, for example, analyte fumes of hazardous materials 3900. Using the monitor systems for detecting and early pinpointing hazardous waste spills 3910. The monitor systems are configured for transmitting the GPS data to a device to plot the path being followed on an area map to display the probable area of the hazardous waste spill 3920 of one embodiment.

Figure 40:
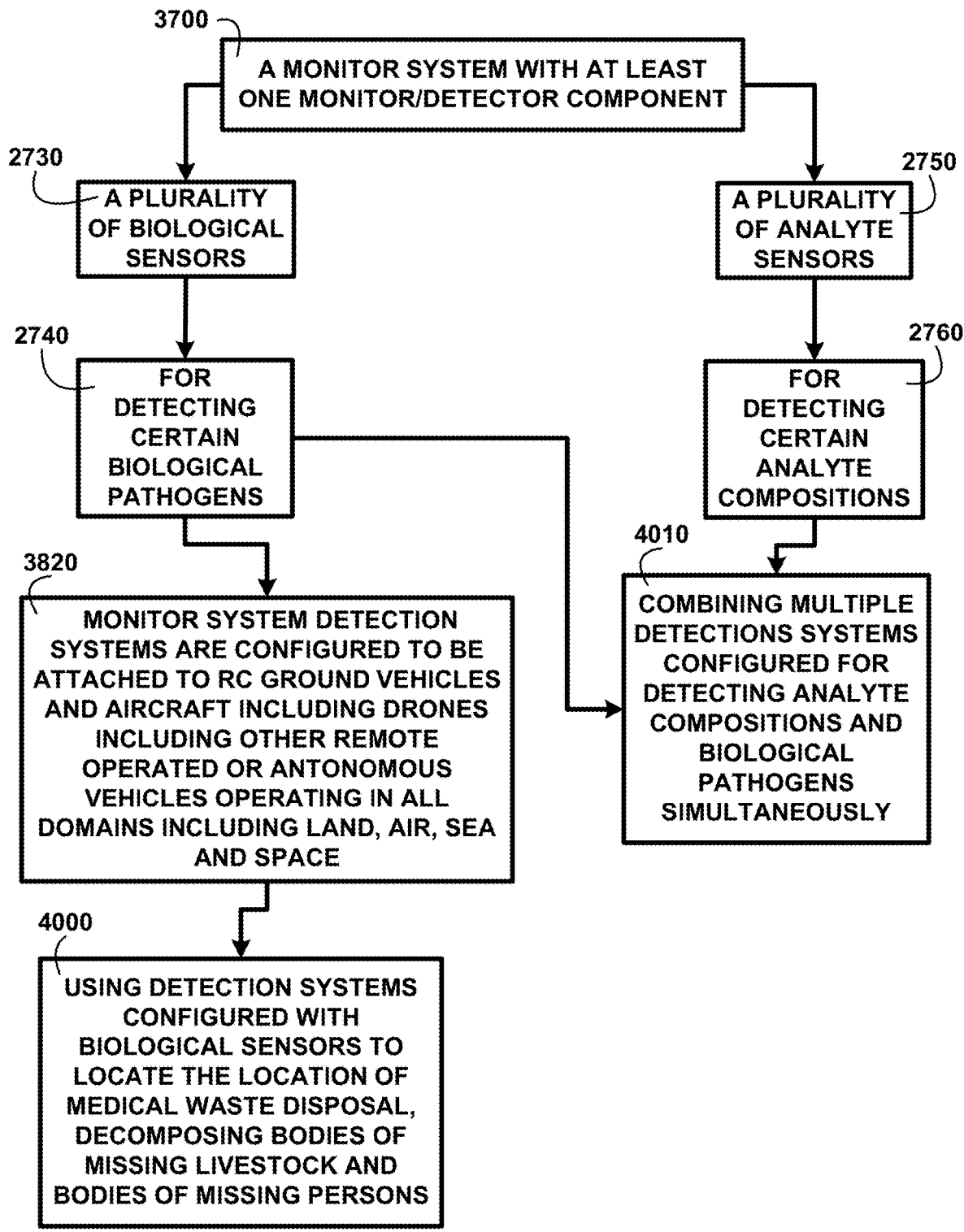
FIG. 40 shows a block diagram of an overview of the location of medical waste disposal of one embodiment.

Location of Medical Waste Disposal:

FIG. 40 shows a block diagram of an overview of the location of medical waste disposal of one embodiment. FIG. 40 shows a monitor system with at least one monitor/detector component 3700 with a plurality of analyte sensors 2750 for detecting certain analyte compositions 2760. In another embodiment, the monitor system is configured with a plurality of biological sensors 2730 for detecting certain biological pathogens 2740. Some applications are configured for combining multiple detection systems configured for detecting analyte compositions and biological pathogens simultaneously 4010. The plurality of biological sensors 4030 for detecting certain biological pathogens 4040 can be used with the monitor system detection systems are configured to be attached to RC ground vehicles and aircraft including drones including other remote operated or autonomous vehicles operating in all domains including land, air, sea, and space 3820. The application includes using detection systems configured with biological sensors to locate the location of medical waste disposal, decomposing bodies of missing livestock, and bodies of missing persons 4000 of one embodiment.

Monitor Systems are Placed in Air Handlers:

FIG. 41 shows a block diagram of an overview of monitor systems placed in air handlers of one embodiment. FIG. 41 shows a monitor system with at least one monitor/detector component 3700 with a plurality of biological sensors 2730 for detecting certain biological pathogens 2740. A plurality of nanosensors 4140 for analytic detection 4142. A plurality of analyte sensors 2750 for analytic detection 4142. Monitor systems are placed in air handlers to detect pathogens in the air 4100. Monitor systems are configured to activate disinfectant dispersing devices when pathogens are detected in the air 4110. Monitor systems GPS chips record the GPS coordinates in a memory device of the detection reader 4120. The monitor systems are configured to transmit detection location GPS coordinates to a sensing platform smartphone app 4130 of one embodiment.

Figure 42A:
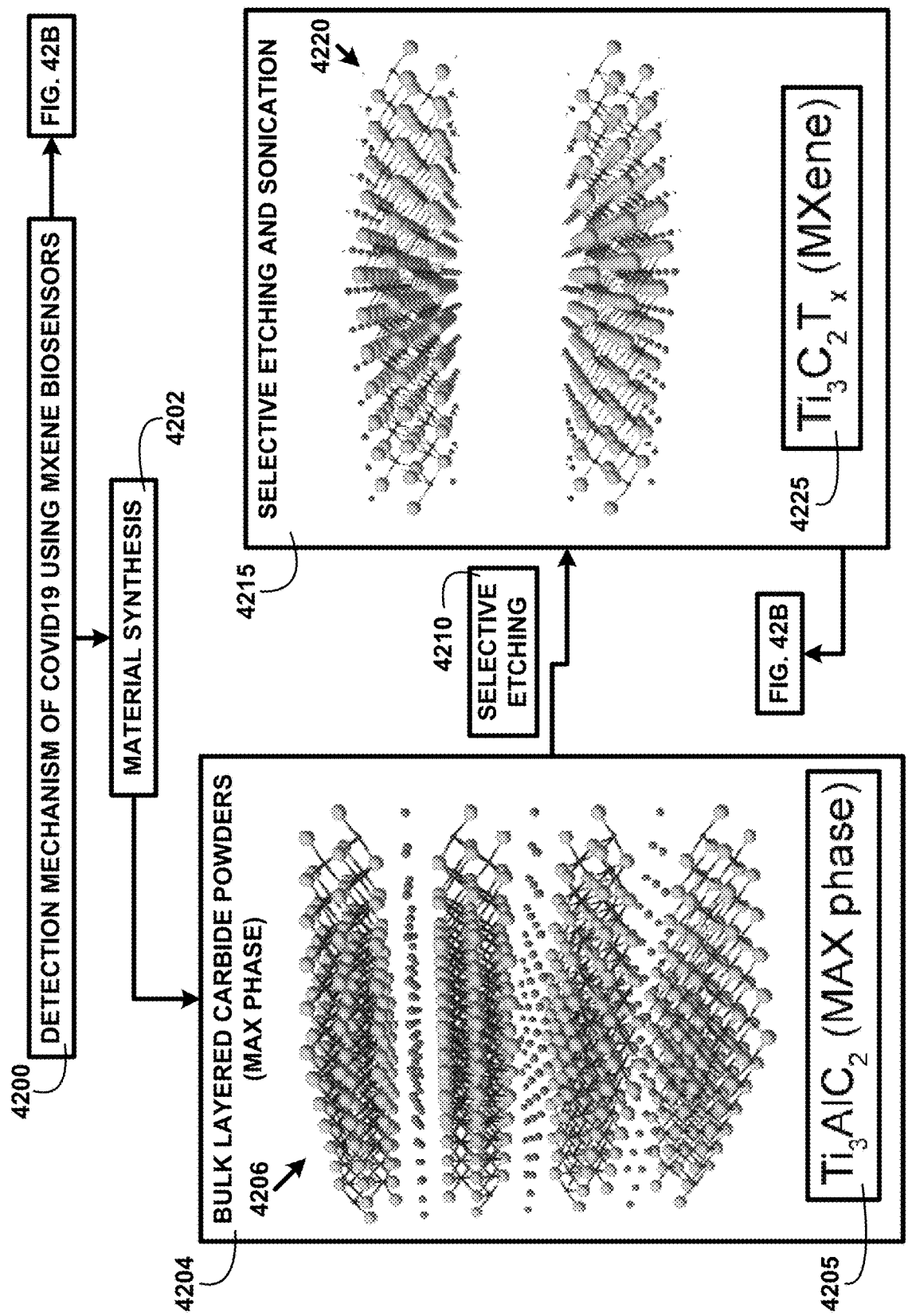
FIG. 42A shows for illustrative purposes only an example of a detection mechanism of COVID-19 using MXene biosensors of one embodiment.

The Detection Mechanism of COVID-19 Using MXene Biosensors:

FIG. 42A shows for illustrative purposes only an example of a detection mechanism of COVID-19 using MXene biosensors of one embodiment. FIG. 42A shows a detection mechanism of COVID-19 using MXene biosensors 4200 with a process for material synthesis 4202 of MXene. Providing bulk layered carbide powders (MAX phase) 4204 as shown with carbide powders molecules 4206 in a Ti3AlC2 (MAX phase) 4205. The process uses selective etching 4210 to transform the bulk layered carbide powders (MAX phase) 4204. A selective etching and sonication 4215 process results in MXene molecules 4220 Ti3C2Tx (MXene) 4225. MXene is one of many Van Der Waal (VDW) materials. In the exemplary embodiment, other VDW materials can be used as a substitute for MXene. The description continues in FIG. 42B of one embodiment.

Figure 42B:
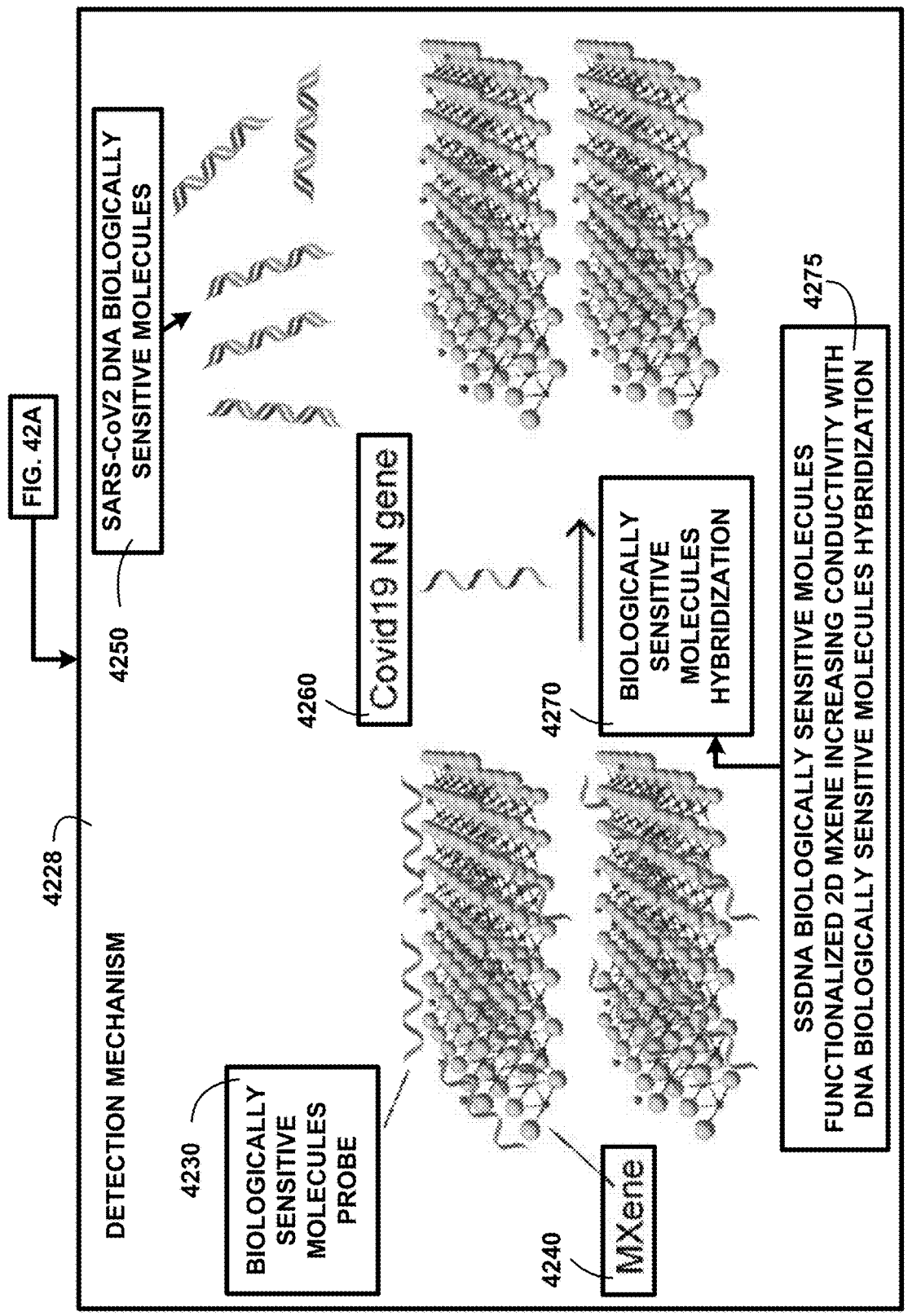
FIG. 42B shows for illustrative purposes only an example of biologically sensitive molecules hybridization and Van Der Waal (VDW) forces of one embodiment.

Biologically Sensitive Molecules Hybridization:

FIG. 42B shows for illustrative purposes only an example of biologically sensitive molecules hybridization and Van Der Waal (VDW) forces of one embodiment. Hybridization is the process of mixing two atomic orbitals to form a new type of hybrid orbital. Van Der Waal forces are relatively weak forces that attract neutral molecules to one another. Examples of hybridized orbitals include sp Hybridization, sp2 Hybridization, sp3 Hybridization, sp3d Hybridization, and sp3d2 Hybridization. Examples of VDW forces include hydrogen bonding, dispersion forces (London Dispersion Forces) and dipole-dipole interactions. Hybridization and VDW forces enable binding biopolymers to conductive nanosensors and combining two complementary single-stranded DNA and/or RNA molecules and allowing them to form a single double-stranded molecule through base pairing. It should be appreciated that other embodiments will include other forms of complementary base-pairing and binding of nucleic acids. FIG. 42B shows a continuation from 42A with a detection mechanism 4228 utilizing a plurality of biologically sensitive molecules probe 4230 and MXene 4240. The plurality in this example of biologically sensitive molecules probes 4230 are SARS-CoV-2 DNA biologically sensitive molecules 4250. The SARS-CoV-2 DNA biologically sensitive molecules 4250 layered onto the MXene 4240 molecules stabilized inductively forming a weak bond and alternatively with other Van der Waal materials. A plurality of COVID-19 N genes 4260 from the SARS-CoV-2 biologically sensitive molecules 4250 undergoes biologically sensitive molecules hybridization 4270. The DNA biologically sensitive molecules hybridization 4270 creates ssDNA biologically sensitive molecules functionalized 2D MXene increasing conductivity with DNA biologically sensitive molecules hybridization 4275. The hybridization process is orienting the biologically sensitive molecules on the surface of the conductive layer consisting of one from a group of graphene, other allotropes of carbon, MXene, and other VDW materials, to ensure that the stronger bond between the biologically sensitive molecules and the target genetic material (RNA of SARS-Cov-2) overpowers the weaker electrostatic bond between the surface of the conductive layer and the biologically sensitive molecules of one embodiment.

It is contemplated that the biologically sensitive molecule hybridization method presented in FIG. 42B applies to wall types of existing and future van der Waal materials. The term van der Waals material refers to a specific class of materials that exhibit significant van der Waals forces and interactions between their constituent atoms or molecules. These materials are often characterized by having weak intermolecular forces and can be layered structures held together by van der Waals forces, resulting in unique properties and behaviors. A well-known example of a van der Waals material is graphene, which is a single layer of carbon atoms arranged in a hexagonal lattice. Graphene's remarkable properties, such as its high electrical conductivity and mechanical strength, are attributed to its unique two-dimensional structure and the strong covalent bonds within each layer, along with the relatively weak van der Waals forces between the layers. Other examples of van der Waals materials include: Transition Metal Dichalcogenides (TMDs), which are materials like molybdenum disulfide (MoS2) and tungsten diselenide (WSe2) are layered compounds with weak van der Waals forces between the layers. Layered Insulators, which are certain insulating materials like hexagonal boron nitride (hBN) that are made up of layers held together by van der Waals forces.

Organic Crystals, which include many organic compounds, such as certain polymers and organic molecules, can form layered structures with weak intermolecular interactions. These materials often have flexible and tunable properties. Metal-Organic Frameworks (MOFs) are made up of metal ions or clusters linked by organic ligands, forming porous structures with weak van der Waals forces between the layers. It should be appreciated that hybridization is a concept commonly associated with the formation of hybrid orbitals in chemistry, specifically in the context of atomic orbitals to create molecular orbitals in any type of molecule. This process is relevant to the arrangement of electrons around atoms to form covalent bonds. Hybridization primarily occurs with atoms in all types of molecules such as organic compounds, inorganic compounds and other chemical species.

Figure 43A:
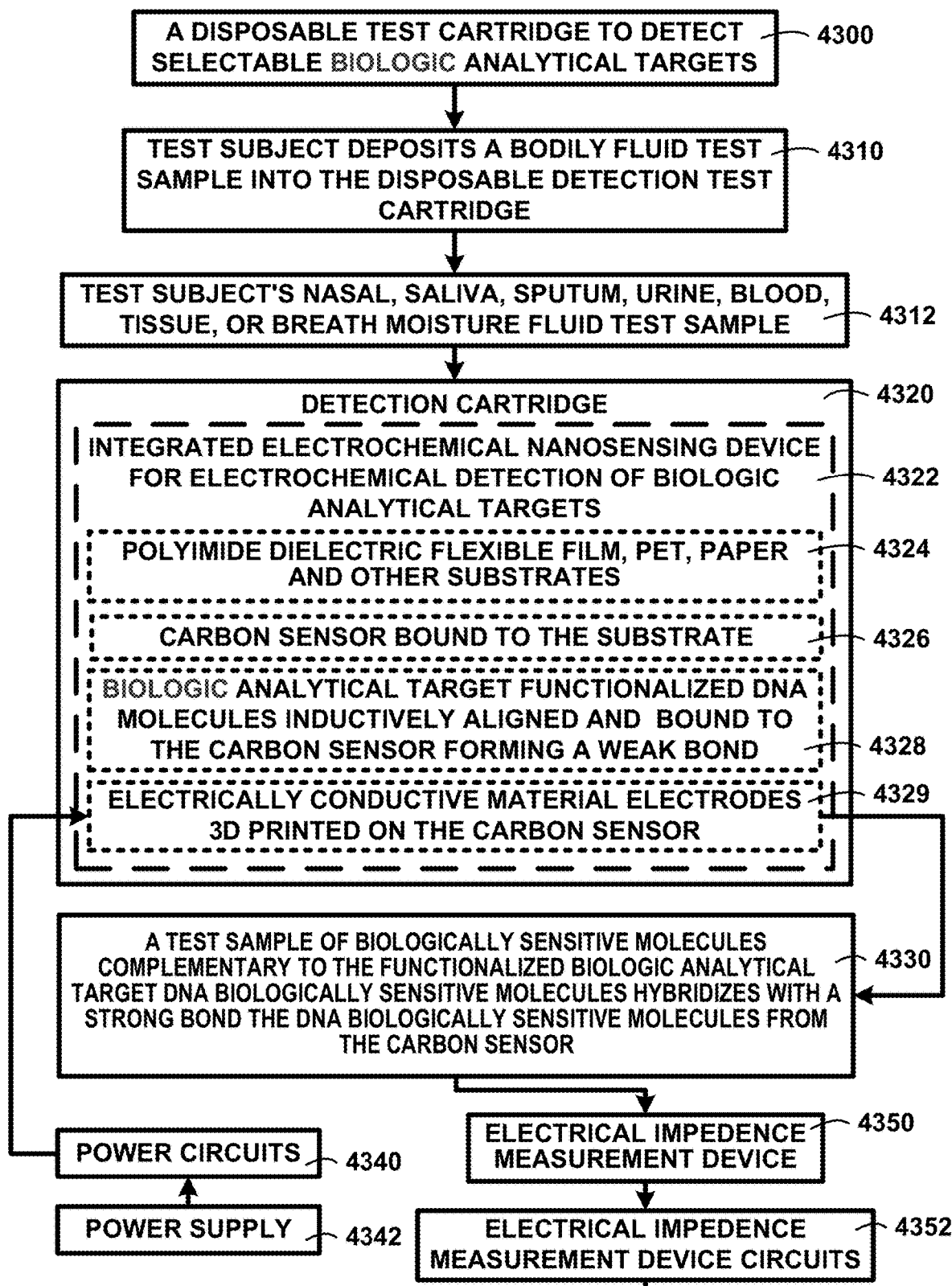
FIG. 43A shows a block diagram of an overview of a disposable detection cartridge of one embodiment.

A Disposable Detection Cartridge:

FIG. 43A shows a block diagram of an overview of a disposable detection cartridge of one embodiment. FIG. 43A shows a disposable detection cartridge to detect selectable biologic analytical targets 4300. A test subject deposits a bodily fluid test sample into the disposable detection test cartridge 4310. The bodily fluid test sample may consist of a test subject's bodily fluid test sample including the test subject's nasal, saliva, sputum, urine, blood, tissue or breath moisture fluid test sample 4312. The bodily fluid test sample is deposited into the detection cartridge 4320. The bodily fluid test sample comes in contact with an integrated electronic nanosensing device for electronic detection of biologic analytical targets 4322.

The integrated electrochemical nanosensing device for electrochemical detection of biologic analytical targets 4322 comprises a polyimide dielectric flexible film, pet, paper and other substrates 4324 with a carbon sensor bound to the substrate 4326. In other embodiments, the substrate comprises thermoplastic polymers, paper or other substrates known in the art of printed electronics. The carbon sensor includes biologic analytical target functionalized DNA biologically sensitive molecules aligned and bound to the carbon sensor forming a weak bond 4328. Electrically conductive material electrodes printed on the carbon sensor 4329.

A test sample of biologically sensitive molecules complementary to the functionalized biologic analytical target DNA biologically sensitive molecules hybridizes with a strong bond the DNA biologically sensitive molecules from the carbon sensor 4330. A power supply 4342 energizes through power circuits 4340 the electrically conductive material electrodes printed on the carbon sensor 4329.

A test sample biologically sensitive molecules complementary to the functionalized biologic analytical target DNA biologically sensitive molecules with a strong bond hybridizes the DNA biologically sensitive molecules from the carbon sensor 4330. The electrical power in two phases arcs across two electrodes to complete the circuit. An electrical impedance measurement device 4350 measures the electrical current in milliamp (mA) or microamp (μA) or nanoamp (nA) and resistance in ohms, milliohms or kiloohms across the electrical impedance measurement device circuits 4352. A temperature measurement device for measuring the temperature of the test sample. A saline or fluid detector for measuring the salt concentration of the test sample. An electrical field and ionic strength measuring device for measuring the electrical field and ionic strength of the test sample. The electrical field, ionic strength, temperature, and salt concentration of the bodily fluid test sample affect the speed of sensing performance. RNase P, the central enzyme of gene expression, which transcribes DNA to RNA is also measured. These factors are measured and recorded on a memory device in the detection cartridge 1110 of FIG. 11A. A digital processor installed in the portable detection cartridge reader 1100 of FIG. 11A reads these factors received from detection cartridge 1110 of FIG. 11A after inserting the detection cartridge 1110 of FIG. 11A into the portable detection cartridge reader 1100 of FIG. 11A. The portable detection cartridge reader 1100 of FIG. 11A digital processor calculates the anticipated optimal sensing performance time and adjusts the time of the operation of the electrical power and current level to complete the electrical current and impedance measurement processing. The description continues in FIG. 43B of one embodiment.

Figure 43B:
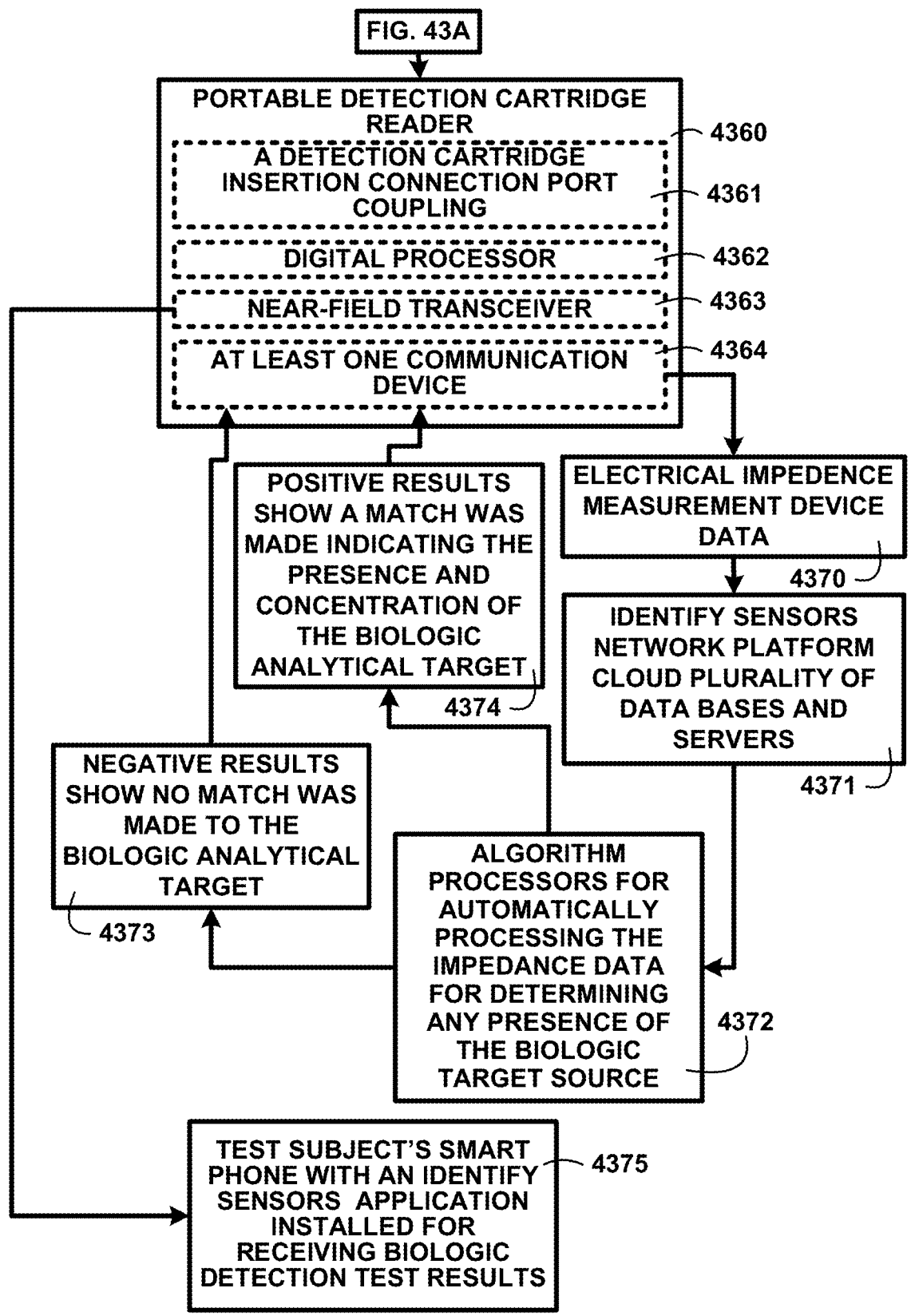
FIG. 43B shows a block diagram of an overview of a portable detection cartridge reader of one embodiment.

A Portable Detection Cartridge Reader:

FIG. 43B shows a block diagram of an overview of a portable detection cartridge reader of one embodiment. FIG. 43B shows a continuation from FIG. 43A with a portable detection cartridge reader 4360. The portable detection cartridge reader 4360 comprises a detection cartridge insertion coupling 4361 connection port with circuits for transferring data from the disposable detection cartridge to detect selectable biologic analytical targets 4300 of FIG. 43A. The portable detection cartridge reader 4360 further comprises a digital processor 4362 for formatting the disposable detection cartridge transferred data automatically. Formatting the disposable detection cartridge transferred data includes adding the portable detection cartridge reader 4360 unique identifying number, the disposable detection cartridge identifying number showing the biologic analytical target identification code, the testing GPS location, date and time, base impedance measured without the test sample, and the impedance data with the test sample in contact with the sensor.

The portable detection cartridge reader 4360 further comprises a near-field transceiver 4363 for communicating with a test subject digital device automatically. At least one communication device 4364 is provided for transmitting electrical current/impedance measurement device data 4370 automatically. After formatting the data is transmitted to identify sensors network platform cloud plurality of databases and servers 4371 automatically. The data is stored on a plurality of databases automatically. The stored data is automatically transmitted to algorithm processors for automatically processing the current/impedance data for determining any presence of the biologic target source 4372. Negative results show no match was made to the biologic analytical target 4373. Positive results show a match was made indicating the presence and concentration of the biologic analytical target 4374.

The test results are transmitted to the portable detection cartridge reader 4360 and displayed automatically within minutes. The near-field transceiver 4363 automatically determines if the test subject's digital device is in close proximity to receive the test results, if so then the results are transmitted to the test subject's digital device. Should the test subject's digital device be out of range for a near-field transmission then at least one communication device 4364 automatically transmits a cellular signal to the test subject's digital device for displaying the test results on the test subject's digital device. The test subject's digital device may for example be a test subject's smartphone with an identify sensors application installed for receiving biologic detection test results 4375 of one embodiment.

Figure 43C:
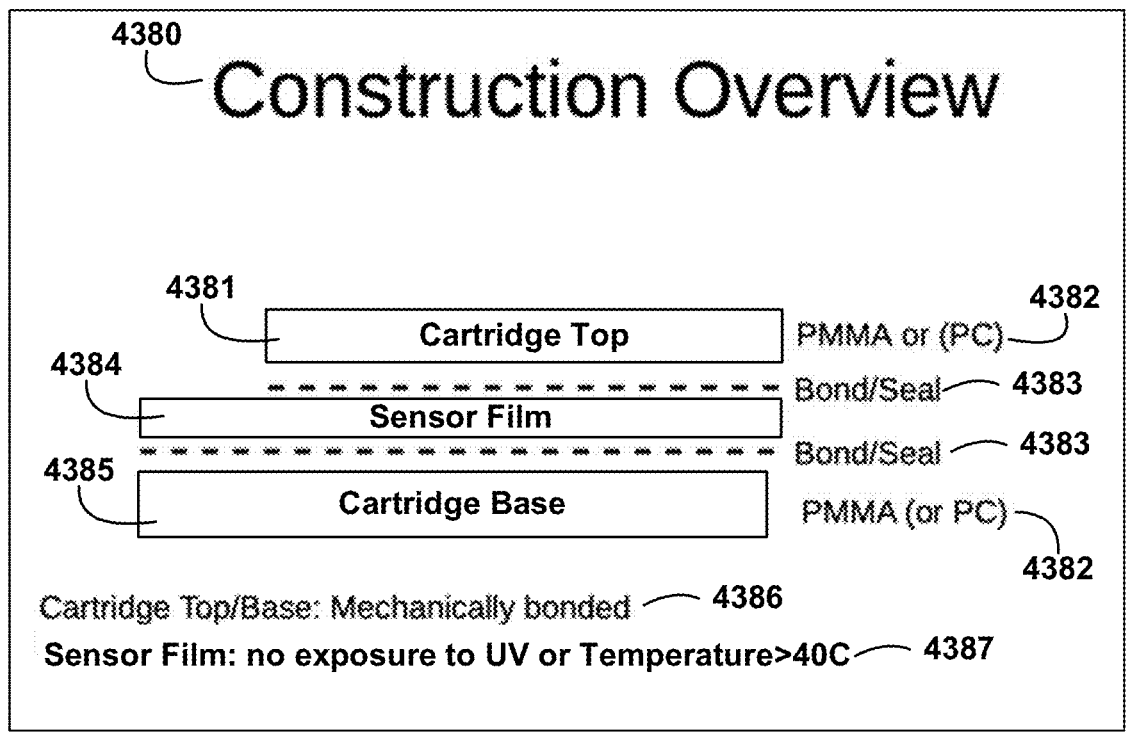
FIG. 43C shows for illustrative purposes only an example of a construction overview of one embodiment.

A Portable Detection Cartridge:

FIG. 43C shows for illustrative purposes only an example of a construction overview of one embodiment. FIG. 43C shows a construction overview 4380 of the portable detection cartridge. The construction overview 4380 shows a cartridge top 4381 made of PMMA or (PC) 4382. A mechanical bond/seal 4383 couples the cartridge top 4381 to the sensor film 4384. A mechanical bond/seal 4383 couples the sensor film 4384 to a cartridge base 4385 made of PMMA or (PC) 4382. A cartridge top/base: mechanically bonded 4386 enclosing the sensor film: no exposure to UV or temperature >40 C 4387 of one embodiment.

Figure 43D:
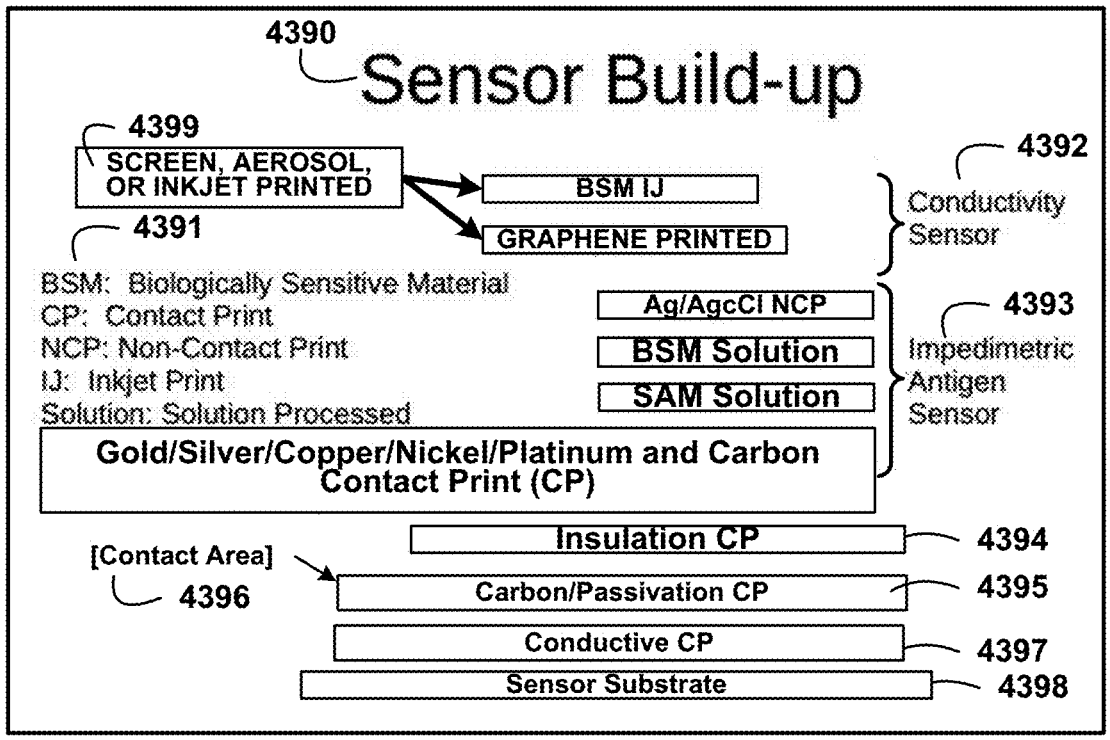
FIG. 43D shows for illustrative purposes only an example of a sensor build-up of one embodiment.

Sensor Build-Up:

FIG. 43D shows for illustrative purposes only an example of a sensor build-up of one embodiment. FIG. 43D shows a sensor build-up for two different types of sensors. The first is the "Conductivity Sensors" and the second sensor is the "Antigen Sensor". The antigen sensor will be used for applications involving detecting proteins, antigens, and antibodies in the liquid phase or gas phase (e.g. in breath or HVAC systems). FIG. 43D shows a sensor build-up 4390 for the two different types of sensors. The following are definitions 4391 used in this figure and include BSM: Biologically Sensitive Material; CP: Contact Print; NCP: Non-Contact Print; IJ: Inkjet Print; and Solution: Solution-Processed. A Conductivity Sensor 4392 includes a BSM IJ and graphene IJ. It should be appreciated that the BSM and graphene layers can also be screen printed or aerosol printed or inkjet printed or gravure printed 4399. An Impedimetric Antigen Sensor 4393 includes an Ag/AgCl NCP, BSM Solution, SAM Solution, and Gold/Silver/Copper/Nickel/Platinum/Carbon contact print (CP). It is contemplated that the sensor made of other conductive material. The two different types of sensors include an Insulation CP 4394, Carbon/Passivation CP 4395 [Contact Area] 4396, Conductive CP 4397, and Sensor Substrate 4398 of one embodiment.

Figure 44:
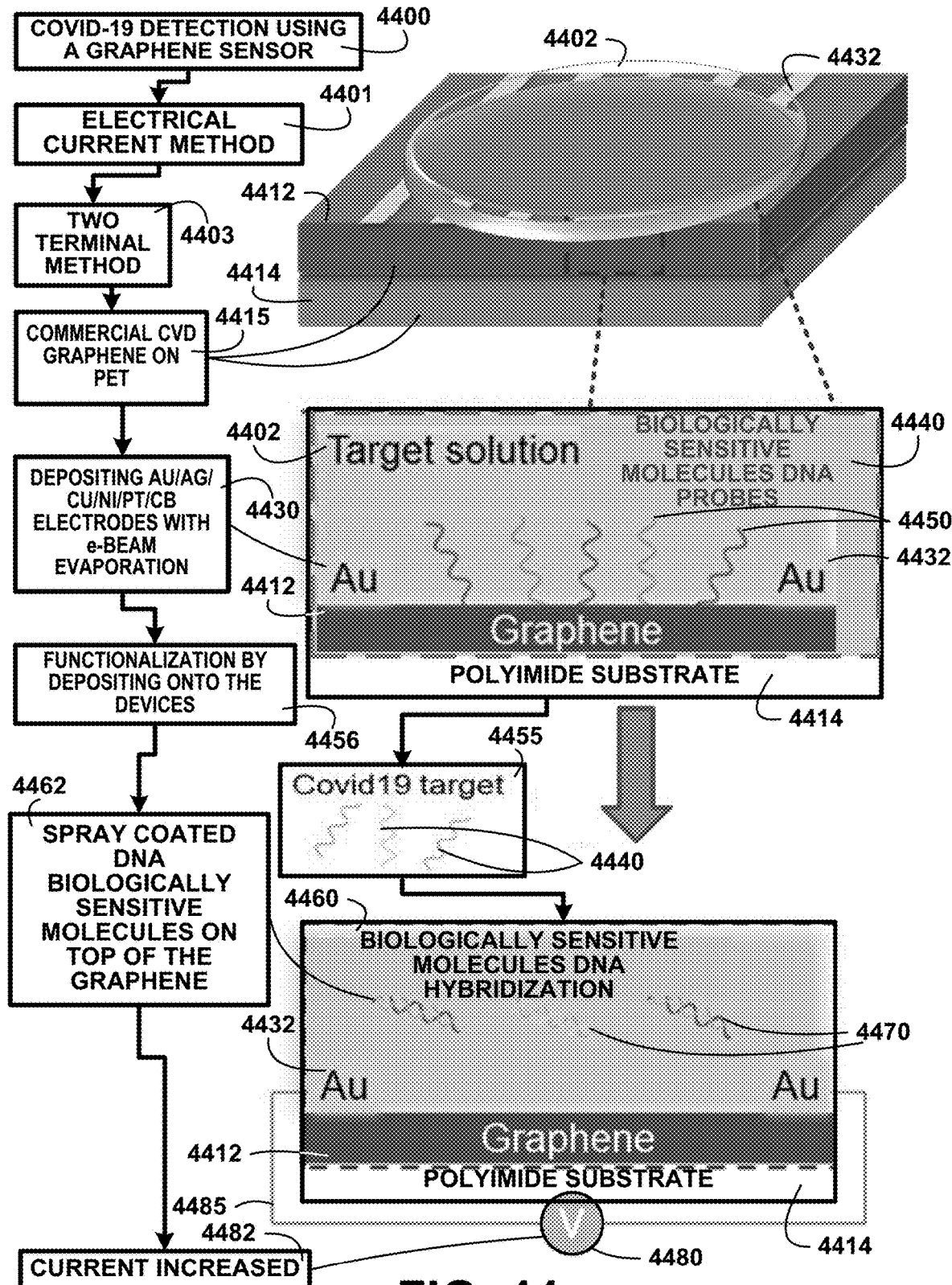
FIG. 44 shows for illustrative purposes only an example of an electrical current method of one embodiment.

An Electrical Current Method:

FIG. 44 shows for illustrative purposes only an example of an electrical current method of one embodiment. FIG. 44 shows a COVID-19 detection using a graphene sensor 4400 for an electrical current method 4401 of detecting selectable biologic analytical targets. A target solution 4402 is deposited on a plurality of an AU/AG/CU/NI/PT/CB electrode 4432 precision printed on a graphene 4412 material bonded to a substrate made of polyimide or other polymers 4414. The electrical current method 4401 uses a two-terminal method 4403.

The sensor structure can be of embodiments including a commercial CVD graphene on PET 4415 or print graphene ink on a polyimide substrate and upon the graphene 4412 depositing AU/AG/CU/NI/PT/CB electrodes with e-beam evaporation 4430. The chemical symbols used herein are AU for gold, AG for silver, CU for copper and NI for nickel, PT for platinum and CB for Carbon. On the surface of the graphene 4412 bonded to the polyimide substrate 4414 and between each AU/AG/CU/NI/PT/CB electrode 4432, biologically sensitive molecules DNA probes 4440 showing biologically sensitive molecules 4450 are polarized and bonded to the graphene 4412.

In this example, the biologically sensitive molecules DNA probes 4440 are COVID-19 target 4455 biologically sensitive molecules DNA probes for detecting the selectable biologic analytical target COVID-19 also referred to herein as SARS-CoV-2. Graphene sensors are processed for functionalization by depositing onto the devices 4456 in a biologically sensitive molecule DNA probes 4440 solution. IDE electrodes can be functionalized by drop cast, dip coat, spray coat, and other deposition or transfer means. The biologically sensitive molecules DNA probes 4440 solutions may include spray-coated DNA biologically sensitive molecules on top of the graphene 4462 for DNA biologically sensitive molecules DNA hybridization 4460. COVID-19 target RNA biologically sensitive molecules 4470 may be present in a test subject's bodily fluid sample target solution 4402.

A power supply 4480 energizes each AU/AG/CU/NI/PT/CB electrode 4432 through power supply circuits 4485. The power supply 4480 current increased 4482 sufficiently to complete a circuit between the pairs of the AU/AG/CU/NI/PT/CB electrode 4432 in the two-terminal methods 4403. Each selectable biologic analytical target produces different impedance results when power is applied. Proprietary experimentation has determined these unique impedance characteristics. No amplification or changes to the raw material (DNA biologically sensitive molecules probes and target RNA biologically sensitive molecules) are made to obtain a pure unadulterated impedance measurement of one embodiment.

Figure 45B:
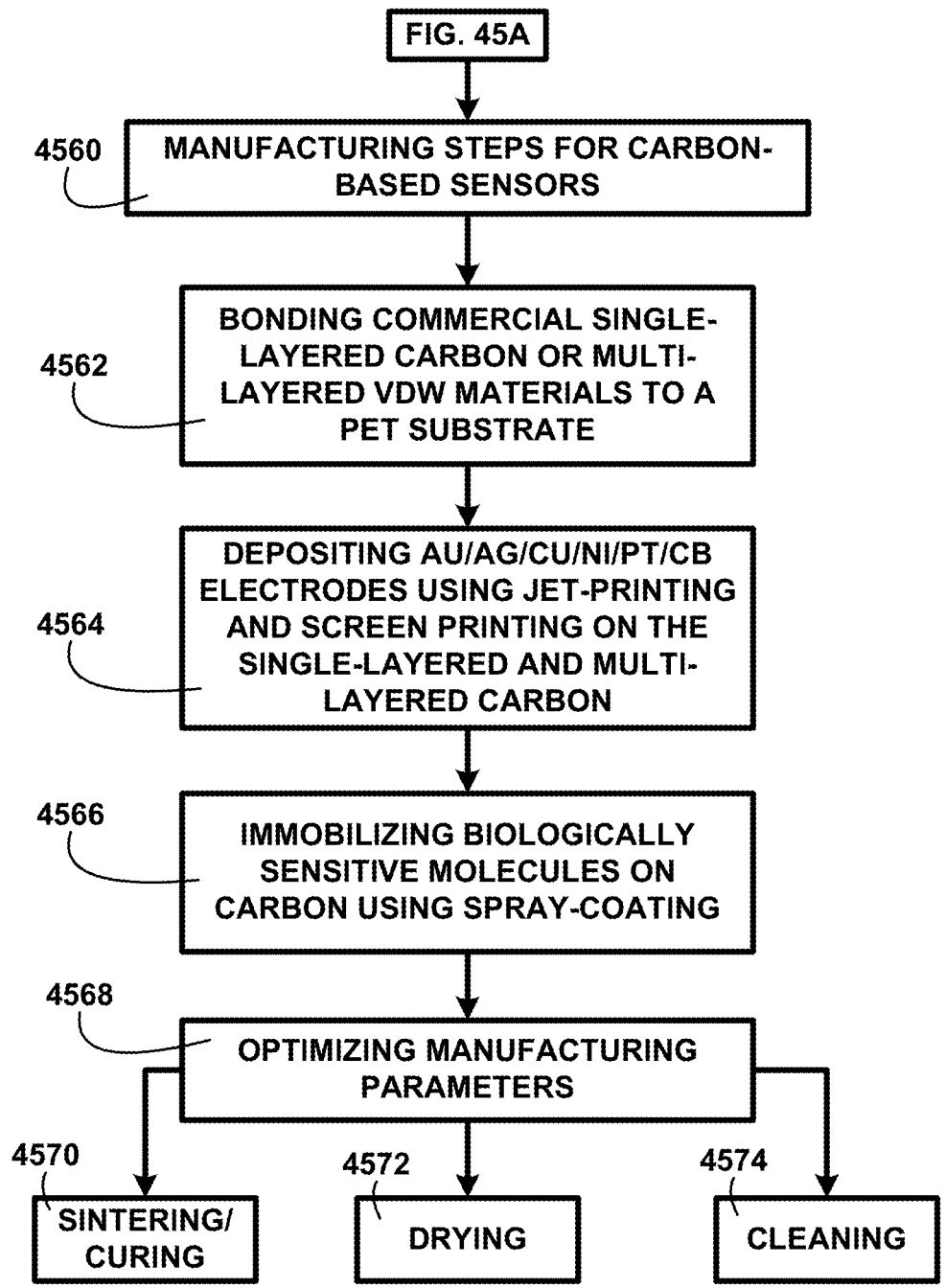
FIG. 45B shows a block diagram of an overview flow chart of manufacturing steps for carbon/VDW-based sensors of one embodiment.

Working Mechanism for Carbon and Van Der Waal (VDW) Material Sensors:

FIG. 45A shows a block diagram of an overview of the working mechanism for carbon sensors of one embodiment. FIG. 45A shows a working mechanism for carbon or VDW sensors 4500. The sensor may provide a 1 D or 2D material one from a group of MXene, graphene, and other carbon and VDW materials with similar characteristics. The 1 D or 2D material element has a large surface to volume ratio 4501. The surface functionalization 4502 with DNA biologically sensitive molecules of a selectable biologic analytical target allows selective detection 4503 of biological organisms for example SARS-CoV-2 virus, influenza virus, swine flu, MSRA, Legionnaires, and many others. Improving reproducibility of carbon/VDW sensors 4508 includes a microgravure system for R2R thin-film deposition 4510 and R2R NIR drying, curing, and sintering processes. The term R2R herein refers to roll-to-roll processing or R2R. Roll-to-roll processing may include a multi-functional R2R system, including in-line electrospray, drying, curing, and sintering processes 4520. Production costs are reduced using scaled production of carbon/VDW-based sensors by using R2R thin film deposition system 4530. The end product of the R2R process creates an integrated structure of carbon and VDW sensors 4532. The detection cartridge 1310 of FIG. 13 provides a selectable biologic target detection system that is field-deployable and rapid detection of SARS-CoV-2 devices 4534 in one embodiment. The description continues in FIG. 45B.

Manufacturing Steps for Carbon/VDW-Based Sensors:

FIG. 45B shows a block diagram of an overview flow chart of manufacturing steps for carbon/VDW-based sensors of one embodiment. FIG. 45B shows a continuation from FIG. 45A and shows manufacturing steps for carbon/VDW-based sensors 4560 including bonding commercial single-layered carbon or multi-layered VDW materials to a PET substrate 4562 or other polymer substrate. Another step is depositing AU/AG/CU/NI/PT/CB electrodes using jet-printing, screen printing, or micro-contact printing on the single-layered carbon or the multi-layered VDW material 4564. In other embodiments, the carbon/VDW material is deposited on top of the AU/AG/CU/NI/PT/CB electrodes. A subsequent step is immobilizing biologically sensitive molecules on carbon/VDW using spray-coating 4566. The manufacturing steps for the production of carbon/VDW-based sensors 4560 provide optimizing manufacturing parameters 4568 including sintering/curing 4570, drying 4572, and cleaning 4574 of one embodiment.

Conductive-Based Sensors Manufacturing Parameters:

FIG. 46 shows a block diagram of an overview of conductive-based sensors manufacturing parameters of one embodiment. FIG. 46 shows conductive-based sensors manufacturing parameters 4600. One manufacturing parameter includes a conductive nanosensor bonded to a polyimide or PET substrate 4602. The conductive nanomaterials include one from a group of VDW materials 4603, graphene 4604, and other carbon materials with similar characteristics.

Other manufacturing parameter includes jet printing, screen printing, inkjet printing, digital printing, 3D printing, micro-contact printing, aerosol printing and additive manufacturing of conductive electrodes 4610. The conductive electrode materials include gold 4611, silver 4612, copper 4613, platinum 4614 nickel 4615, or carbon 4616. Another manufacturing parameter includes depositing materials using ink-jet print or aerosol print or screen print at least one layer of graphene or other nano ink. This step may require multiple layers, at different ink viscosities, print densities, drop sizes, and drops per inch (DPI).

Another manufacturing parameter includes using various methods of drying/curing including but not limited to thermal, IR, NIR, laser, microwave, photonic, filter, paddle, and spherical and can be used at different speeds, pulses of light, wavelengths of light, and power settings. Another manufacturing parameter includes cleaning/washing treatment using various methods of rinsing, plasma treatment, or UV treatment to remove interfering ions.

Another manufacturing parameter includes binding sensors and optimizing sensor conductivity using various ink deposition, drying, curing, cleaning, washing, and functionalization methods 4630. In one embodiment, depositing the target biologic material includes an aerosol spray/air-spray 4632. The aerosol spray/air-spray 4632 produces a spray coating biologically sensitive molecules solution on conductive nanosensor surface 4633. The drying/curing parameter includes various methods of drying/curing including but not limited to (thermal, IR, NIR, laser, UV, microwave, photonic, pulse, plasma, etc. . . . ) and can be used at different speeds, power, wavelengths of light, pulses of light and distance settings. In another embodiment, depositing target biologic material includes an electrostatic spray 4634. The electrostatic spray 4634 is controlled according to nozzle size, operating pressure/voltage, operating distance between the spray nozzle and the substrate, material temperature, and platen drying temperature 4635. In another embodiment, deposition includes piezo-driven dispensing biologically sensitive molecules solution on conductive carbon sensor surface 4636. In another embodiment, deposition includes dip-coating, drop casting, aerosol printing, micro pipetting, misting, or other forms of precise and uniform deposition of biologically sensitive molecules solution on conductive nanosensor surface 4637.

Electrochemical Detection of SARS-CoV-2 Biologic Analytical Target:

FIG. 47A shows for illustrative purposes only an example of electronic detection of SARS-CoV-2 biologic analytical target of one embodiment. FIG. 47A shows a detection sensor for electronic detection of SARS-CoV-2 biologic analytical target 4700. The detection sensor for electronic detection of SARS-CoV-2 biologic analytical target 4700 comprises a bodily fluid deposition port 4710 for depositing bodily fluid 4711 onto the detection sensor. The detection sensor base is a polyimide, PET or paper flexible film substrate 4720 or other polymer or plastic substrates. On the substrate, a carbon sensor is bonded to the polyimide, PET, paper or other plastic substrate 4702. It should be appreciated that any substrate type known in the art of printed electronics can be used. A plurality of target biologically sensitive molecules specific for SARS-CoV-2 are bound to the carbon sensor and stabilized inductively 4724. Printed electrodes 4725 are positioned on the surface of the carbon sensor or positioned below the surface of the carbon sensor.

Biologic analytical target RNA biologically sensitive molecules 4740 in the bodily fluid showing in these examples SARS-CoV-2 RNA biologically sensitive molecules, if present in the bodily fluid creates a unique impedance and current flow to the electrical circuit flowing through the printed electrodes 4725. A measured power level is delivered through, for example, a first IDE 4730. The electrical power flows through the first IDE 4730 electrodes from printed IDEs 4722. The electrical power from a first IDE circuit 4732 is conducted by the plurality of target biologic DNA molecules specific for SARS-CoV-2 and SARS-CoV-2 RNA biologically sensitive molecules to the second IDE 4731 electrodes completing the circuit to a second IDE circuit 4734.

The plurality of target biologic DNA biologically sensitive molecules specific for SARS-CoV-2 and SARS-CoV-2 RNA biologically sensitive molecules create a resistance to the flow of the electricity (impedance). The resulting reduction in the flow of electricity (impedance) is measured. In this example, the impedance of the plurality of target biologic DNA biologically sensitive molecules specific for SARS-CoV-2 and SARS-CoV-2 RNA biologically sensitive molecules is known through proprietary experimentation. A positive test result shows the impedance measurement decreases and the current measurement increases. Should the measured impedance match the experimentally determined known SARS-CoV-2 impedance, it indicates the presence of the SARS-CoV-2 virus. If the measured impedance does not match the experimentally determined known SARS-CoV-2 impedance, it indicates the SARS-CoV-2 virus is not present in the bodily fluid sample of one embodiment.

Breathe Moisture Test Sampling:

FIG. 47B shows for illustrative purposes only an example of breath moisture test sampling of one embodiment. FIG. 47B shows a test subject blowing moist breath 4750 into the bodily fluid deposition port 4710 of the detection cartridge 1310. A test subject breath moisture bodily fluid test sample 4314 deposits biologic analytical target RNA biologically sensitive molecules 4740. If present, the detection sensor for electronic detection of SARS-CoV-2 biologic analytical target 4700 test results will be positive of one embodiment.

Figure 48A:
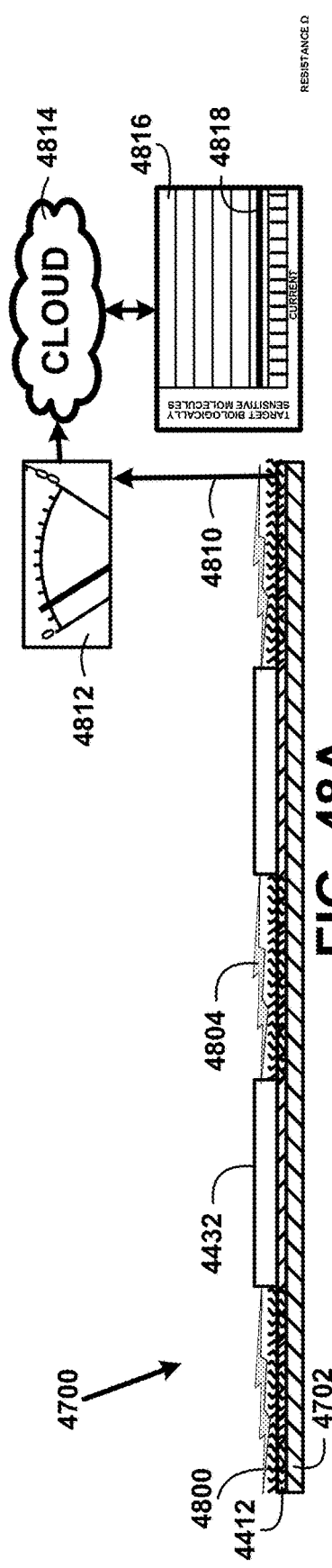
FIG. 48A shows for illustrative purposes only an example of a no-test sample impedance and current measurement of one embodiment.

No Test Sample Impedance Measurement:

FIG. 48A shows for illustrative purposes only an example of a no-test sample impedance and current measurement of one embodiment. FIG. 48A shows the detection sensor for electronic detection of SARS-CoV-2 biologic analytical target 4700. The detection sensor includes the polyimide or PET or paper or other plastic substrate or other substrate known in the art of printed electronics 4702, in one embodiment graphene 4412, target biologically sensitive molecules deposited onto the graphene 4800, and at least one AU/AG/CU/NI/PT/CB electrodes 4432. In one embodiment, the biologically sensitive molecules are drop cast onto the sensor surface. Other embodiments include spray coating, aersol spray, piezo-driven dispensing, micropippeting, pipetting, or dip coating the biologically sensitive molecules onto the sensor surface. It should be appreciate that other methods of depositing the target biologically sensitive molecule on the graphene is contemplated.

At least one AU/AG/CU/NI/PT/CB electrodes 4432 carry an electrical current 4804 flow between two poles AU/AG/CU/NI/PT/CB electrodes. An electrode measurement circuit 4810 passes the electrical current 4804 in this example through a meter to measure the circuit electrical current 4804. The meter reading with no bodily fluid sample present 4812 shows the base current. The meter reading data is transmitted to a cloud 4814 for recording and analysis. A graph of detection cartridge data 4816 is shown with the flat line base current and determined by an algorithmic analysis of detection cartridge data no test sample present 4818 of one embodiment.

Figure 48B:
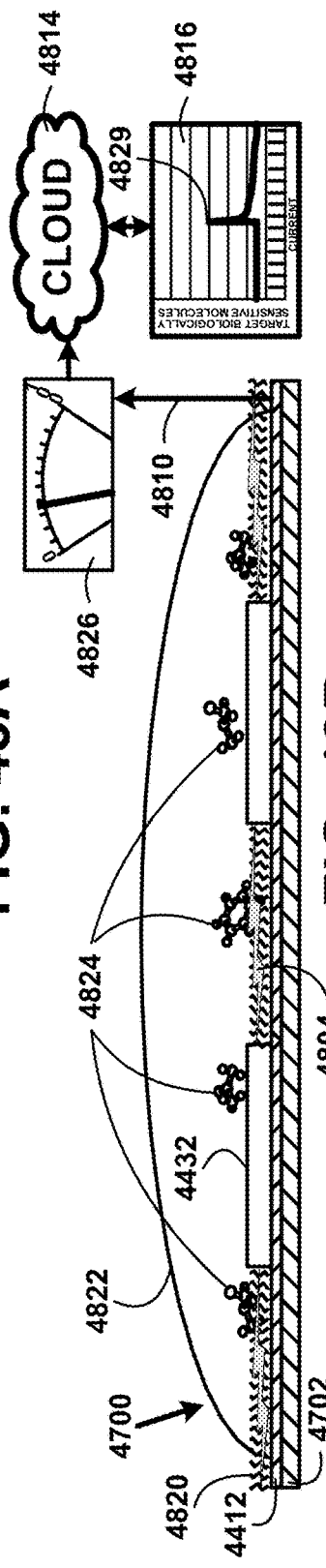
FIG. 48B shows for illustrative purposes only an example of a test sample with low biologic target concentration electrical current impedance measurement of one embodiment.

Test Sample with Low Biologic Target Concentration Impedance Measurement:

FIG. 48B shows for illustrative purposes only an example of a test sample with low biologic target concentration electrical current impedance measurement of one embodiment. FIG. 48B shows the detection sensor for electrochemical detection of SARS-CoV-2 biologic analytical target 4700. The detection sensor includes a polyimide, PET, paper or other plastic substrate or other substrates known in the art of printed electronics 4702, graphene 4412; target biologically sensitive molecules layered onto the graphene 4800, and at least one AU/AG/CU/NI/PT/CB electrodes 4432.

The bodily fluid sample 4822 in this example deposits target biologically sensitive molecules 4824 onto the target biologic molecules layered onto the graphene 4800 of FIG. 48A. The weak bond of the target biologically sensitive molecules layered onto the graphene 4800 is broken and hybridizes the target biological molecules due to the stronger bond with the biologically sensitive molecules 4820 causing an increase in electrical current and decrease in electrical resistance. The detection sensor automatically initiates an electrical current 4804 in the electrode measurement circuit 4810. The meter reading within a low concentration of target biologic biologically sensitive molecules 4826 measures the current through the biologically sensitive molecules.

The current data is automatically transmitted to the cloud 4814. The graph of detection cartridge data 4816 displays the algorithmic analysis of detection cartridge data of low concentration of target biologically sensitive molecules 4829 showing a spike in the current. The current measurement identifies the biologically sensitive molecules as the SARS-CoV-2 biologic analytical target and in some embodiments, the magnitude of the impedance measurement indicates the low concentration of the numbers of COVID-19 biologically sensitive molecules. These test findings produce a positive result that the test subject is infected with COVID-19 of one embodiment.

Figure 48C:
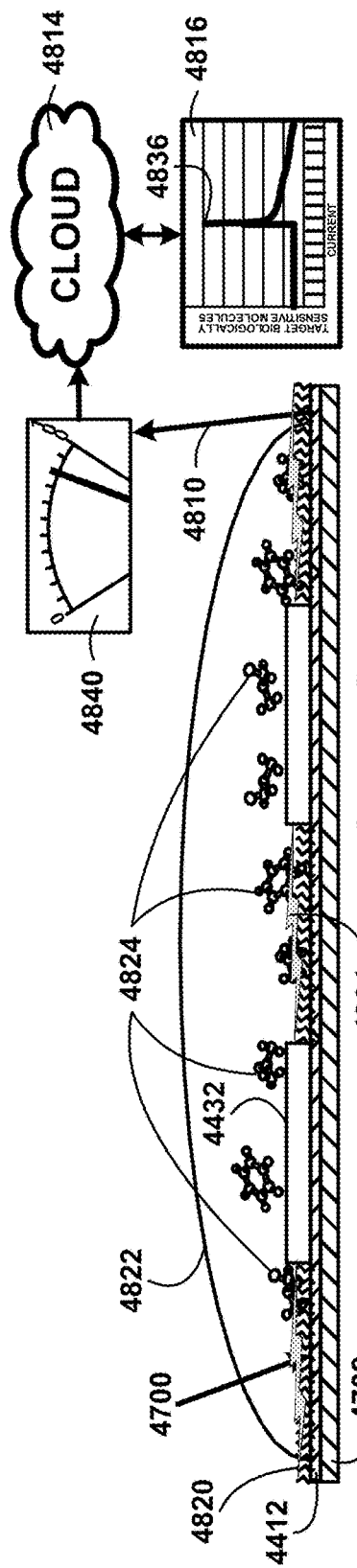
FIG. 48C shows for illustrative purposes only an example of a test sample with high biologic target concentration current impedance measurement of one embodiment.

Test Sample with High Biologic Target Concentration Current Impedance Measurement:

FIG. 48C shows for illustrative purposes only an example of a test sample with high biologic target concentration current impedance measurement of one embodiment. FIG. 48C shows the detection sensor for electrochemical detection of SARS-CoV-2 biologic analytical target 4700. The detection sensor includes a polyimide, PET, paper or other plastic substrate or other substrate known in the art of printed electronics 4702, graphene 4412; target biologic molecules layered onto the graphene 4800, and at least one AU/AG/CU/NI/PT/CB electrodes 4432.

The bodily fluid sample 4822 in this example deposits target biologically sensitive molecules 4824 onto the target biologic molecules layered onto the graphene 4800 of FIG. 48A. The weak bond of the target biologic DNA molecules layered onto the graphene 4800 is broken and hybridizes the target biologic DNA molecules due to the stronger bond of the biologically sensitive molecules 4820. The detection sensor automatically initiates an electrical current 4804 in the electrode measurement circuit 4810.

The meter reading of the higher concentration of target biologically sensitive molecules 4840 measures the current through the biologically sensitive molecules. The current data is automatically transmitted to the cloud 4814. The graph of detection cartridge data 4816 displays the algorithmic analysis of detection cartridge data of high concentration of target biologically sensitive molecules 4836 showing a spike in the current. The current measurement identifies the biologically sensitive molecules as the SARS-CoV-2 biologic analytical target and in some embodiments, the magnitude of the current measurement indicates the higher concentration of the numbers of COVID-19 biologically sensitive molecules. These test findings produce a positive result that the test subject is infected with COVID-19 of one embodiment.

Opened Test Cartridge Showing Sensor:

FIG. 49A shows for illustrative purposes only an example of an opened test cartridge showing a sensor of one embodiment. FIG. 49A shows the detection cartridge 1110 opened with a detection cartridge top cover 4900 to one side and an interior view of the detection cartridge bottom case 4905. The interior view shows the detection sensor for electrochemical detection of SARS-CoV-2 biologic analytical target 4700 installed in the detection cartridge bottom case 4905 of one embodiment. In one embodiment the detection cartridge bottom case 4905 includes a heater 4906 to test cartridge samples.

Closed Test Cartridge:

FIG. 49B shows for illustrative purposes only an example of a closed test cartridge of one embodiment. FIG. 49B shows the detection cartridge 1110 closed with the detection sensor for electronic detection of SARS-CoV-2 biologic analytical target 4700 of FIG. 47A installed one embodiment.

Test Subject Depositing Sample:

FIG. 49C shows for illustrative purposes only an example of a test subject depositing a sample of one embodiment. FIG. 49C shows the test subject blowing moist breath into the detection cartridge bodily fluid deposition port 4920. A bodily fluid deposition port 4930 includes a passageway for the moisture in the test subject's breath to deposit on the detection sensor for electronic detection of SARS-CoV-2 biologic analytical target 4700 of FIG. 47A within the detection cartridge 1110 of one embodiment.

Test Cartridge Inserting into Portable Detection Cartridge Reader:

FIG. 49D shows for illustrative purposes only an example of a test cartridge inserting into a portable detection cartridge reader of one embodiment. FIG. 49D shows the detection cartridge 1110 after a test subject deposits bodily fluid into the detection cartridge 1110. Inserting the detection cartridge into the portable detection cartridge reader 4940 allows the portable detection cartridge reader 1100 to read the detection data from the detection cartridge 1110 automatically upon insertion including a unique device identification code and a biologic analytical target identification code number. The portable detection cartridge reader display 1130 will display progress milestones as the processing of the test proceeds of one embodiment.

Figure 50A:
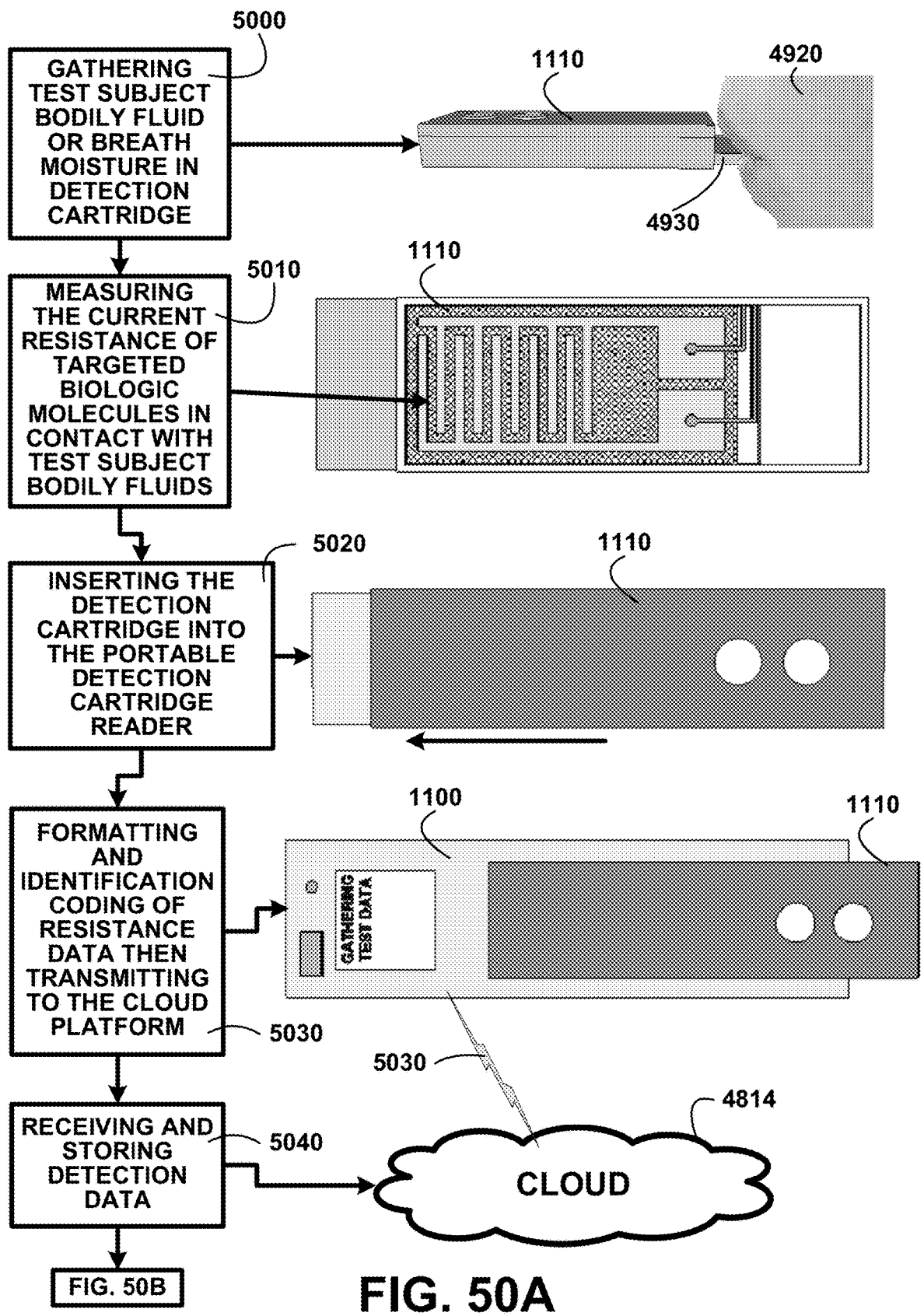
FIG. 50A shows for illustrative purposes only an example of an overview flow chart of gathering test subject samples of one embodiment.

Gathering Test Subject Sample:

FIG. 50A shows for illustrative purposes only an example of an overview flow chart of gathering test subject samples of one embodiment. FIG. 50A shows gathering test subject bodily fluid or breathe moisture in detection cartridge 5000. Gathering test subject test samples include for example a test subject blowing moist breath into the bodily fluid deposition port 4920. A bodily fluid deposition port 4930 provides a passageway for the test subject's bodily fluids to be deposited on the detection cartridge 1110 detection sensor surface.

The detection cartridge 1110 is for measuring the current resistance of targeted biologic molecules in contact with test subject bodily fluids 5010.

Inserting the detection cartridge into the portable detection cartridge reader 5020 begins the electrical current impedance measuring process. The electrical current impedance data is transmitted from the detection cartridge 1110 to the portable detection cartridge reader 1100 for formatting and identification coding of resistance data then transmitting to the cloud platform 5030 the formatted and identified data. The cloud 4814 is receiving and storing detection data 5040 for further processing as described in FIG. 50B of one embodiment.

Figure 50B:
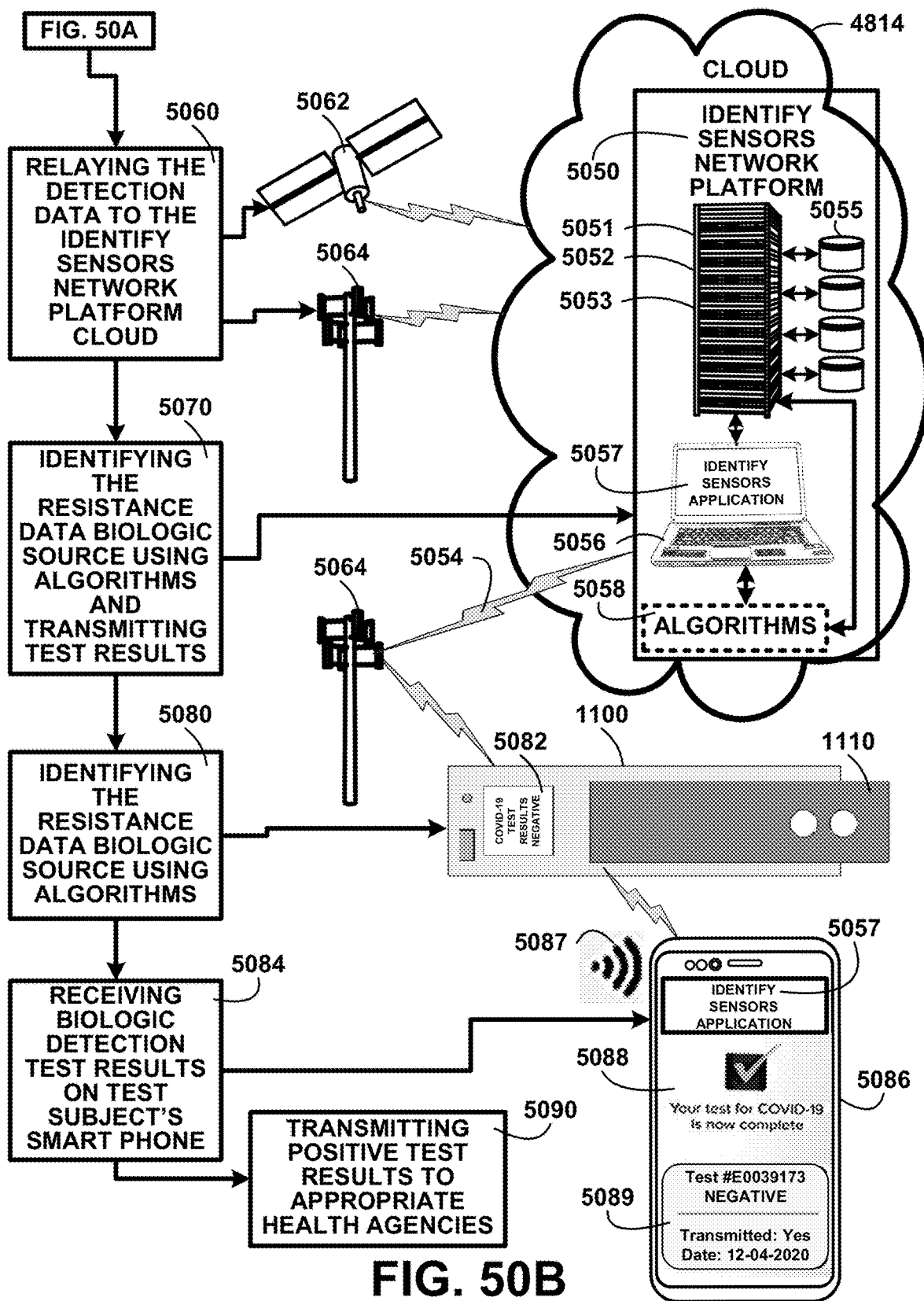
FIG. 50B shows for illustrative purposes only an example of an overview flow chart of identifying the electrical current resistance data biologic source of one embodiment.

Identifying the Electrical Current Resistance Data Biologic Source:

FIG. 50B shows for illustrative purposes only an example of an overview flow chart of identifying the electrical current resistance data biologic source of one embodiment. FIG. 50B shows a continuation from FIG. 50A including alternates of communication using satellite 5062 and cellular 5064 communications for relaying the detection data to the identify sensors network platform cloud 5060. It should be appreciated that in other embodiments, the test data is communicated directly to an electronic device through Bluetooth. This other embodiment does not rely on connectivity to transmit test results.

The detection data received in the cloud 4814 is processed using an IdentifySensors network platform 5050. The IdentifySensors network platform 5050 provides at least one server 5051, at least one digital processor 5052, at least one communication device 5053, a plurality of databases 5055, at least one network computer 5056, an IdentifySensors application 5057 and algorithms 5058 for analyzing the detection data. The algorithm 5058 analysis provides identifying the resistance data biologic source using algorithms 5070 and transmitting test results.

Transmitting test results 5054 for example over cellular 5064 communications to the portable detection cartridge reader 1100 and alternatively to a test subject's smartphone 5086. In this example COVID-19 test results negative 5082 are determined after identifying the resistance data biologic source using algorithms 5080 does not show the presence of the SARS-CoV-2 biologically sensitive molecules in the test subject's bodily fluids. The COVID-19 test results negative 5082 are transmitted to the portable detection cartridge reader 1100.

The test results are displayed on the portable detection cartridge reader 1100. The portable detection cartridge reader 1100 transmits the test results to a test subject's smartphone 5086. Receiving biologic detection test results on the test subject's smartphone 5084 is convenient for the test subject. The test results message in this example can be audible using Bluetooth 5087 technology and also displayed on the test subject's smartphone 5086. The display of the test results may include as shown in this example "Your Test for COVID-19 is now complete" 5088 and "Test #E0039173 NEGATIVE Transmitted: Yes Date: Dec. 4, 2020" 5089. In instances where the test results are determined to be positive for COVID-19 transmitting positive test results to appropriate health agencies 5090 may be required of one embodiment.

Figure 51:
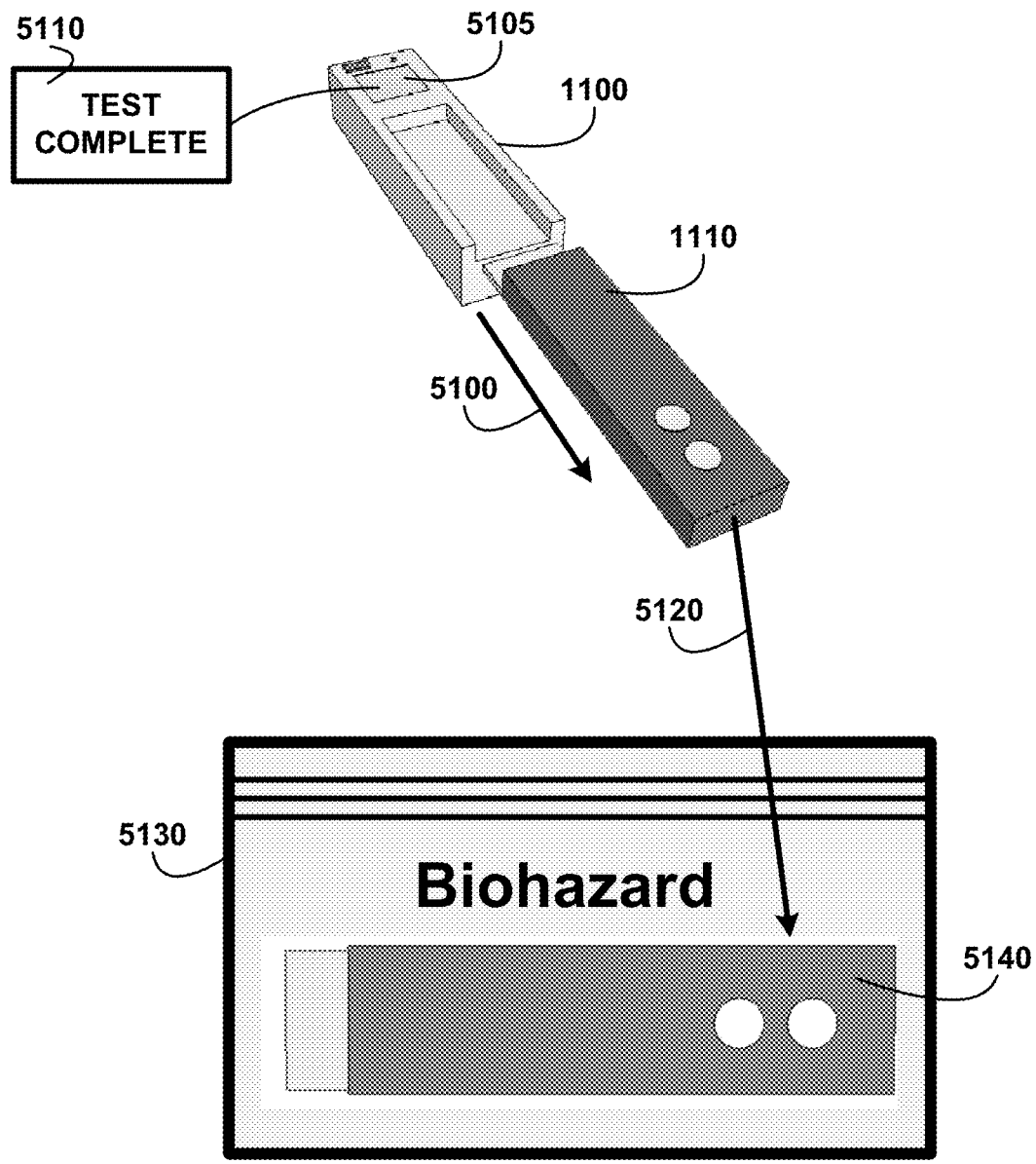
FIG. 51 shows for illustrative purposes only an example of the disposal of a used test cartridge of one embodiment.

Disposal of Used Test Cartridge:

FIG. 51 shows for illustrative purposes only an example of the disposal of a used test cartridge of one embodiment. FIG. 51 shows the portable detection cartridge reader 1100, detection cartridge 1110, and display 5105 with the message test complete 5110. After test results are transmitted to the test subject, removing the disposable detection cartridge after completion of the test 5100 is performed for appropriate disposal of the detection cartridge 5120. In those instances where the target biologic is transmittable infectious biological materials that are showing as positive a sealable biohazard container 5130 may be required for appropriate disposal of the detection cartridge 5120. The detection cartridge in the biohazard container 5140 may be required to be taken to a facility designated for approved biohazard disposal of one embodiment.

Figure 52:
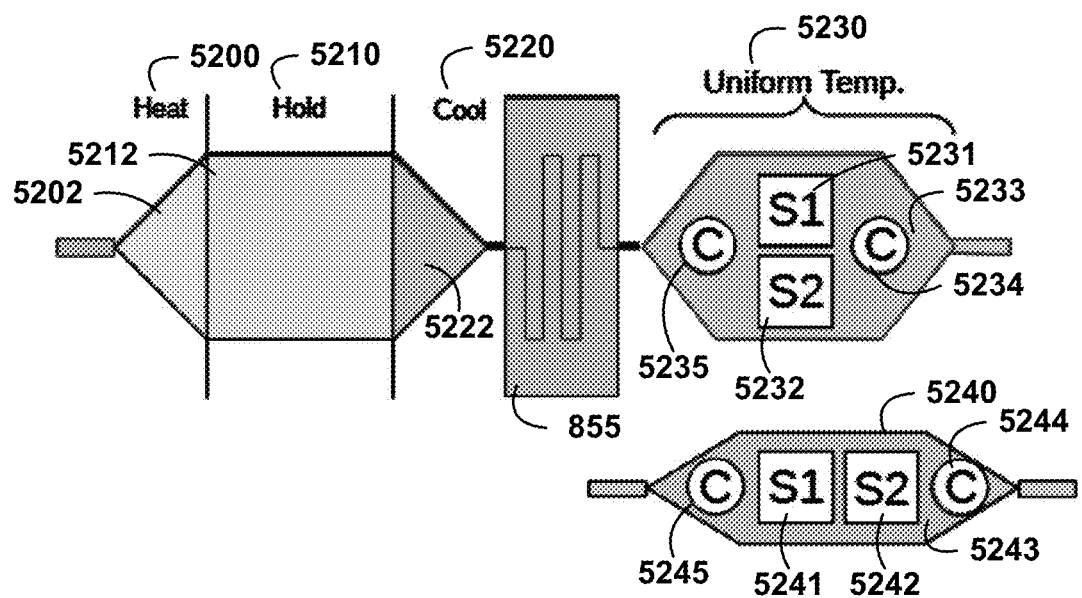
FIG. 52 shows for illustrative purposes only an example of a temperature control device of one embodiment.

Temperature Control Device:

FIG. 52 shows for illustrative purposes only an example of a temperature control device of one embodiment. FIG. 52 shows a temperature control device arrangement for testing samples. An initial area for applying heat 5200 in a heater section 5202 for a period of time measured in seconds. A hold 5210 stage for the heated sample is held in the hold section 5212. An area to cool 5220 the sample in a cooling section 5222 for a period of time measured in seconds. The temperature control device 855 applies heat or cooling to regulate the sample at a uniform temp. 5230, wherein the temperature is known by resistance values. In certain embodiments, the hold 5210 is not included and in yet another embodiment, the cool 5220 is not included. In yet another embodiment, the hold 5210 and the cool 5220 are not included. A sensing section 5233 includes sensors S1 5231 and S2 5232, sensing section 5233, first C (sample outlet) 5234, second C (sample inlet) 5235. In this example FIG. 52A shows an alternative configuration for the sensing section 5240 with sensors S1 5241 and S2 5242 in the sensing section 5243 with the first C (sample outlet) 5244 and second C (sample inlet) 5245 of one embodiment. This alternative exemplary embodiment does not include a temperature control device.

Figure 53:
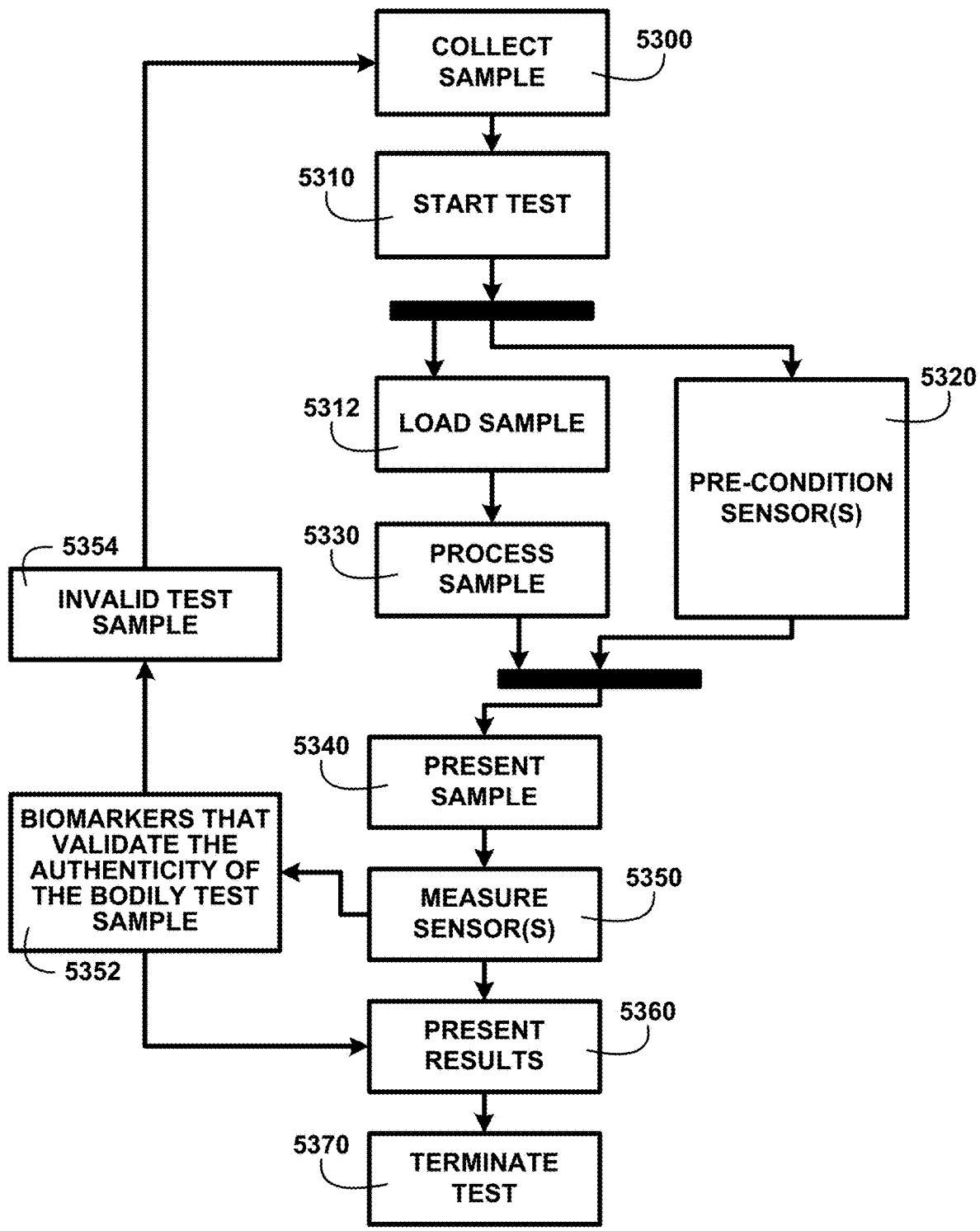
FIG. 53 shows a block diagram of an overview of a general test flow of one embodiment.
Figure 55:
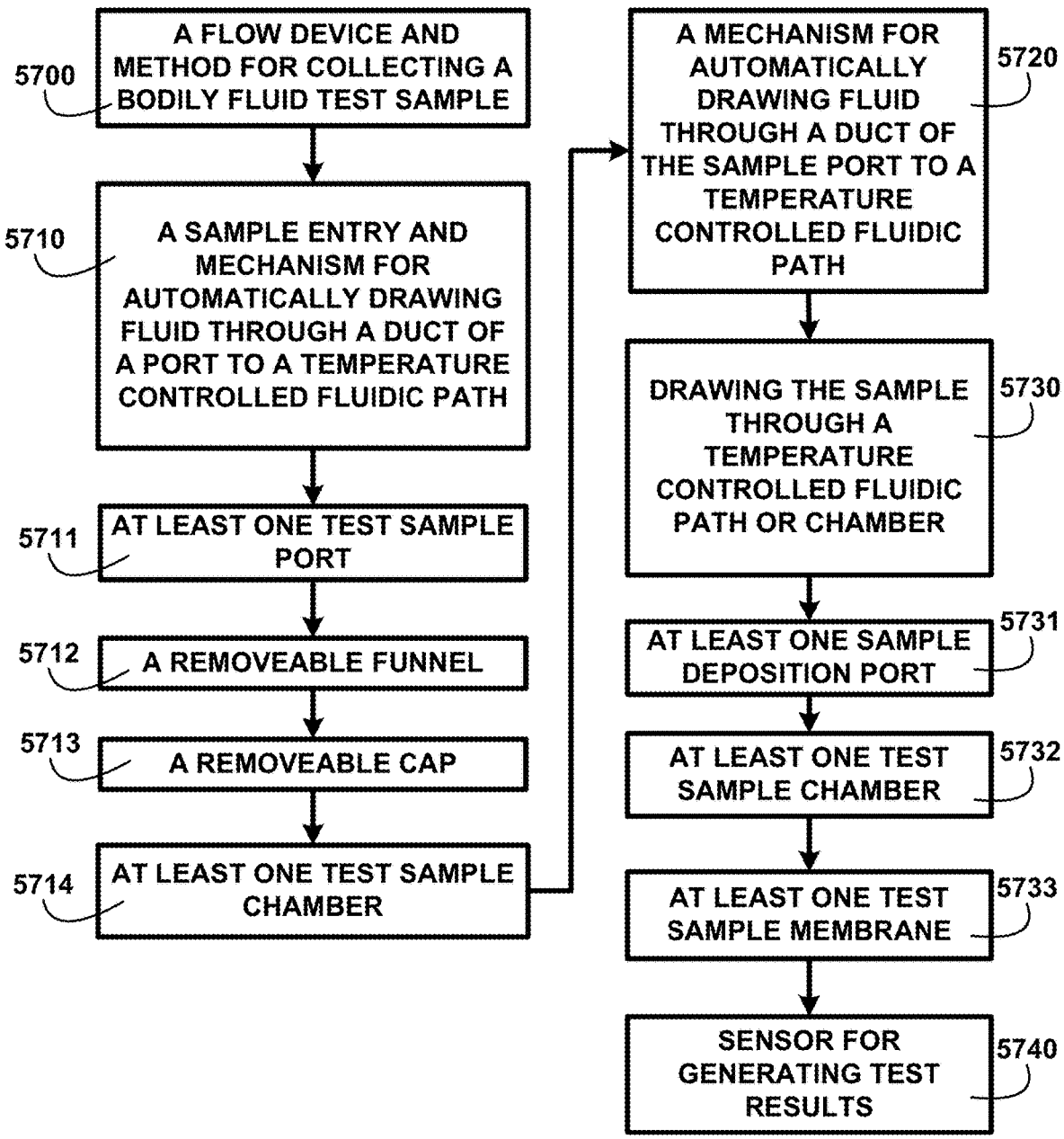
FIG. 55 shows a block diagram of an overview of a flow device of one embodiment.
Figure 56:
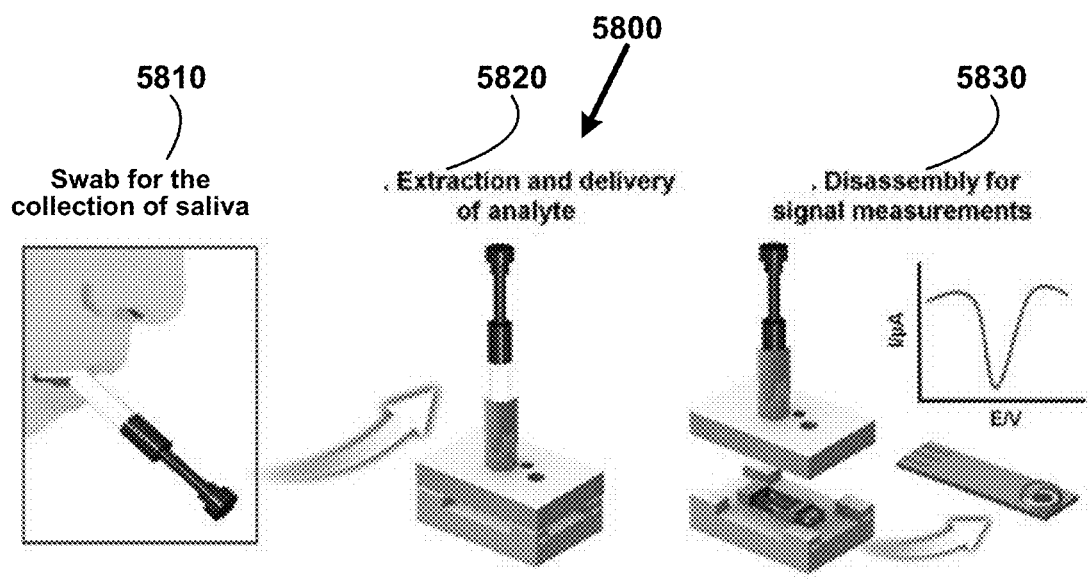
FIG. 56 shows for illustrative purposes only an example of a swabbing device for collecting and processing bodily test samples of one embodiment.
Figure 57:
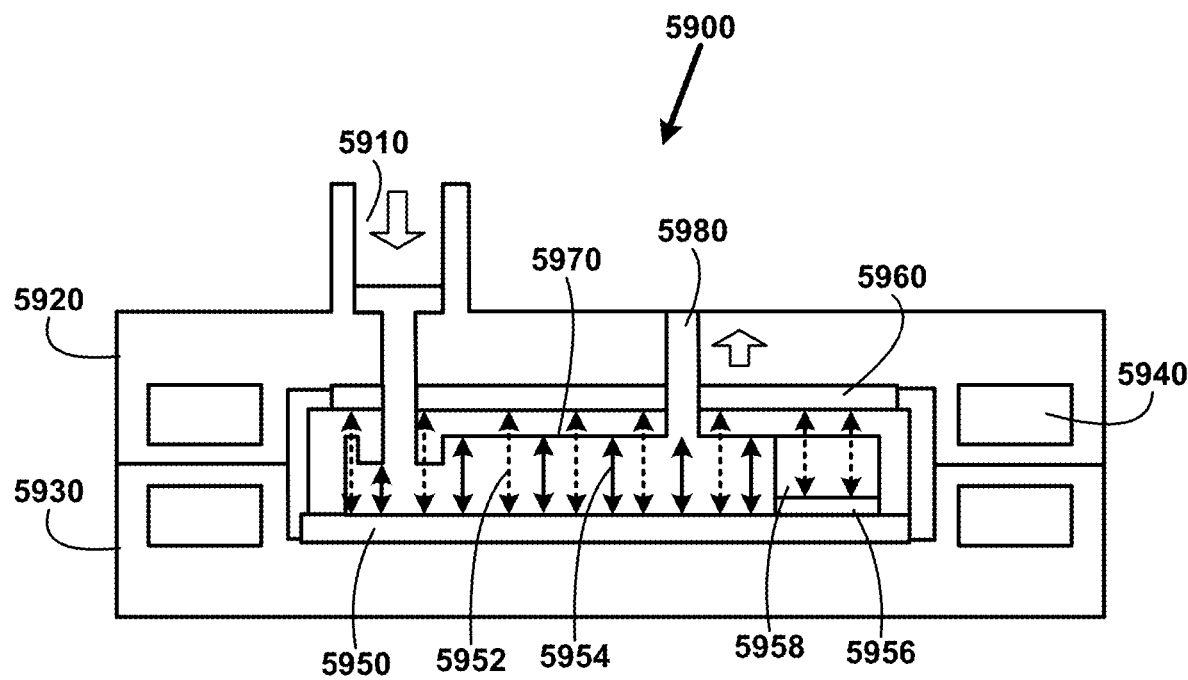
FIG. 57 shows for illustrative purposes only an example of a platform for processing and flowing the test sample of one embodiment.
Figure 58:
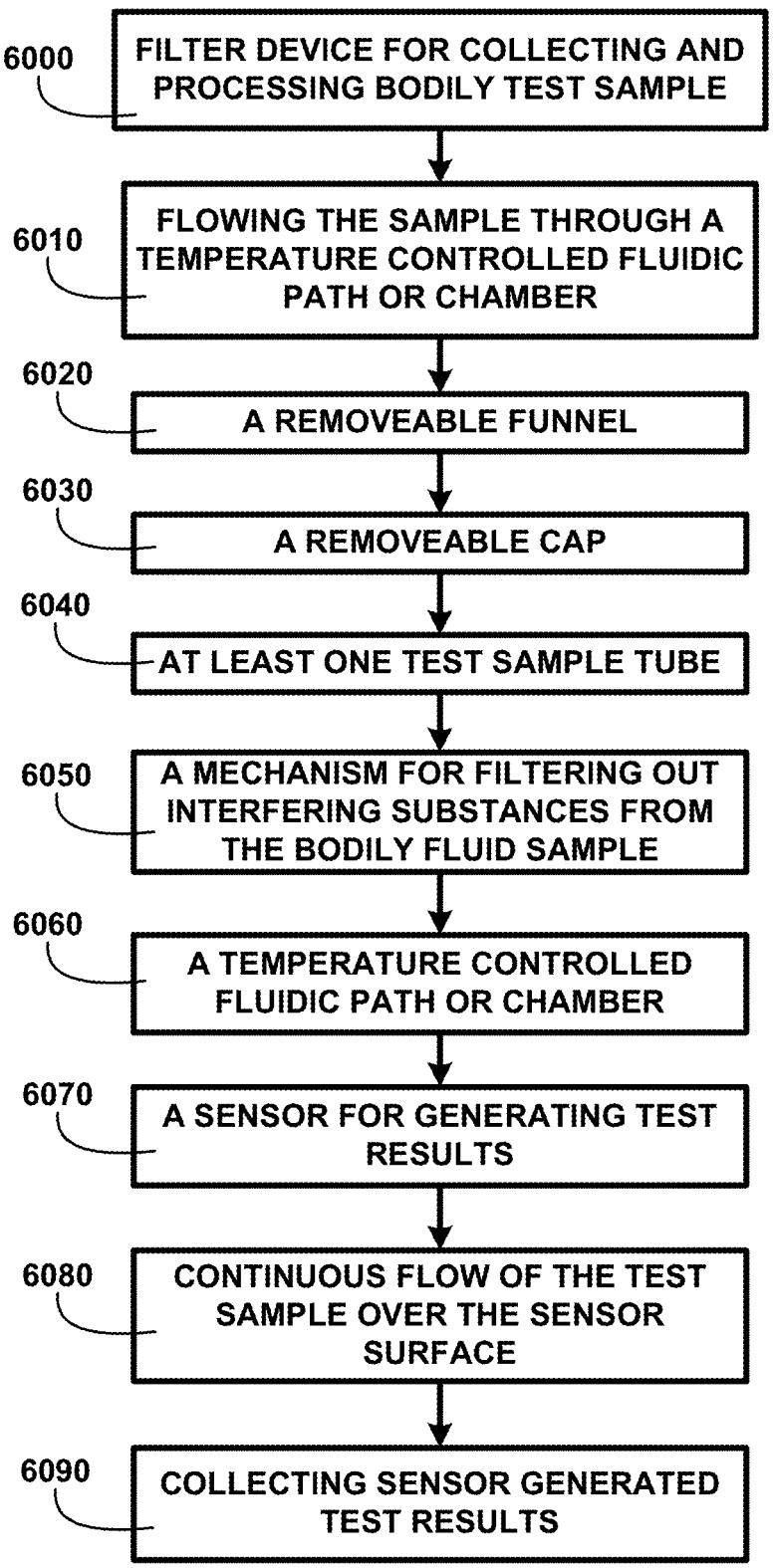
FIG. 58 shows a block diagram of an overview of a filter device of one embodiment.
Figure 59A:
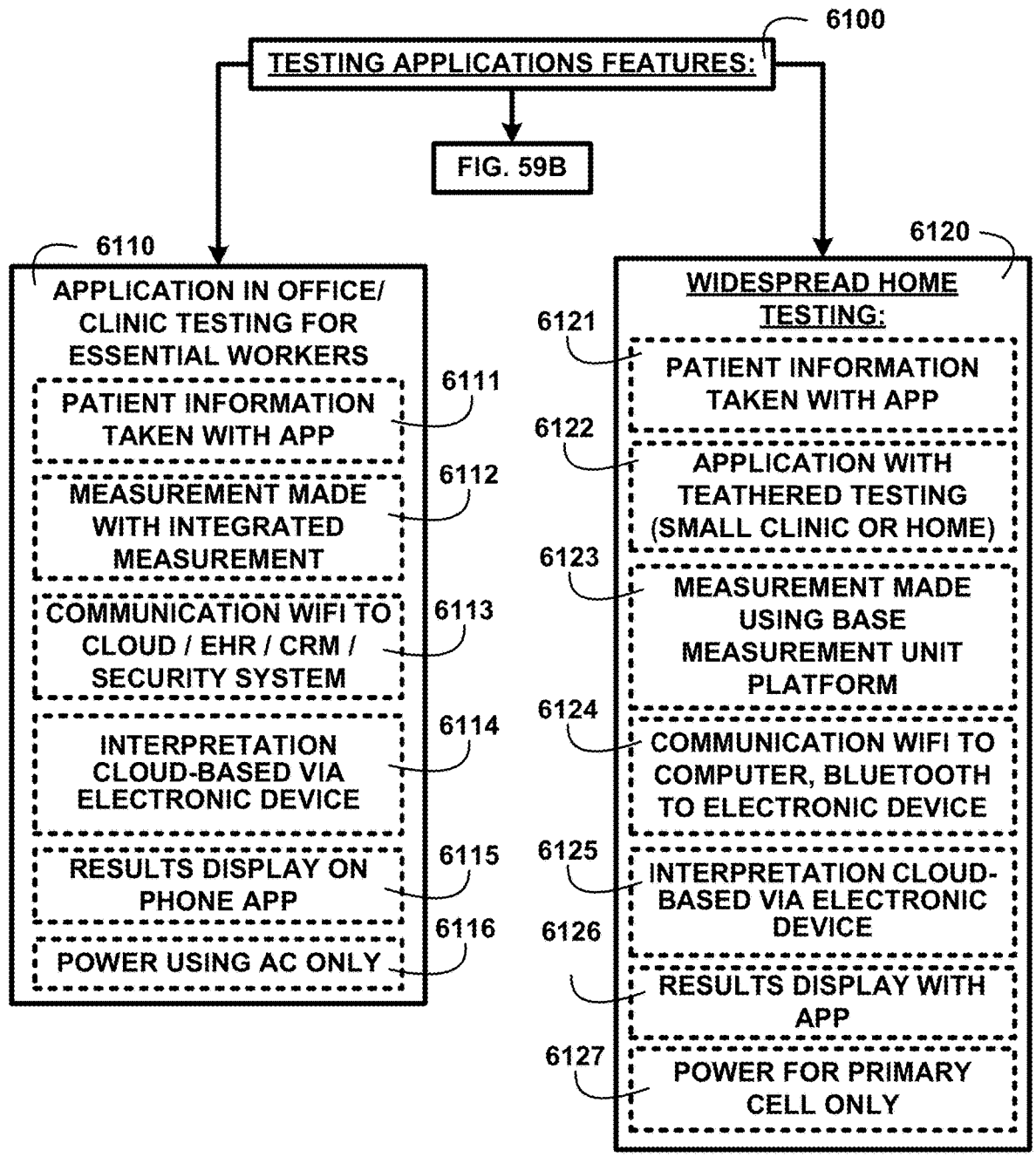
FIG. 59A shows a block diagram of an overview of testing applications features: of one embodiment.
Figure 59B:
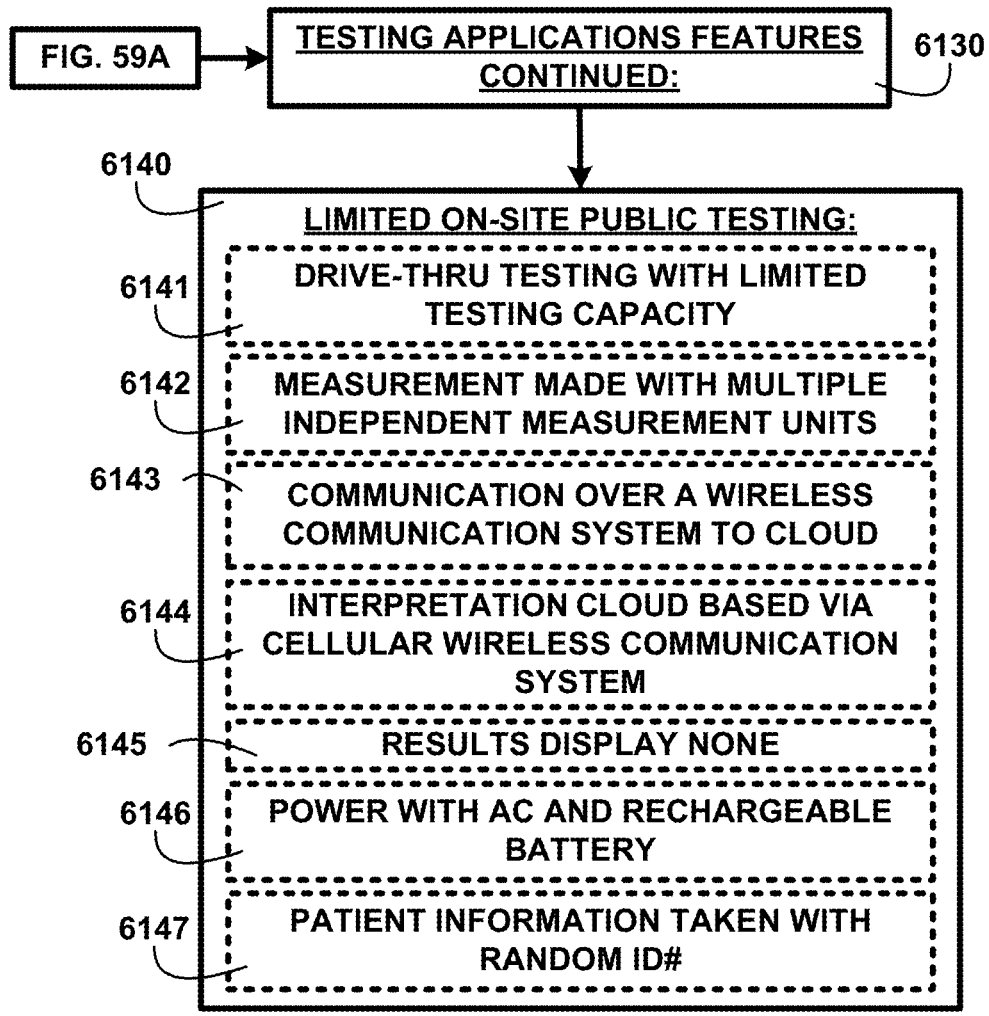
FIG. 59B shows a block diagram of an overview of testing applications features continued: of one embodiment.

General Test Flow:

FIG. 53 shows a block diagram of an overview of a general test flow of one embodiment. FIG. 53 shows a general test flow for the detection of infectious viruses and bacterial pathogens and biomarkers indicative of pathogens and general health conditions. The test starts with collecting sample 5300 and starts test 5310. The test continues with load sample 5312 for processing and a portion of the sample for pre-condition sensor(s) 5320 to determine a baseline. The testing includes a process sample 5330 stage and then to present sample 5340 to measure sensor(s) 5350 for measuring factors in the sample. Among the factors measured in the sample include biomarkers, enzymes, genes that validate the authenticity of the bodily test sample 5352. For example, the biomarker RNase P is used for the CoVID-19 authentication of test samples. If the test sample is an invalid test sample 5354 the test is invalid and a new test sample is taken. The final step is to present results 5360 for evaluation and then terminate test 5370 of one embodiment.

Chemical and Pathogen Detection Air Sample and HVAC:

FIG. 54 shows a block diagram of an overview of chemical and pathogen detection in an air sample and HVAC system of one embodiment. FIG. 54 shows a process for analyte and pathogen detection in the air sample and HVAC 5400. The process begins with an air sample collected and electrically charged (usually negatively charged) 5410. A nebulizer containing a solution (buffer or other solutions) creates electrically charged (usually positively charged) aerosols 5420. The negatively charged air sample is attracted to the positively charged aerosols forming a uniform aerosolized test sample 5430.

Figure 60:
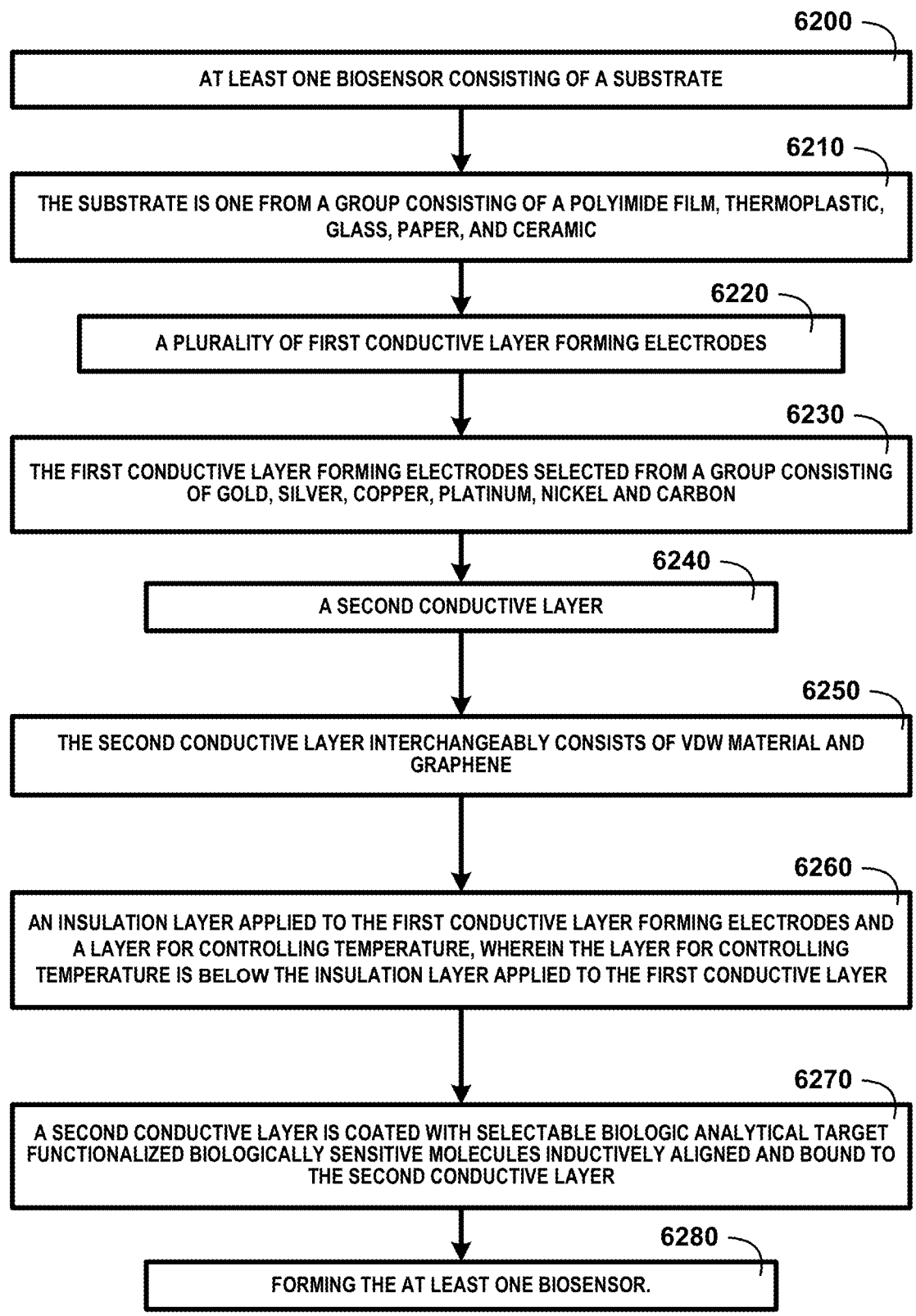
FIG. 60 shows for illustrative purposes only an example of two carbon layer biosensor of one embodiment.

The aerosolized test sample is transformed into a liquid test sample using an impactor jet nozzle to spray the aerosolized sample into an impaction plate, which causes the sample to transform into a liquid 5440. The liquid test sample is captured by a temperature-controlled fluidic path or chamber where the liquid sample can be electrically charged again if necessary 5450. The liquid test sample is presented to the sensor array for measurement through the temperature-controlled fluidic path or chamber 5460 of one embodiment. The test sample is disposed of in a waste reservoir using various active or passive induction devices such as vacuums or pumps 5470 of one embodiment.

Flow Device:

FIG. 55 shows a block diagram of an overview of a flow device of one embodiment. FIG. 55 shows a flow device and method for collecting a bodily fluid test sample 5700. The flow device includes a sample entry and mechanism for automatically drawing fluid through a test sample port to a temperature-controlled fluidic path 5710. The flow device includes at least one test sample port 5711, a removable funnel 5712, a removable cap 5713, and at least one test sample chamber 5714. The flow device and method include a mechanism for automatically drawing fluid through a duct of the test sample port to a temperature-controlled fluidic path 5720. The mechanism is used for drawing the test sample through a temperature-controlled fluidic path or chamber 5730. The temperature-controlled fluidic path or chamber includes at least one test sample deposition port 5731, at least one test sample chamber 5732, and at least one test sample membrane 5733. The flow device and method include a sensor for generating test results 5740 of one embodiment.

Swab Device for Collecting and Processing Bodily Test Samples:

FIG. 56 shows for illustrative purposes only an example of a swabbing device for collecting and processing bodily test samples of one embodiment. FIG. 56 shows a device and method for collecting a bodily fluid test sample and flowing the sample through a temperature-controlled fluidic path or chamber to the sensor for generating test results 5800. The device includes a bodily fluid test sample collection swab type for the collection of saliva 5810. It should be appreciated that the swab is made of a variety of materials that are most suitable for collecting a biospecimen. The device includes a port with an embedded membrane for extracting test sample fluid from the swab. The extraction and delivery of analyte 5820 to test the sample fluid is processed. The device includes a printed component for flowing the bodily test sample through a temperature-controlled fluidic path or chamber to the sensor for measurement and disposal of the bodily fluid test sample. A disassembly for signal measurements 5830 removes the sensor for electronic collection of the sensor signal measurements of one embodiment.

A Platform for Processing and Flowing the Test Sample to a Sensor for Measurement:

FIG. 57 shows for illustrative purposes only an example of a platform for processing and flowing the test sample of one embodiment. FIG. 57 shows a platform for processing a bodily fluid test sample and flowing the sample through a temperature-controlled fluidic path or chamber to the sensor for generating test results 5900. The exemplary platform includes a cover 5920, a holder 5930, an inlet 5910, an outlet 5980, PDMS 5970, jig 5960, a sensor 5950 including a working electrode 5956, and connectors 5940 that securely join the cover 5920 and holder 5930. The exemplary platform can also include a filter for removing interfering substances. Once the bodily fluid test sample in the swab is compressed by the extraction port, the bubble-depleted bodily fluid is injected into the temperature-controlled fluidic path or chamber through the inlet. The sample then flows on top of the working electrode then onto the outlet and is deposited in a waste reservoir.

The cover includes a jig on the bottom of the cover. The jig applies magnetic force 5952 to the outer wall of the PDMS channel 5954. The holder includes a grip on the top of the holder to hold the temperature-controlled fluidic chip and sensor in position. In the exemplary embodiment, the fluidic path or chamber 5958 is separate from the sensor. In other embodiments, the fluidic path or chamber is printed on the sensor film.

Filter Device:

FIG. 58 shows a block diagram of an overview of a filter device of one embodiment. FIG. 58 shows a filter device for collecting and processing bodily test sample 6000 and flowing the sample through a temperature-controlled fluidic path or chamber 6010. The filter device includes a removable funnel 6020, a removable cap 6030, at least one test sample tube 6040, a mechanism for filtering out interfering substances from the bodily fluid sample 6050, a temperature-controlled fluidic path or chamber 6060, a sensor for generating test results 6070. The filter device creates a continuous flow of the test sample over the sensor surface 6080. The filter device includes collecting sensor-generated test results 6090 of one embodiment.

Testing Applications Features:

FIG. 59A shows a block diagram of an overview of testing applications features: of one embodiment. FIG. 59A shows testing applications features: 6100. In one embodiment the testing applications features: 6100 include an application in office/clinic testing for essential workers 6110. This application includes patient information taken with an app. 6111. Testing measurement was made with integrated measurement 6112. Communication WIFI to cloud/EHR/CRM/security system 6113 is performed for Interpretation cloud-based via electronic device 6114. Testing results are displayed on an app 6115. The application devices connect to power using AC only 6116.

In another embodiment, a widespread home testing: 6120 testing application includes features including patient information taken with an app 6121. Application with tethered testing (small clinic or home) 6122 is used for a measurement made using base measurement unit platform 6123.

Communication WIFI to computer, Bluetooth to electronic device 6124 is used to perform interpretation cloud-based via electronic device 6125. Test results display with an app 6126. The testing uses power for primary cell only 6127. Another testing application is described in FIG. 59B.

Testing Applications Features Continued:

FIG. 59B shows a block diagram of an overview of testing applications features continued: of one embodiment. FIG. 59B shows a continuation from FIG. 59A of testing applications features continued: 6130 in an embodiment of limited on-site public testing: 6140. Limited on-site public testing: 6140 is an application with patient information taken with random id #6147. Limited on-site public testing: 6140 is performed with drive-thru testing with limited testing capacity 6141. Testing measurement made with multiple independent measurement units 6142. Communication over a wireless communication system to cloud 6143 is used for interpretation cloud-based via cellular wireless communication system 6144. Results display none 6145 as the cars are driving through with only a brief time for the test sampling. Power with AC and rechargeable battery 6146 is used to operate the devices of one embodiment.

Two Conductive Layer Biosensor:

FIG. 60 shows for illustrative purposes only an example of two carbon layer biosensor of one embodiment. FIG. 60 shows at least one biosensor consisting of a substrate 6200. The substrate is one from a group consisting of a polyimide film, thermoplastic, glass, ceramic and paper and other substrates known in the art of printed electronics 6210. A plurality of first conductive layer forming electrodes 6220 are deposited on the substrate. The first conductive layer forming electrodes selected from a group consisting of gold, silver, copper, platinum, nickel and carbon 6230. A second conductive layer 6240 is deposited onto the substrate and plurality of first conductive layer forming electrodes. The second conductive layer interchangeably consists of VDW material and Graphene 6250. An insulation layer applied to the first conductive layer forming electrodes and a layer for controlling temperature, wherein the layer for controlling temperature is below the insulation layer applied to the first conductive layer 6260. On top of the insulation layer and layer for controlling temperature 6260 the second conductive layer 6240 is coated with selectable biologic analytical target functionalized biologically sensitive molecules inductively aligned and bound to the second conductive layer 6270 forming at least one biosensor 6280 of one embodiment.

Figure 61:
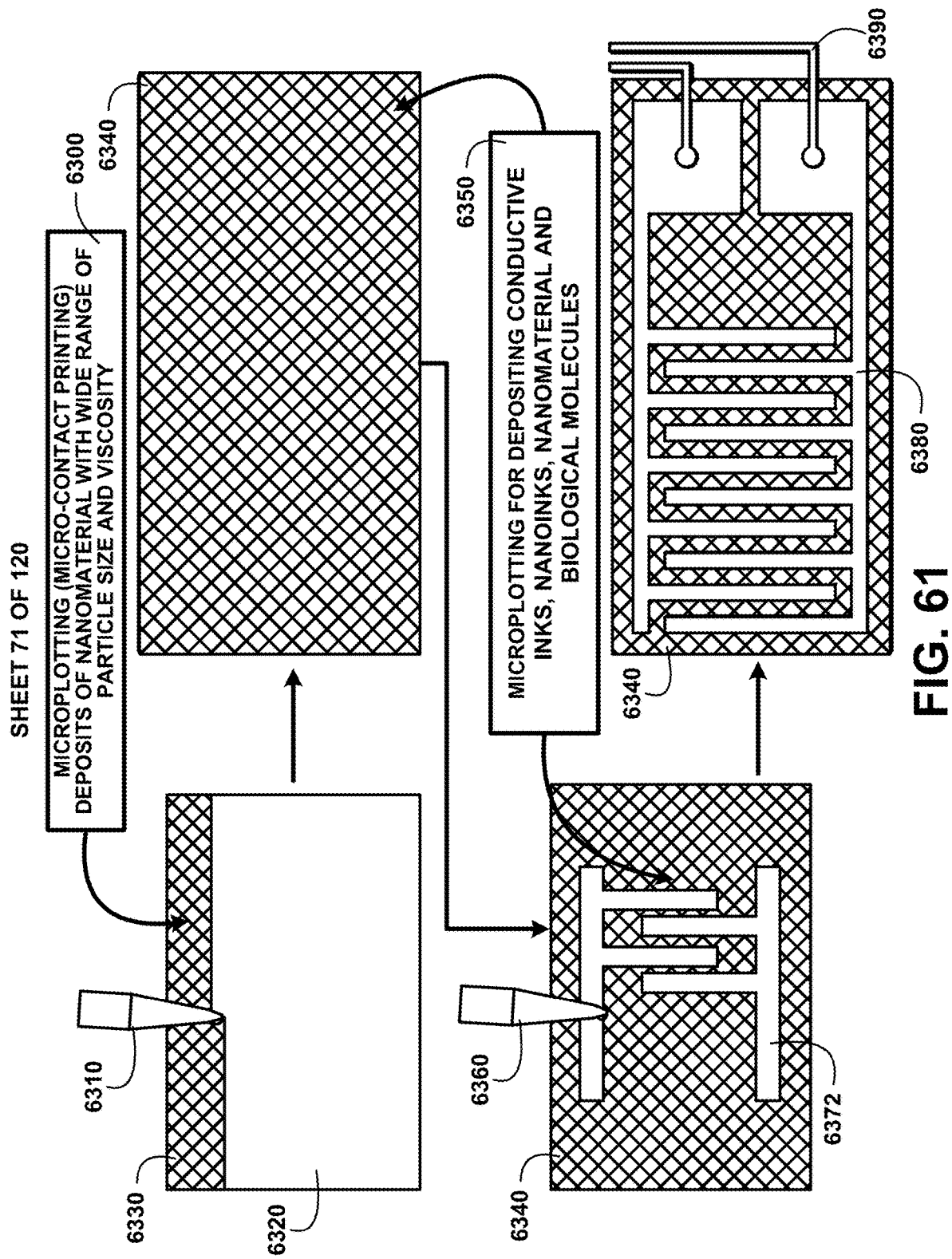
FIG. 61 shows for illustrative purposes only an example of an overview of a micro plotter depositing material with a wide range of particle size and viscosity of one embodiment.

Microplotter Depositing Inks with a Wide Range of Particle Size and Viscosity:

FIG. 61 shows for illustrative purposes only an example of an overview of a micro plotter depositing material with a wide range of particle size and viscosity of one embodiment. This method of depositing material is also known as micro-contact printing. FIG. 61 shows a process for depositing of nanomaterial and biological material with micropipettes across a wide range of particle size and viscosity. Microplotting (micro-contact printing) deposits of nanomaterial and biological material with a wide range of particle size and viscosity 6300. Microplotting depositing graphene and biological material with higher or lower concentrations of solvents, binders, polymers, and solids, minimizing the time, temperature, and energy required for solvents, binders, and polymers to evaporate, enabling a simplified curing process. A micro plotter depositing materials with a wide range of particle size and viscosity 6310 on the substrate 6320 applies a wide range of inks with ultrasonic pumping directly onto the substrate 6320 in continuous lines having high-precision positioning rather than eject droplets over a distance to a surface. Graphene 6330 is a conductive layer. Microplotting over the substrate with graphene 6340 provides conductivity for impedance current flow between electrodes. The process includes micro plotting for depositing conductive inks, nano inks, nanomaterials, and biological molecules 6350. FIG. 61 shows a micro plotter depositing conductive ink 6360 on top of the substrate micro plotted with graphene 6340. Conductive inks include conductive ink 6372. On the substrate micro plotted with graphene 6340 is a plurality of micro plotted electrodes 6380 and micro plotted electronic circuits 6390 to carry the impedimetric detection current of one embodiment.

Figure 62:
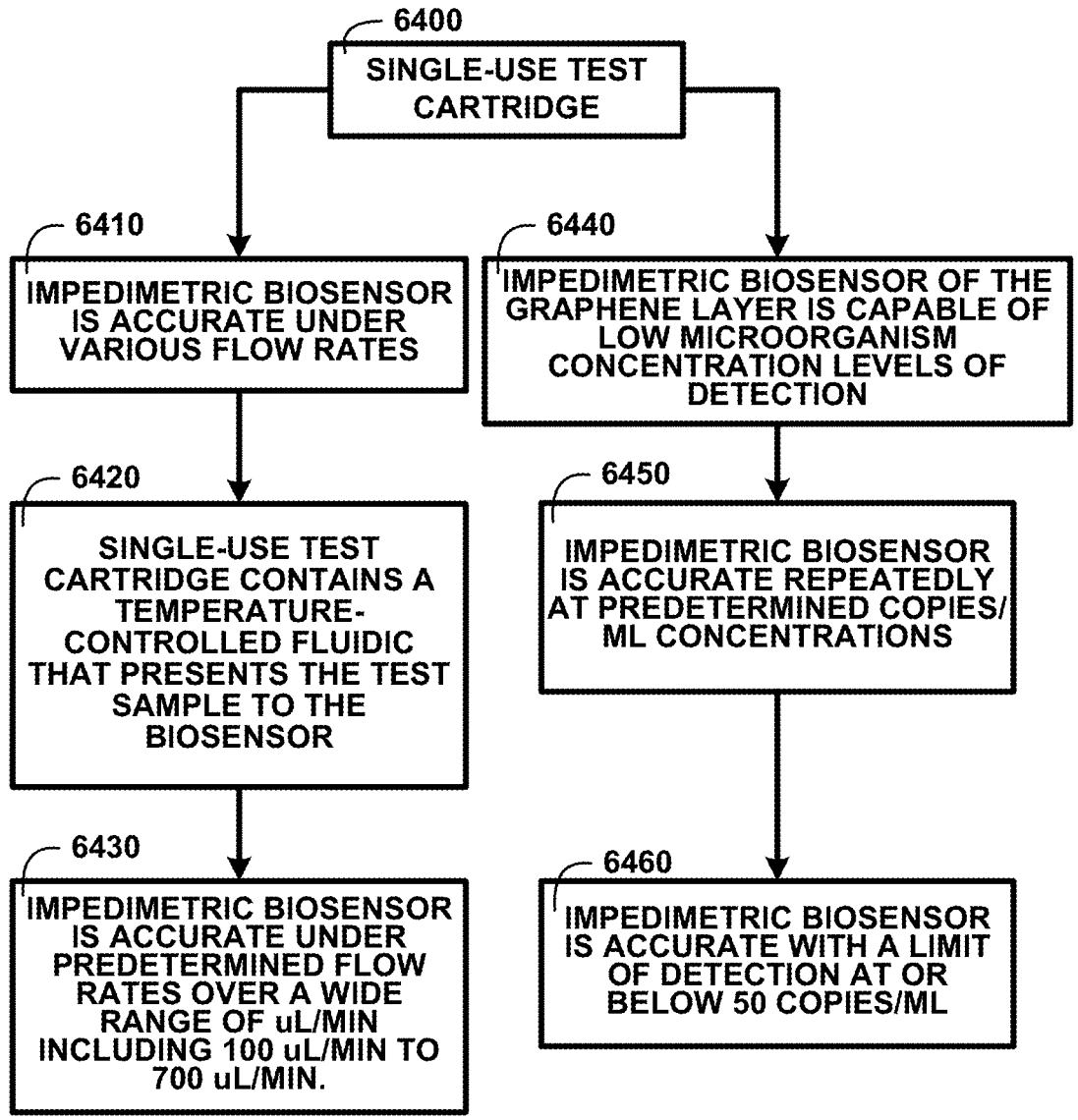
FIG. 62 shows a block diagram of an overview of a single-use test cartridge of one embodiment.

Single-Use Test Cartridge:

FIG. 62 shows a block diagram of an overview of a single-use test cartridge of one embodiment. FIG. 62 shows a single-use test cartridge 6400 capable of a plurality of impedimetric biosensors for detecting multiple different disease targets simultaneously. The single-use test cartridge 6400 biosensor performs well under various flow rates 6410. A single-use test cartridge contains a temperature-controlled fluidic that presents the test sample to the sensor 6420. The biosensor performs well under predetermined flow rates over a wide range of uL/min including 100 uL/min. to 700 uL/min. 6430.

An impedimetric biosensor is capable of low microorganism concentration levels of detection 6440. A biosensor is accurate repeatedly at predetermined copies/mL concentrations 6450. Including the biosensor is accurate with a limit of detection at or below 15 copies/mL 6460 of concentration of one embodiment.

Figure 63:
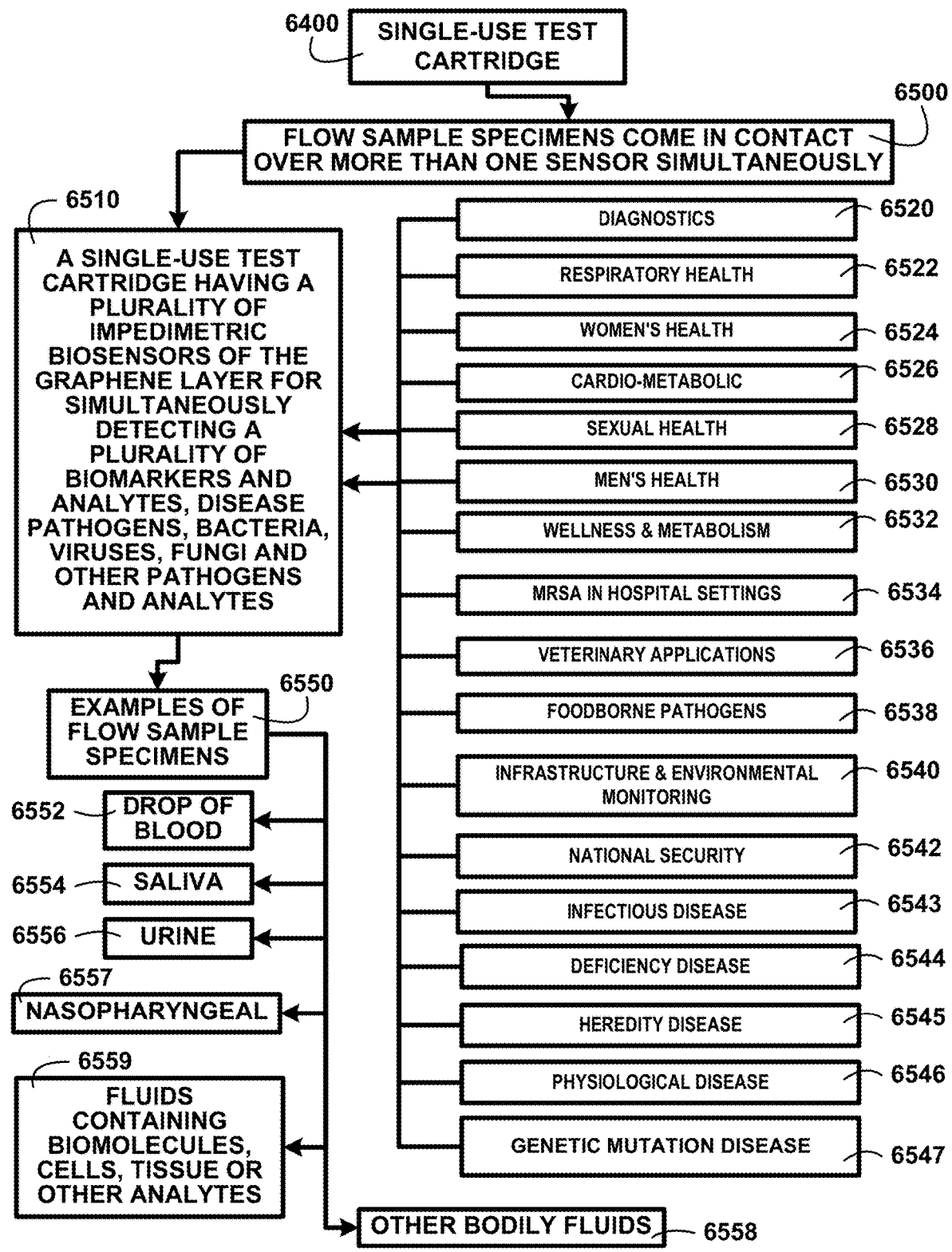
FIG. 63 shows for illustrative purposes only an example of flow sample specimens of one embodiment.

Flow Sample Specimens:

FIG. 63 shows for illustrative purposes only an example of flow sample specimens of one embodiment. FIG. 63 shows the single-use test cartridge 6400 having flow sample specimens come in contact over more than one sensor simultaneously 6500. A single-use test cartridge having a plurality of biosensors for simultaneously detecting a plurality of biomarkers and analytes, disease pathogens, bacteria, viruses, fungi, and other pathogens and analytes 6510.

The categories of health issues impacted by the diseases include diagnostics for disease (infectious, deficiency, heredity, and physiological diseases) 6520, respiratory health 6522, women's health 6524, cardio-metabolic 6526, sexual health 6528, men's health 6530, wellness & metabolism 6532, MRSA in hospital settings 6534, veterinary applications 6536, foodborne pathogens 6538, infrastructure & environmental monitoring (e.g. water & air) 6540, national security 6542, infectious disease 6543, deficiency disease 6544, heredity disease 6545, physiological disease 6546 and genetic mutation disease 6547 (Cancer, Cystic Fibrosis, Sickel Cell Anemia, Huntington's Disease, Muscular Dystrophy, Tay-Sachs Disease, Down Syndrome, Fragile X Syndrome, Hemophilia, Cystinuria, Phenylketonuria among other diseases caused by genetic mutations.

Examples of flow sample specimens 6550 include a drop of blood (serum and plasma) 6552, saliva 6554, nasopharyngeal 6557, urine 6556, fluids containing biomolecules, cells, tissue, or other analytes 6559, and other bodily fluids 6558 and fluids containing biomolecules, cells, tissue, clots, coagulants or other target analytes. Other bodily fluids include amniotic fluid, aqueous humor, bile, blood plasma, breast milk, cerebrospinal fluid, cerumen, chyle, exudates, gastric juice, lymph, mucus, pericardial fluid, peritoneal fluid, pleural fluid, pus, saliva, sebum, serous fluid, semen, sputum, synovial fluid, sweat, tears, urine and vomit. The nano-scaled impedimetric biosensors allow for example the low flow rates of flow sample specimens and low concentration levels capacity for accurate detection in this example of blood flow sample specimens 6550. Typically, lab tests require at least one vile of blood to be drawn from a patient. The nano-scaled impedimetric biosensors are capable of accurate detection with a drop of blood. This is less inconvenient for patients and produces fast and most importantly high accuracy in detection which provides improved diagnostics and earlier treatment for the patient. If the results of the single-use test cartridge 7100 are negative for one or more infectious diseases under examination the fast and accurate detection results provide the patient with peace of mind.

The plurality of infectious diseases or target analytes are detectable using the single-use test cartridge 7100 includes depositing a plurality of flow sample specimens 6550 from which multiple diseases or target analytes are detectable with low flow rates and concentrations. Examples of the flow sample specimens 6550 and diseases and target analytes detectable in the specimens include saliva specimen samples common in several health issues including Respiratory Health: COVID, Coronavirus, Influenza, Respiratory Syncytial Virus (RSV), Rhinovirus, and Strep Throat; Men's Health: Testosterone; Sexual Health: *Chlamydia*/Gonorrhea, HIV, and Herpes; Wellness & Metabolism: Cortisol; hospital settings: Methicillin-resistant *Staphylococcus aureus* (MRSA) common in a hospital setting. Other disease targets include single-stranded RNA viruses such as Hepatitis, Dengue, Yellow Fever, Zika, Norwalk, Norovirus, Polio, HIV, Measles, Mumps, and Ebola. Other disease targets include DNA viruses such as Parvovirus, Anellovirdae, Lyme, HPV, Adenovirus, Shingles and Chickenpox, *Streptococcus pneumonia, Yersinia pestis*, and *Acinetobacter baumannii*. Other detectable targets include proteins, enzymes, hormones, antibodies, nanobodies, and other small molecules and large molecules. Another group is Urine specimen samples including Women's Health: Fertility, and Pregnancy; Sexual Health: *Chlamydia*/Gonorrhea. One group of health issues for blood specimen samples includes Cardio-Metabolic: Inflation, Cholesterol, and diabetes testing (HbA1C); Sexual Health: Hep C; and Wellness & Metabolism: Vitamin D and other essential minerals and vitamins of one embodiment and Genetic Mutation Disease: (Cancer, Cystic Fibrosis, Sickel Cell Anemia, Huntington's Disease, Muscular Dystrophy, Tay-Sachs Disease, Down Syndrome, Fragile X Syndrome, Hemophilia, Cystinuria, Phenylketonuria among other diseases caused by genetic mutations).

Figure 64:
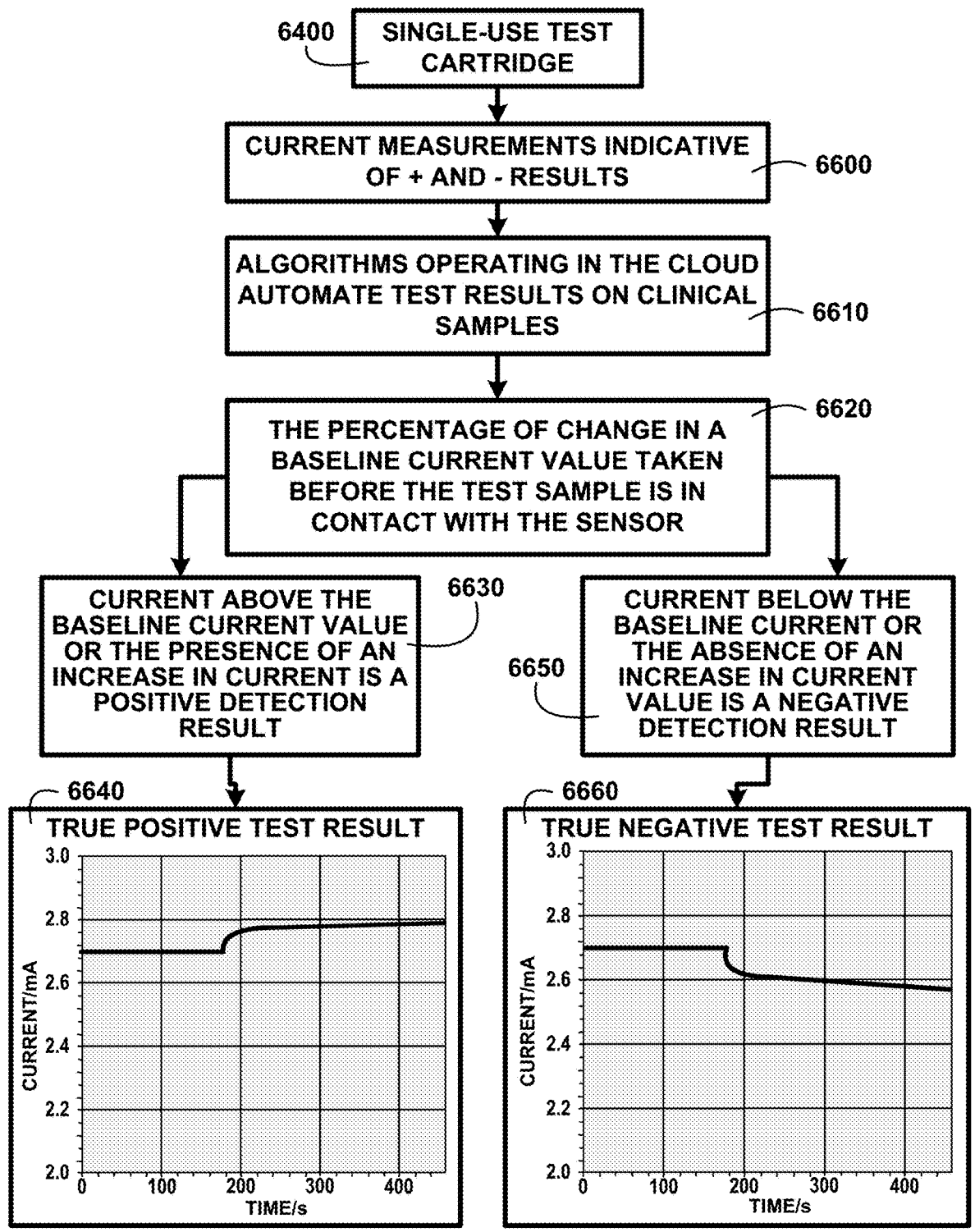
FIG. 64 shows for illustrative purposes only an example of current measurements of one embodiment.

Current Measurements:

FIG. 64 shows for illustrative purposes only an example of current measurements of one embodiment. FIG. 64 shows the single-use test cartridge 6400 having the capacity for performing and recording impedimetric current measurements indicative of + and − results 6600. The current measurements are automatically transmitted to a system cloud. Algorithms operating in the cloud automate test results on clinical samples 6610. The current measurements are made to determine the percentage of change in a baseline current value taken before the test sample is in contact with the sensor 6620.

Current measurements showing a current above the baseline current value or the presence of an increase in current is a positive detection result 6630 indicating the presence of the particular disease or target analyte in the sample. A true positive test result 6640 is confirmed with the algorithm analysis of based on verified clinical sample lab-based evaluations. A true positive test result 6640 is confirmed with the algorithm analysis of current measurements from the test sample.

Current measurements showing a current below the baseline current value or the absence of an increase in current value is a negative detection result 6650 indicating the lack of presence of the particular disease or target analyte in the sample. A true negative test result 6660 is confirmed with the algorithm analysis of current measurements from the test sample.

Figure 65:
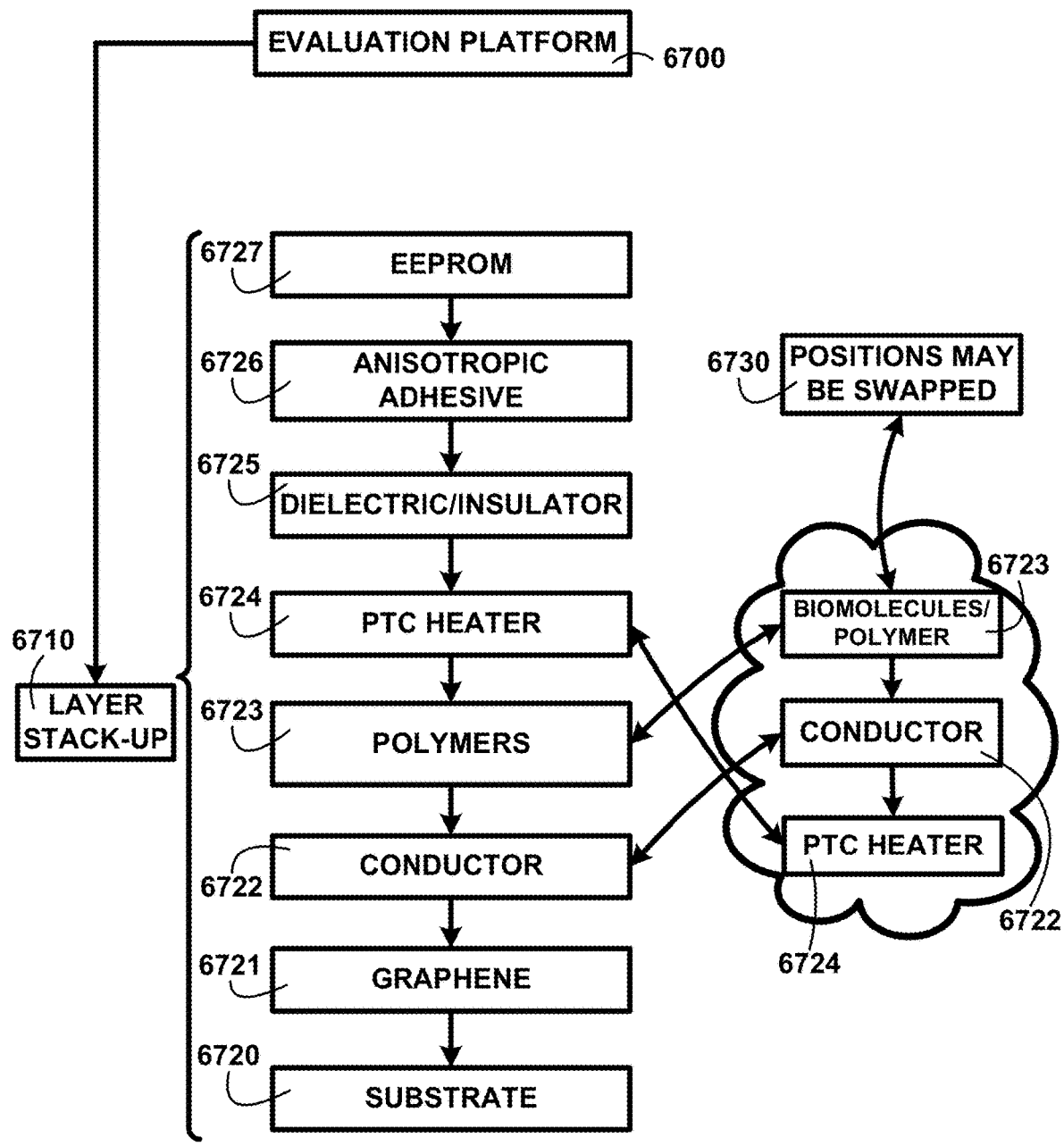
FIG. 65 shows for illustrative purposes only an example of an evaluation platform of one embodiment.

Evaluation Platform:

FIG. 65 shows for illustrative purposes only an example of an evaluation platform of one embodiment. FIG. 65 shows an evaluation platform 6700 layers stack up 6710 of layered components. The layer stack-up 6710 comprises at the bottom layer a substrate 6720. Graphene 6721 is applied to the surface of the substrate 6720. A pattern of electrodes and circuits are deposited onto the graphene 6721 with a plurality of a conductor 6722 material. The electrodes are functionalized with polymers 6723. Each evaluation platform 6700 includes electrodes functionalized with different polymers 6723 for the detection of a specific disease or target analytes. A PTC heater 6724 is a positive temperature coefficient (PTC) temperature control device. The PTC heater 6724 applies heat to the deposited sample specimen in an incubating process of the patient's sample. A dielectric/insulator 6725 is applied over the conductive materials. An anisotropic adhesive 6726 is applied before the placement of an EEPROM 6727. An electrically erasable programmable read-only memory (EEPROM) records the current measurements. In another embodiment positions may be swapped 6730 as follows with the PTC heater 6724 below the conductor 6722 patterns, and the polymers 6723 applied on the conductors of one embodiment. It shall be appreciated that other layer stack-up embodiments are contemplated and disclosed in FIGS. 98-104.

Figure 66:
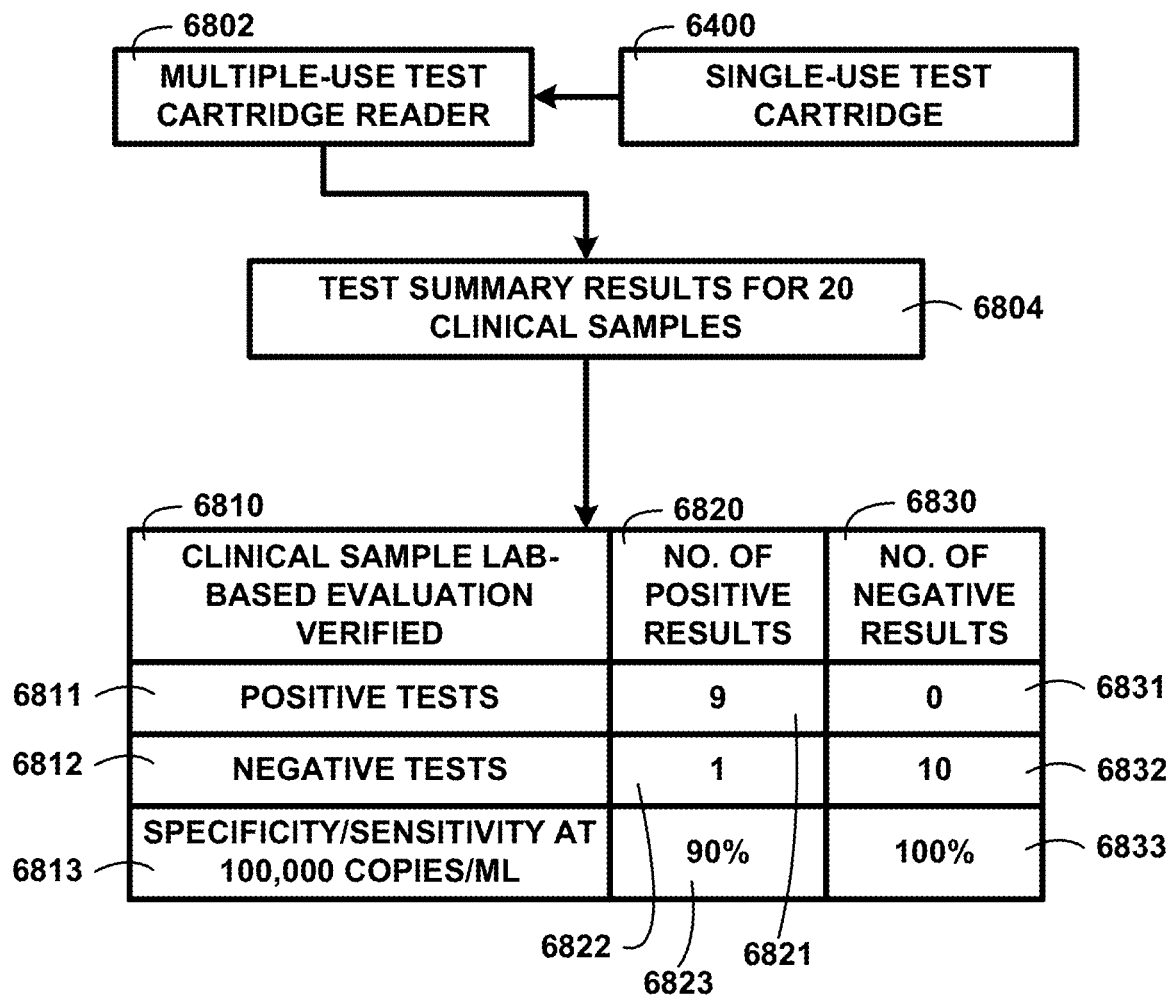
FIG. 66 shows for illustrative purposes only an example of a multiple-use test cartridge reader of one embodiment.

Multiple-Use Test Cartridge Reader:

FIG. 66 shows for illustrative purposes only an example of a multiple-use test cartridge reader of one embodiment. FIG. 66 shows the single-use test cartridge 6400 that inserts into a multiple-use test cartridge reader 6802 to determine if the test performed was positive or negative for the presence of a disease or target analyte. The test summary results for 20 clinical samples 6804 were processed for a clinical sample lab-based evaluation verified 6810 on accuracy. The lab-based test shows positive tests 6811 and negative tests 6812 at a specificity/sensitivity at 100,000 copies/ml 6813. The lab-based evaluations found the no. of positive results 6820 included 9 6821 accurate for positive and 1 6822 of the 10 was negative for a verified 90% 6823 accuracy. The no. of negative results 6830 evaluation found 0 6831 for a positive result and all 10 6832 for a verified 100% 6833 accuracy of one embodiment.

Figure 67:
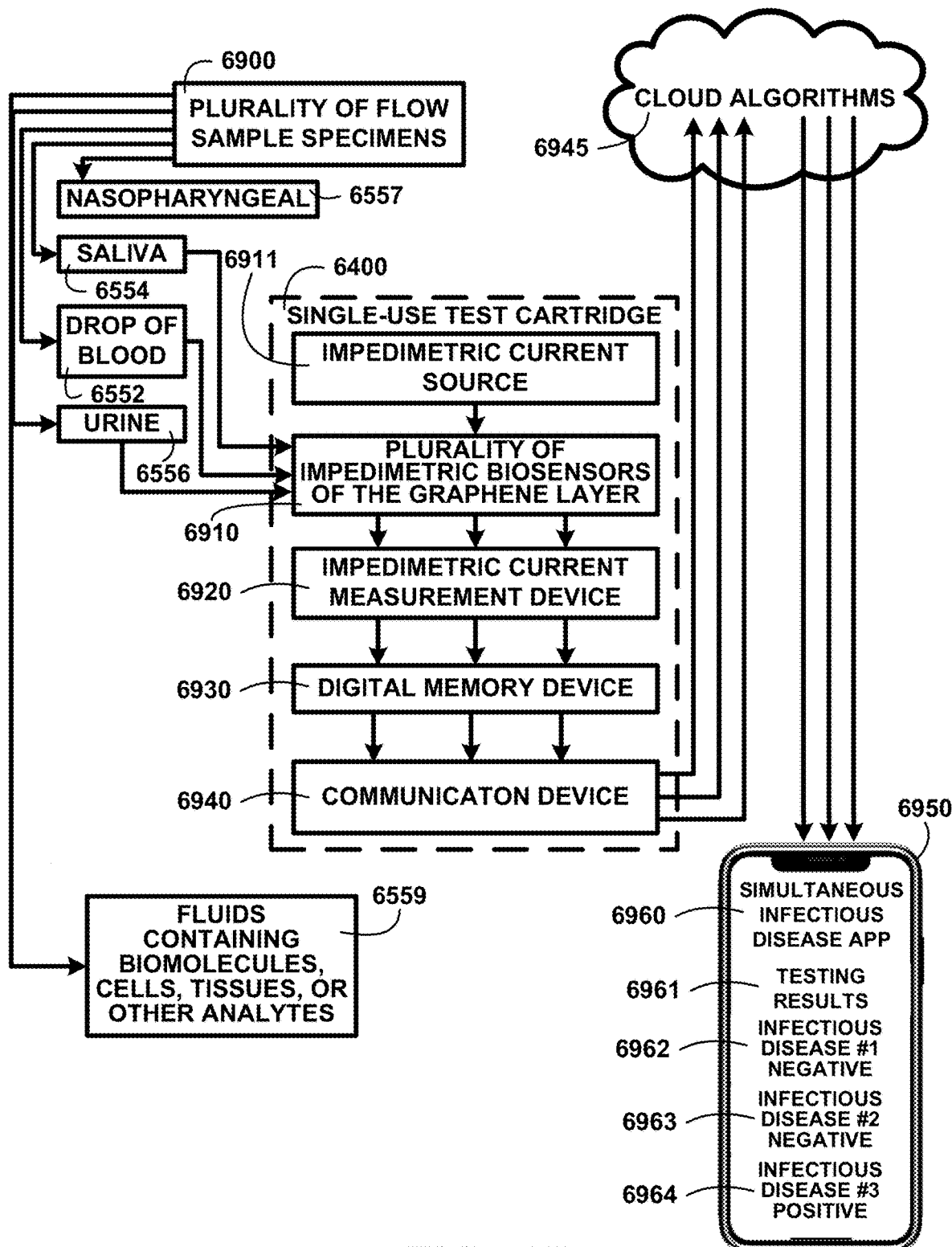
FIG. 67 shows for illustrative purposes only an example of a simultaneous disease or target analyte app of one embodiment.

Simultaneous Infectious Disease or Target Analyte App:

FIG. 67 shows for illustrative purposes only an example of a simultaneous disease or target analyte app of one embodiment. FIG. 67 shows the plurality of flow sample specimens 6900 selected for these tests including saliva 6554, nasopharyngeal 6557, drop of blood 6552, urine 6556, and other fluids containing biomolecules, cells, tissue or other analytes 6559. The selected flow sample specimens saliva 6554, nasopharyngeal 6557, a drop of blood 6552, urine 6556, and fluids containing biomolecules, cells, tissue or other analytes 6559 are deposited into the plurality of impedimetric biosensors 6910 of the single-use test cartridge 6400.

The single-use test cartridge 6400 includes an impedimetric current source 6911 for conducting impedimetric testing with the plurality of impedimetric biosensors 6910. An impedimetric current measurement device 6920 measures any changes in the impedance occurring in the plurality of impedimetric biosensors 6910 with the depositions of the selected flow sample specimens. The impedimetric current measurements are recorded in a digital memory device 6930.

The recorded impedimetric current measurement data is transmitted with a communication device 6940 to the cloud algorithm 6945 for analysis and determinations of the testing results. The cloud wirelessly transmits the testing results to a user's smartphone 6950 having a simultaneous disease or target analyte app 6960. The simultaneous disease or target analyte app 6960 displays the testing results 6961 including for this example disease #1 negative 6962, infectious disease #2 negative 6963, and infectious disease #3 positive 6964. The user-patient is now aware of the infection and can contact a healthcare provider to discuss treatment of one embodiment.

Figure 68:
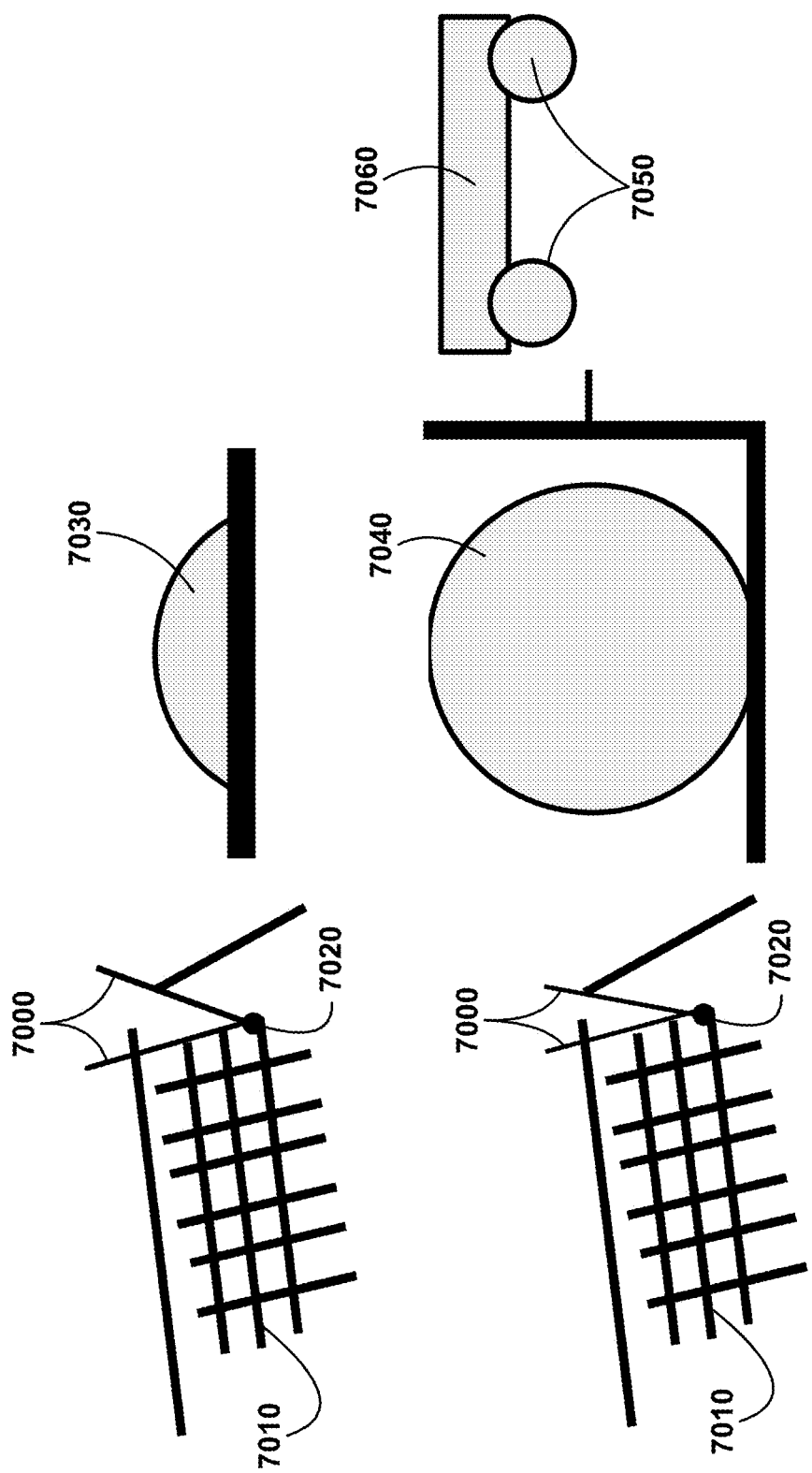
FIG. 68 shows for illustrative purposes only an example of an overview of inkjet printing high-resolution patterns uniformly at predetermined ink particle size, surface tension, and viscosity of one embodiment.

Inkjet Printing High-Resolution Patterns Uniformly with Drop-On-Demand:

FIG. 68 shows for illustrative purposes only an example of an overview of (piezo-driven) inkjet printing high-resolution patterns uniformly at predetermined ink particle size, surface tension, and viscosity of one embodiment. FIG. 68 shows resolution of inkjet printing 7000 patterns 7010 is determined in part by the volume of the drop 7020, dots per inch (DPI), number of print layers, the drop's impact with the underlying substrate, and the spreading 7030 or retracting 7040 of the ink on the surface of the substrate. As the drop impacts the substrate after being jetted from the printer, it may rebound, splash or spread, depending on whether the surface of the substrate is wetting or non-wetting. Rebounding, splashing, or spreading affects the overall resolution of the printed feature. To help avoid the wetting or de-wetting of the printed droplets, the surface tension or energy of the substrate can be lowered. In the exemplary disclosure, changing the surface tension is accomplished by cleaning the substrate surface to be printed on with a polar, hydrophilic substance or changing the ink viscosity. Gaps between materials 7050 are filled with subsequent materials 7060. The rebound of the drop can also be avoided, specifically by adding small amounts of flexible polymer to the solvent, lowering nozzle diameter, and increasing platen temperature and ink cartridge temperature. The method of inkjet printing results in high electrical conductivity of the conductive graphene layer and an extended shelf-life.

Figure 69:
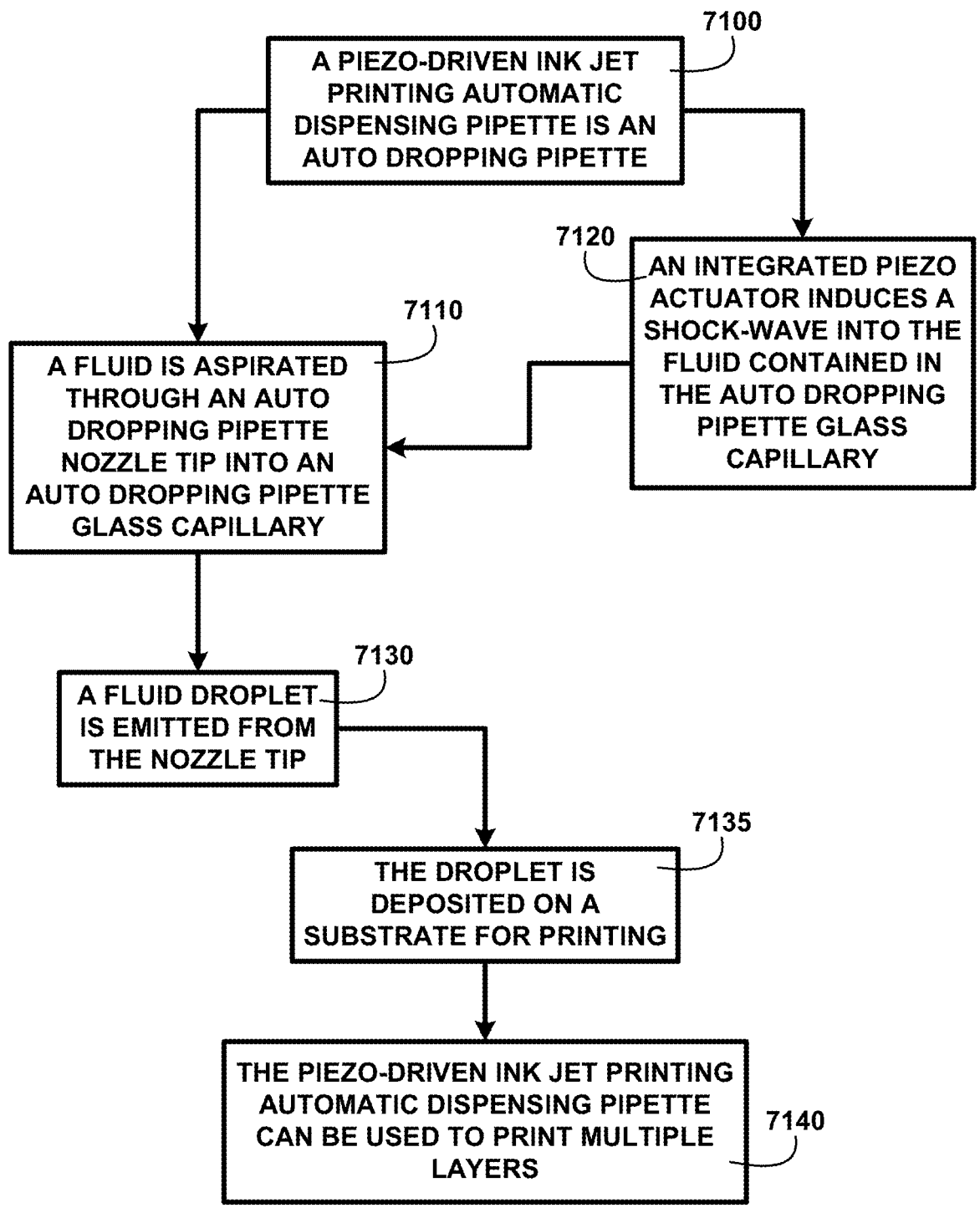
FIG. 69 shows for illustrative purposes only an example of piezo-driven ink jet printing automatic dispensing pipettes of one embodiment.

Automatic Dispensing Pipettes Based on Piezo-Driven Inkjet Printing:

FIG. 69 shows for illustrative purposes only an example of piezo-driven inkjet printing automatic dispensing pipettes of one embodiment. FIG. 69 shows a piezo-driven inkjet printing automatic dispensing pipette is an auto dropping pipette 7100. A fluid is aspirated through an auto-dropping pipette nozzle tip into an auto-dropping pipette glass capillary 7110. An integrated piezo actuator induces a shock wave into the fluid contained in the auto-dropping pipette glass capillary 7120. A droplet is emitted from the nozzle tip 7130. The droplet is deposited on a substrate for printing 7135. The piezo-driven inkjet printing automatic dispensing pipette can be used to print multiple layers 7140.

Figure 70:
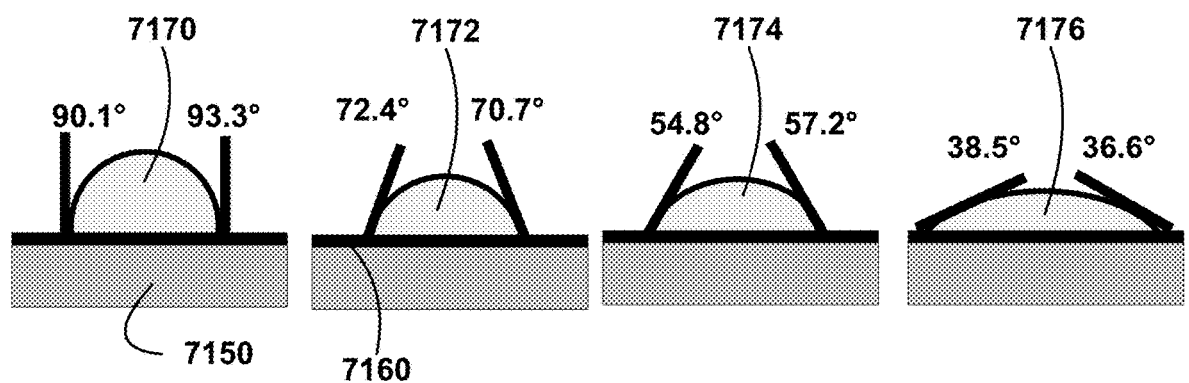
FIG. 70 shows for illustrative purposes only an example of inkjet printing contact angles of one embodiment.

Contact Angle:

FIG. 70 shows for illustrative purposes only an example of piezo-driven inkjet printing contact angles of one embodiment. FIG. 70 shows contact angles for different ink viscosities used for piezo-driven inkjet printing of high-resolution patterns on graphene 7160 deposited on a substrate 7150. After piezo-driven inkjet printing the graphene layer wettability and contact angle is measured to be between 0 and 180 degrees. An exemplary retracted drop 7170 has contact angles ranging from 90.1° to 93.3°. Exemplary drop 7172 has contact angles ranging from 72.4° to 70.7°. Exemplary drop spreading increases the contact angle reduces as seen in drop 7174 with contact angles ranging from 54.8° to 57.2° and exemplary drop 7176 contact angles ranging from 38.5° to 36.6° of one embodiment. It should be appreciated that contact angle measurements and analysis can be conducted for a wide range of print methods, including screen printing and the typical range of analysis is between 0 and 180 degrees.

Figure 71:
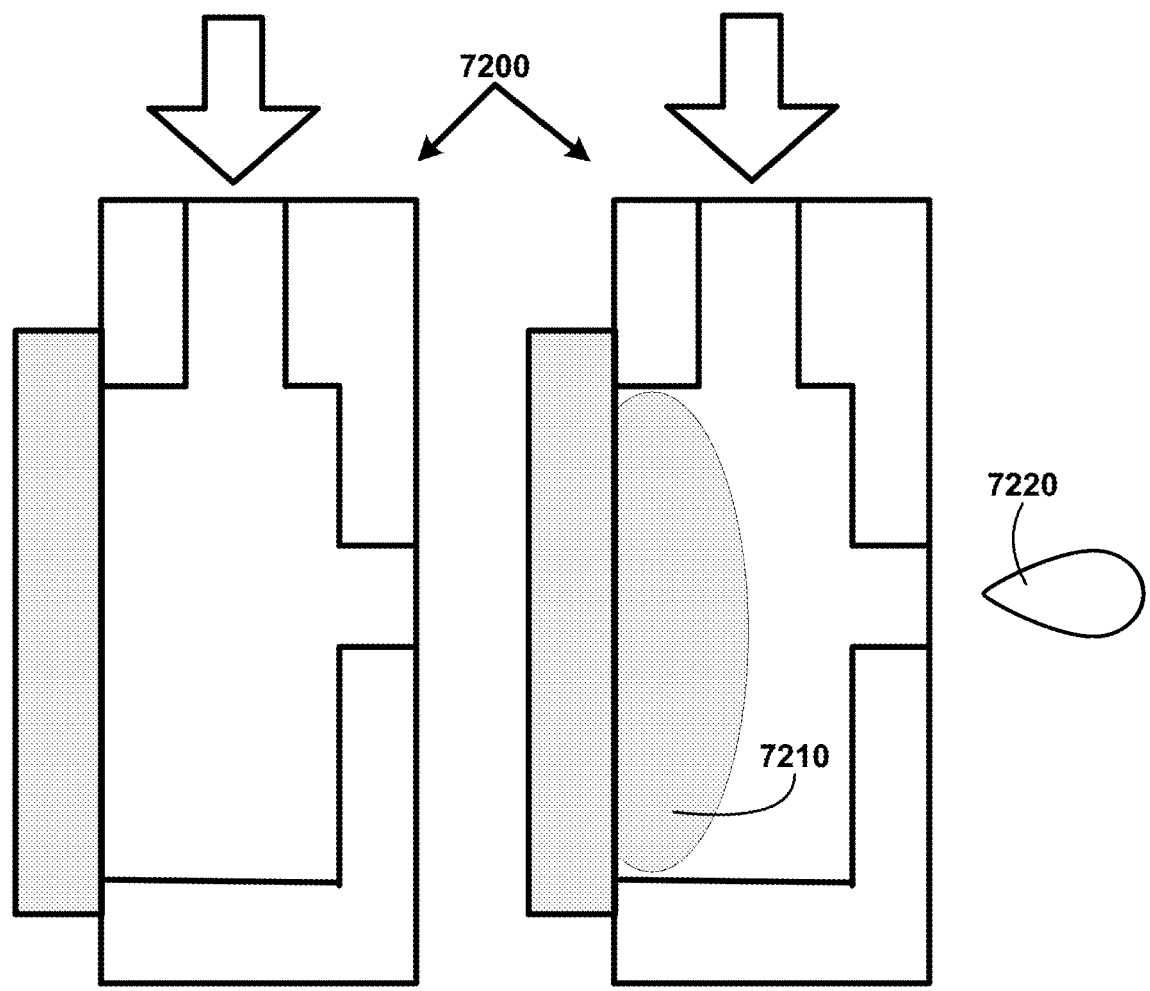
FIG. 71 shows for illustrative purposes only an example of an overview of inkjet valve printing of one embodiment.

Valve Printing Patterns for a Wide Range of Particle Sizes and Viscosities:

FIG. 71 shows for illustrative purposes only an example of an overview of inkjet valve printing of one embodiment. FIG. 71 shows traditional drop-on-demand inkjet print can be limited by fine tuning of ink viscosity and surface tension, with high viscosity inks tending to clog and not disperse uniformly. Thermal valve 7200 printing is used to overcome these challenges by applying heat to the ink, which causes bubbles 7210 to form and discharge ink particles 7220. The heating element is attached to the component that is filled with ink. An advantage to using this method is an increased print resolution of one embodiment.

Figure 72:
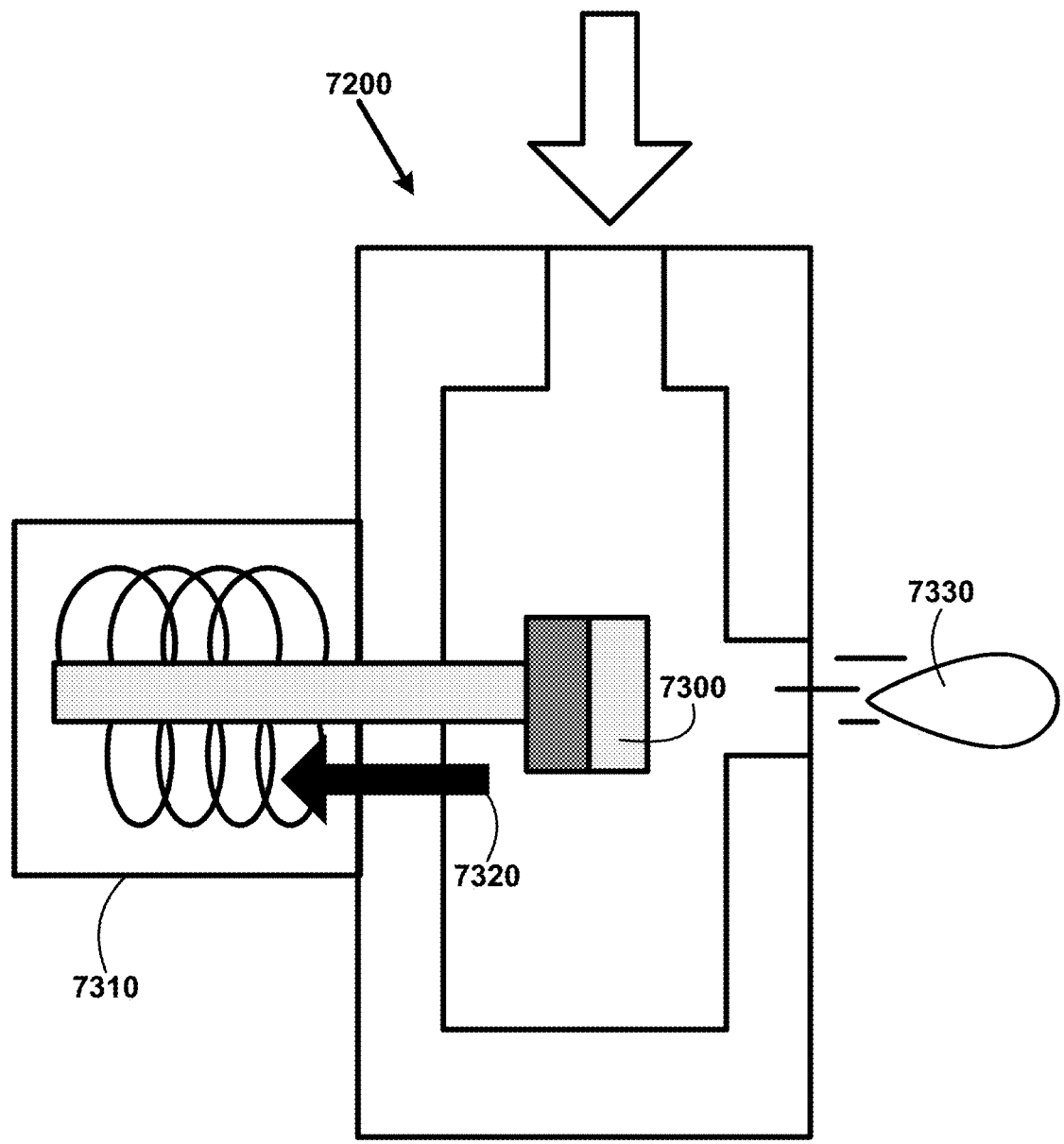
FIG. 72 shows for illustrative purposes only an example of an overview of a solenoid thermal valve inkjet printing of one embodiment.

Solenoid Thermal Valve:

FIG. 72 shows for illustrative purposes only an example of an overview of a solenoid thermal valve inkjet printing of one embodiment. FIG. 72 shows thermal valve 7200 printing with another type of thermal valve 7300 printing uses a solenoid 7310 to open and close the nozzle cover, which discharges ink particles. By opening and closing 7320 the valve, the pressurized ink is discharged from the nozzle 7330 this allows the distance between the nozzle and target to be increased of one embodiment.

Figure 73:
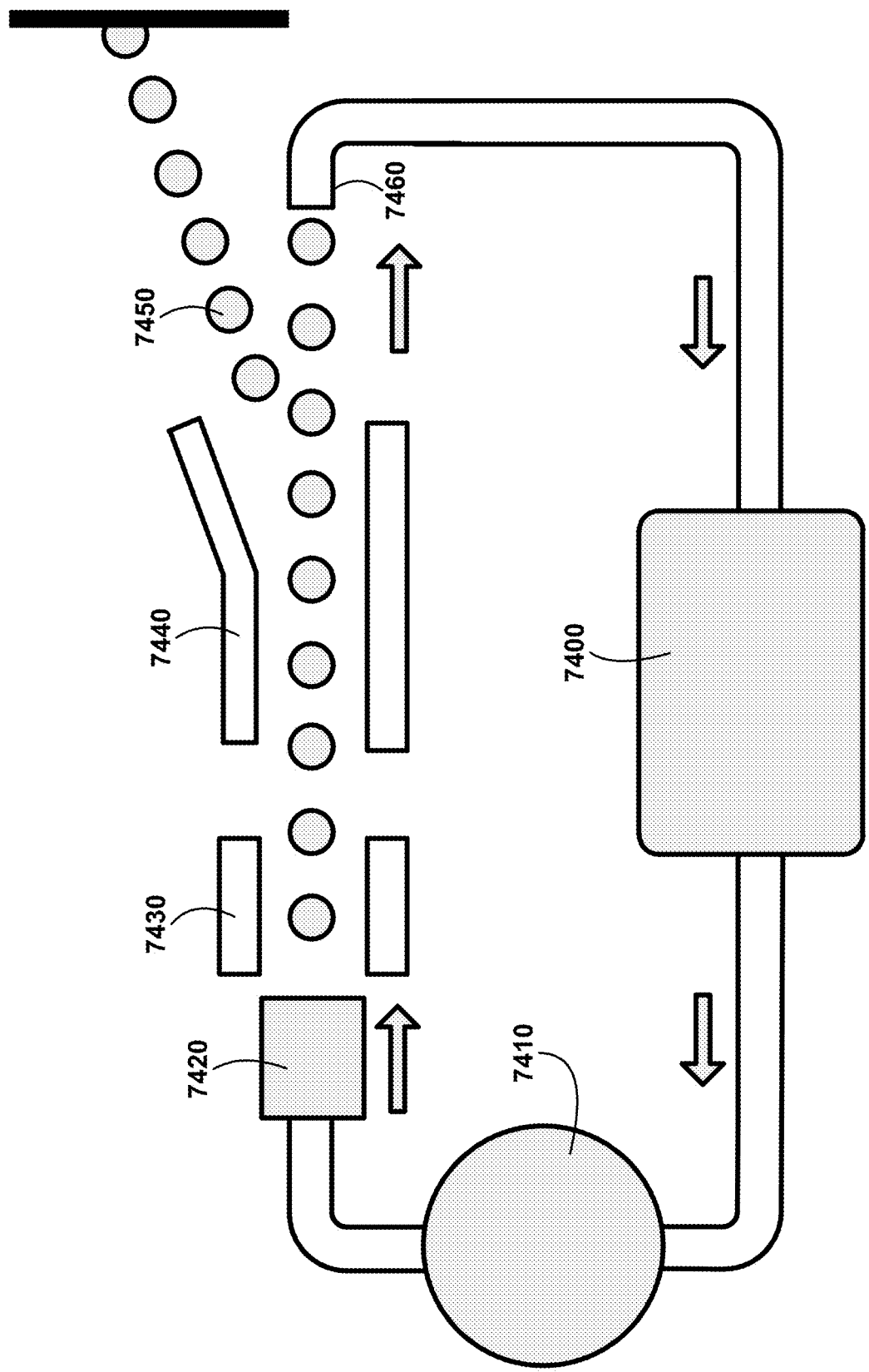
FIG. 73 shows for illustrative purposes only an example of Continuous Valve printing of one embodiment.

Continuous Valve Printing:

FIG. 73 shows for illustrative purposes only an example of Continuous Valve printing of one embodiment. FIG. 73 shows valve printing can also be performed in a continuous fashion with a pump 7410, whereby the ink particles 7450 are continuously discharged from the nozzle 7420. The ink particles 7450 pass-through charging electrodes 7430 and are charged with electrostatic and deflecting electrodes 7440 are used to deflect the ink particles so that they are sprayed on the printing surface. Ink particles that are not deflected are collected with a gutter 7460, returned to the ink tank 7400, and reused. Even when printing is not being performed, ink is continuously discharged at all times, which prevents inks from drying and clogging the print heads of one embodiment.

Figure 74:
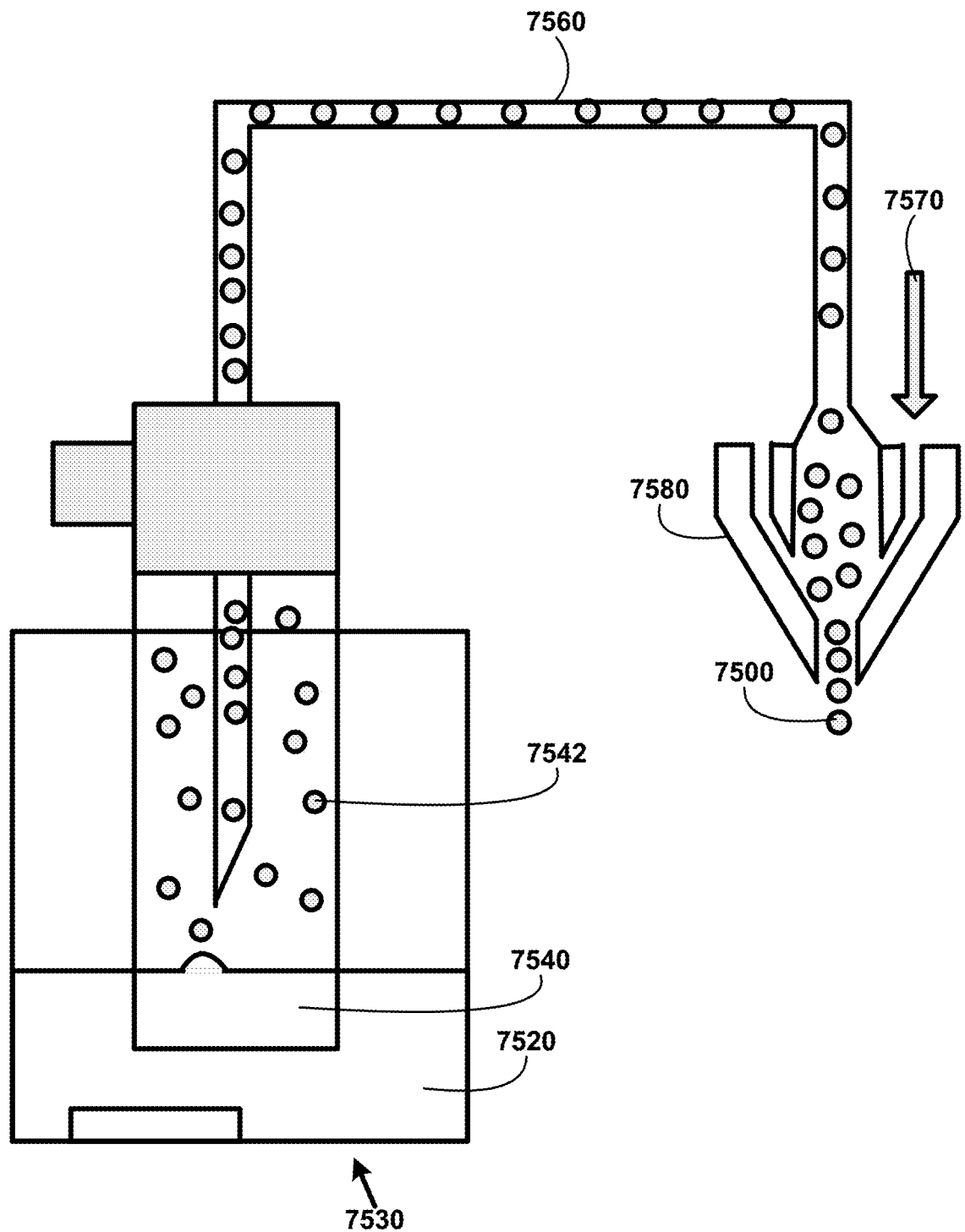
FIG. 74 shows for illustrative purposes only an example of aerosol printing of one embodiment.

Aerosol Printing for Uniform Deposition of Thin Layers:

FIG. 74 shows for illustrative purposes only an example of aerosol printing of one embodiment. FIG. 74 shows the uniform deposition of a thin layer of nanomaterial. The method uses aerodynamic focusing 7500 to deposit electronic inks precisely and accurately onto substrates. The ink 7540 is placed into an atomizer 7530 with water or other solvents 7520, which creates a dense mist of material-laden droplets 7542. The aerosol mist is then delivered 7560 to the deposition head 7580 where it is focused by a sheath gas 7570, which surrounds the aerosol 7500 as an annular ring of one embodiment. The aerosol jet process minimizes graphene ink utilization and waste by only depositing graphene ink or other nano inks at a thickness of less than 1 micron.

Ultrasonic Spray Coating for Tight Drop Distribution without Clogging:

FIG. 75 is a block diagram of an overview of ultrasonic spray coating of one embodiment. FIG. 75 shows ultrasonic spray coating, a low-velocity spray that creates uniform micron or sub-micron thickness layers. Ultrasonic nozzles operate by converting high-frequency sound waves into mechanical energy that is transferred to a liquid, creating standard waves. Ultrasonic spray coating is used for tight drop distribution without clogging 7600. Ultrasonic spray coating is a low-velocity spray that creates uniform micron or sub-micron and sub-micron thickness layers typically ranging from 10μ to 39μ 7610. Ultrasonic nozzle frequency is measured in kHz 7620. Ultrasonic nozzles operate at a specific resonance frequency, which dictates the median droplet size 7630. As the liquid exists on the atomizing surface of the nozzle, it is broken into a fine mist of uniform micron or sub-micron-sized droplets. Unlike pressure nozzles, ultrasonic nozzles do not force liquids through a small orifice using high pressure to produce a spray. The liquid is fed through the center of a nozzle with a relatively large orifice, without pressure, and is atomized due to ultrasonic vibrations in the nozzle. Ultrasonic nozzles operate at a specific resonance frequency, which dictates the median droplet size. Droplet sizes have little variance and can be calculated to fall within a tight predicted drop size distribution. For example, a 120 kHz nozzle produces a drop size of 13 microns. The higher the frequency, the smaller the median drop size. Drop size can be as large as 39 microns and as small as less than 10 microns.

Figure 76:
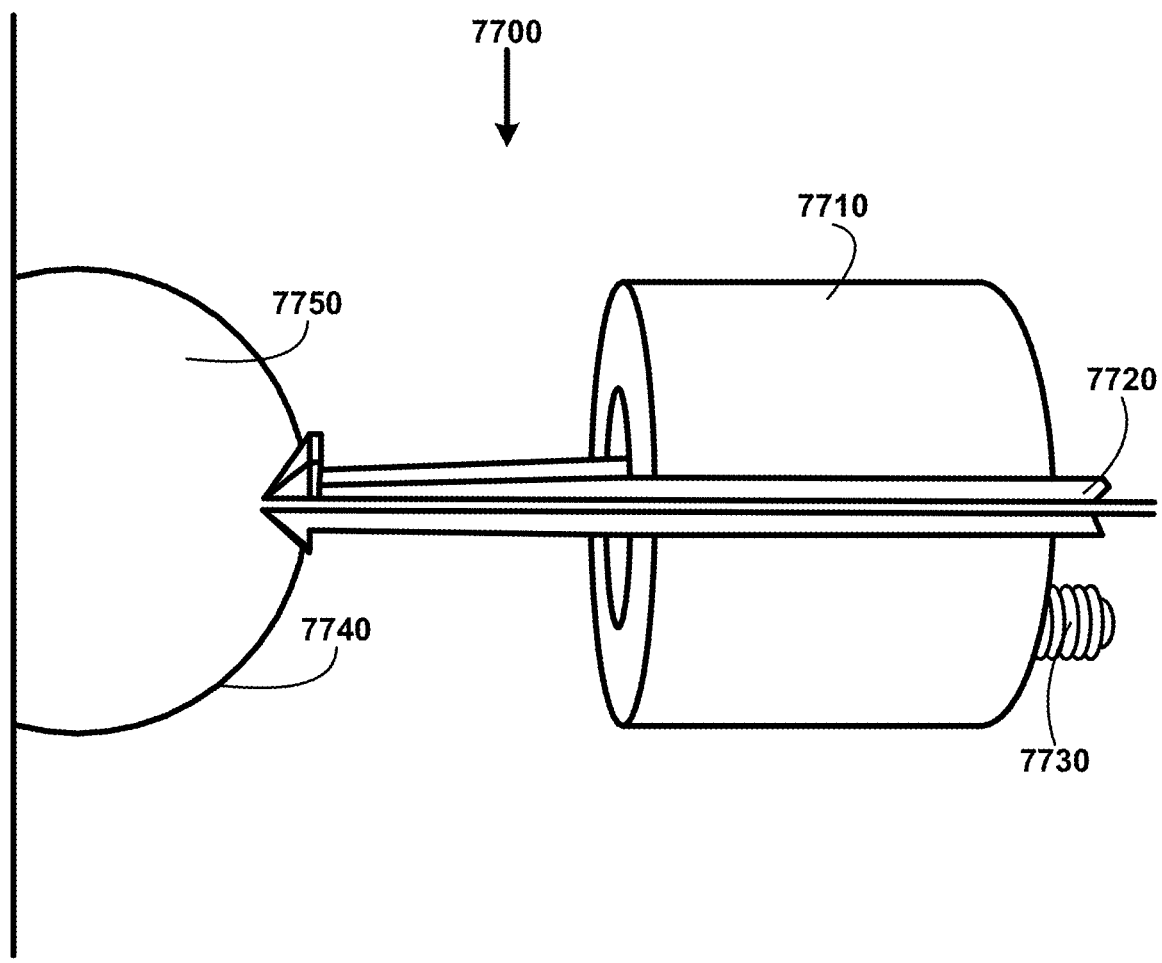
FIG. 76 shows for illustrative purposes only an example of an ultrasonic nozzle of one embodiment.

Ultrasonic Nozzle:

FIG. 76 shows for illustrative purposes only an example of an ultrasonic nozzle of one embodiment. FIG. 76 shows an ultrasonic nozzle 7700. The ultrasonic nozzle 7700 includes a housing 7710, liquid feed channel 7720, and an electrical connector to the ultrasonic generator. The liquid is applied to an atomizing surface 7740. The atomized liquid creates a soft, low-velocity spray 7750 of one embodiment. In one embodiment, a nozzle is used to generate low-velocity air to produce a precise spray plume shape of droplets that limits overspray. A dry spray method allows for very thin, multi-pass layers, while the wet coat method relies heavily on the chemical properties of the solution. Dot pattern spraying each sensor and purging the nozzle before each spray is a quick method to disperse graphene onto the sensor. Area pattern spray, a heated vacuum plate is used to dry the sensor after printing, and air pressure is used to achieve a uniform deposition of materials. In some embodiments, a stencil or mask can be used to limit overspray and generate more precise dispositions and cleaner resolutions.

Figure 77:
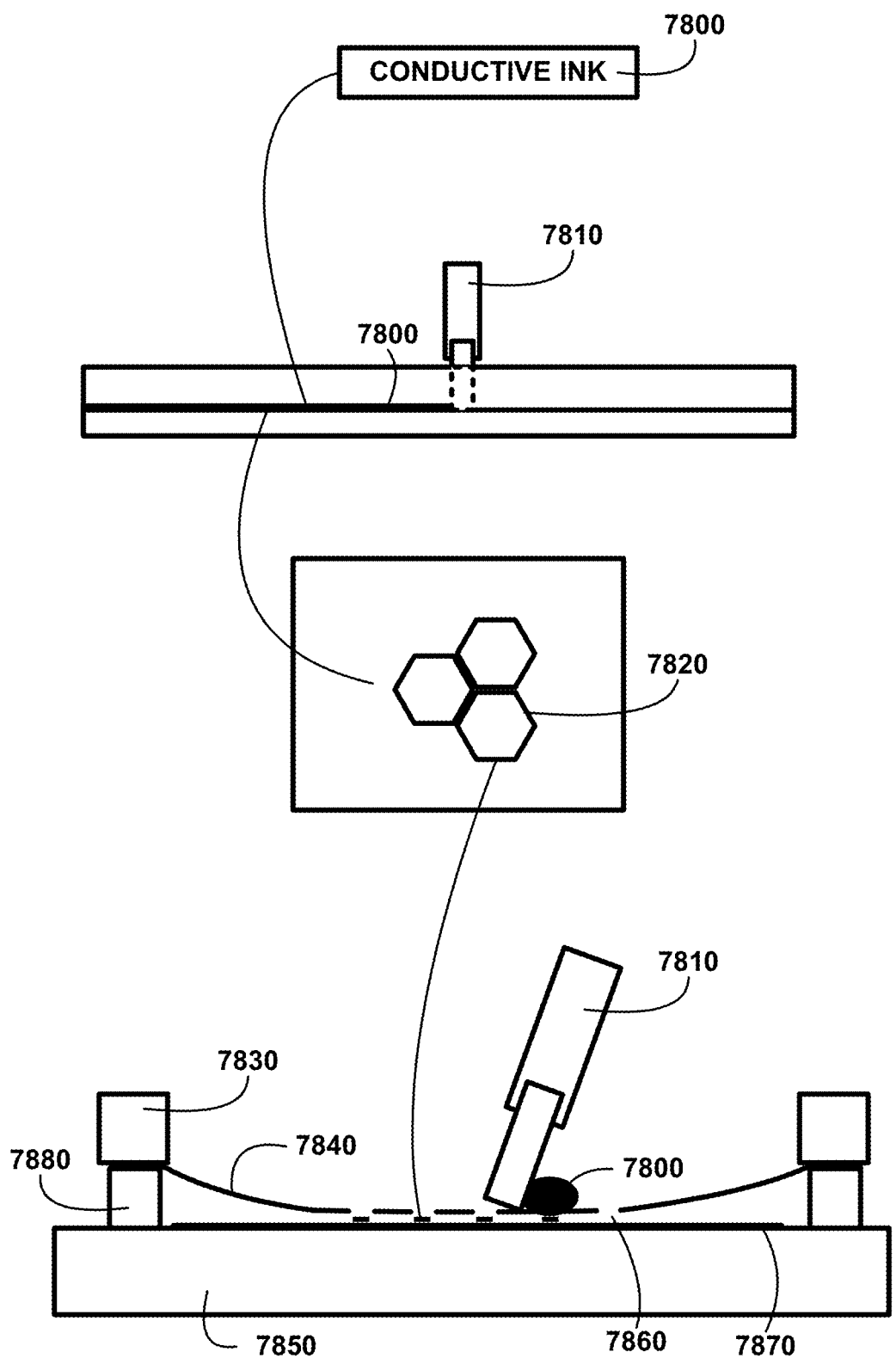
FIG. 77 shows for illustrative purposes only an example of screen-printing of one embodiment.

Screen-Printing Graphene Ink for Improved Resolution:

FIG. 77 shows for illustrative purposes only an example of screen-printing of one embodiment. FIG. 77 shows achieving high-resolution patterns of pristine graphene using screen printing remains a major challenge, primarily because of the material's inherent tendency to aggregate or clump. Conventional screen-printing methods are restricted to resolutions greater than 1 μm, impeding the drive for the fabrication of finer patterns to facilitate higher integration density and improved performance. The screen printing applies a conductive ink 7800 with a squeegee 7810 through a graphene pattern 7820. A screen frame 7830 on top of a spacer 7880 supports a screen mesh 7840 that incorporates the pattern 7860 to be printed. A base plate 7850 is covered with a substrate 7870 upon which the screen-printing pattern is applied. The resolution of screen printing is highly dependent on the quality of the stencil, which is generally prepared using a photochemically defined emulsion coated on a screen mesh. Although finer patterns of the stencil are expected to improve printing resolution, the low lithography resolution of the emulsion layer and mesh dimensions restricts the improvement in printing resolution. Thus, it is a challenge to develop sub-micron high-resolution stencils that can be applied to screen-printing of graphene for printed electronics. In certain embodiments, achieving a sub-micron print requires diluting the graphene ink with solvents, then adding a polymer binder to increase graphene ink viscosity of 5 to 100 Pa·s. or a viscosity range suitable for screen printing. Ink solvents can include organic solvents in any of four isomeric monoterpenoids such as terpineol, cyclohexanone or other relative organic solvents such as amines, acetone, acetonitrile, alcohols, dichloromethane, dimethylformamide, dimethylsulfoxide, esters, ethers, ethanol, butanol, formaldehyde, ethyl acetate, ethyl lactate, octyl acetate, ethylene glycol diacetate, diethylene glycol, propylene glycol, diacetone acrylamide, hexane, heptane, toluene, tetrahydrofuran, xylene, methanol, methylene chloride, nitrates, chloroform, bromoform, and mixtures containing both halogenated and nonhalogenated organic solvents. Polymer binders can include conductive insulating semiconducting polymers such as: ethyl cellulose, nitrocellulose, or other derivatives of cellulose in which some of the hydroxyl groups on the repeating glucose units are converted into ethyl ether groups. Other polymers that can be used include polyethylene (PE), polypropylene (PP), polyvinyl chloride (PVC), polystyrene (PS), p-phenylenediamine (PPD), nylon, Teflon® (polytetrafluoroethylene), thermoplastic polyurethane (TPU), PEDOT (Poly(3,4-ethylenedioxythiophene), PSS (Poly(styrenesulfonate), Polyaniline (PANI), Polypyrrole (PPy), Polythiophene (PT), Polyacetylene, Poly(p-phenylene vinylene) (PPV), Polyfluorene, Poly(3-hexylthiophene) (P3HT), Polyaniline-Poly(methyl methacrylate) (PANI-PMMA) Blends, Poly(3,4-propylenedioxythiophene) (PProDOT), Poly(3,4-ethylenedioxypyrrole) (PEDOP), Poly[2-methoxy-5-(2-ethylhexyloxy)-1,4-phenylenevinylene] (MEH-PPV), Poly(3-methylthiophene) (P3MT), Polyindole (Pln), Poly(3,4-ethylenedioxythiophene)-poly(styrenesulfonate) (PEDOT:PSS). Other ink properties suitable for screen printing include a solid content between 1% and 50%; a sub-micron film thickness after curing; a particle size of less than 10 microns and a density of 0.5-1.5 g/mL.

Figure 78:
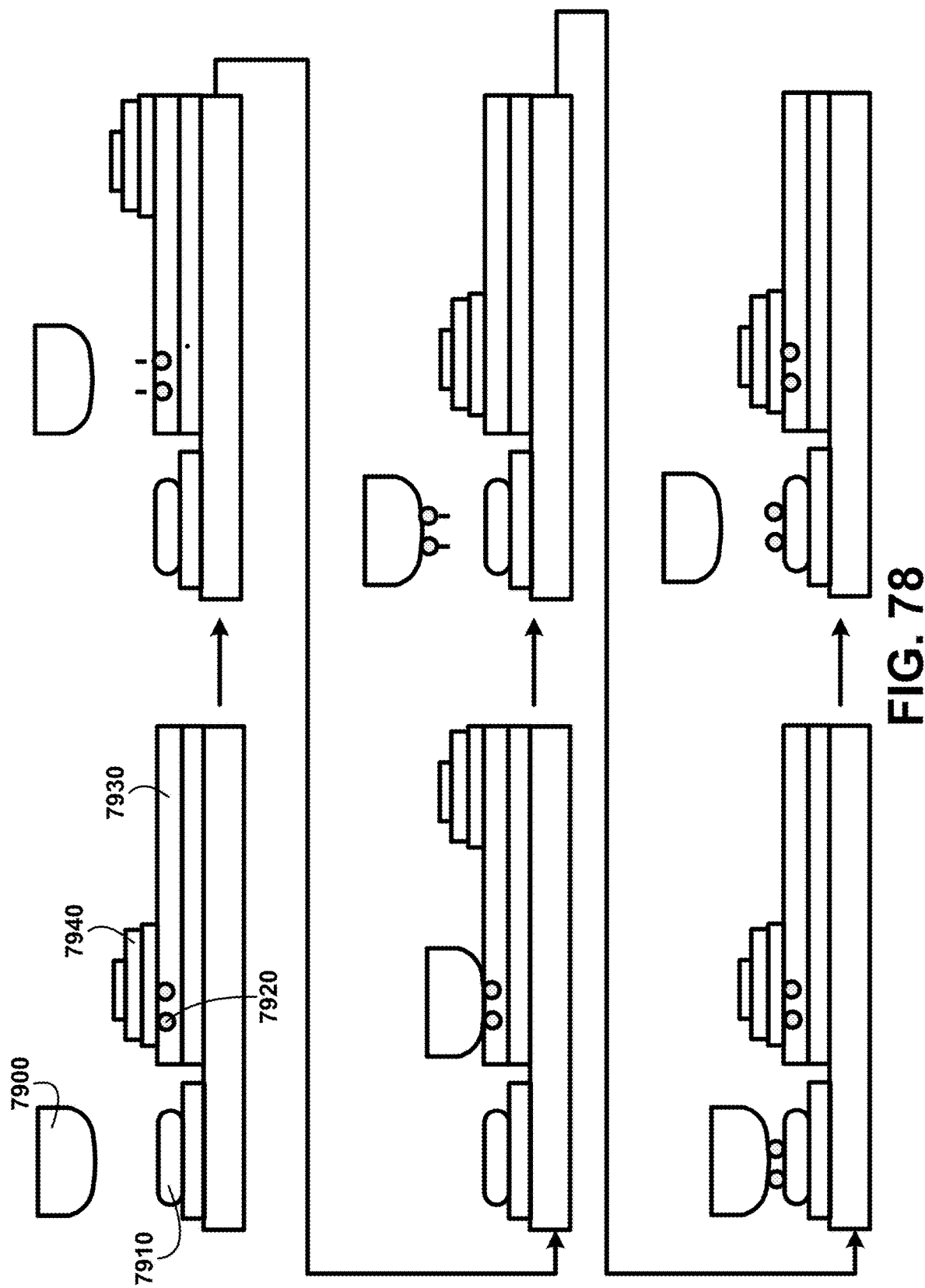
FIG. 78 shows for illustrative purposes only an example of an overview of pad printing multiple thicknesses and dimensions of one embodiment.

Pad Printing Material with Varying Patterns, Thicknesses, and Dimensions:

FIG. 78 shows for illustrative purposes only an example of an overview of pad printing multiple thicknesses and dimensions of one embodiment. FIG. 78 shows the process involves an offset printing process whereby an image is transferred from a pad onto a substrate. Pad printing is used to print on surfaces that can be damaged by other forms of printing or whereby other methods of printing do not produce the required level of adhesion. Physical changes within the ink film allow it to leave an etched image area for adhering to the pad and subsequently releasing from the pad as it adheres to the substrate. The unique properties of the pad enable the pad to transfer ink to the sensor substrate. The pad printing cycle takes place in several steps: (A) rest position with (1) pad 7900, (2) substrate 7910, (3) inked engraved pattern 7920, (4) cliché 7930, and (5) ink cup 7940. (B) The ink cup moves to allow the thinner from the top surface of the inked engraved pattern to evaporate. At the same time, the pad moves laterally to the position above the ink to be transferred. (C) The pad moves down to pick up the patterned ink film. (D) The pad moves up first and then moves laterally above the substrate. During this time, the thinner from the lower surface of the ink film evaporates. (E) The pad moves down in contact with the substrate to deposit the ink film while the ink cup returns over the cliché pattern to fill it with ink. (F) The pad goes up and the ink layer is deposited on the substrate of one embodiment.

Figure 79:
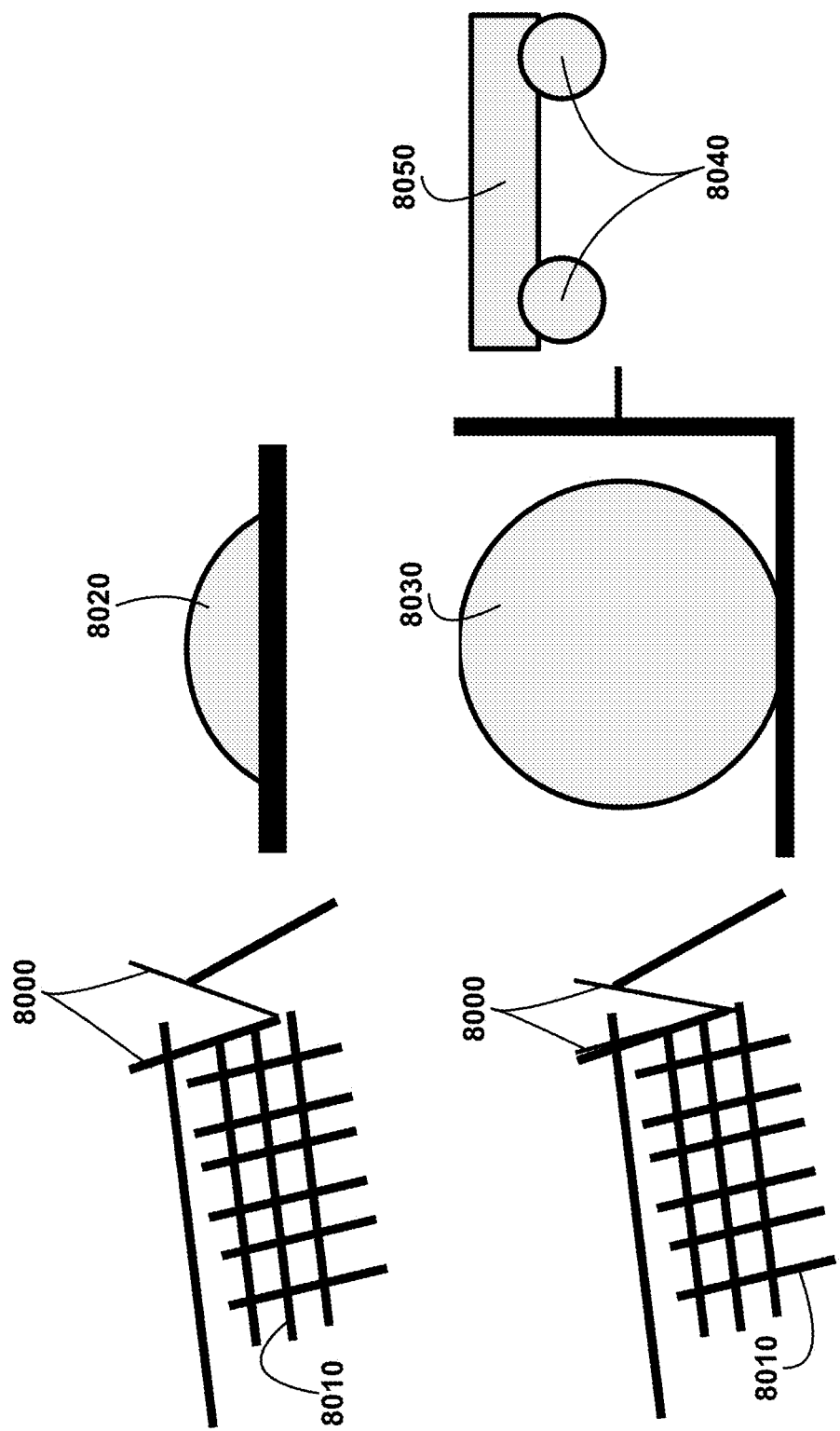
FIG. 79 shows for illustrative purposes only an example of an overview of 3D printing material with varying dimensions and densities of one embodiment.

3D Printing Material with Varying Dimensions, Densities, and Structures:

FIG. 79 shows for illustrative purposes only an example of an overview of 3D printing material with varying dimensions and densities of one embodiment. FIG. 79 shows that 3D inks can be printed into volumetric structures comprised of one or more layers. The inks have moderate viscosity; have rapid drying times; are self-supporting upon deposition and have an extended shelf-life. 3D printed inks and related materials employ an evaporation-driven solidification mechanism, whereby an ink is formulated by dissolving a polymer in a fast-evaporating solvent such as chloroform, trichloromethane, dichloromethane or other organochlorine or chloromethane compounds. The ink is extruded at ambient or near ambient temperatures and rapidly solidifies as the solvent evaporates and the polymer comes out of the solution. 3D printing graphene ink has a moderate viscosity requirement (25-35 Pa·s) and graphene suspension comprises graphene, dissolved elastomeric polymer binder, and a mixture of solvents that can be 3D printed (or used with any standard syringe 8000) from a nozzle (50-2,000 μM) in diameter under ambient conditions to rapidly create 3D graphene-based constructs in a continuous line 8010 that can be handled immediately with no drying time required. The Ink viscosity may create the spreading 8020 or retracting 8030 of the ink on the surface of the substrate. Gaps between 3D materials 8040 are filled with subsequent 3D materials 8050. Typically, 3D-printed ink produces a film thickness of greater than 1 μM. In certain embodiments, achieving a sub-micron print requires diluting the ink with solvents, then adding a polymer binder to increase graphene ink viscosity to a range suitable for 3D printing. Ink solvents can include organic solvents such as terpineol, cyclohexanone or other relative organic solvents such as amines, acetone, acetonitrile, alcohols, dichloromethane, dimethylformamide, dimethylsulfoxide, esters, ethers, ethanol, butanol, formaldehyde, ethyl acetate, ethyl lactate, octyl acetate, ethylene glycol diacetate, diethylene glycol, propylene glycol, diacetone acrylamide, hexane, heptane, toluene, tetrahydrofuran, xylene, methanol, methylene chloride, nitrates, chloroform, bromoform, and mixtures containing both halogenated and nonhalogenated organic solvents. Polymer binders can include ethyl cellulose or other derivatives of cellulose in which some of the hydroxyl groups on the repeating glucose units are converted into ethyl ether groups. Other polymers that can be used include polyethylene (PE), polypropylene (PP), polyvinyl chloride (PVC), polystyrene (PS), p-phenylenediamine (PPD), nylon, Teflon® (polytetrafluoroethylene) or thermoplastic polyurethane (TPU), PEDOT (Poly (3,4-ethylenedioxythiophene), PSS (Poly(styrenesulfonate), Polyaniline (PANI), Polypyrrole (PPy), Polythiophene (PT), Polyacetylene, Poly(p-phenylene vinylene) (PPV), Polyfluorene, Poly(3-hexylthiophene) (P3HT), Polyaniline-Poly(methyl methacrylate) (PANI-PMMA) Blends, Poly(3, 4-propylenedioxythiophene) (PProDOT), Poly(3,4-ethyl-enedioxypyrrole) (PEDOP), Poly[2-methoxy-5-(2-ethylhexyloxy)-1,4-phenylenevinylene] (MEH-PPV), Poly (3-methylthiophene) (P3MT), Polyindole (Pln), Poly(3,4-ethylenedioxythiophene)-poly(styrenesulfonate) (PEDOT: PSS).

Figure 80:
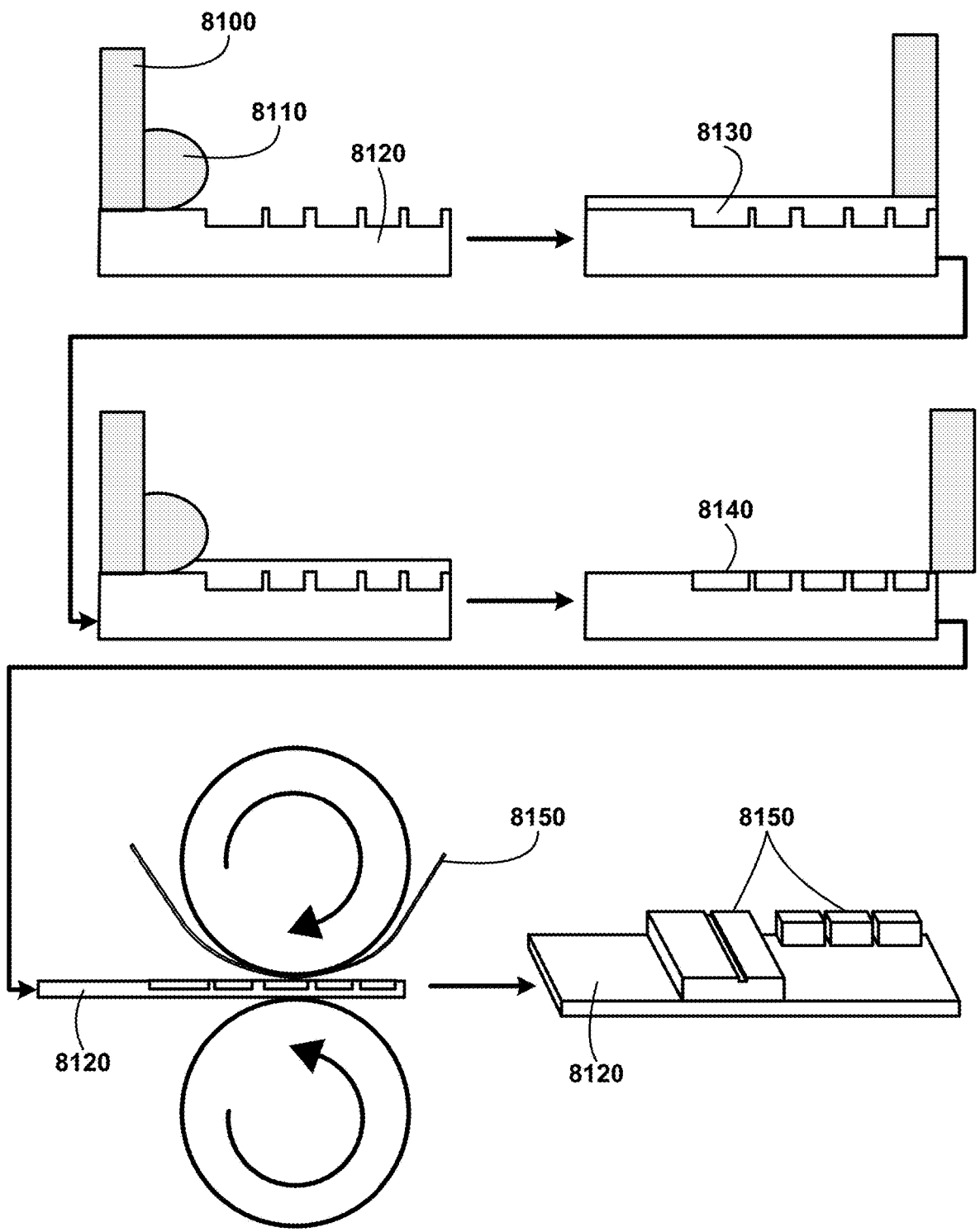
FIG. 80 shows for illustrative purposes only an example of an overview of gravure printing of material at the high-speed, roll-to-roll deposition of functional materials with high resolutions of one embodiment.

Gravure Printing Material with Uniform Characteristics and Sub-Micron Particles:

FIG. 80 shows for illustrative purposes only an example of an overview of gravure printing of material at the high-speed, roll-to-roll deposition of functional materials with high resolutions of one embodiment. FIG. 80 shows gravure printing requires a smaller particle size. The exemplary embodiment of few-layer graphene flakes, with a typical thickness of ~2 nm and a lateral size of approximately 50 nm×50 nm. Other major factors that impact gravure printing include viscosity and surface tension. Surface tension is determined largely by binders and solvents in the ink 8110 and viscosity determines printed dot size. Low-viscosity inks produce larger dot sizes than high-viscosity inks. This is due to greater ink spreading on the gravure plate 8120 substrate for low-viscosity inks. Lower viscosity inks also tend to produce anisotropic dots with an empty center and an extended tail of ink residue along the direction of doctoring. During the flooding 8130 step (C), the graphene ink (0.1 g) was flooded onto the gravure plate 8120 using the doctor blade 8100 at 70 degrees and a typical speed of 5 cm/s. Doctor blading 8140 was then performed at 55 degrees, also at a typical speed of 5 cm/s. The ink in the cells is transferred to the substrate through a nip consisting of a soft and a hard roll at a speed equivalent to the doctoring speed. To print patterns the first printed layer is dried in air for 5 minutes before printing the second layer. Other methods involve not drying layers between prints. The substrate orientation relative to the printing direction was maintained, while the gravure pattern 8150 was rotated, such that the process more closely resembles a continuous web process.

Figure 81:
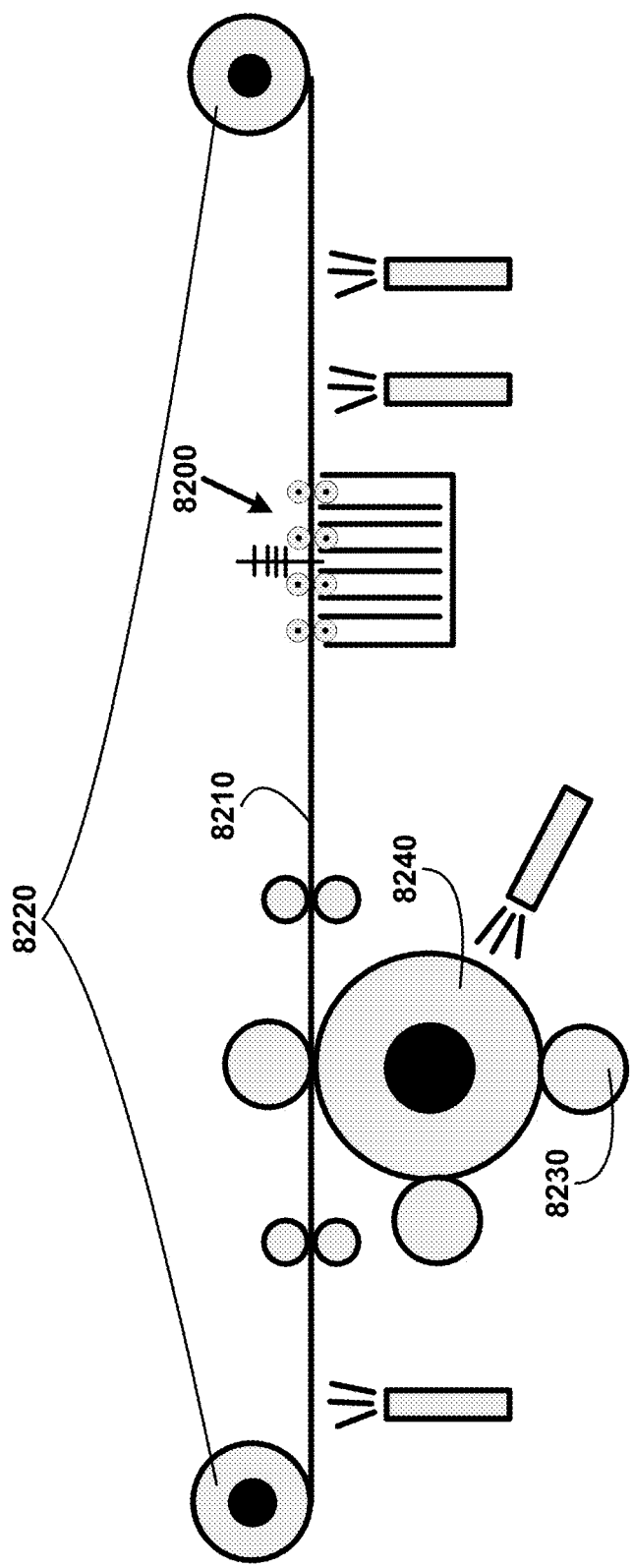
FIG. 81 shows for illustrative purposes only an example of an overview of flexographic microcontact printing of material at the high-speed, roll-to-roll deposition of functional materials with micron and sub-micron resolutions, and more than one dimension of one embodiment.

Flexographic Microcontact Printing with Improved Resolution:

FIG. 81 shows for illustrative purposes only an example of an overview of flexographic microcontact printing of material at the high-speed, roll-to-roll deposition of functional materials with micron and sub-micron resolutions and more than one dimension of one embodiment. FIG. 81 shows the exemplary embodiment presents using an elastomeric stamp 8200 to transfer sub-micron patterns onto a substrate 8210 via ink monolayers. The integration of microcontact printing into a roll-to-roll system 8220 enables continuous printing at high resolutions. The typical flexography system comprises four rollers. Ink is collected by the collecting cylinder 8230 and transferred to the Anilox roller 8240 or a cylinder with engraved patterns. The patterns on the Anilox roller are filled with ink and doctored off to remove the excessive ink. Then, the printed pattern is transferred intermediately to the substrate through the printing roller. This direct contact printing process benefits from the printing roller made of rubber (or polymer), which can be more pliable to reduce the impact of the rollers onto the thin film, minimizing the creases and scratches on the substrates. The process is simple and industrially scalable, which is highly applicable for the printing of inks with graphene and other Van Der Waal materials.

Figure 82:
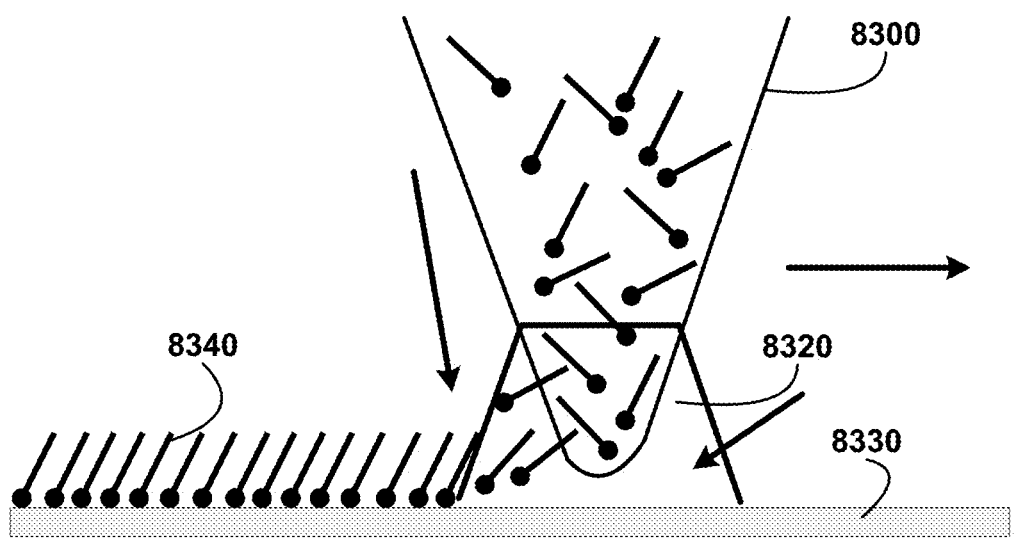
FIG. 82 shows for illustrative purposes only an example of an overview of methods of nanolithography printing of material at the nanometer scale of one embodiment.

Nanolithography Methods for Patterning, Etching, Depositing, Writing, and Printing of Nanomaterials:

FIG. 82 shows for illustrative purposes only an example of an overview of methods of nanolithography printing of material at the nanometer scale of one embodiment. FIG. 82 shows nanolithographic methods include: photolithography, scanning lithography, soft lithography, and other miscellaneous nanolithography techniques. Photolithography or optical lithography uses light to produce a patterned thin film of nanomaterials 8340 over a substrate 8330 to protect the selected areas with a water meniscus 8320 during subsequent etching, deposition, or implantation operations. Typically, ultraviolet light is used to transfer a geometric design from an optimal mask to a light-sensitive chemical coated on the substrate. Other types of light that can be used include ultraviolet and X-rays. The wavelength of light used determines the minimum feature size that the light can impress on the photoresist. Quantum optical lithography is a diffraction-unlimited method able to write at a resolution as low as 1 nanometer.

Scanning lithography is another technique for patterning at the nanometer scale down to individual atoms using scanning probes, either by etching away unwanted material or by directly writing new material onto the substrate. Some of the important techniques leveraged include dip-pen nanolithography, thermochemical nanolithography, thermal scanning probe lithography, and local oxidation nanolithography. Dip-pen nanolithography, where an atomic force microscope (AFM) tip 8300 is used to create patterns directly on a range of substances with a variety of inks is the most widely used of these techniques.

Protein beam writing uses a focused beam of high energy (MeV) protons to pattern-resist material at nano dimensions well below 100 nanometers. Charged-particle techniques include ion- and electronic projection lithographies. Soft lithography uses elastomer material made from different chemical compounds such as polydimethylsiloxane. Elastomers are used to make a stamp, mold, or mask (photomask) which in turn is used to generate micro patterns and microstructures. Examples of soft lithography techniques include PDMS lithography, microcontact printing, and multilayer soft lithography. Examples of miscellaneous nanolithography techniques include nanoimprint lithography, magnetolithography, nanofountain drawing, nanosphere lithography, neutral particle lithography, plasmonic lithography, and stencil lithography.

Figure 83:
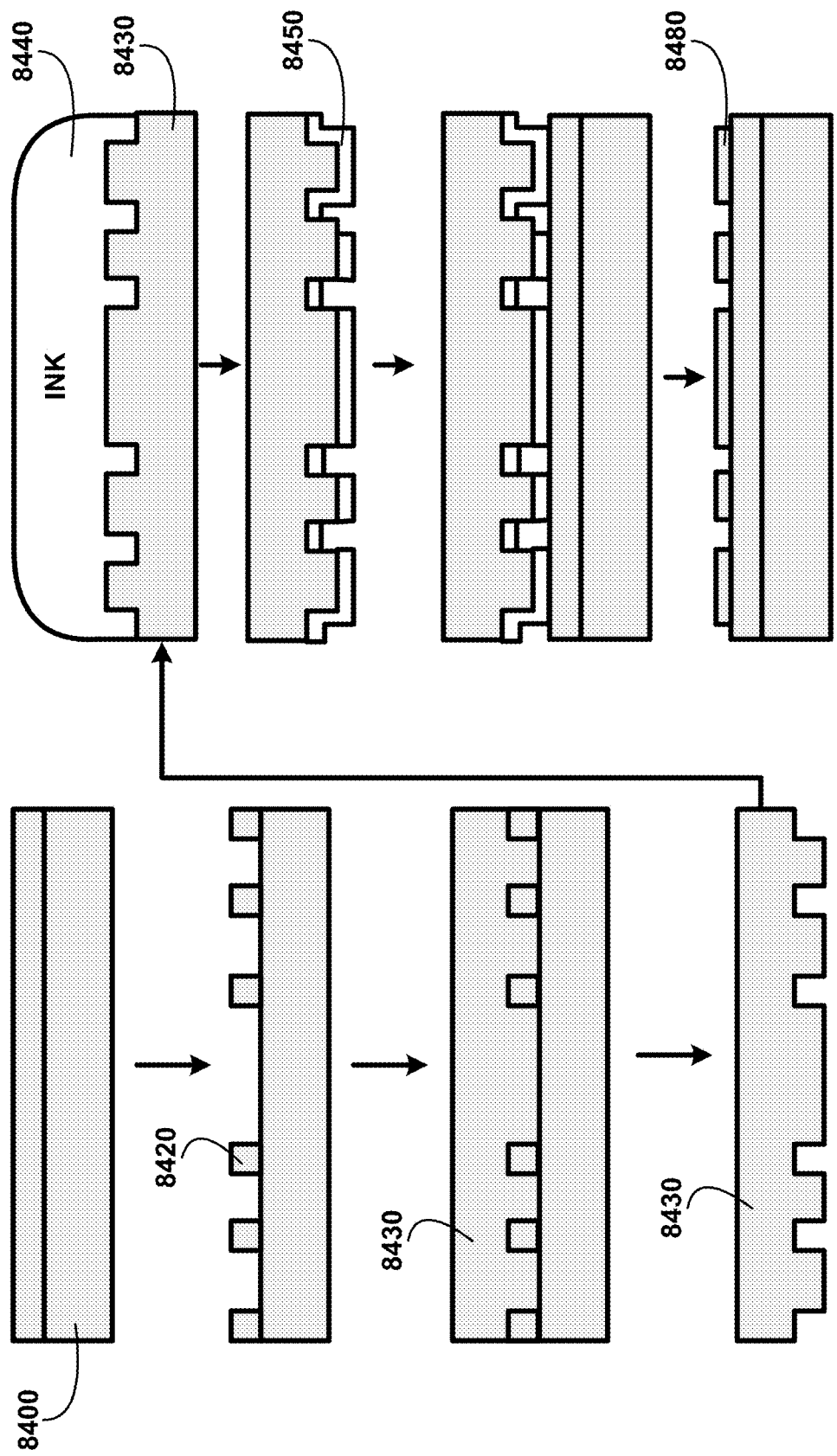
FIG. 83 shows for illustrative purposes only an example of an overview of methods of microcontact printing of nanomaterial, DNA, and other biomolecules at the nanometer scale of one embodiment.

Microcontact Printing for Patterning Nanomaterial, DNA, and Other Biomolecules:

FIG. 83 shows for illustrative purposes only an example of an overview of methods of microcontact printing of nanomaterial, DNA, and other biomolecules at the nanometer scale of one embodiment. FIG. 83 shows microcontact printing uses relief patterns 8420 on a master polydimethylsiloxane (PDMS) stamp 8430 or Urethane rubber micro stamp to form patterns of self-assembled monolayers of ink 8440 on the surface of the substrate 8400 through conformal contact. The PDMS master stamp is created by patterning metals, non-metals, and metalloids such as silicon, pouring and curing PDMS 8450, and peeling away from the substrate. Thiol is poured over the stamp 8480 and let to dry. Conformal contacts are made with the substrate and the pattern is left behind.

Figure 84:
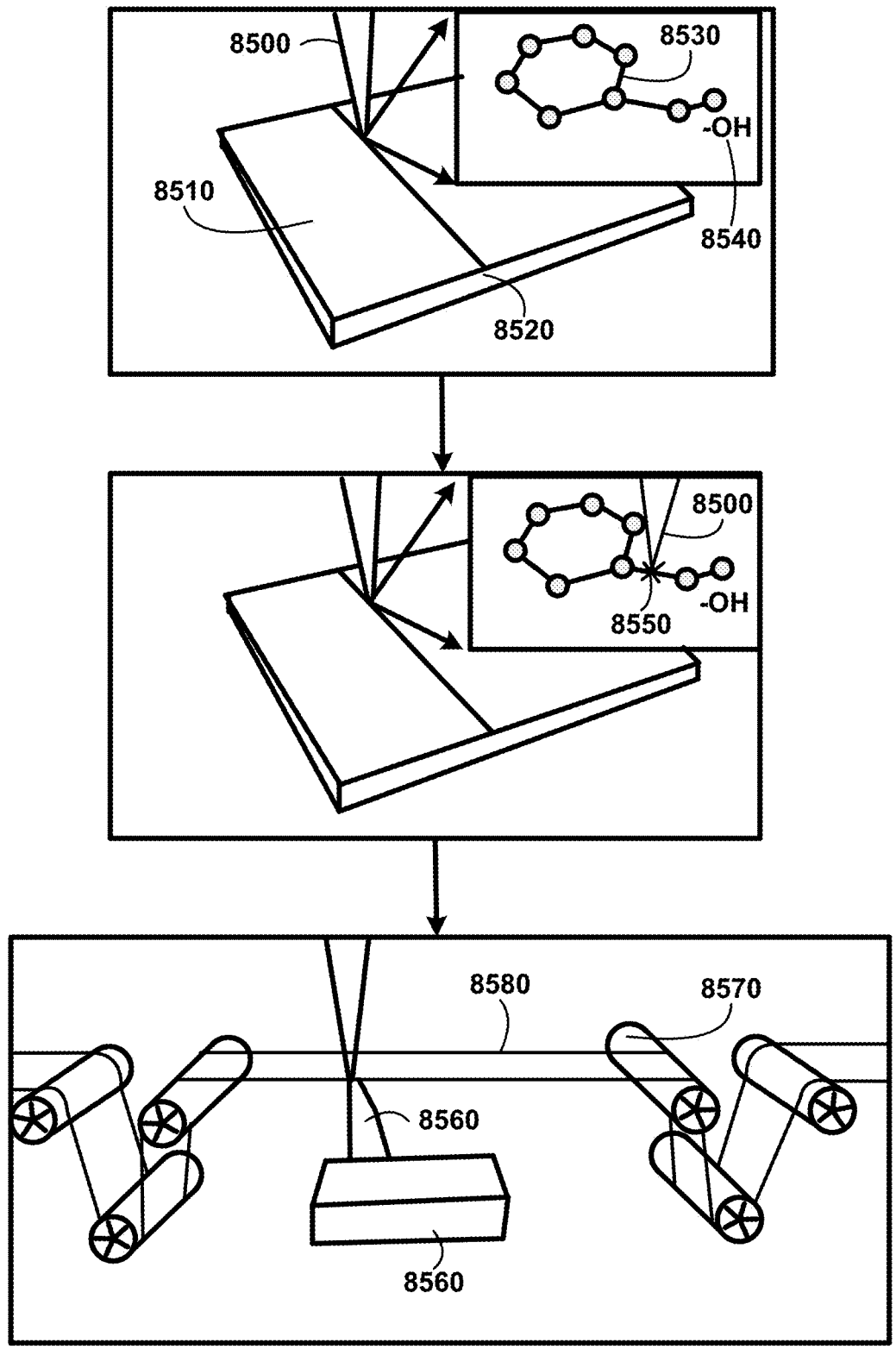
FIG. 84 shows for illustrative purposes only an example of an overview of methods of rapid fabrication of multidimensional carbon electronic materials using lasers and etching of one embodiment.

Laser-Induced Graphene for Rapid and Inexpensive Scalable Production:

FIG. 84 shows for illustrative purposes only an example of an overview of methods of rapid fabrication of multidimensional carbon electronic materials using lasers and etching of one embodiment. FIG. 84 shows direct laser writing 8500 of graphene 8510 and other allotropes of carbon or Van Der Waal materials can be categorized into three groups: photothermal, photochemical, and 3D printing. Photothermal has two types including photothermal reduction of carbon and direct synthesis through laser-induced thermal heating for the thermal reorganization of the carbon atoms into graphene structures 8530. Photothermal reduction of carbon removes chemical bonding 8550 of the graphene skeleton such as —COOH and —OH 8540 through thermal treatment using the high energy density of the laser that can reach temperatures over 2000° C. Graphene or other allotropes of carbon or Van Der Waal materials can also be synthesized directly from the carbon source under laser heating using the presence of metal catalyst materials. The solute atoms on the metallic catalyst surfaces can be directly grown to the graphene structure under a suitable thermal environment brought about by laser heating.

Photochemical effects will significantly influence the synthesis of graphene by removing the oxygen residuals on the graphene skeleton by using photon energy to directly break the chemical bonding 8550 such as —COOH and —OH 8540. The breaking down of the chemical bonding occurs when the photon energy is larger than the dissociation energy. When the laser wavelength is small, the energy of each photon is increased. When the wavelength of external light is approaching the UV region (typically smaller than 400 nm), the photochemical effects will significantly influence the synthesis of graphene, removing the oxygen residuals.

Synthesized graphene 8560 can also be deposited onto substrates 8520 using additive manufacturing.

The laser heating causes kinetic momentum, which is generated due to the volume expansion of the synthesized graphene from the polyimide precursor and the gaseous by-products, such as $CO_2$ and NOx. By utilizing the layer-by-layer approach, graphene desired in 3D structures can be artificially fabricated as a computer-aided design, as illustrated in FIG. 78.

The photothermal process within the laser writing of graphene electrodes proceeds by the thermal breaking between C and O—H bonds. The photochemical process within the laser writing of graphene electrodes shows the photon-induced disassociation of the band between C and O—H. The laser-induced forward transfer of graphene based on the roll-to-roll production 8570 with a polyimide film 8580. Laser-induced graphene on polyimide film with interdigital patterns.

Figure 85:
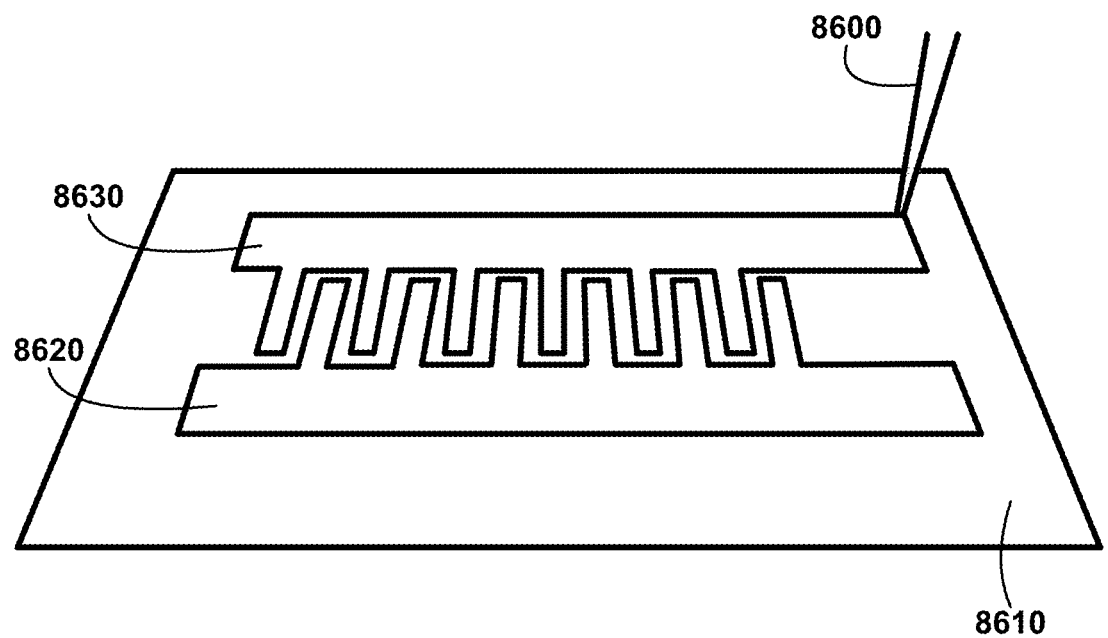
FIG. 85 shows for illustrative purposes only an example of interdigital patterns of one embodiment.

Interdigital Patterns:

FIG. 85 shows for illustrative purposes only an example of interdigital patterns of one embodiment. FIG. 85 shows laser-induced graphene 8600 on polyimide film 8610 or another polymer film with interdigital patterns 8620 and 8630. The interdigital patterns 8620 and 8630 are conductive electrodes that are integrated into biosensors of one embodiment.

Figure 86:
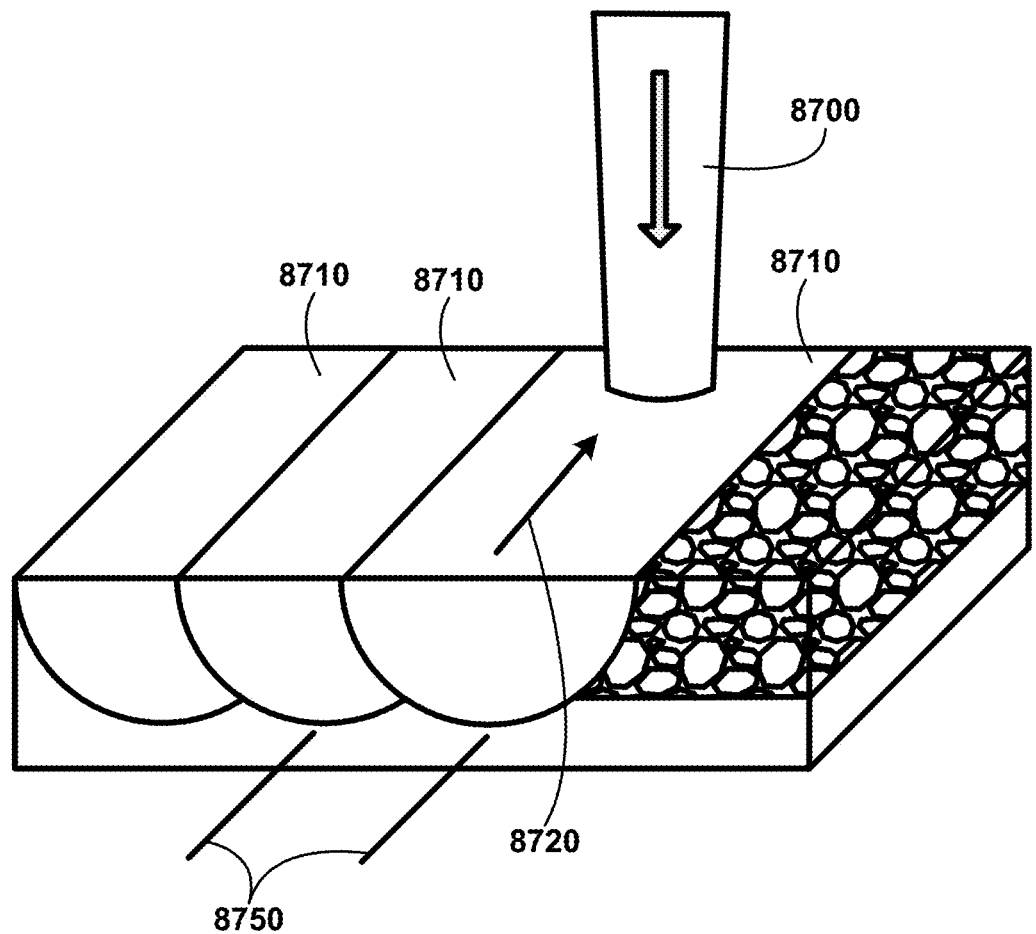
FIG. 86 shows for illustrative purposes only an example of laser-based texturing of graphene to locally tune electrical potential, surface chemistry, and surface morphology of one embodiment.

Laser Texturing of Van Der Waals Materials for Optimal Surface Morphology, Wettability and Resistance:

FIG. 86 shows for illustrative purposes only an example of laser-based texturing of graphene to locally tune electrical potential, surface chemistry, and surface morphology of one embodiment. FIG. 86 shows the laser 8700 texturing produces three-dimensional blisters 8710 of graphene through irradiation of the visible ranger laser. The produced blisters are consistently formed in altitude and functionality by increasing the surface area of the graphene. The laser irradiation leads to lattice expansion of carbon atoms and introduced oxygenic functional groups with the structural disorder. The defect density of graphene is a direct function of the displacement of material as a result of laser-based texturing or laser ablation. Laser texturing using monochromatic light through an optical amplification process. The process variables include laser power (W), scanning speed 8720 (mm/sec), distance from the laser source, and scan line spacing (Hatch distance 8750) of one embodiment.

Figure 87:
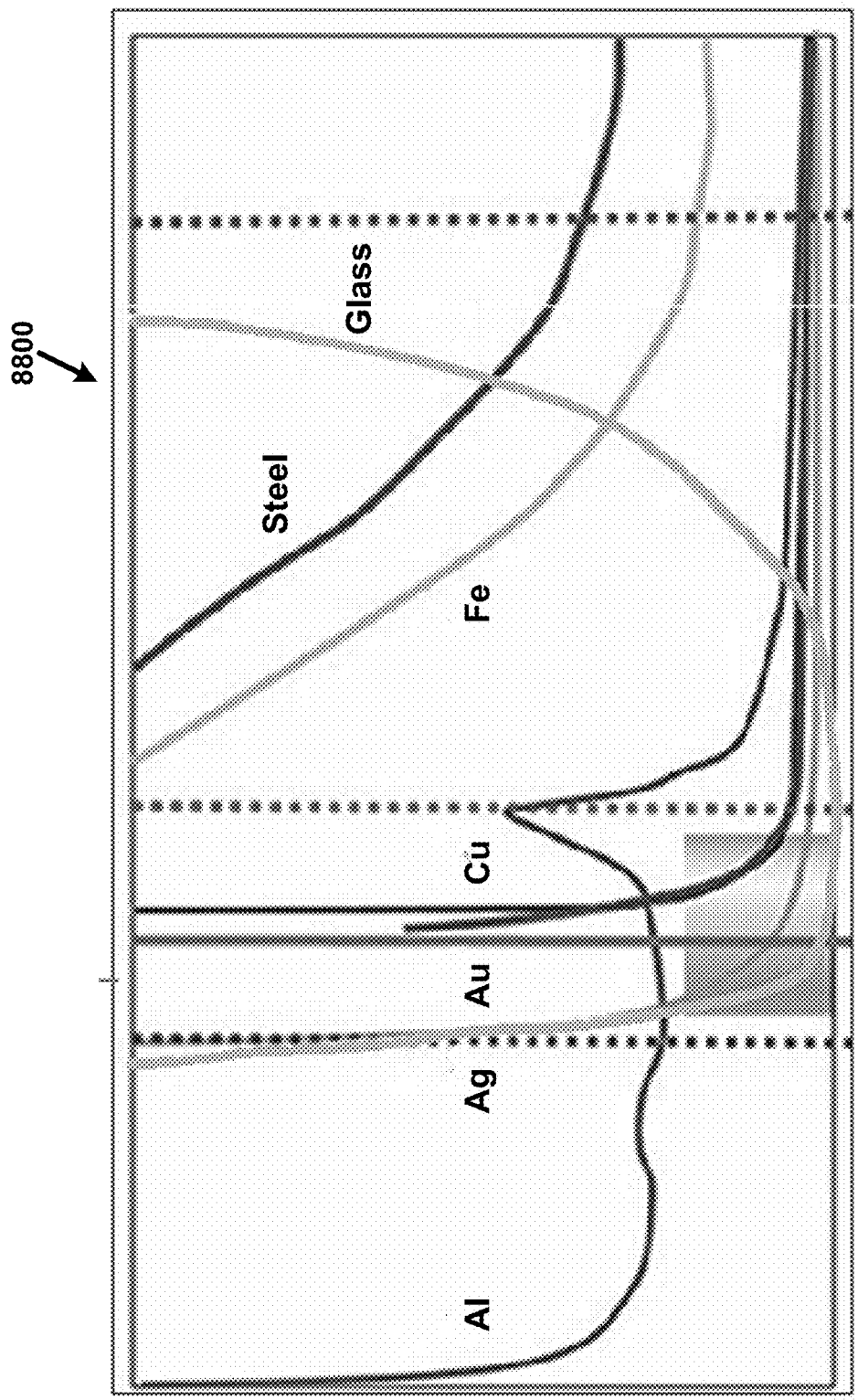
FIG. 87 shows for illustrative purposes only an example of the material absorption of one embodiment.

Material Absorption:

FIG. 87 shows for illustrative purposes only an example of the material absorption of one embodiment. FIG. 87 shows material absorption 8800 (%) for conductive metals (e.g. Al, Ag, Au, Cu, Fe, Pt, Zn, Ni, Steel, and Glass) at various wavelengths of light produced by different lasers (Direct Diode Laser, Fiber Laser, Nd:Yag Fiber Laser of one embodiment. Non-conductive materials with conductive coatings can be used in the exemplary embodiment.

Figure 88:
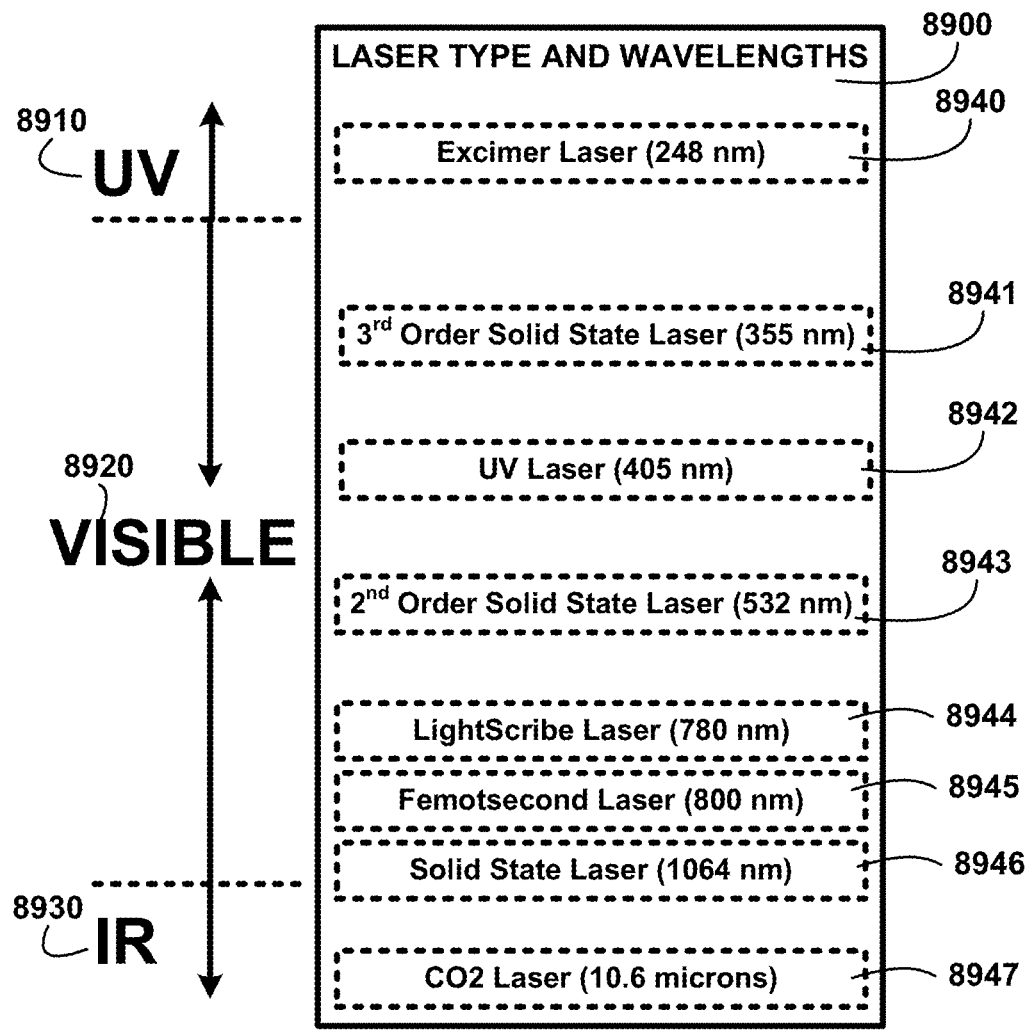
FIG. 88 shows for illustrative purposes only an example of the types of lasers used for rapid fabrication of multi-dimensional carbon electronic materials on polymers such as polyimide of one embodiment.

Types of Lasers Used to Texture and Induce Van Der Waals Materials on Substrates:

FIG. 88 shows for illustrative purposes only an example of the types of lasers used for rapid fabrication of multi-dimensional carbon electronic materials on polymers such as polyimide of one embodiment. FIG. 88 shows wavelength groups including UV 8910, VISIBLE 8920, and IR 8930. Also showing are laser type and wavelengths 8900. These laser types include Excimer Laser (248 nm) 8940, $3^{rd}$ Order Solid State Laser (355 nm) 8941, UV Laser (405 nm) 8942, $2^{nd}$ Order Solid State Laser (532 nm) 8943, LightScribe Laser (780 nm) 8944, Femotsecond Laser (800 nm) 8945, Solid State Laser (1064 nm) 8946, and CO2 Laser (10.6 microns) 8947. Polyimide and other polymers like it present several advantages for direct laser synthesis of graphene. For example, polyimide has abundant hexagonal crystalline carbon within the imide structures, which can serve as a precursor for the synthesis of graphene. Polyimide also has a large absorption at the IR region and near the UV region, so many types of lasers can directly carbonize the polyimide film to graphene structures. In addition, the film form of polyimide can be easily integrated into roll-to-roll production, which can be straightforwardly scaled up for mass production.

Figure 89:
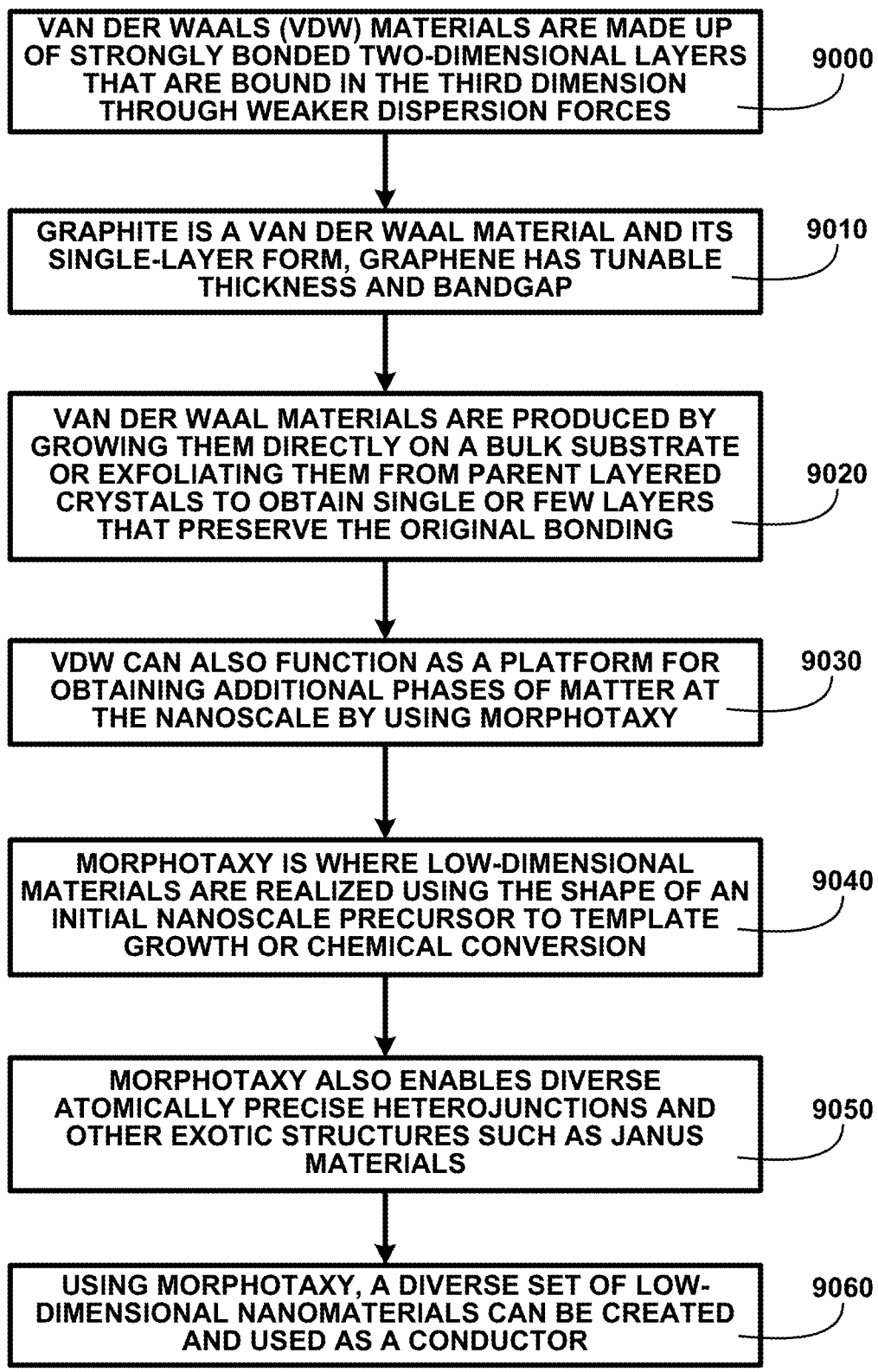
FIG. 89 shows a block diagram of an overview of growing layered Van Der Waals that preserves the original bonding of the nanomaterial of one embodiment.

Growing Layered Van Der Waals Materials that Preserve Original Bonding:

FIG. 89 shows a block diagram of an overview of growing layered Van Der Waals that preserve the original bonding of the nanomaterial of one embodiment. FIG. 89 shows Van Der Waals (VDW) materials are made up of strongly bonded two-dimensional layers that are bound in the third dimension through weaker dispersion forces 9000. Graphite is a Van der Waal material and its single-layer form, graphene has tunable thickness and bandgap 9010. Van der Waal materials are produced by growing them directly on a bulk substrate or exfoliating them from parent layered crystals to obtain a single or few layers that preserve the original bonding 9020. VDW can also function as a platform for obtaining additional phases of matter at the nanoscale by using morphotaxy 9030. Morphotaxy is where low-dimensional materials are realized using the shape of an initial nanoscale precursor to template growth or chemical conversion 9040. Morphotaxy also enables diverse atomically precise heterojunctions and other exotic structures such as Janus materials 9050. Using morphotaxy, a diverse set of low-dimensional nanomaterials can be created and used as a conductor 9060 of one embodiment.

Figure 90:
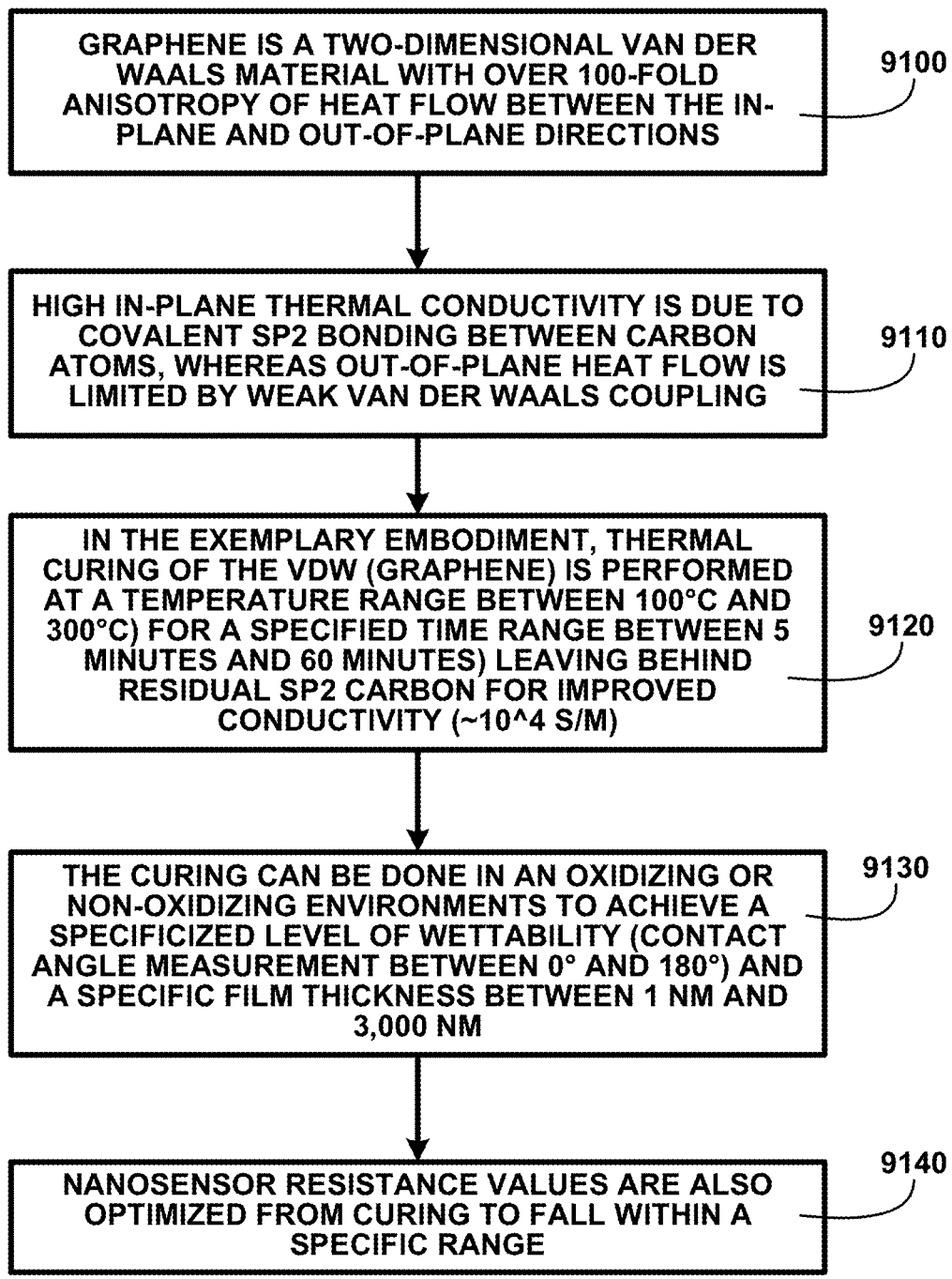
FIG. 90 shows a block diagram of an overview of the thermal curing of Van Der Waals materials for optimal surface area, conductivity, hydrophilicity/hydrophobicity, and resistance of one embodiment.

Thermal Curing of Van Der Waals Materials for Optimal Surface Area, Conductivity, and Wettability:

FIG. 90 shows a block diagram of an overview of the thermal curing of Van Der Waals materials for optimal surface area, conductivity, wettability, and resistance of one embodiment. FIG. 90 shows graphene is a two-dimensional Van Der Waals material with over 100-fold anisotropy of heat flow between the in-plane and out-of-plane directions 9100. High in-plane thermal conductivity is due to covalent sp2 bonding between carbon atoms, whereas out-of-plane heat flow is limited by weak Van Der Waals coupling 9110. In the exemplary embodiment, thermal curing of the VDW (graphene) is performed at a temperature range between 100° C. and 300° C.) for a specified time range between 5 minutes and 60 minutes) leaving behind residual sp2 carbon for improved conductivity (~$10^4$ S/m) 9120. The curing can be done in oxidizing or non-oxidizing environments to achieve a specificized level of wettability (contact angle measurement between 0° and 180°) and a specific film thickness between (1 nm and 3,000 nm) 9130. Nanosensor resistance values are also optimized from curing to fall within a specific range 9140 of one embodiment.

Photocuring of Van Der Waals Materials for High-Volume Production:

FIG. 91A shows a block diagram of an overview of the photocuring of Van Der Waals materials for high-volume production of one embodiment. FIG. 91A shows the processes include the photocuring of Van Der Waals materials for high volume production 9200. Photocuring is the process of hardening a substance by exposing it to a specific wavelength of light 9210. The photocuring transient process can be performed rapidly on inexpensive, low-temperature substrates such as plastics, polymers, or paper without damaging the substrate 9220. Photocuring processes can be performed in an in-line or roll-to-roll process 9230. The rapid, higher temperature processing afforded by photonic curing reduces the processing time exponentially, from hours down to milliseconds or microseconds or nanoseconds, which increases throughput with a small machine footprint 9240. Photonic curing uses radiative heat transfer from a lamp to the object of interest during the time that the flashlamp is on (usually between 100 μs and 100 ms) 9250. After radiative heat impinges on this object, thermal conduction through the object and convective loss to the atmosphere in contact with the material will occur until the object nears thermal equilibrium 9260. Because of the intensity and short duration of the flashlamp pulse, extreme thermal gradients can occur in the object of interest 9262. The description continues in FIG. 91B.

Photocuring of Van Der Waals Materials for High-Volume Production Continuation:

FIG. 91B shows a block diagram of an overview of the photocuring of Van Der Waals materials for high-volume production of one embodiment. FIG. 91B shows a continuation from FIG. 91A. Extreme thermal gradients can be useful in exposing only certain parts of an object to high temperatures 9270. Process parameters of photonic curing including intensity of wavelength of light, number of pulses of wavelengths of light, and the length of the wavelengths of light are used to produce a cured VDW material with a thickness of >50 nm; a contract angle measurement within the range of 0° and 180° and a conductivity of ~$10^4$ s/m 9280. The photocuring also achieves a specific range of nanosensor resistance values 9290. Photocuring uses a plasma arc lamp or UV lamp or xenon lamp or flash lamp 9292.

The foregoing has described the principles, embodiments, and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

In one embodiment FIGS. 91 through 110 describe the manufacturing of the sensing, detection, and analysis systems that are the components of the analyte detection system of the invention.

Figure 92:
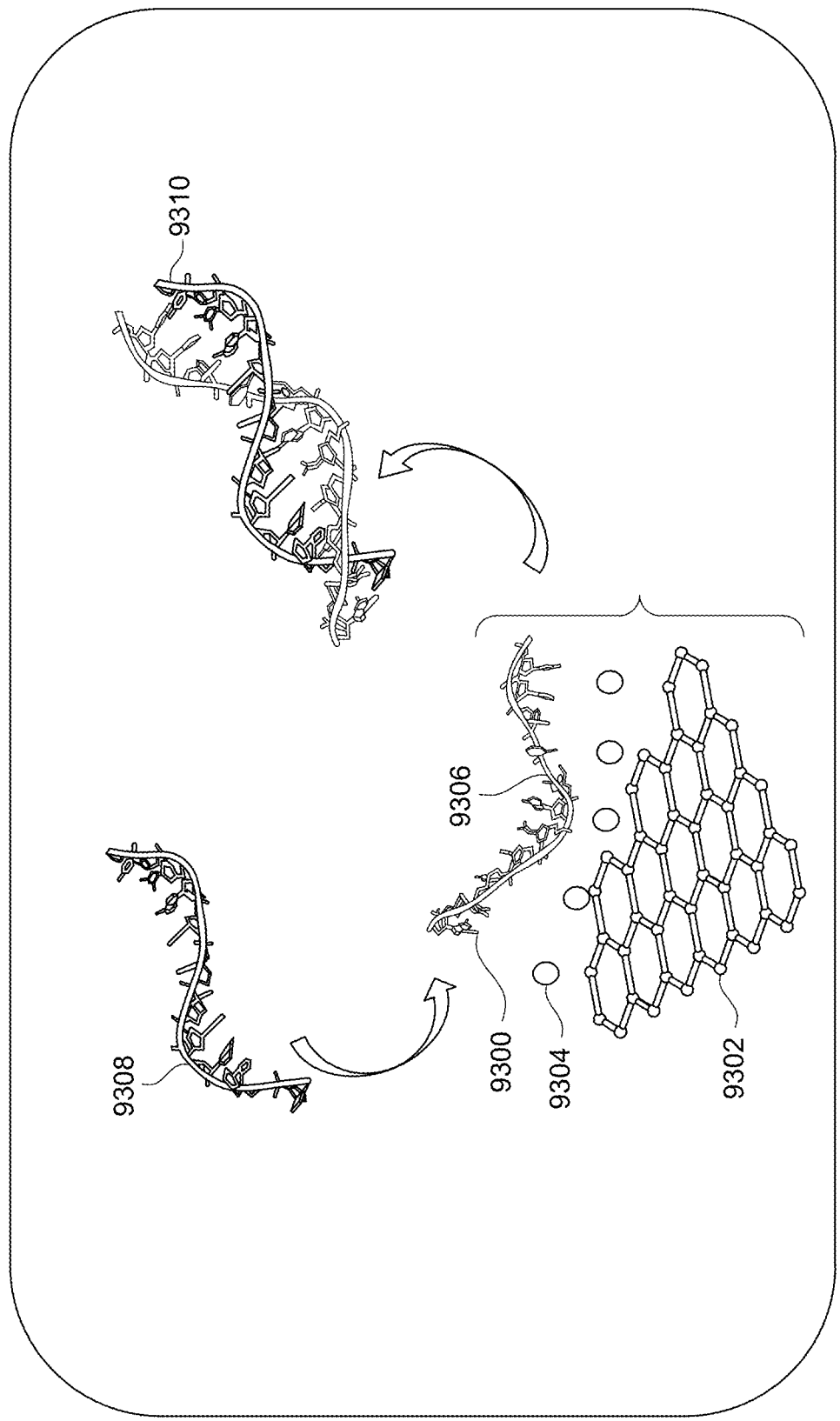
FIG. 92 shows for illustrative purposes only an example of the adsorption and desorption of molecules on the surface of Van der Waal (VDW) materials of one embodiment.

Adsorption and Desorption of Molecules on the Surface of Van Der Waals Materials:

FIG. 92 shows for illustrative purposes only an example of the adsorption and desorption of molecules on the surface of Van der Waal (VDW) materials of one embodiment. Adsorption occurs when one compound attaches to the surface of another compound. In the adsorption process, two important terms are adsorbate and adsorbent. An adsorbate is a molecule, and the adsorbent is the surface to which the adsorbate attaches. There are two main ways among other ways in which attachment can occur. One way is when Van der Waals forces refer to the cumulative effects of the attraction and repulsion between atoms, molecules, and surfaces. The other way occurs when chemical bonding takes place between the adsorbate and the adsorbent. Adsorption can occur amongst many types of substances, including gases, liquids, and solids. Desorption represents the reverse process of adsorption. Desorption occurs when one compound is released from the surface of another compound. When desorption occurs, the Van der Waals forces and chemical bonds attaching the adsorbate to the surface of the adsorbent can weaken or be disrupted. This enables the adsorbate to detach from the surface of the adsorbent.

In the present embodiment, molecules 9300 are layered onto the Van der Waal material 9302 stabilized by Van der Waals forces. The Van der Waal forces are enabled by molecules 9304 deposited on the surface of the Van der Waal material 9302. The molecules 9304 create a bridge-like coupling affect between the Van der Waal material 9302 and the molecule 9300. The desorption of the molecules 9300 occurs when the molecules 9300 undergo an interaction known as hybridization 9306. Hybridization is a process in which two complementary single-stranded DNA 9300 and/or RNA molecules 9308 bond together to form a double-stranded molecule 9310. It should be appreciated that in this exemplary embodiment biomolecules and molecules can be used interchangeably with the only difference between the two being that biomolecules are present in living organisms. Biomolecules can be aptamers, proteins, and other chemical molecules. The exemplary adsorption and desorption can occur using any type of molecule across the various forms of matter such as solids, liquids, and gases.

Figure 93:
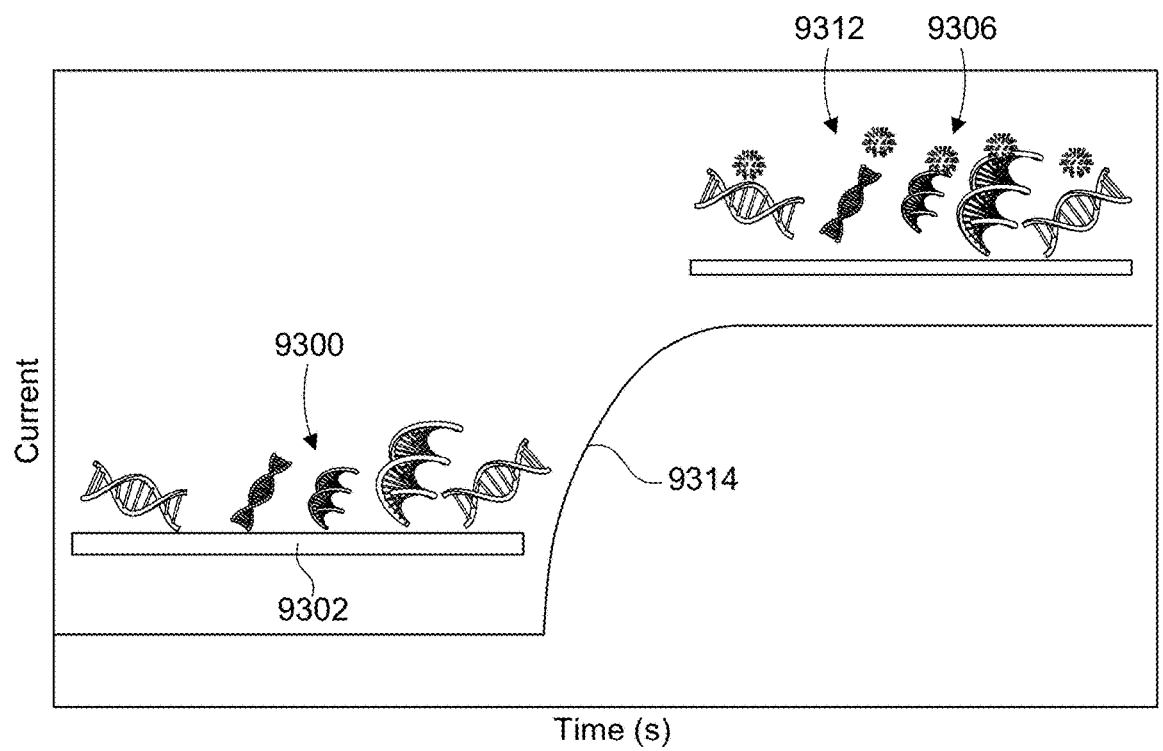
FIG. 93 shows for illustrative purposes only an example of surface functionalization and molecule lifting of one embodiment.

Van Der Waal Material Surface Functionalization and Hybridization:

FIG. 93 shows for illustrative purposes only an example of Van der Waal material surface functionalization of the monitor/detector and molecule hybridization occurring on the surface of the Van der Waal material monitor/detector of one embodiment. Surface functionalization occurs when molecules 9300 are deposited on the surface of the Van der Waal material 9302. The molecules bind to the surface of the Van der Waal material 9302 through Van der Waal forces. Hybridization 9312 occurs when the test sample, containing the target molecule, is presented to the sensor. The hybridization occurs because of the base-pair binding of complimentary molecules, an interaction known as hybridization 9306. Base-pair binding occurs when two complimentary stands are held together by hydrogen bonds between pairs of bases such as adenine pairs with thymine and cytosine pairs with guanine. The molecule hybridization 9312 occurs because the hydrogen bonds between the pairs of bases are stronger than the bond created by Van der Waal forces inductively aligning the biomolecule on the surface of the Van der Waal material. Molecule hybridization occurs when positive test samples are presented to the monitor/detector. Molecule hybridization does not occur when negative test samples are presented to the monitor/detector. The molecule hybridization causes an increase in measured electrical current 9314. This measured increase in electrical current is indicative of a positive test, defined by the presence of targeted molecules.

Figure 94:
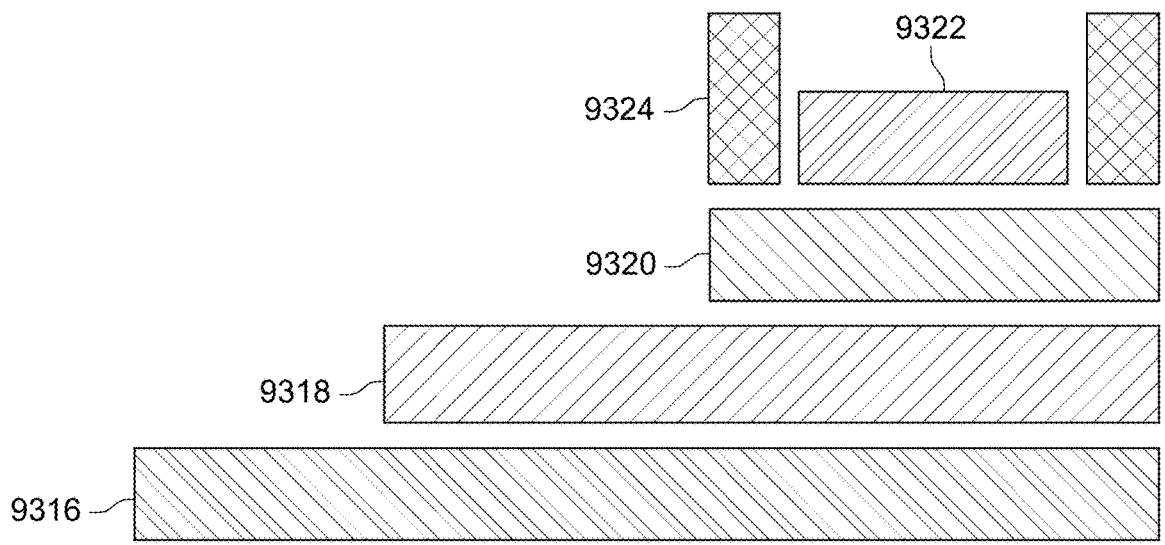
FIG. 94 shows for illustrative purposes only an example of a monitor/detector material layers and stack-up of one embodiment.

Monitor/Detector Material Layers and Stack-Up:

FIG. 94 shows for illustrative purposes only an example of a monitor/detector material layers and stack-up of one embodiment. The first exemplary layer is the substrate 9316. The substrate can be any material that can receive a deposited material and typically consists of polyimide, polyethylene terephthalate (PET), plastics, polymers, glass, and paper among other substrates that deposited materials are adhered to that are known in the art of printed electronics. The second exemplary layer is the first conductive layer 9318. The first conductive layer 9318 can be any conductive material and typically consists of at least one conductive metal, a conductive nanomaterial, a Van der Waal material, a polymer, a semiconductor, ionic conductors, metal oxides, a solvent, a binder, and an adhesion promoter. Conductive metals include gold, silver, copper, platinum, aluminum, zinc, nickel, brass, bronze, iron, steel, and lead. Conductive nanomaterials include inorganic-based nanomaterials, organic-based nanomaterials, carbon-based nanomaterials, and composite-based nanomaterials. Van der Waal materials are any material that exhibits Van der Waal forces. Conductive materials are typically created by infusing any material that has the ability to conduct electric current due to the presence of charged particles with a solvent material, a binder material, and an adhesion promoter material. The solvent material enables the proper viscosity for material deposition. The binder material is typically a polymer that enables the proper cohesion, adhesion, stability and film-forming properties of the material for deposition. The adhesion promoter material enables the proper adhesion of the material to the substrate 9316.

It should be appreciated that conductive layers presented in the exemplary embodiment can consist of any combination of conductive materials, polymers, solvents, binders, and adhesion promoters. The third exemplary layer is the second conductive layer 9320. The second conductive layer 9320 can be any conductive material and typically consists of at least one of a conductive polymer, a conductive nanomaterial, a conductive metal, and a Van der Waal material. Conductive polymers are any polymer that has the ability to conduct electricity. Exemplary conductive nanomaterials are carbon-based, metal-based, dendrimers, and nanocomposites. Other exemplary conductive materials are Van der Waal materials, which exhibit Van der Waal forces. The second conductive layer 9320 is typically created by infusing any conductive material with a solvent material, a binder material, and an adhesion promoter material. The solvent material enables the proper viscosity for material deposition. The binder material is typically a polymer that enables the proper cohesion, adhesion, dispersion and stability of the material for deposition. The adhesion promoter material enables the proper adhesion of the material to the substrate. It should be appreciated that conductive layers presented in the exemplary embodiment can consist of any combination of conductive materials, solvents, binders, and adhesion promoters. The fourth exemplary layer is the molecule layer 9322. The molecule layer 9322 can be any type of layer containing molecules 9300 that bind to the second conductive layer 9320. The molecule layer helps promote inductive alignment of the molecule 9300 on the surface of the second conductive layer 9320. The fifth exemplary layer is the insulating layer 9324. The insulating layers 9324 include dielectrics, which can be in the form of a solid, liquid, or gas. The insulating layers 9324 is deposited on a portion of the monitor/detector material layers and stack-up.

Figure 95:
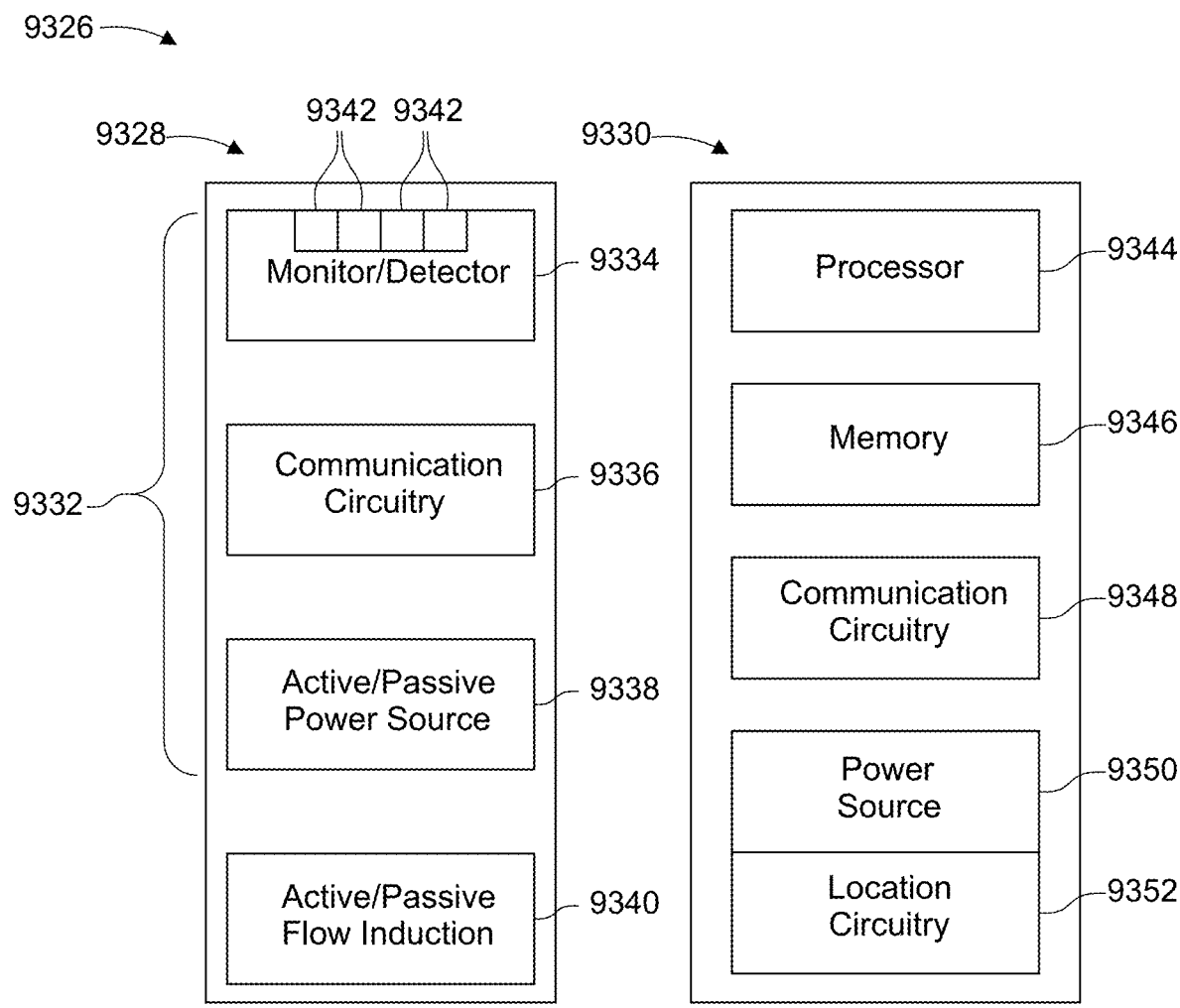
FIG. 95 shows for illustrative purposes only an example of an analyte detection system of one embodiment.

Analyte Detection System:

FIG. 95 shows for illustrative purposes only an example of the analyte detection system of one embodiment. The system 9326 comprising a sensor 9328 and an associated receiver 9330. The sensor comprising a detection device 9332. The detection device comprising a monitor/detector 9334, communication circuitry 9336 and an active/passive power source 9338. In one exemplary embodiment, the detection device 9332 is a removable and replaceable component of the sensor 9328. In other exemplary embodiments, the detection device 9332 is not a removable and replaceable component of the sensor 9328. The sensor 9328 also comprises an active/passive flow induction 9340. The monitor/detector 9334, comprises a plurality of detectors 9342 that detect analytes. The associated receiver 9330 comprises a processor 9344, memory 9346, communication circuitry 9348, location circuitry 9352, and a power source 9350. The power source 9350 is operatively coupled to the detection device 9332. It should be appreciated that in some embodiments, location circuitry 9352 may not be necessary and therefore shall not be included in the analyte detection system.

Figure 96:
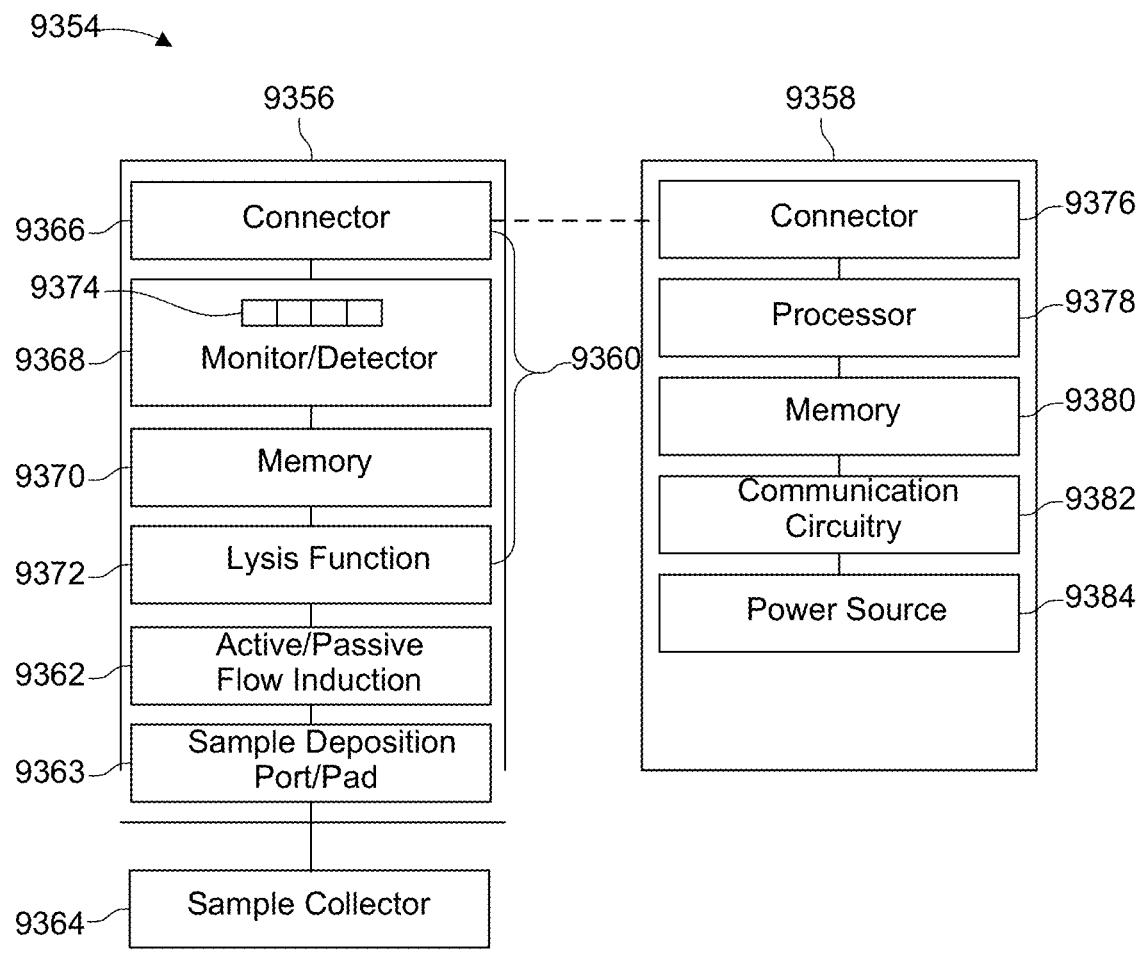
FIG. 96 shows for illustrative purposes only an example of an analyte detection system with lysing component of one embodiment.

Analyte Detection System with Lysing Component:

FIG. 96 shows for illustrative purposes only an example of an analyte detection system with a lysing component of one embodiment. The system 9354 comprises a sensor 9356 and an associated receiver 9358. The sensor comprises a detection device 9360, an active/passive flow induction device 9362, and a sample deposition port/pad 9363. A sample collector 9364 is selectively attachable to the sensor 9356. The sample collector 9364 mates with the sample deposition port/pad 9363 enabling transfer of the test sample to the sensor 9356 from the sample collector 9364. The detection device 9360 comprises a connector 9366, monitor detector 9368, memory 9370, and a lysing function 9372. The monitor detector 9368 comprises a plurality of detectors 9374. In the exemplary embodiment, the connector of the sensor 9356 mates with the connector 9376 of the associated receiver 9358. The connection between the associated receiver 9358 and the sensor 9356 facilitates power to the detection device 9360 from the power source 9384 of the associated receiver 9358. In the exemplary embodiment, the detection device 9360 can be a removable and replaceable component of the sensor 9356. It should be appreciated that in other exemplary embodiments, the detection device 9360 is not removable/replaceable. The associated receiver 9358 comprises a connector 9376, processor 9378, memory 9380, communication circuitry 9382, and a power source 9384, operatively coupled to at least one of the detection devices 9360 and the active/passive flow induction 9362 of the sensor 9356. It should be appreciated that in some embodiments, location circuitry 9352 is shown in FIG. 95 may be necessary and therefore shall be included in the analyte detection system with the lysing component of FIG. 96.

Figure 97B:
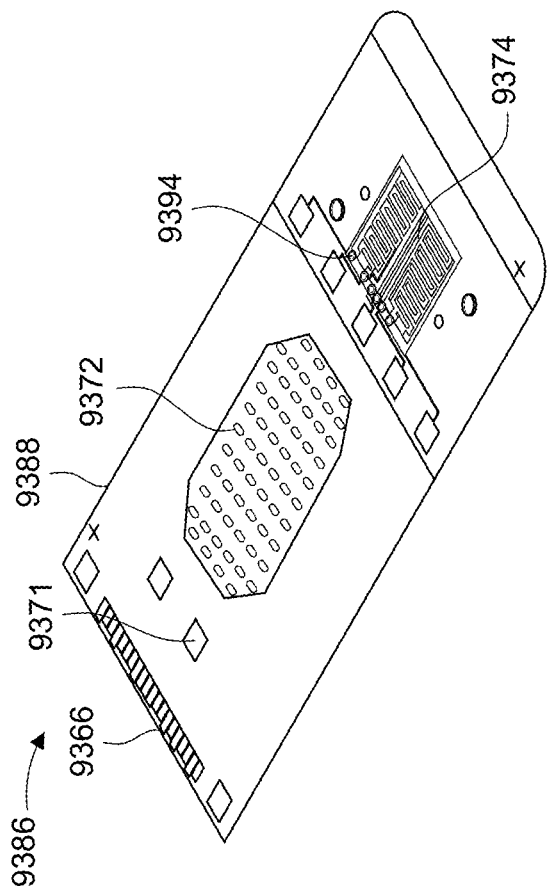
Figure 97A:
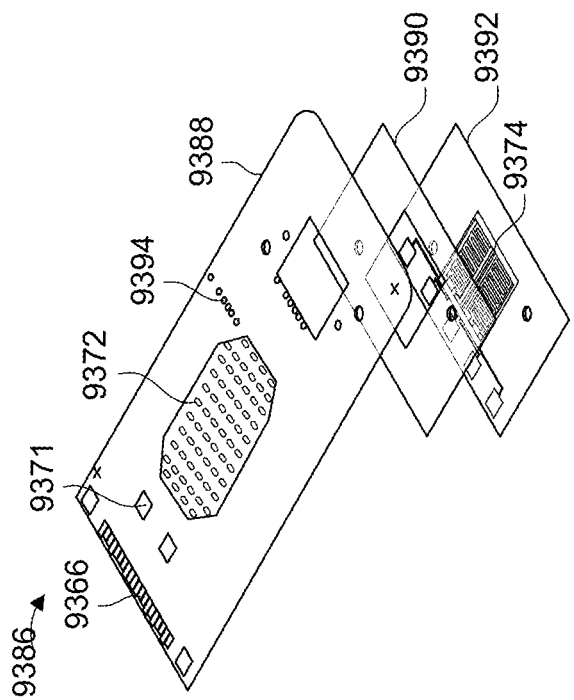

Dual-Film Sensor:

FIG. 97A shows for illustrative purposes only an example of a dual-film sensor of one embodiment. FIG. 97A shows the dual-film sensor 9386 comprising a thin film 9388, an adhesive layer 9390, and a sensor layer 9392. The thin film 9388 comprises a connector 9366, a memory 9371, a lysis function 9372, and shunts 9394 that electrically connect the thin film 9388 and the sensor film 9392. The adhesive layer 9390 physically connects the thin film 9388 and the sensor film 9392. The sensor layer 9392 comprises a plurality of detectors 9374. The descriptions continue in FIG. 97B.

FIG. 97B shows for illustrative purposes only an example of an assembled dual-film sensor 9386 of one embodiment. FIG. 97B shows a continuation from FIG. 97A of the assembled dual-film sensor comprises a thin film 9388, an adhesive layer 9390, and a sensor layer 9392. The thin film 9388 comprises a connector 9366, a memory 9371, a lysis function 9372, and shunts 9394 that electrically connect the thin film 9388 and the sensor film 9392. The adhesive layer 9390 physically connects the thin film 9388 and the sensor film 9392. The sensor layer 9392 comprises a plurality of detectors 9374.

Figure 98:
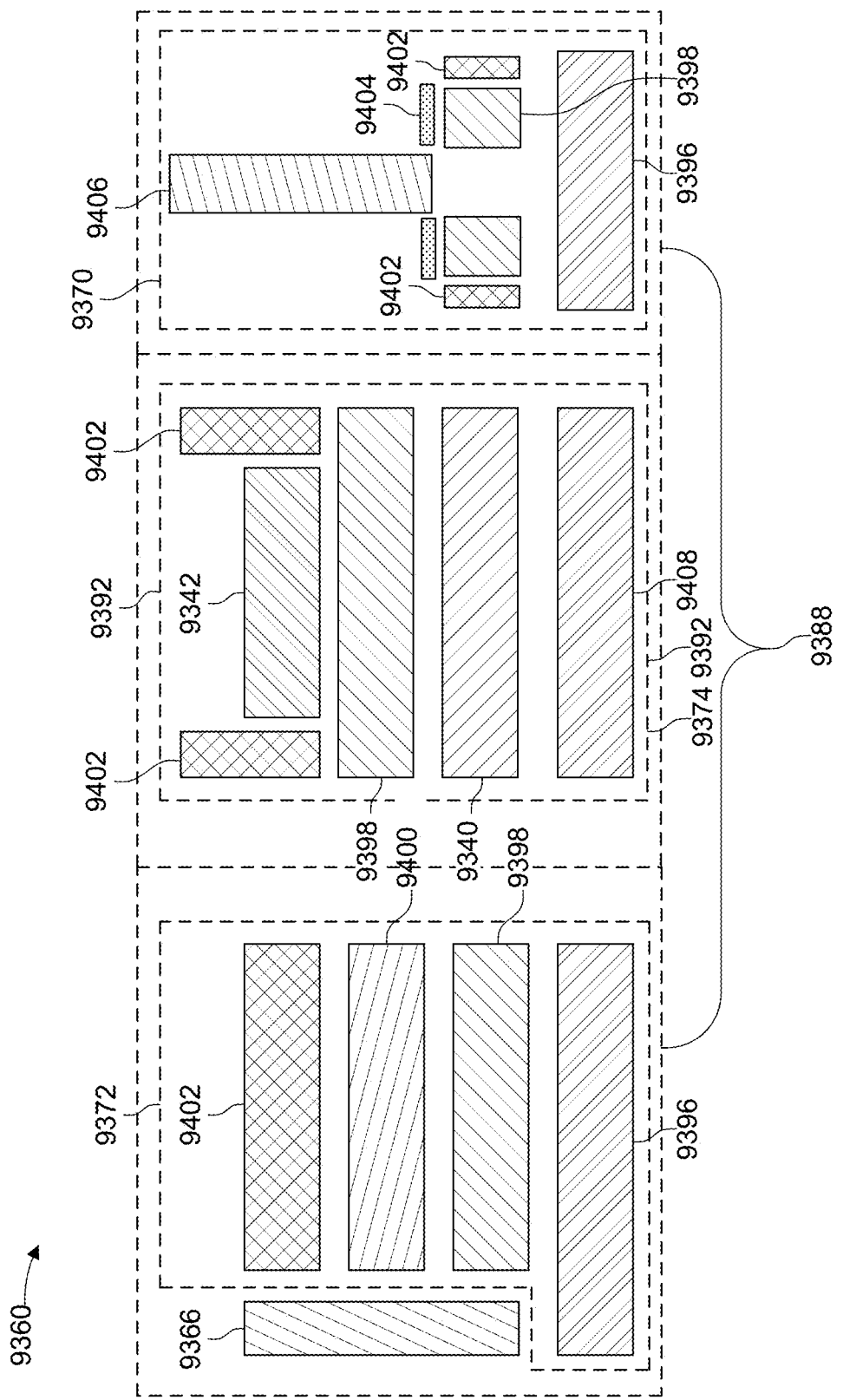

Dual-Film Sensor Material Layers and Stack-Up:

FIG. 98 shows for illustrative purposes only an example of a dual-film material layers and stack-up of one embodiment. In the exemplary embodiment, the detection device 9360 comprises two films, a thin film 9388 and a sensor film 9392 joined by an adhesive layer 9390 as presented in FIGS. 97A-97B. The thin film 9388 comprises a connector layer 9366 and material layer lysing function 9372 and a materials layer memory 9370. The material layer sensor film 9392 comprises a plurality of material layer monitors/detectors 9374. The material layer lysing function 9372 comprises a substrate 9396, a first conductive layer 9398, a temperature-controlling conductive layer 9400, and an insulating layer 9402. The material layer memory 9370 comprises a substrate 9396, a first conductive layer 9398, an insulating layer 9402, an adhesive layer 9404, and a memory chip 9406. The material layer sensor film 9392 comprises a substrate 9408, a first conductive layer 9398, a second conductive layer 9340, a molecule layer 9342, and an insulating layer 9402.

Figure 99:
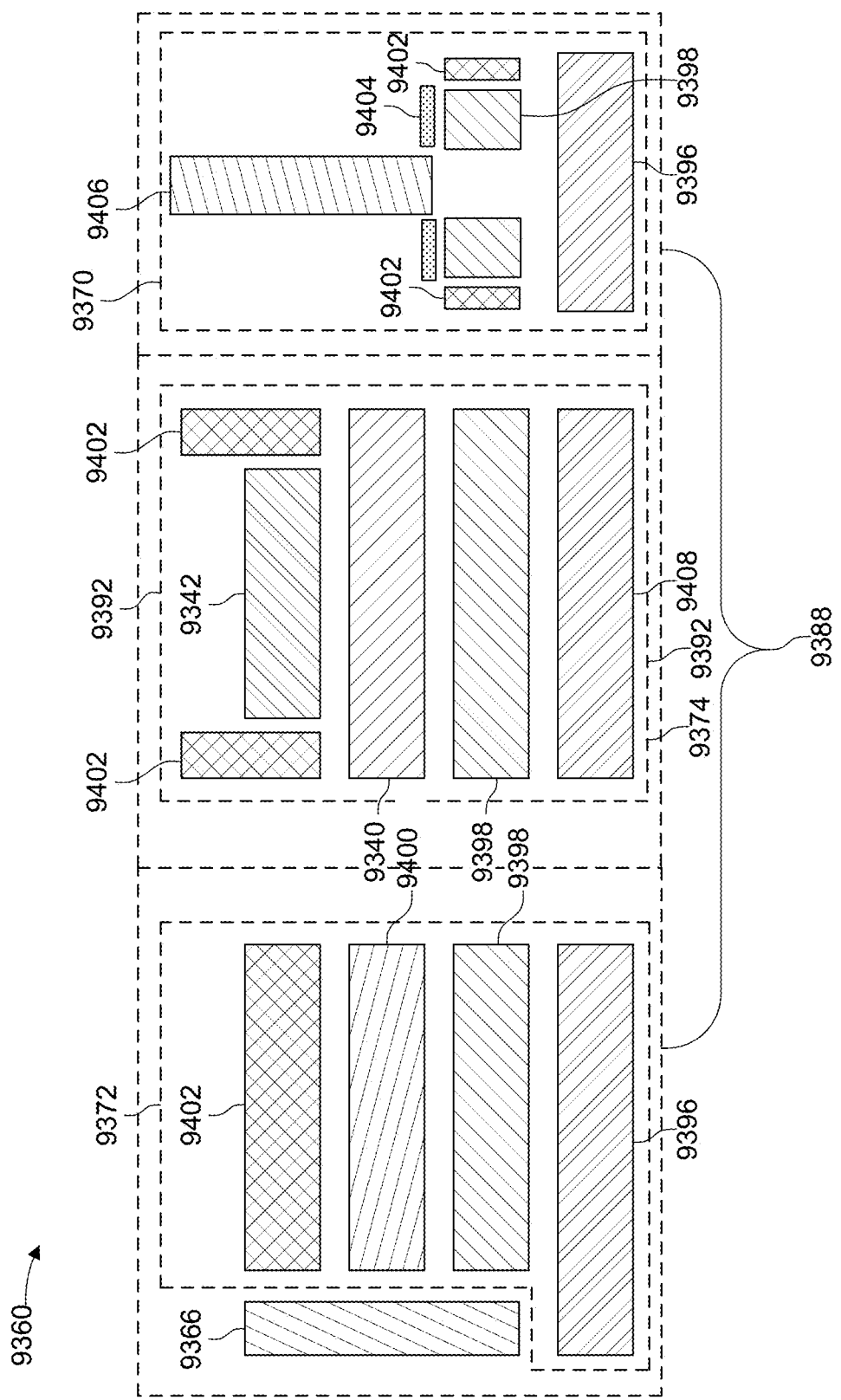

Dual-Film Sensor Material Layers and Stack-Up with Swapped First and Second Conductive Layers:

FIG. 99 shows for illustrative purposes another example of a dual-film material layers and stack-up with the first and second conductive material layers of the sensor film swapped of one embodiment. In the exemplary embodiment, the detection device 9360 comprises two films, a thin film 9388 and a sensor film 9392 joined by an adhesive layer as presented in FIG. 94. The thin film 9388 comprises a connector 9366, a material layer lysing function 9372, and a materials layer memory 9370. The material layer sensor film 9392 comprises a plurality of material layer monitor/detectors 9374. The material layer lysing function 9372 comprises a substrate 9396, a first conductive layer 9398, a temperature-controlling conductive layer 9400, and an insulating layer 9402. The material layer memory 9370 comprises a substrate 9396, a first conductive layer 9398, an insulating layer 9402, an adhesive layer 9404, and a memory chip 9406. The material layer sensor film 9392 comprises a substrate 9408, a second conductive layer 9340, a first conductive layer 9398, a molecule layer 9342, and an insulating layer 9402. The material layer sensor 9392 comprises a plurality of monitors/detectors as shown in FIG. 96.

Figure 100:
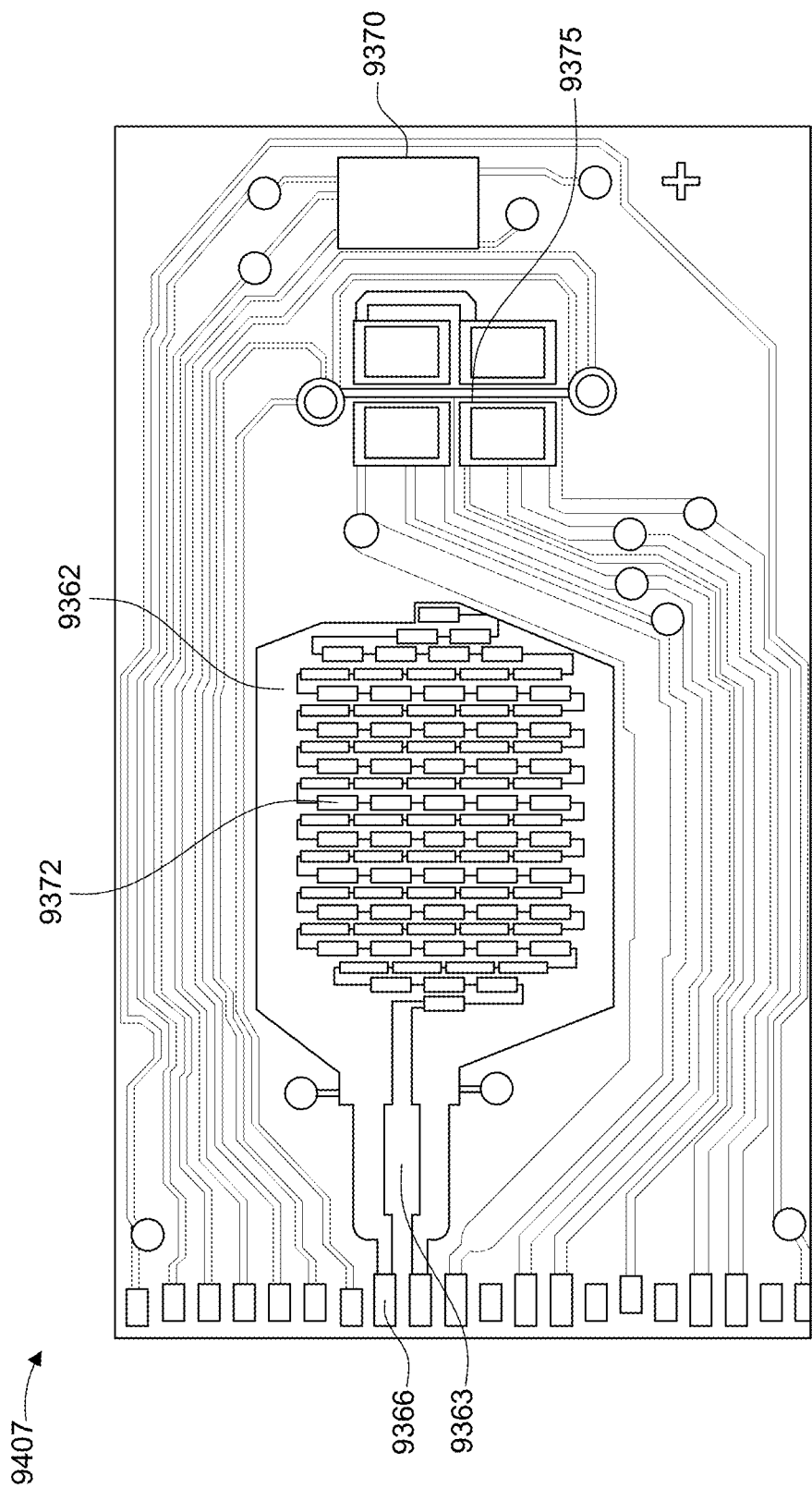

Mono-Film Sensor:

FIG. 100 shows for illustrative purposes a mono-film sensor, whereby all material layers are printed on a single substrate of one embodiment. The mono-film sensor 9407 comprises a connector 9366, material layer lysing function 9372, material layer monitor/detector array 9374, and a materials layer memory 9370. An active/passive flow induction 9362 transfers the test sample from the lysis function 9372 to the monitor/detector array 9374. The sample deposition port/pad 9363 connects with the sample collector 9364, such that the test sample is transferred from the sample collector 9364 to the lysis function 9372, then onto the monitor/detector array 9374 for analyte detection. It should be appreciated that the material layer monitor/detector array comprises a plurality of material layer monitors/detectors 9375. It should also be appreciated that other methods of moving the test sample from the material layer lysing function 9372 to the material layer monitor/detector array 9374 are contemplated. Such methods include using gravity, magnetics and other forms of non-mechanical active/passive flow induction.

Figure 101:
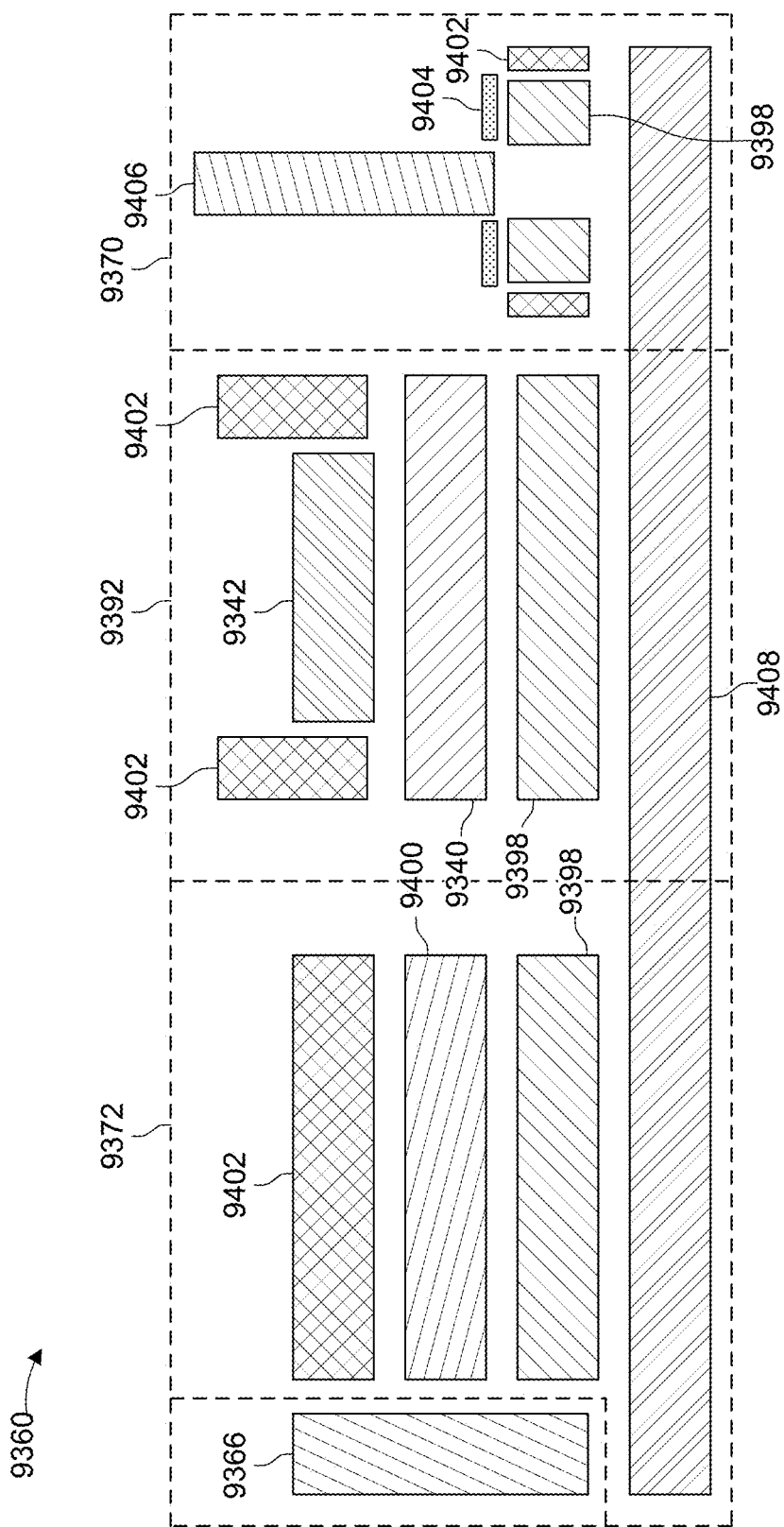

Mono-Film Sensor Material Layers and Stack-Up:

FIG. 101 shows for illustrative purposes a mono-film sensor material layers and stack-up of one embodiment. In the exemplary embodiment, the detection device 9360 comprises a connector 9366 material layer lysing function 9372, a material layer detector array 9392, and a materials layer memory 9370. The material layer lysing function 9372 comprises a substrate 9408, a first conductive layer 9398, a temperature-controlling conductive layer 9400, and an insulating layer 9402. The material layer detector array 9392 comprises a substrate 9408, a first conductive layer 9398, a second conductive layer 9340, a molecule layer 9342, and an insulating layer 9402, whereby the insulating layer is applied to a portion of the first conductive layer 9398 and the temperature controlling conductive layer 9400. The material layer memory 9406 comprises a substrate 9408, a first conductive layer 9398, an insulating layer 9402, an adhesive layer 9404, and a memory chip 9406.

Figure 102:
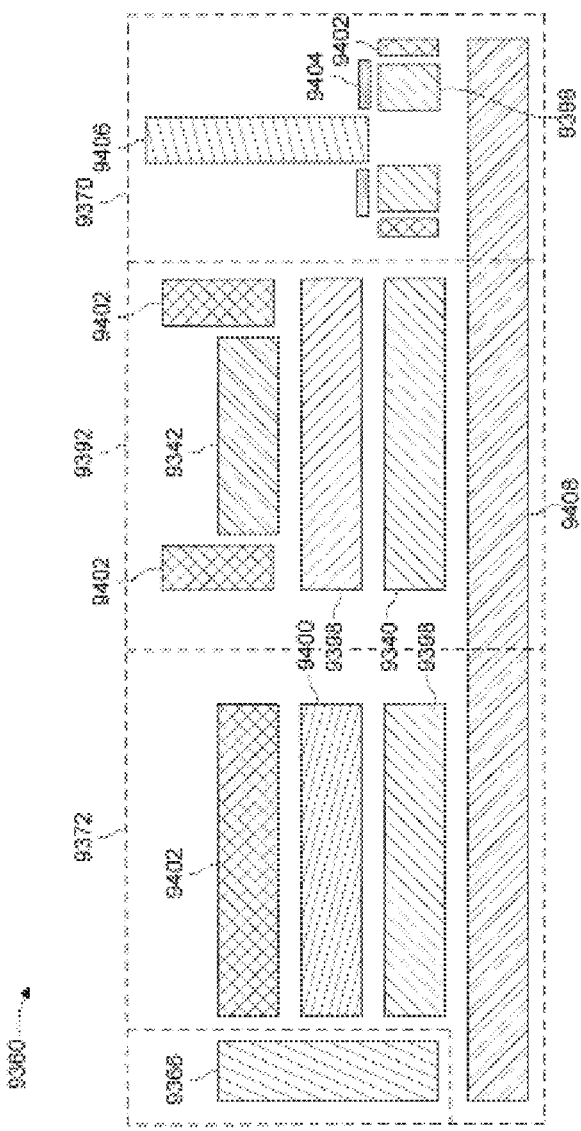

Mono-Film Sensor Material Layers and Stack-Up with Swapped First and Second Conductive Layers:

FIG. 102 shows for illustrative purposes a mono-film sensor material layers and stack-up with swapped first and second conductive layers of one embodiment. In the exemplary embodiment, the detection device 9360 comprises a connector 9366, material layer lysing function 9372, material layer detector array 9392, and a materials layer memory 9370. The material layer lysing function 9372 comprises a substrate 9408, a first conductive layer 9398, a temperature-controlling conductive layer 9400, and an insulating layer 9402, whereby the insulating layer is applied to at least one of the first conductive layer 9398 and the temperature controlling conductive layer 9400 and is applied to a portion of the second conductive layer 9340. The material layer detector array 9392 comprises a substrate 9408, a second conductive layer 9340, a first conductive layer 9398, a molecule layer 9342, and an insulating layer 9402. In the exemplary embodiment, the deposition sequence of the first conductive layer and the second conductive layer is swapped. The material layer memory 9370 comprises a substrate 9408, a first conductive layer 9398, an insulating layer 9402, an adhesive layer 9404, and a memory chip 9406.

Figure 103:
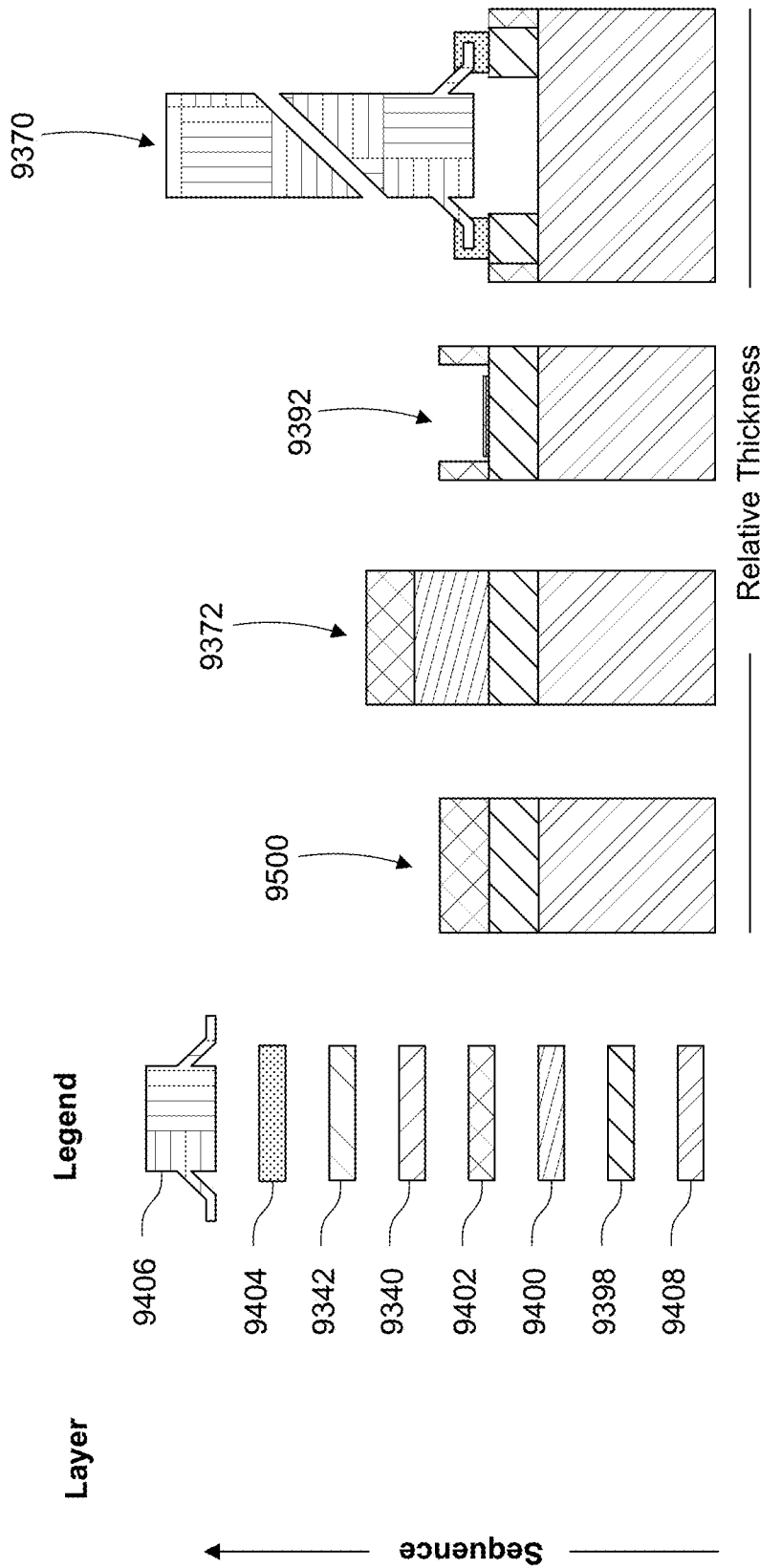

Mono-Film Sensor Material Deposition Sequence and Relative Thickness:

FIG. 103 shows for illustrative purposes the mono-film sensor material deposition sequence and relative thickness of one embodiment. In the exemplary embodiment, the printed material deposition sequence begins with stack-up 9500 showing depositing an insulating layer 9402 on top of a first layer of conductive material 9398 deposited on top of a substrate 9408. Next, a temperature-controlling conductive material 9400 is deposited on top of the first conductive layer material 9398. Deposition of the temperature-controlling conductive material 9400 creates a heating element that serves as the lysis function 9372. In other exemplary embodiments, the lysis function can be performed using mortar and pestle, bead beating, sonication, homogenization, freeze-thaw, enzymatic, chemical treatment, or other lysis methods in the art. After depositing the temperature-controlling conductive material 9400, an insulation layer 9402 is deposited, which insulates the first conductive layer 9398 and the temperature-controlling conductive material 9400 completing the fabrication of the lysis function 9372. The insulating layer 9402 is only deposited on a portion of the surface of the monitor/detector. Next, a second conductive layer 9340 is deposited on top of the first conductive layer 9398, and then the molecule layer 9342 is deposited on top of the second conductive layer completing the fabrication of the material layer detector array 9392. A component adhesive 9404 is deposited, followed by a memory component 9406 and a materials layer memory 9370.

It should be appreciated that the deposition of the first conductive layer material 9398 and the second conductive layer material 9340 can be swapped as shown in FIG. 99 and FIG. 102.

Figure 104:
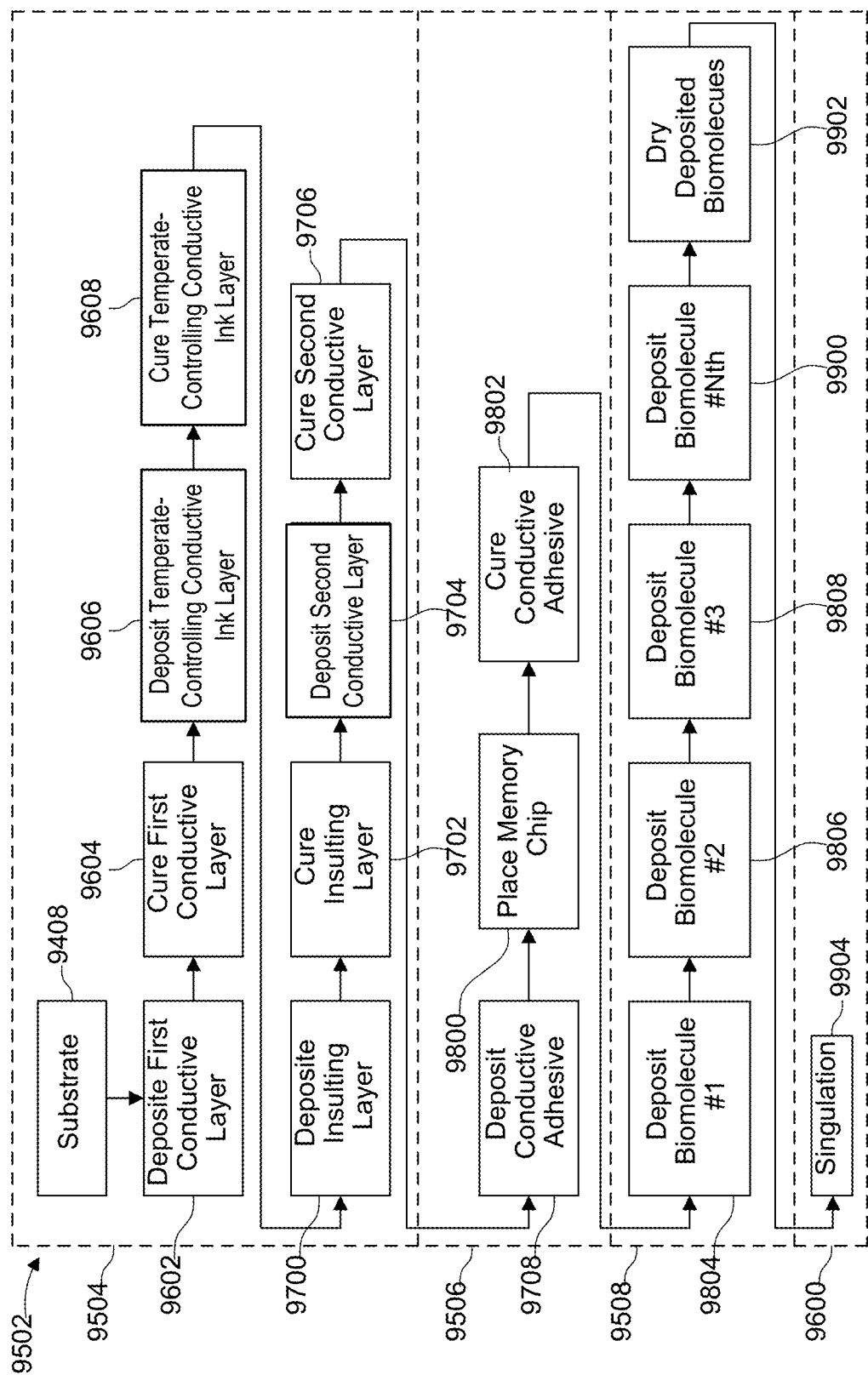

Sensor Material Manufacturing Process:

FIG. 104 shows for illustrative purposes the sensor material manufacturing process of one embodiment. In the exemplary embodiment, the manufacturing process comprising 9502 has four phases: depositing and curing conductive materials 9504, placing the memory chip 9506, depositing and drying molecules 9508, and sensor material processing and singulation 9600. The first phase, depositing and curing conductive material 9504, begins with depositing the first conductive layer 9602 on a substrate 9408 and curing the first conductive layer 9604. Next, the temperature-controlling conductive layer is deposited 9606 and then the temperature-conductive layer is cured 9608. Next, the insulating layer is deposited 9700 and then the insulating layer is cured 9702. Next, the second conductive layer is deposited 9704 and then the second conductive layer is cured 9706. After all the conductive layers and insulating layers are deposited and cured, phase two can begin.

In the second phase, placing the memory chip 9506 begins with depositing a conductive adhesive 9708. Next, the memory chip is placed on the conductive adhesive 9800 and then the conductive adhesive is cured 9802, creating a secure physical and electrical connection with the deposited first conductive layer 9602. After the memory chip is securely connected using a conductive adhesive, phase three can begin. The third phase, depositing and drying molecules 9508, begins with the deposition of molecule solution #1 9804, followed by deposition of molecule solution #2 9806, followed by deposition of molecule solution #3 9808, followed by deposition of molecule #Nth 9900. It should be appreciated that any number of molecule solutions can be deposited. Next, the deposited molecule solutions are dried 9902 in a furnace, completing phase three depositing and drying molecules 9508. After all the molecule layers are deposited and dried, phase four can begin. The fourth phase, sensor material processing 9600 involves the singulation of the sensor materials 9904. After all the sensor materials are singulated the sensor materials are ready for cartridge assembly.

Figure 105:
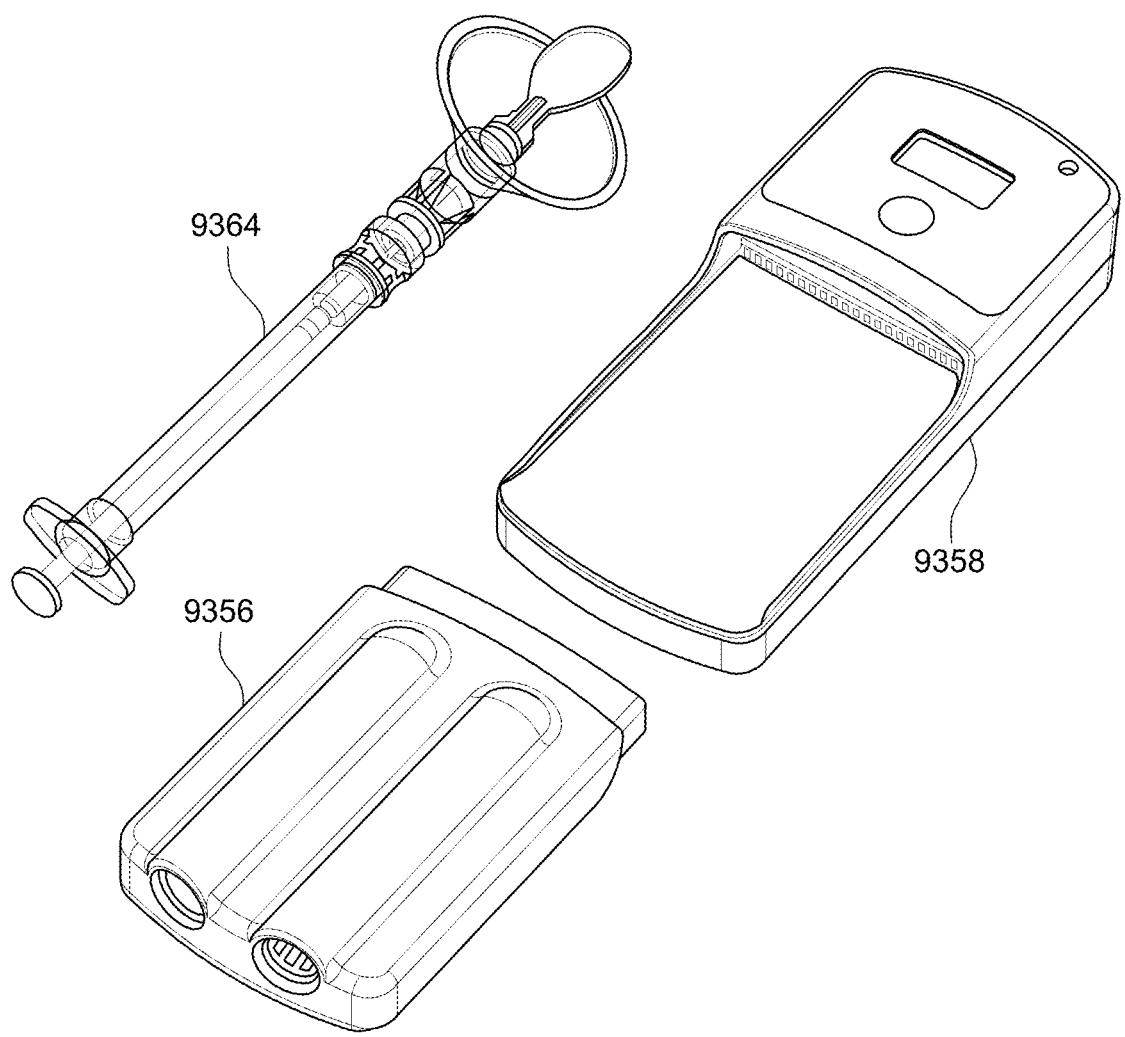

Analyte Detection System Components:

FIG. 105 shows for illustrative purposes the analyte detection system components of one embodiment. In the exemplary embodiment the analyte detection system comprising a sample collector 9364, a sensor detector cartridge 9356, and an associated receiver reader 9358.

Figure 106B:
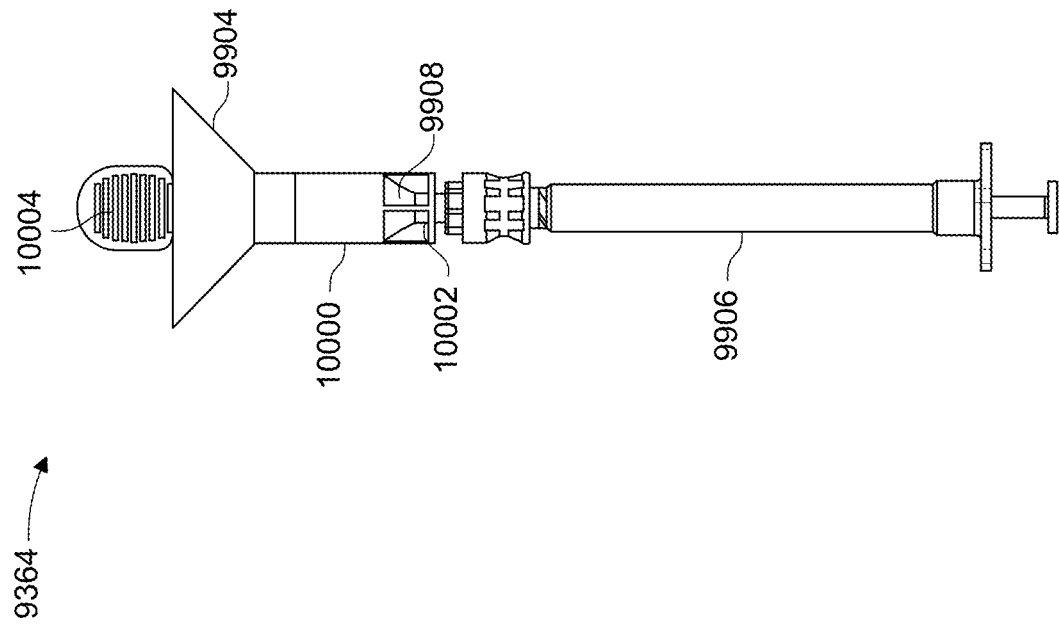
Figure 106A:
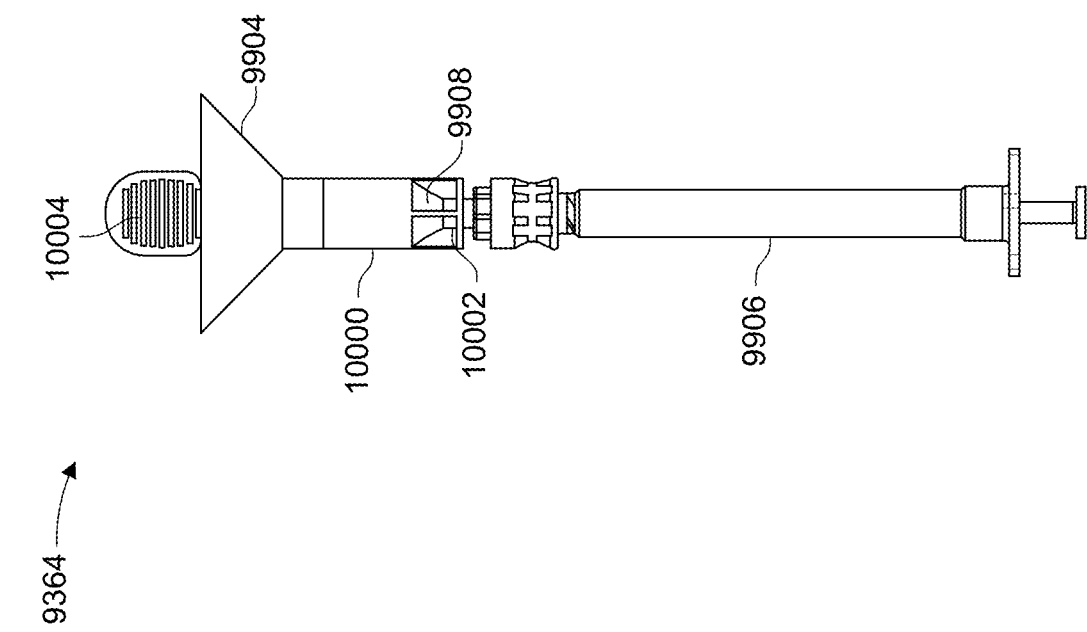

Sample Collector:

FIGS. 106A-106B presents an exemplary sample collector of one embodiment. FIG. 106A shows for illustrative purposes only an example of an exemplary sample collector assembled as a single unit of one embodiment. FIG. 106A shows the sample collector 9364 comprises a sample collection cup or funnel 9904, a syringe 9906, a connector 9908, a sample collection assembly 10000, and a sample collection stopper 10004. The syringe 9906 is selectively attachable to the sample collection assembly 10000 of the sample collector 9363 and the sample deposition port/pad 9363 shown in FIG. 96. In one exemplary embodiment, the syringe 9906 has a luer-lock tip 10002 or like screw mechanism or fitting for establishing a secure connection with the sample collection assembly 10000 of the sample collector 9363 and the sample deposition port/pad 9363 of the sensor 9356 as shown in FIG. 96. The sample collection stopper 10004 establishes pressure in the sample collector 9364 of FIG. 96, enabling the sample to be drawn to the syringe 9906 from the sample collection assembly 10000. In other embodiments, a filter for filtering the test sample can be part of the sample collection cup or funnel 9904 or be part of the sample collection assembly 10000 or be part of the syringe 9906. In yet other embodiments, a chemical lysis can be placed in at least one of the sample collection assembly 10000, syringe 9906, or elements of sensor 9356 such as the sample deposition port/pad 9363 or active/passive flow induction 9362 or the monitor/detector 9368 as shown in FIG. 96. The descriptions continue in FIG. 106B.

FIG. 106B shows for illustrative purposes only an example of an exemplary removeable sample collection component continuation of one embodiment. FIG. 106B shows a continuation from FIG. 106A of the exemplary sample collection component 10006 comprising a sample collection cup or funnel 9904 modified or molded to fit with the sample collection vial assembly 10000, a sample collection stopper 10004, and a connector 9908 for enabling the test sample to flow to the syringe 9906 from the sample collection assembly 10000. The sample collection stopper 10004 is in a position to restrict airflow through the sample collector 9364 of FIG. 96, creating pressure and enabling the test sample to be drawn to the syringe 9906 from the sample collection vial assembly 10000.

Figure 107:
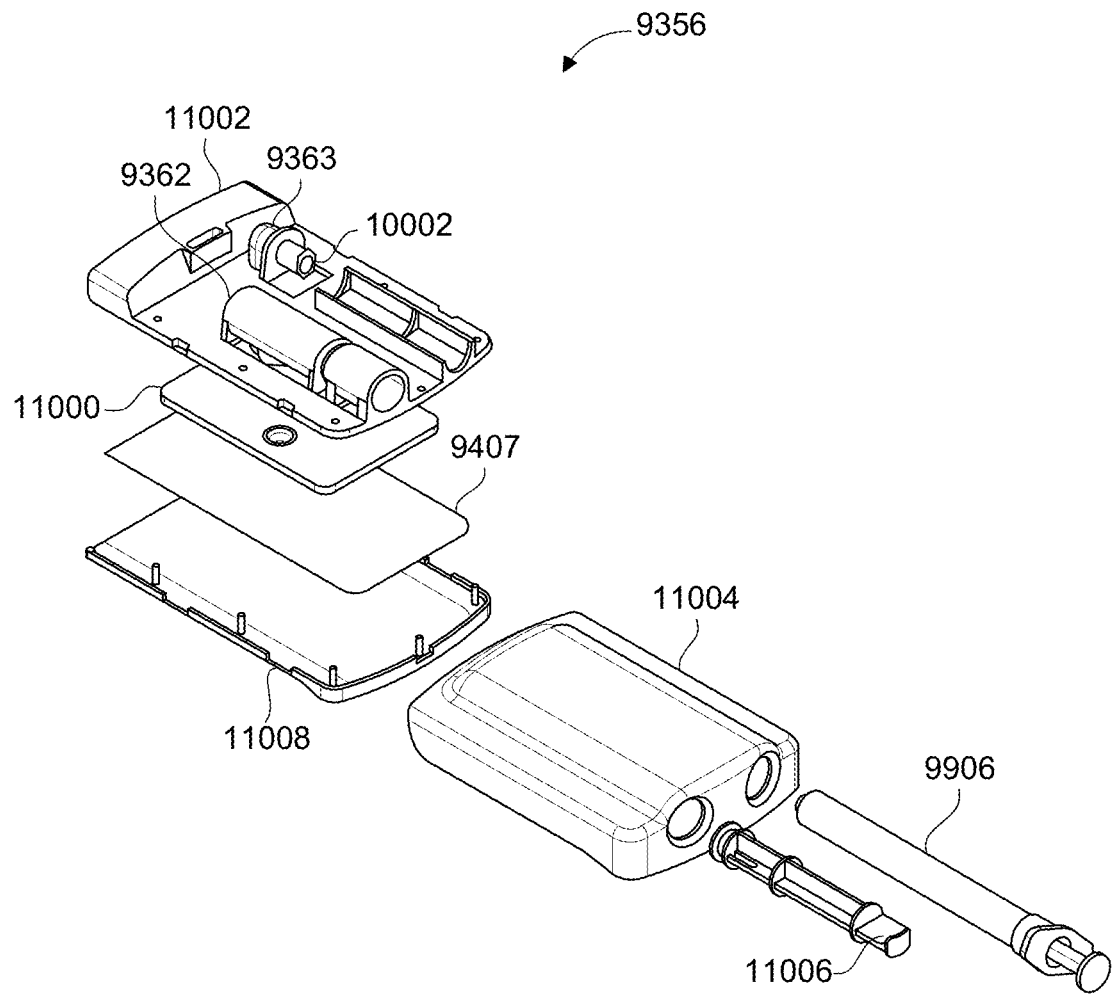

Sensor Cartridge Components:

FIG. 107 shows for illustrative purposes exemplary sensor 9356 in the form of the analyte detection sensor cartridge of one embodiment. In the exemplary embodiment, the sensor 9356 or analyte detection cartridge components comprising a lower molded housing 10008, a sensor 9407, a test sample active/passive inductive device 11000, a middle-molded part 11002, an upper molded cover 11004, a syringe 9906 and a molded plunger part 11006. The lower molded housing 10008 properly aligns the sensor 9407 and the test sample active/passive inductive device 11000. The test sample active/passive inductive device 11000 receives the test sample from the syringe 9906. The syringe 9906 is selectively attachable to the middle-molded part 11002 through the sample deposition port/pad 9363. In the exemplary embodiment, the sample deposition port/pad 9363 has a luer-lock tip 10002 or like screw mechanism or fitting for a secure connection. Upon transferring the test sample to the test sample active/passive inductive device 11000 from the syringe 9906, the test sample is processed using a lysing step from the lysis function 9372 as shown in FIG. 96. After processing the test sample, the molded plunger part 11006 is activated, creating a pressurized vacuum for flowing the test sample to the monitor/detector 9368 as shown in FIG. 96.

Test Sample Flow Induction Mechanism:

FIGS. 108A-108B shows for illustrative purposes an exemplary mechanism for inducing the flow of the test sample within the analyte detection cartridge components of one embodiment.

FIG. 108A shows for illustrative purposes only an example of an exemplary mechanism for inducing the flow of the test sample within the analyte detection cartridge components of one embodiment. FIGS. 108A-108B shows for illustrative purposes an exemplary mechanism for inducing the flow of the test sample within the analyte detection cartridge components of one embodiment. FIG. 108A shows the flow induction mechanism 9362 as shown in FIG. 96, creates a vacuum source for moving the test sample to the monitor/detector 9368 as shown in FIG. 96 for analyte detection. FIG. 108A shows for illustrative purposes the test sample active flow induction mechanism in the closed position 11008. In the closed position, the plunger 11006 is fully engaged in the plunger pathway 12000 such that the plunger 11006 is blocking the vent 12002 of the flow induction mechanism 9362 of FIG. 96. In the closed position the active flow induction mechanism is not activated.

FIG. 108B shows for illustrative purposes only an example of an exemplary mechanism for inducing the flow of the test sample within the analyte detection cartridge components of one embodiment. FIG. 108B shows a continuation from FIG. 108A of an example of an exemplary mechanism for inducing the flow of the test sample within the analyte detection cartridge components the flow induction mechanism in the open position 12004 of one embodiment. FIG. 108B shows in the open position, the active flow induction mechanism activated, enabling the test sample to flow to the monitor/detector 9368 as shown in FIG. 96, for analyte detection. In the open position, the plunger 11006 is not fully engaged in the plunger pathway 12000 such that the plunger 11006 is not blocking the vent 12002 of the flow induction mechanism 9362 of FIG. 96. In the open position, the plunger 11006 is securely in place of the plunger pathway 12000 such that the plunger 11006 cannot be moved back into the closed position without using excessive force.

Sensor Cartridge Assembled Components:

FIG. 109 shows for illustrative purposes an exemplary assembled sensor cartridge components of one embodiment. The assembled sensor cartridge-1206 12006 comprising of sensor 9356 components as shown in FIG. 96. The assembled sensor cartridge 12006 comprises a sample collector 9364 that mates with the sample deposition port/pad 9363 and a connector 9366. Upon injecting the test sample from the sample collector 9364 through the sample deposition port/pad 9363 to the lysis function 9372, the test sample is processed. Using the active/passive flow induction 9362, the test sample is moved to the monitor/detector 9368 for analyte detection. The analyte detection data is stored in memory 9370 of the sensor 9356 as shown in FIG. 96.

Analyte Detection Reader Components:

FIG. 110 shows for illustrative purposes exemplary components of the analyte detection reader of one embodiment. In the exemplary embodiment, the analyte detection reader 12008 components comprising a lower molded housing 13000, a power source 13002 with a rechargeable port 13004, a printed circuit board assembly (PCBA) 13006, a display 13008, an upper molded housing 14000 and a display cover 14002. In the exemplary embodiment, the lower molded housing 13000 and the upper molded housing 14000 is held together with screws 14004. It should be appreciated that any mechanism in the art can be used to hold together the reader housings. Other exemplary embodiments can include snap fits, tabs, fasteners, and welds. In other exemplary embodiments, the analyte detection reader 12008 does not include a display 13008 and does not include a display cover 14002.

What is claimed is:

1. An apparatus comprising:
   a first conductive layer deposited and cured to couple to a substrate configured for a lysis function;
   wherein the substrate is configured to support deposited materials;
   a temperature controlling conductive layer deposited and cured to couple on top of a portion of the first conductive layer configured to create a heating element that serves as the lysis function;
   an insulating layer deposited and cured to couple on top of a temperature controlling conductive ink and a portion of the first conductive layer configured to insulate the temperature controlling conductive layer and a portion of the first conductive layer;
   a second conductive layer deposited and cured to couple on top of a portion of first conductive layer configured to bind with at least one molecule;
   a memory chip conductively coupled to the first conductive layer;
   wherein the memory chip is configured to store analyte signatures; and
   at least one molecule layer deposited and dried to couple on top of the second conductive layer configured to promote hybridization of the atomic orbitals of the at least one molecule on the surface of the second conductive layer with at least one biomolecule in a test sample.

2. The apparatus of claim 1, wherein the substrate is at least one of a material from a group of at least one polyimide, polyethylene terephthalate (PET), plastics, polymers, glass, ceramics and paper.

3. The apparatus of claim 1, wherein the binding of the second conductive layer and the at least one molecule is at least one of non van der Waals force and covalent interactions.

4. The apparatus of claim 1, wherein the layered materials are configured to be cured with at least one of thermal curing, energy transfer, conduction, radiative heat transfer, infrared (IR), near infrared (NIR), laser, microwave, and photonic at different speeds, pulses of light, wavelengths of light, and power settings.

5. The apparatus of claim 1, further comprising a detector array coupled to the apparatus including a substrate, a first conductive layer, a temperature controlling conductive layer, an insulating layer, a second conductive layer, an adhesive layer, a memory chip, and at least one molecule layer.

6. The apparatus of claim 1, wherein at least one molecule layer includes all types of molecules configured to bind to the second conductive layer.

7. An apparatus comprising:
a first conductive layer deposited and cured to couple to a substrate configured for a lysis function;
wherein the substrate is configured to support deposited materials;
a temperature controlling conductive layer deposited and cured to couple on top of a portion of the first conductive layer configured to create a heating element that serves as the lysis function;
an insulating layer deposited and cured to couple on top of the temperature controlling conductive layer and a portion of the first conductive layer configured to insulate the temperature controlling conductive layer and a portion of the first conductive layer;
a second conductive layer deposited and cured to couple on top of a portion of first conductive layer configured to bind with at least one molecule;
an adhesive layer deposited on a portion of the first conductive layer and having a memory chip placed on the adhesive layer configured to adhere the memory chip to the first conductive layer;
wherein the memory chip is conductively coupled to the first conductive layer and configured to store analyte signatures;
wherein the memory chip is further configured to communicate the stored analyte signatures to an app for identifying a detected analyte using the stored analyte signatures; and
at least one molecule layer deposited and dried to couple on top of the second conductive layer configured to promote hybridization of the atomic orbitals of the at least one molecule on the surface of the second conductive layer and the atomic orbitals of the at least one molecule in a test sample.

8. The apparatus of claim 7, wherein the substrate is at least one of a material from a group of at least one polyimide, polyethylene terephthalate (PET), plastics, polymers, glass, ceramics, and paper configured to adhere to deposited materials.

9. The apparatus of claim 7, wherein the adhesive layer includes a conductive adhesive.

10. The apparatus of claim 7, wherein the layered materials are configured to be cured with at least one of thermal curing, energy transfer, conduction, radiative heat transfer, infrared (IR), near infrared (NIR), laser, microwave, and photonic at different speeds, pulses of light, wavelengths of light, and power settings.

11. The apparatus of claim 7, further comprising a detector array coupled to the apparatus including a substrate, a first conductive layer, a temperature controlling conductive layer, an insulating layer, a second conductive layer, an adhesive layer, a memory chip, and at least one molecule layer.

12. The apparatus of claim 7, wherein at least one molecule layer can be any type of layer containing all types of molecules configured to bind to the second conductive layer and promote atomic orbital hybridization of the molecule configured to bind to the second conductive layer and at least one molecule in the test sample.

* * * * *